(12) United States Patent
Brown, Jr. et al.

(10) Patent No.: US 6,673,909 B1
(45) Date of Patent: Jan. 6, 2004

(54) OLIGONUCLEOTIDES FOR DYSFERLIN, A GENE MUTATED IN DISTAL MYOPATHY AND LIMB GIRDLE MUSCULAR DYSTROPHY

(75) Inventors: Robert H. Brown, Jr., Needham, MA (US); Jing Liu, Outremont (CA); Masashi Aoki, Sendai (JP); Meng F. Ho, Singapore (SG); Chie Matsuda-Asada, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/382,552

(22) Filed: Aug. 25, 1999

Related U.S. Application Data
(60) Provisional application No. 60/097,927, filed on Aug. 25, 1998.

(51) Int. Cl.[7] ........................... C12N 15/12; C07H 21/00
(52) U.S. Cl. .................. 536/23.1; 536/24.3; 536/24.31
(58) Field of Search .............................. 536/23.1, 23.5, 536/24.3, 24.31; 435/320.1, 325, 252.3

(56) References Cited

U.S. PATENT DOCUMENTS 6,165,748 A * 12/2000 Racie et al. ................ 435/69.1

OTHER PUBLICATIONS

Rudinger, In "Peptide Hormones" (ed. J.A. Parsons) University Park Press, Baltimore pp. 1–7, 1976.*
Achanzar, et al. "A nematode gene required for sperm vesicle fusion," *Journal of Cell Science*, 110: 1073–1081 (1997).
Argon & Ward, "Caenorhabditis Elegans Fertilization–Defective Mutants with Abnormal Sperm" *J. Cell Science*, 110:1073–81 (1997).
Bashir, et al. "Genetic and Physical Mapping at the Limb–Girdle Muscular Dystrophy Locus (LGMD2B) on Chromosome 2p", *Genomics*, 33:46–52 (1996).
Bashir, et al. "A gene related to Caenorhabditis elegans spermatogenesis factor fer–1 mutated in limb–girdle muscular dystrophy type 2B", *Nature Genetics*, 20:37–42 (1998).
Bejaoui, et al. "Linkage of Miyoshi myopathy (distal autosomal recessive muscular dystrophy) locus to chromosome 2p12–14", *Neurology*,45:768–775 (1995).
Bejaoui et al., "Genetic fine mapping of the Miyoshi myopathy locus and exclusion of eight candidate genes," *Neurogenetics* 1:189–96 (1998).
Cameron, "Recent Advances in Transgenic Technology," *Molecular Biotechnology*, 7:253–265 (1997).
Hudson, et al. "An STS–Based Map of the Human Genome," *Science*, 270:1945–1954 (1995).
Gastier, et al., "Survey of trinucleotide repeats in the human genome: assessment of their utility as genetic markers," *Hum. Molecular Genetics* 4:1829–36 (1995).
Liu, et al. "Generation of a 3–Mb PAC Contig Spanning the Miyoshi Myopathy/Limb–Girdle Muscular Dystrophy (MM/LGMD2B) Locus on Chromosome 2p13", Genomics, 49:23–29 (1998).
Liu, "Dysferlin, a novel skeletal muscle gene, is mutated in Miyoshi myopathy and limb girdle muscular dystrophy," *Nature Genetics*, 20:31–36 (1998).
Ahlberg et al., "Genetic Linkage of Elander Distal Myopathy to Chormosome 2p13" Annals of Neurology 46(3):399–404, 1999.
Bittner et al., "Dysferlin deletion in SJL mice (SJL–Dysf) defines a natural model for limb girdle muscular dystrophy 2B" Nature Genetics 23:141–142, 1999.
National Cancer Institute, Database GenCore, Accession No. AI128455, 1998.
Waye et al., Database GenCore, Accession No. R41062, 1995.
Marra et al., Database GenCore, Accession No. AA718275, 1997.
Hillier et al., Database GenCore, Accession No. R76778, 1995.
Koenig et al., "Complete Cloning of the Duchenne Muscular Dystrophy (DMD) cDNA and Preliminary Genomic Organization of the DMD Gene . . . "Cell 50:509–517, 1987.
Matsuda et al., "Dysferlin is a surface membrane–associated protein that is absent in Miyoshi myopathy" Neurology 53(5):1119–1122, 1999.
Moreira et al., "The Seventh Form of Autosomal Recessive Limb–Girdle Muscular Dystrophy is Mapped to 17q11–12" Amer. J. Hum. Genet. 61:151–159, 1997.
Weiler et al., "Limb–Girdle Muscular Dystrophy and Miyoshi Myopathy in an Aborignal Canadian Kindred Map to LGMD2B and . . . "Amer. J. Hum. Genet. 59:872–878, 1996.

* cited by examiner

*Primary Examiner*—Gary Kunz
*Assistant Examiner*—Robert C. Hayes
(74) *Attorney, Agent, or Firm*—Fish & Richardson P.C.

(57) ABSTRACT

A novel gene and the protein encoded therein, i.e., dysferlin, are disclosed. This gene and its expression products are associated with muscular dystrophy, e.g., Miyoshi myopathy and limb girdle musclular dystrophy 2B.

1 Claim, 10 Drawing Sheets

```
   1  MLRVEILYAE NVHTPDTDIS DAYCSAVFAG VKKRTKVIKN SVNPVWNEGF
  51  EWDLKGIPLD CGSELHVVVK DHETMGRNRF LGEAKVPLRE VLATPSLSAS
 101  FNAPLLDTKK QPTGASLVLQ VSYTPLPGAV PLFPPPTPLE PSPTLPDLDV
 151  VADTGGEEDT EDQGLTGDEA EPFLDQSGGP GAPTTPRKLP SRPPPHYPGI
 201  KRKRSAPTSR KLLSDKPQDF QIRVQVIEGR QLPGVNIKPV VKVTAAGQTK
 251  RTRIHKGNSP LFNETLFFNL FDSPGELFDE PIFITVVDSR SLRTDALLGE
 301  FRMDVGTIYR EPRHAYLRKW LLLSDPDDFS AGARGYLKTS LCVLGPGDEA
 351  PLERKDPSED KEDIESNLLR PTGVALRGAH FCLKVFRAED LPQMDDAVMD
 401  NVKQIFGFES NKKNLVDPFV EVSFAGKMLC SKILEKTANP QWNQNITLPA
 451  MFPSMCEKMR IRIIDWDRLT HNDIVATTYL SMSKISAPGG EIEEEPAGAV
 501  KPSKASDLDD YLGFLPTFGP CYINLYGSPR EFTGFPDPYT ELNTGKGEGV
 551  AYRGRLLLSL ETKLVEHSEQ KVEDLPADDI LRVEKYLRRR KYSLFAAFYS
 601  ATMLQDVDDA IQFEVSIGNY GNKFDMTCLP LASTTQYSRA VFDGCHYYYL
 651  PWGNVKPVVV LSSYWEDISH RIETQNQLLG IADRLEAGLE QVHLALKAQC
 701  STEDVDSLVA QLTDELIAGC SQPLGDIHET PSATHLDQYL YQLRTHHLSQ
 751  ITEAALALKL GHSELPAALE QAEDWLLRLR ALAEEPQNSL PDIVIWMLQG
 801  DKRVAYQRVP AHQVLFSRRG ANYCGKNCGK LQTIFLKYPM EKVPGARMPV
 851  QIRVKLWFGL SVDEKEFNQF AEGKLSVFAE TYENETKLAL VGNWGTTGLT
 901  YPKFSDVTGK IKLPKDSFRP SAGWTWAGDW FVCPEKTLLH DMDAGHLSFV
 951  EEVFENQTRL PGGQWIYMSD NYTDVNGEKV LPKDDIECPL GWKWEDEEWS
1001  TDLNRAVDEQ GWEYSITIPP ERKPKHWVPA EKMYYTHRRR RWVRLRRRDL
1051  SQMEALKRER QAEAEGEGWE YASLFGWKFH LEYRKTDAFR RRRWRRRMEP
1101  LEKTGPAAVF ALEGALGGVM DDKSEDSMSV STLSFGVNRP TISCIFDYGN
1151  RYHLRCYMYQ ARDLAAMDKD SFSDPYAIVS FLHQSQKTVV VKNTLNPTWD
1201  QTLIFYEIEI FGEPATVAEQ PPSIVVELYD HDTYGADEFM GRCICQPSLE
1251  RMPRLAWFPL TRGSQPSGEL LASFELIQRE KPAIHHIPGF EVQETSRILD
1301  ESEDTDLPYP PPQREANIYM VPQNIKPALQ RTAIEILAWG LRNMKSYQLA
1351  NISSPSLVVE CGGQTVQSCV IRNLRKNPNF DICTLFMEVM LPREELYCPP
1401  ITVKVIDNRQ FGRRPVVGQC TIRSLESFLC DPYSAESPSP QGGPDDVSLL
1451  SPGEDVLIDI DDKEPLIPIQ EEEFIDWWSK FFASIGEREK CGSYLEKDFD
1501  TLKVYDTQLE NVEAFEGLSD FCNTFKLYRG KTQEETEDPS VIGEFKGLFK
1551  IYPLPEDPAI PMPPRQFHQL AAQGPQECLV RIYIVRAFGL QPKDPNGKCD
1601  PYIKISIGKK SVSDQDNYIP CTLEPVFGKM FELTCTLPLE KDLKITLYDY
1651  DLLSKDEKIG ETVVDLENRL LSKFGARCGL PQTYCVSGPN QWRDQLRPSQ
1701  LLHLFCQQHR VKAPVYRTDR VMFQDKEYSI EEIEAGRIPN PHLGPVEERL
1751  ALHVLQQQGL VPEHVESRPL YSPLQPDIEQ GKLQMWVDLF PKALGRPGPP
1801  FNITPRRARR FFLRCIIWNT RDVILDDLSL TGEKMSDIYV KGWMIGFEEH
1851  KQKTDVHYRS LGGEGNFNWR FIFPPFDYLPA EQVCTIAKKD AFWRLDKTES
1901  KIPARVVFQI WDNDKFSFDD FLGSLQLDLN RMPKPAKTAK KCSLDQLDDA
1951  FHPEWFVSLF EQKTVKGWWP CVAEEGEKKI LAGKLEMTLE IVAESEHEER
2001  PAGQGRDEPN MNPKLEDPRR PDTSFLWFTS PYKTMKFILW RRFRWAIILF
2051  IILFILLLFL AIFIYAFPNY AAMKLVKPES
```

(SEQ ID NO:2)

FIG. 2

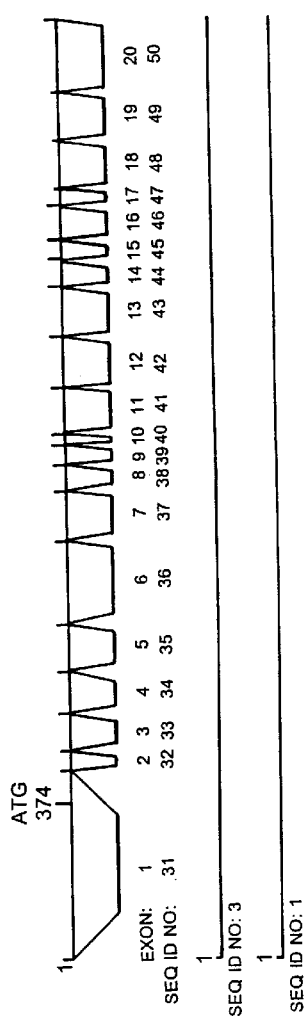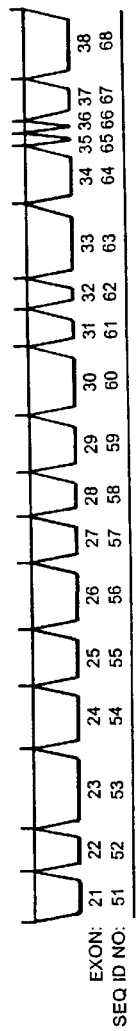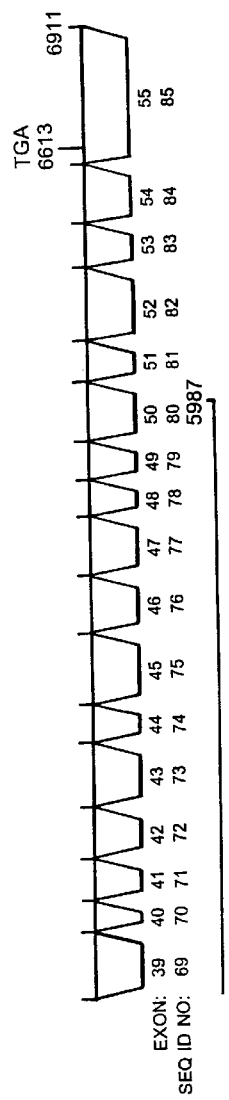
FIG. 5

FIG. 6A

```
811/271
att gtg gtg gag ctg tac gac cat gac act tat ggt gca gac gag ttt atg ggt cgc tgc atc tgt caa ccg agt ctg gaa cgg atg cca
 I   V   V   E   L   Y   D   H   D   T   Y   G   A   D   E   F   M   G   R   C   I   C   Q   P   S   L   E   R   M   P
901/301                                                                             871/291
cgg ctg gcc tgg ttc cca ctg acg agg ggc agc cag ccg tcg ggg gag ctg gcc tct ttt gag ctc atc cag gag gag aag ccg gcc
 R   L   A   W   F   P   L   T   R   G   S   Q   P   S   G   E   L   A   S   F   E   L   I   Q   R   E   K   P   A
991/331                                                                             961/321
atc cac cat att cct ggt ttt gag gtg cag gag aca tca agg atc ctg gat gag tct gag gac aca gac ctg ccc tac cca ccc cag
 I   H   H   I   P   G   F   E   V   Q   E   T   S   R   I   L   D   E   S   E   D   T   D   L   P   Y   P   P   Q
1081/361                                                                            1051/351
agg gag gcc aac atc tac atg gtt cct cag aac atc aag cca gcg ctc cag agt acc gcc atc gag atc ctg gca tgg ggc ctg cgg aac
 R   E   A   N   I   Y   M   V   P   Q   N   I   K   P   A   L   Q   S   T   A   I   E   I   L   A   W   G   L   R   N
1171/391                                                                            1141/381
atg aag agt tac cag ctg gcc aac ccc atc tcc tgc agc ctc gtg gta gaa gtg atg gtg cag acg gtg ggc tcc tgc ccc atc acc gtc
 M   K   S   Y   Q   L   A   N   P   I   S   C   S   L   V   V   E   V   M   V   Q   T   V   G   S   C   P   I   T   V
1261/421                                                                            1231/411
ctc cgg aag tac cag ctg gcc aac ccc atc tgc agc ctc gtg gta gaa gtg atg gtg cag acg gtg ggc tcc tgc ccc atc acc gtc
```

FIG. 6B

```
1711/571
acc ttc aag ctg tac cgg ggc aag acg cag                                                      1741/581
 T   F   K   L   Y   R   G   K   T   Q   gag gag aca gaa gat cca tct gtg att ggc              1771/591
1801/601                                   E   E   T   E   D   P   S   V   I   G   gaa ttt aag ggc ctc ttc aaa att tat ccc
ctc cca gaa gac gcc atc ccc atg cca cag                                                       E   F   K   G   L   F   K   I   Y   P
 L   P   E   D   A   I   P   M   P   Q   ttc cac cag ctg gcc gcc cag           1861/621
1891/631                                   F   H   Q   L   A   A   Q           gga ccc cag gag tgc ctg tgt gtc atc tac
att gtc cga gca ttt ggc ctg cag ccc aag                                        1951/651       G   P   Q   E   C   L   V   R   I   Y
 I   V   R   A   F   G   L   Q   P   K   gac ccc aat ggc tac atc tcc ata ggg aag aaa tca gtg agt
1981/661                                   D   P   N   G   Y   I   S   I   G   K   K   S   V   S
gac cag gat aac tac atc ccc tgc acg ctg   2041/681
 D   Q   D   N   Y   I   P   C   T   L   gag ccc gta ttt gga aag atg ttc gag ctg cct ctg gag aag gac cta
2071/691                                   E   P   V   F   G   K   M   F   E   L   P   L   E   K   D   L
aag atc act ctc gac tat gac ctc cca cag   2131/711
 K   I   T   L   D   Y   D   L   P   Q   acc tgc act gtc gac ctg gag aac agg ctg ctg tcc aag
2161/721                                   T   C   T   V   D   L   E   N   R   L   L   S   K
ttt ggg gct cgc tgt gga ctc cca cag acc   2221/741
 F   G   A   R   C   G   L   P   Q   T   gtc gac ctg gag acg gtc tcc ccc cag ctc cac
2251/751                                   V   D   L   E   T   V   S   P   Q   L   H
ctc ttc tgc cag cag cat aga gtc aag gca   2311/771
 L   F   C   Q   Q   H   R   V   K   A   gac cag ctc gga ccg aac cag tgg cgg gat aaa gaa gag ata gag
2341/781                                   D   Q   L   G   P   N   Q   W   R   D   K   E   E   I   E
gag gct ggc agg atc cca aac cca cac ctg   2401/801
 E   A   G   R   I   P   N   P   H   L   cag gat gta atg ttt cag gac aag gtc att atc tgg aat acc aga gat gtg
2431/811                                   Q   D   V   M   F   Q   D   K   V   I   I   W   N   T   R   D   V
cac gtg gag tca cgg ccc tac agc ctg cca   2491/831
 H   V   E   S   R   P   Y   S   L   P   gtg ctt cag cat ctg gct cgt ctg cag cag cag cag ctg gac cta ttt ccg aag gcc
2521/841                                   V   L   Q   H   L   A   R   L   Q   Q   Q   Q   L   D   L   F   P   K   A
ctg cag cgg cct gga cct ccc ttc aac atc   2581/861
 L   Q   R   P   G   P   P   F   N   I   acc cca cgg aga agg gcc aga agg ttt ttc ctg cgt tgt att atc cag atg tgg gtc cag atg ttc
2611/871                                   T   P   R   R   R   A   R   R   F   F   L   R   C   I   I   Q   M   W   V   Q   M   F
atc ctg gag gac ctg agc acg ctc acc ggg   2671/891
 I   L   D   D   L   S   T   L   T   G   ttt gcg act ggc tgg aaa ggt tat gtg aaa gag cac aag caa aag
 2641/881                                  F   A   T   G   W   K   G   Y   V   K   E   H   K   Q   K
aag aag gag ggg gag aag atg agc gac att
 E   K   M   S   D   I
```

```
2701/901
aca gac gtg cat tat cgt tcc ctg gga ggt gaa ggc aac ttc aac ttc att ttc ccc ttc gac tac ctg cca gct gag caa gtc
 T   D   V   H   Y   R   S   L   G   G   E   G   N   F   N   F   I   F   P   F   D   Y   L   P   A   E   Q   V
2791/931                                                          2731/911                      2761/921
tgt acc att gcc aag aag gat gcc ttc tgg agg ctg gac aag act gac aag agc aaa atc cca gca cga gtg gtg ttc cag atc tgg gac aat
 C   T   I   A   K   K   D   A   F   W   R   L   D   K   T   D   K   S   K   I   P   A   R   V   V   F   Q   I   W   D   N
2881/961                                      2821/941                                    2851/951
gac aag ttc tcc gat gat gat ttt ctg ggc tcc ctg cag ctc gat ctc aac cgc atg ccc aag cca gcc aag aag tgc tcc
 D   K   F   S   D   D   D   F   L   G   S   L   Q   L   D   L   N   R   M   P   K   P   A   K   K   C   S
2971/991                                      2911/971                                    2941/981
ttg gac cag ctg gat gat gct ttc cac cca gaa tgg ttt gtg tcc ctt ttt gag cag aaa aca gtg aag ggc tgg tgg ccc tgt gta gca
 L   D   Q   L   D   D   A   F   H   P   E   W   F   V   S   L   F   E   Q   K   T   V   K   G   W   W   P   C   V   A
3061/1021                                     3001/1001                                   3031/1011
gaa gag ggt gag aag aaa ata ctg gcg ggc aag ctg gaa atg acc gag agt gag cat gag tgg ctg ctg ctg ttt acc tcc cca tac aag
 E   E   G   E   K   K   I   L   A   G   K   L   E   M   T   E   S   E   H   E   W   L   L   L   F   T   S   P   Y   K
3151/1051                                     3091/1031                                   3121/1041
cag ggc cgg gat gag ccc aac atg aac cct aag ctt gag gac cca agg cgc cga gac ccc gac acc atc atc ttc atc ctg ttc gcc atc ttc
 Q   G   R   D   E   P   N   M   N   P   K   L   E   D   P   R   R   R   D   P   D   T   I   I   F   I   L   F   A   I   F
3241/1081                                     3181/1061                                   3211/1071
acc atg aag ttc atc ttc tgg tgg cgg cgg ttc cgg tgg cgg ttc atg ctg gtg gtg cct gtc gaa ggg gcc gtg ggg tcc
 T   M   K   F   I   F   W   W   R   R   F   R   W   R   F   M   L   V   V   P   V   E   G   A   V   G   S
3331/1111                                     3271/1091                                   3301/1101
atc tac gcc ttc ccg aac tat gct gcc atg aag ctg gtg gtg aag ccc ttc tcc ctc ctc tcc tgc tga ttg tcc tgc cag gtg ggg cag
 I   Y   A   F   P   N   Y   A   A   M   K   L   V   V   K   P   F   S   L   L   S   C   *   L   S   C   Q   V   G   Q
3421/1141                                     3361/1121                                   3391/1131
cct cca gca tgg gac tgg ccc gcc tcc gcc cag ctc ggc gag gct ctg aga cag acc tca ccc cac ttc cat ccc ttc ctc ccc caa ccc
 P   P   A   W   D   W   P   A   S   A   Q   L   G   E   A   L   R   Q   T   S   P   H   F   H   F   L   P   Q   P
3511/1171                                     3451/1151                                   3481/1161
aca gac aga tgg acc ggc cca cac tcc cag agt tgc taa cat gga tca aga ctg aga tca tgc
 T   D   R   W   T   G   P   H   S   Q   S   C   *   H   G   S   R   L   R   S   C
3601/1201                                     3541/1181                                   3571/1191
aac gct ttt ttg gat cag ctc aga cat att tca gta taa aac cac aaa aaa aaa aa
 N   A   F   L   D   Q   L   R   H   I   S   V   *   N   H   K   K   K   K
                                              3631/1211                                   3661/1221

(SEQ ID NO:232)
                        (SEQ ID NO:233)
```

SEQUENCE LISTING

<160> NUMBER OF SEQ ID NOS: 233

<210> SEQ ID NO 1
<211> LENGTH: 6911
<212> TYPE: DNA
<213> ORGANISM: Homo sapiens
<220> FEATURE:
<221> NAME/KEY: CDS
<222> LOCATION: (374)...(6613)

<400> SEQUENCE: 1

```
tcgaccgccc agccaggtgc aaaatgccgt gtcattggga gactccgcag ccggagcatt      60
agattacagc tcgacggagc tcgggaaggg cggcgggggt ggaagatgag cagaagcccc     120
tgttctcgga acgccggctg acaagcgggg tgagcgcagg cggggcgggg acccagccta     180
gcccactgga gcagccgggg gtggcccgtt ccccttaag agcaactgct ctaagccagg      240
agccagagat tcgagccggc ctcgcccagc cagccctctc cagcgagggg acccacaagc     300
ggcgcctcgg ccctcccgac ctttccgagc cctctttgcg ccctgggcgc acggggcct      360 acacgcgcca agc atg ctg agg gtc ttc atc ctc tat gcc gag aac gtc       409
            Met Leu Arg Val Phe Ile Leu Tyr Ala Glu Asn Val
              1               5                  10 cac aca ccc gac acc gac atc agc gat gcc tac tgc tcc gcg gtg ttt     457
His Thr Pro Asp Thr Asp Ile Ser Asp Ala Tyr Cys Ser Ala Val Phe
         15                  20                  25 gca ggg gtg aag aag aga acc aaa gtc atc aag aac agc gtg aac cct     505
Ala Gly Val Lys Lys Arg Thr Lys Val Ile Lys Asn Ser Val Asn Pro
     30                  35                  40
```

```
gta tgg aat gag gga ttt gaa tgg gac ctc aag ggc atc ccc ctg gac      553
Val Trp Asn Glu Gly Phe Glu Trp Asp Leu Lys Gly Ile Pro Leu Asp
 45              50                  55                  60 cag ggc tct gag ctt cat gtg gtg gtc aaa gac cat gag acg atg ggg      601
Gln Gly Ser Glu Leu His Val Val Val Lys Asp His Glu Thr Met Gly
             65                  70                  75 agg aac agg ttc ctg ggg gaa gcc aag gtc cca ctc cga gag gtc ctc      649
Arg Asn Arg Phe Leu Gly Glu Ala Lys Val Pro Leu Arg Glu Val Leu
         80                  85                  90 gcc acc cct agt ctg tcc gcc agc ttc aat gcc ccc ctg ctg gac acc      697
Ala Thr Pro Ser Leu Ser Ala Ser Phe Asn Ala Pro Leu Leu Asp Thr
             95                 100                 105 aag aag cag ccc aca ggg gcc tcg ctg gtc ctg cag gtg tcc tac aca      745
Lys Lys Gln Pro Thr Gly Ala Ser Leu Val Leu Gln Val Ser Tyr Thr
        110                 115                 120 ccg ctg cct gga gct gtg ccc ctg ttc ccg ccc cct act cct ctg gag      793
Pro Leu Pro Gly Ala Val Pro Leu Phe Pro Pro Thr Pro Leu Glu
125                 130                 135                 140 ccc tcc ccg act ctg cct gac ctg gat gta gtg gca gac aca gga gga      841
Pro Ser Pro Thr Leu Pro Asp Leu Asp Val Val Ala Asp Thr Gly Gly
                145                 150                 155 gag gaa gac aca gag gac cag gga ctc act gga gat gag gcg gag cca      889
Glu Glu Asp Thr Glu Asp Gln Gly Leu Thr Gly Asp Glu Ala Glu Pro
            160                 165                 170 ttc ctg gat caa agc gga ggc ccg ggg gct ccc acc acc cca agg aaa      937
Phe Leu Asp Gln Ser Gly Gly Pro Gly Ala Pro Thr Thr Pro Arg Lys
        175                 180                 185 cta cct tca cgt cct ccg ccc cac tac ccc ggg atc aaa aga aag cga      985
Leu Pro Ser Arg Pro Pro Pro His Tyr Pro Gly Ile Lys Arg Lys Arg
    190                 195                 200 agt gcg cct aca tct aga aag ctg ctg tca gac aaa ccg cag gat ttc     1033
Ser Ala Pro Thr Ser Arg Lys Leu Leu Ser Asp Lys Pro Gln Asp Phe
205                 210                 215                 220 cag atc agg gtc cag gtg atc gag ggg cgc cag ctg ccg ggg gtg aac     1081
Gln Ile Arg Val Gln Val Ile Glu Gly Arg Gln Leu Pro Gly Val Asn
                225                 230                 235 atc aag cct gtg gtc aag gtt acc gct gca ggg cag acc aag cgg acg     1129
Ile Lys Pro Val Val Lys Val Thr Ala Ala Gly Gln Thr Lys Arg Thr
            240                 245                 250 cgg atc cac aag gga aac agc cca ctc ttc aat gag act ctt ttc ttc     1177
Arg Ile His Lys Gly Asn Ser Pro Leu Phe Asn Glu Thr Leu Phe Phe
        255                 260                 265 aac ttg ttt gac tct cct ggg gag ctg ttt gat gag ccc atc ttt atc     1225
Asn Leu Phe Asp Ser Pro Gly Glu Leu Phe Asp Glu Pro Ile Phe Ile
    270                 275                 280 acg gtg gta gac tct cgt tct ctc agg aca gat gct ctc ctc ggg gag     1273
Thr Val Val Asp Ser Arg Ser Leu Arg Thr Asp Ala Leu Leu Gly Glu
285                 290                 295                 300 ttc cgg atg gac gtg ggc acc att tac aga gag ccc cgg cac gcc tat     1321
Phe Arg Met Asp Val Gly Thr Ile Tyr Arg Glu Pro Arg His Ala Tyr
                305                 310                 315 ctc agg aag tgg ctg ctg ctc tca gac cct gat gac ttc tct gct ggg     1369
Leu Arg Lys Trp Leu Leu Leu Ser Asp Pro Asp Asp Phe Ser Ala Gly
            320                 325                 330 gcc aga ggc tac ctg aaa aca agc ctt tgt gtg ctg ggg cct ggg gac     1417
Ala Arg Gly Tyr Leu Lys Thr Ser Leu Cys Val Leu Gly Pro Gly Asp
        335                 340                 345 gaa gcg cct ctg gag aga aaa gac ccc tct gaa gac aag gag gac att     1465
Glu Ala Pro Leu Glu Arg Lys Asp Pro Ser Glu Asp Lys Glu Asp Ile
    350                 355                 360
```

```
gaa agc aac ctg ctc cgg ccc aca ggc gta gcc ctg cga gga gcc cac      1513
Glu Ser Asn Leu Leu Arg Pro Thr Gly Val Ala Leu Arg Gly Ala His
365                 370                 375                 380 ttc tgc ctg aag gtc ttc cgg gcc gag gac ttg ccg cag atg gac gat      1561
Phe Cys Leu Lys Val Phe Arg Ala Glu Asp Leu Pro Gln Met Asp Asp
                385                 390                 395 gcc gtg atg gac aac gtg aaa cag atc ttt ggc ttc gag agt aac aag      1609
Ala Val Met Asp Asn Val Lys Gln Ile Phe Gly Phe Glu Ser Asn Lys
            400                 405                 410 aag aac ttg gtg gac ccc ttt gtg gag gtc agc ttt gcg ggg aaa atg      1657
Lys Asn Leu Val Asp Pro Phe Val Glu Val Ser Phe Ala Gly Lys Met
        415                 420                 425 ctg tgc agc aag atc ttg gag aag acg gcc aac cct cag tgg aac cag      1705
Leu Cys Ser Lys Ile Leu Glu Lys Thr Ala Asn Pro Gln Trp Asn Gln
    430                 435                 440 aac atc aca ctg cct gcc atg ttt ccc tcc atg tgc gaa aaa atg agg      1753
Asn Ile Thr Leu Pro Ala Met Phe Pro Ser Met Cys Glu Lys Met Arg
445                 450                 455                 460 att cgt atc ata gac tgg gac cgc ctg act cac aat gac atc gtg gct      1801
Ile Arg Ile Ile Asp Trp Asp Arg Leu Thr His Asn Asp Ile Val Ala
                465                 470                 475 acc acc tac ctg agt atg tcg aaa atc tct gcc cct gga gga gaa ata      1849
Thr Thr Tyr Leu Ser Met Ser Lys Ile Ser Ala Pro Gly Gly Glu Ile
            480                 485                 490 gaa gag gag cct gca ggt gct gtc aag cct tcg aaa gcc tca gac ttg      1897
Glu Glu Glu Pro Ala Gly Ala Val Lys Pro Ser Lys Ala Ser Asp Leu
        495                 500                 505 gat gac tac ctg ggc ttc ctc ccc act ttt ggg ccc tgc tac atc aac      1945
Asp Asp Tyr Leu Gly Phe Leu Pro Thr Phe Gly Pro Cys Tyr Ile Asn
    510                 515                 520 ctc tat ggc agt ccc aga gag ttc aca ggc ttc cca gac ccc tac aca      1993
Leu Tyr Gly Ser Pro Arg Glu Phe Thr Gly Phe Pro Asp Pro Tyr Thr
525                 530                 535                 540 gag ctc aac aca ggc aag ggg gaa ggt gtg gct tat cgt ggc cgg ctt      2041
Glu Leu Asn Thr Gly Lys Gly Glu Gly Val Ala Tyr Arg Gly Arg Leu
                545                 550                 555 ctg ctc tcc ctg gag acc aag ctg gtg gag cac agt gaa cag aag gtg      2089
Leu Leu Ser Leu Glu Thr Lys Leu Val Glu His Ser Glu Gln Lys Val
            560                 565                 570 gag gac ctt cct gcg gat gac atc ctc cgg gtg gag aag tac ctt agg      2137
Glu Asp Leu Pro Ala Asp Asp Ile Leu Arg Val Glu Lys Tyr Leu Arg
        575                 580                 585 agg cgc aag tac tcc ctg ttt gcg gcc ttc tac tca gcc acc atg ctg      2185
Arg Arg Lys Tyr Ser Leu Phe Ala Ala Phe Tyr Ser Ala Thr Met Leu
    590                 595                 600 cag gat gtg gat gat gcc atc cag ttt gag gtc agc atc ggg aac tac      2233
Gln Asp Val Asp Asp Ala Ile Gln Phe Glu Val Ser Ile Gly Asn Tyr
605                 610                 615                 620 ggg aac aag ttc gac atg acc tgc ctg ccg ctg gcc tcc acc act cag      2281
Gly Asn Lys Phe Asp Met Thr Cys Leu Pro Leu Ala Ser Thr Thr Gln
                625                 630                 635 tac agc cgt gca gtc ttt gac ggg tgc cac tac tac cta ccc tgg          2329
Tyr Ser Arg Ala Val Phe Asp Gly Cys His Tyr Tyr Leu Pro Trp
            640                 645                 650 ggt aac gtg aaa cct gtg gtg gtg ctg tca tcc tac tgg gag gac atc      2377
Gly Asn Val Lys Pro Val Val Val Leu Ser Ser Tyr Trp Glu Asp Ile
        655                 660                 665 agc cat aga atc gag act cag aac cag ctg ctt ggg att gct gac cgg      2425
Ser His Arg Ile Glu Thr Gln Asn Gln Leu Leu Gly Ile Ala Asp Arg
    670                 675                 680
```

-continued

| | |
|---|---|
| ctg gaa gct ggc ctg gag cag gtc cac ctg gcc ctg aag gcg cag tgc<br>Leu Glu Ala Gly Leu Glu Gln Val His Leu Ala Leu Lys Ala Gln Cys<br>685                        690                         695                        700 | 2473 |
| tcc acg gag gac gtg gac tcg ctg gtg gct cag ctg acg gat gag ctc<br>Ser Thr Glu Asp Val Asp Ser Leu Val Ala Gln Leu Thr Asp Glu Leu<br>                     705                         710                         715 | 2521 |
| atc gca ggc tgc agc cag cct ctg ggt gac atc cat gag aca ccc tct<br>Ile Ala Gly Cys Ser Gln Pro Leu Gly Asp Ile His Glu Thr Pro Ser<br>                720                         725                        730 | 2569 |
| gcc acc cac ctg gac cag tac ctg tac cag ctg cgc acc cat cac ctg<br>Ala Thr His Leu Asp Gln Tyr Leu Tyr Gln Leu Arg Thr His His Leu<br>           735                         740                        745 | 2617 |
| agc caa atc act gag gct gcc ctg gcc ctg aag ctc ggc cac agt gag<br>Ser Gln Ile Thr Glu Ala Ala Leu Ala Leu Lys Leu Gly His Ser Glu<br>750                        755                         760 | 2665 |
| ctc cct gca gct ctg gag cag gcg gag gac tgg ctc ctg cgt ctg cgt<br>Leu Pro Ala Ala Leu Glu Gln Ala Glu Asp Trp Leu Leu Arg Leu Arg<br>765                        770                        775                        780 | 2713 |
| gcc ctg gca gag gag ccc cag aac agc ctg ccg gac atc gtc atc tgg<br>Ala Leu Ala Glu Glu Pro Gln Asn Ser Leu Pro Asp Ile Val Ile Trp<br>                     785                         790                        795 | 2761 |
| atg ctg cag gga gac aag cgt gtg gca tac cag cgg gtg ccc gcc cac<br>Met Leu Gln Gly Asp Lys Arg Val Ala Tyr Gln Arg Val Pro Ala His<br>           800                         805                        810 | 2809 |
| caa gtc ctc ttc tcc cgg cgg ggt gcc aac tac tgt ggc aag aat tgt<br>Gln Val Leu Phe Ser Arg Arg Gly Ala Asn Tyr Cys Gly Lys Asn Cys<br>815                        820                        825 | 2857 |
| ggg aag cta cag aca atc ttt ctg aaa tat ccg atg gag aag gtg cct<br>Gly Lys Leu Gln Thr Ile Phe Leu Lys Tyr Pro Met Glu Lys Val Pro<br>830                        835                        840 | 2905 |
| ggc gcc cgg atg cca gtg cag ata cgg gtc aag ctg tgg ttt ggg ctc<br>Gly Ala Arg Met Pro Val Gln Ile Arg Val Lys Leu Trp Phe Gly Leu<br>845                        850                        855                        860 | 2953 |
| tct gtg gat gag aag gag ttc aac cag ttt gct gag ggg aag ctg tct<br>Ser Val Asp Glu Lys Glu Phe Asn Gln Phe Ala Glu Gly Lys Leu Ser<br>                     865                         870                        875 | 3001 |
| gtc ttt gct gaa acc tat gag aac gag act aag ttg gcc ctt gtt ggg<br>Val Phe Ala Glu Thr Tyr Glu Asn Glu Thr Lys Leu Ala Leu Val Gly<br>880                        885                        890 | 3049 |
| aac tgg ggc aca acg ggc ctc acc tac ccc aag ttt tct gac gtc acg<br>Asn Trp Gly Thr Thr Gly Leu Thr Tyr Pro Lys Phe Ser Asp Val Thr<br>           895                         900                        905 | 3097 |
| ggc aag atc aag cta ccc aag gac agc ttc cgc ccc tcg gcc ggc tgg<br>Gly Lys Ile Lys Leu Pro Lys Asp Ser Phe Arg Pro Ser Ala Gly Trp<br>910                        915                        920 | 3145 |
| acc tgg gct gga gat tgg ttc gtg tgt ccg gag aag act ctg ctc cat<br>Thr Trp Ala Gly Asp Trp Phe Val Cys Pro Glu Lys Thr Leu Leu His<br>925                        930                        935                        940 | 3193 |
| gac atg gac gcc ggt cac ctg agc ttc gtg gaa gag gtg ttt gag aac<br>Asp Met Asp Ala Gly His Leu Ser Phe Val Glu Glu Val Phe Glu Asn<br>                     945                         950                        955 | 3241 |
| cag acc cgg ctt ccc gga ggc cag tgg atc tac atg agt gac aac tac<br>Gln Thr Arg Leu Pro Gly Gly Gln Trp Ile Tyr Met Ser Asp Asn Tyr<br>           960                         965                        970 | 3289 |
| acc gat gtg aac ggg gag aag gtg ctt ccc aag gat gac att gag tgc<br>Thr Asp Val Asn Gly Glu Lys Val Leu Pro Lys Asp Asp Ile Glu Cys<br>975                        980                        985 | 3337 |
| cca ctg ggc tgg aag tgg gaa gat gag gaa tgg tcc aca gac ctc aac<br>Pro Leu Gly Trp Lys Trp Glu Asp Glu Glu Trp Ser Thr Asp Leu Asn<br>    990                        995                        1000 | 3385 |

-continued

| | |
|---|---|
| cgg gct gtc gat gag caa ggc tgg gag tat agc atc acc atc ccc ccg<br>Arg Ala Val Asp Glu Gln Gly Trp Glu Tyr Ser Ile Thr Ile Pro Pro<br>1005                           1010                     1015                1020 | 3433 |
| gag cgg aag ccg aag cac tgg gtc cct gct gag aag atg tac tac aca<br>Glu Arg Lys Pro Lys His Trp Val Pro Ala Glu Lys Met Tyr Tyr Thr<br>                      1025                     1030                     1035 | 3481 |
| cac cga cgg cgg cgc tgg gtg cgc ctg cgc agg agg gat ctc agc caa<br>His Arg Arg Arg Arg Trp Val Arg Leu Arg Arg Arg Asp Leu Ser Gln<br>           1040                     1045                     1050 | 3529 |
| atg gaa gca ctg aaa agg cac agg cag gcg gag gcg gag ggc gag ggc<br>Met Glu Ala Leu Lys Arg His Arg Gln Ala Glu Ala Glu Gly Glu Gly<br>              1055                     1060                     1065 | 3577 |
| tgg gag tac gcc tct ctt ttt ggc tgg aag ttc cac ctc gag tac cgc<br>Trp Glu Tyr Ala Ser Leu Phe Gly Trp Lys Phe His Leu Glu Tyr Arg<br>1070                           1075                     1080 | 3625 |
| aag aca gat gcc ttc cgc cgc cgc cgc tgg cgc cgt cgc atg gag cca<br>Lys Thr Asp Ala Phe Arg Arg Arg Arg Trp Arg Arg Arg Met Glu Pro<br>1085                           1090                     1095                1100 | 3673 |
| ctg gag aag acg ggg cct gca gct gtg ttt gcc ctt gag ggg gcc ctg<br>Leu Glu Lys Thr Gly Pro Ala Ala Val Phe Ala Leu Glu Gly Ala Leu<br>                   1105                     1110                     1115 | 3721 |
| ggc ggc gtg atg gat gac aag agt gaa gat tcc atg tcc gtc tcc acc<br>Gly Gly Val Met Asp Asp Lys Ser Glu Asp Ser Met Ser Val Ser Thr<br>              1120                     1125                     1130 | 3769 |
| ttg agc ttc ggt gtg aac aga ccc acg att tcc tgc ata ttc gac tat<br>Leu Ser Phe Gly Val Asn Arg Pro Thr Ile Ser Cys Ile Phe Asp Tyr<br>                   1135                     1140                     1145 | 3817 |
| ggg aac cgc tac cat cta cgc tgc tac atg tac cag gcc cgg gac ctg<br>Gly Asn Arg Tyr His Leu Arg Cys Tyr Met Tyr Gln Ala Arg Asp Leu<br>1150                           1155                     1160 | 3865 |
| gct gcg atg gac aag gac tct ttt tct gat ccc tat gcc atc gtc tcc<br>Ala Ala Met Asp Lys Asp Ser Phe Ser Asp Pro Tyr Ala Ile Val Ser<br>1165                           1170                     1175                1180 | 3913 |
| ttc ctg cac cag agc cag aag acg gtg gtg gtg aag aac acc ctt aac<br>Phe Leu His Gln Ser Gln Lys Thr Val Val Val Lys Asn Thr Leu Asn<br>                   1185                     1190                     1195 | 3961 |
| ccc acc tgg gac cag acg ctc atc ttc tac gag atc gag atc ttt ggc<br>Pro Thr Trp Asp Gln Thr Leu Ile Phe Tyr Glu Ile Glu Ile Phe Gly<br>              1200                     1205                     1210 | 4009 |
| gag ccg gcc aca gtt gct gag caa ccg ccc agc att gtg gtg gag ctg<br>Glu Pro Ala Thr Val Ala Glu Gln Pro Pro Ser Ile Val Val Glu Leu<br>                   1215                     1220                     1225 | 4057 |
| tac gac cat gac act tat ggt gca gac gag ttt atg ggt cgc tgc atc<br>Tyr Asp His Asp Thr Tyr Gly Ala Asp Glu Phe Met Gly Arg Cys Ile<br>1230                           1235                     1240 | 4105 |
| tgt caa ccg agt ctg gaa cgg atg cca cgg ctg gcc tgg ttc cca ctg<br>Cys Gln Pro Ser Leu Glu Arg Met Pro Arg Leu Ala Trp Phe Pro Leu<br>1245                           1250                     1255                1260 | 4153 |
| acg agg ggc agc cag ccg tcg ggg gag ctg ctg gcc tct ttt gag ctc<br>Thr Arg Gly Ser Gln Pro Ser Gly Glu Leu Leu Ala Ser Phe Glu Leu<br>                   1265                     1270                     1275 | 4201 |
| atc cag aga gag aag ccg gcc atc cac cat att cct ggt ttt gag gtg<br>Ile Gln Arg Glu Lys Pro Ala Ile His His Ile Pro Gly Phe Glu Val<br>              1280                     1285                     1290 | 4249 |
| cag gag aca tca agg atc ctg gat gag tct gag gac aca gac ctg ccc<br>Gln Glu Thr Ser Arg Ile Leu Asp Glu Ser Glu Asp Thr Asp Leu Pro<br>                   1295                     1300                     1305 | 4297 |
| tac cca cca ccc cag agg gag gcc aac atc tac atg gtt cct cag aac<br>Tyr Pro Pro Pro Gln Arg Glu Ala Asn Ile Tyr Met Val Pro Gln Asn<br>1310                           1315                     1320 | 4345 |

```
atc aag cca gcg ctc cag cgt acc gcc atc gag atc ctg gca tgg ggc    4393
Ile Lys Pro Ala Leu Gln Arg Thr Ala Ile Glu Ile Leu Ala Trp Gly
1325                1330                1335                1340 ctg cgg aac atg aag agt tac cag ctg gcc aac atc tcc tcc ccc agc    4441
Leu Arg Asn Met Lys Ser Tyr Gln Leu Ala Asn Ile Ser Ser Pro Ser
            1345                1350                1355 ctc gtg gta gag tgt ggg ggc cag acg gtg cag tcc tgt gtc atc agg    4489
Leu Val Val Glu Cys Gly Gly Gln Thr Val Gln Ser Cys Val Ile Arg
1360                1365                1370 aac ctc cgg aag aac ccc aac ttt gac atc tgc acc ctc ttc atg gaa    4537
Asn Leu Arg Lys Asn Pro Asn Phe Asp Ile Cys Thr Leu Phe Met Glu
        1375                1380                1385 gtg atg ctg ccc agg gag gag ctc tac tgc ccc ccc atc acc gtc aag    4585
Val Met Leu Pro Arg Glu Glu Leu Tyr Cys Pro Pro Ile Thr Val Lys
1390                1395                1400 gtc atc gat aac cgc cag ttt ggc cgc cgg cct gtg gtg ggc cag tgt    4633
Val Ile Asp Asn Arg Gln Phe Gly Arg Arg Pro Val Val Gly Gln Cys
1405                1410                1415                1420 acc atc cgc tcc ctg gag agc ttc ctg tgt gac ccc tac tcg gcg gag    4681
Thr Ile Arg Ser Leu Glu Ser Phe Leu Cys Asp Pro Tyr Ser Ala Glu
            1425                1430                1435 agt cca tcc cca cag ggt ggc cca gac gat gtg agc cta ctc agt cct    4729
Ser Pro Ser Pro Gln Gly Gly Pro Asp Asp Val Ser Leu Leu Ser Pro
                1440                1445                1450 ggg gaa gac gtg ctc atc gac att gat gac aag gag ccc ctc atc ccc    4777
Gly Glu Asp Val Leu Ile Asp Ile Asp Asp Lys Glu Pro Leu Ile Pro
        1455                1460                1465 atc cag gag gaa gag ttc atc gat tgg tgg agc aaa ttc ttt gcc tcc    4825
Ile Gln Glu Glu Glu Phe Ile Asp Trp Trp Ser Lys Phe Phe Ala Ser
1470                1475                1480 ata ggg gag agg gaa aag tgc ggc tcc tac ctg gag aag gat ttt gac    4873
Ile Gly Glu Arg Glu Lys Cys Gly Ser Tyr Leu Glu Lys Asp Phe Asp
1485                1490                1495                1500 acc ctg aag gtc tat gac aca cag ctg gag aat gtg gag gcc ttt gag    4921
Thr Leu Lys Val Tyr Asp Thr Gln Leu Glu Asn Val Glu Ala Phe Glu
            1505                1510                1515 ggc ctg tct gac ttt tgt aac acc ttc aag ctg tac cgg ggc aag acg    4969
Gly Leu Ser Asp Phe Cys Asn Thr Phe Lys Leu Tyr Arg Gly Lys Thr
        1520                1525                1530 cag gag gag aca gaa gat cca tct gtg att ggt gaa ttt aag ggc ctc    5017
Gln Glu Glu Thr Glu Asp Pro Ser Val Ile Gly Glu Phe Lys Gly Leu
1535                1540                1545 ttc aaa att tat ccc ctc cca gaa gac cca gcc atc ccc atg ccc cca    5065
Phe Lys Ile Tyr Pro Leu Pro Glu Asp Pro Ala Ile Pro Met Pro Pro
1550                1555                1560 aga cag ttc cac cag ctg gcc gcc cag gga ccc cag gag tgc ttg gtc    5113
Arg Gln Phe His Gln Leu Ala Ala Gln Gly Pro Gln Glu Cys Leu Val
1565                1570                1575                1580 cgt atc tac att gtc cga gca ttt ggc ctg cag ccc aag gac ccc aat    5161
Arg Ile Tyr Ile Val Arg Ala Phe Gly Leu Gln Pro Lys Asp Pro Asn
            1585                1590                1595 gga aag tgt gat cct tac atc aag atc tcc ata ggg aag aaa tca gtg    5209
Gly Lys Cys Asp Pro Tyr Ile Lys Ile Ser Ile Gly Lys Lys Ser Val
                1600                1605                1610 agt gac cag gat aac tac atc ccc tgc acg ctg gag ccc gta ttt gga    5257
Ser Asp Gln Asp Asn Tyr Ile Pro Cys Thr Leu Glu Pro Val Phe Gly
        1615                1620                1625 aag atg ttc gag ctg acc tgc act ctg cct ctg gag aag gac cta aag    5305
Lys Met Phe Glu Leu Thr Cys Thr Leu Pro Leu Glu Lys Asp Leu Lys
1630                1635                1640
```

-continued

| | |
|---|---|
| atc act ctc tat gac tat gac ctc ctc tcc aag gac gaa aag atc ggt<br>Ile Thr Leu Tyr Asp Tyr Asp Leu Leu Ser Lys Asp Glu Lys Ile Gly<br>1645                  1650                  1655                  1660 | 5353 |
| gag acg gtc gtc gac ctg gag aac agg ctg ctg tcc aag ttt ggg gct<br>Glu Thr Val Val Asp Leu Glu Asn Arg Leu Leu Ser Lys Phe Gly Ala<br>              1665                  1670                  1675 | 5401 |
| cgc tgt gga ctc cca cag acc tac tgt gtc tct gga ccg aac cag tgg<br>Arg Cys Gly Leu Pro Gln Thr Tyr Cys Val Ser Gly Pro Asn Gln Trp<br>1680                  1685                  1690 | 5449 |
| cgg gac cag ctc cgc ccc tcc cag ctc ctc cac ctc ttc tgc cag cag<br>Arg Asp Gln Leu Arg Pro Ser Gln Leu Leu His Leu Phe Cys Gln Gln<br>              1695                  1700                  1705 | 5497 |
| cat aga gtc aag gca cct gtg tac cgg aca gac cgt gta atg ttt cag<br>His Arg Val Lys Ala Pro Val Tyr Arg Thr Asp Arg Val Met Phe Gln<br>          1710                  1715                  1720 | 5545 |
| gat aaa gaa tat tcc att gaa gag ata gag gct ggc agg atc cca aac<br>Asp Lys Glu Tyr Ser Ile Glu Glu Ile Glu Ala Gly Arg Ile Pro Asn<br>1725                  1730                  1735                  1740 | 5593 |
| cca cac ctg ggc cca gtg gag gag cgt ctg gct ctg cat gtg ctt cag<br>Pro His Leu Gly Pro Val Glu Glu Arg Leu Ala Leu His Val Leu Gln<br>              1745                  1750                  1755 | 5641 |
| cag cag ggc ctg gtc ccg gag cac gtg gag tca cgg ccc ctc tac agc<br>Gln Gln Gly Leu Val Pro Glu His Val Glu Ser Arg Pro Leu Tyr Ser<br>                    1760                  1765                  1770 | 5689 |
| ccc ctg cag cca gac atc gag cag ggg aag ctg cag atg tgg gtc gac<br>Pro Leu Gln Pro Asp Ile Glu Gln Gly Lys Leu Gln Met Trp Val Asp<br>              1775                  1780                  1785 | 5737 |
| cta ttt ccg aag gcc ctg ggg cgg cct gga cct ccc ttc aac atc acc<br>Leu Phe Pro Lys Ala Leu Gly Arg Pro Gly Pro Pro Phe Asn Ile Thr<br>1790                  1795                  1800 | 5785 |
| cca cgg aga gcc aga agg ttt ttc ctg cgt tgt att atc tgg aat acc<br>Pro Arg Arg Ala Arg Arg Phe Phe Leu Arg Cys Ile Ile Trp Asn Thr<br>1805                  1810                  1815                  1820 | 5833 |
| aga gat gtg atc ctg gat gac ctg agc ctc acg ggg gag aag atg agc<br>Arg Asp Val Ile Leu Asp Asp Leu Ser Leu Thr Gly Glu Lys Met Ser<br>              1825                  1830                  1835 | 5881 |
| gac att tat gtg aaa ggt tgg atg att ggc ttt gaa gaa cac aag caa<br>Asp Ile Tyr Val Lys Gly Trp Met Ile Gly Phe Glu Glu His Lys Gln<br>              1840                  1845                  1850 | 5929 |
| aag aca gac gtg cat tat cgt tcc ctg gga ggt gaa ggc aac ttc aac<br>Lys Thr Asp Val His Tyr Arg Ser Leu Gly Gly Glu Gly Asn Phe Asn<br>              1855                  1860                  1865 | 5977 |
| tgg agg ttc att ttc ccc ttc gac tac ctg cca gct gag caa gtc tgt<br>Trp Arg Phe Ile Phe Pro Phe Asp Tyr Leu Pro Ala Glu Gln Val Cys<br>1870                  1875                  1880 | 6025 |
| acc att gcc aag aag gat gcc ttc tgg agg ctg gac aag act gag agc<br>Thr Ile Ala Lys Lys Asp Ala Phe Trp Arg Leu Asp Lys Thr Glu Ser<br>1885                  1890                  1895                  1900 | 6073 |
| aaa atc cca gca cga gtg gtg ttc cag atc tgg gac aat gac aag ttc<br>Lys Ile Pro Ala Arg Val Val Phe Gln Ile Trp Asp Asn Asp Lys Phe<br>              1905                  1910                  1915 | 6121 |
| tcc ttt gat gat ttt ctg ggc tcc ctg cag ctc gat ctc aac cgc atg<br>Ser Phe Asp Asp Phe Leu Gly Ser Leu Gln Leu Asp Leu Asn Arg Met<br>              1920                  1925                  1930 | 6169 |
| ccc aag cca gcc aag aca gcc aag aag tgc tcc ttg gac cag ctg gat<br>Pro Lys Pro Ala Lys Thr Ala Lys Lys Cys Ser Leu Asp Gln Leu Asp<br>              1935                  1940                  1945 | 6217 |
| gat gct ttc cac cca gaa tgg ttt gtg tcc ctt ttt gag cag aaa aca<br>Asp Ala Phe His Pro Glu Trp Phe Val Ser Leu Phe Glu Gln Lys Thr<br>1950                  1955                  1960 | 6265 |

-continued

```
gtg aag ggc tgg tgg ccc tgt gta gca gaa gag ggt gag aag aaa ata       6313
Val Lys Gly Trp Trp Pro Cys Val Ala Glu Glu Gly Glu Lys Lys Ile
1965                1970                1975                1980 ctg gcg ggc aag ctg gaa atg acc ttg gag att gta gca gag agt gag       6361
Leu Ala Gly Lys Leu Glu Met Thr Leu Glu Ile Val Ala Glu Ser Glu
            1985                1990                1995 cat gag gag cgg cct gct ggc cag ggc cgg gat gag ccc aac atg aac       6409
His Glu Glu Arg Pro Ala Gly Gln Gly Arg Asp Glu Pro Asn Met Asn
2000                2005                2010 cct aag ctt gag gac cca agg cgc ccc gac acc tcc ttc ctg tgg ttt       6457
Pro Lys Leu Glu Asp Pro Arg Arg Pro Asp Thr Ser Phe Leu Trp Phe
        2015                2020                2025 acc tcc cca tac aag acc atg aag ttc atc ctg tgg cgg cgt ttc cgg       6505
Thr Ser Pro Tyr Lys Thr Met Lys Phe Ile Leu Trp Arg Arg Phe Arg
    2030                2035                2040 tgg gcc atc atc ctc ttc atc atc ctc ttc atc ctg ctg ctg ttc ctc       6553
Trp Ala Ile Ile Leu Phe Ile Ile Leu Phe Ile Leu Leu Leu Phe Leu
2045                2050                2055                2060 gcc atc ttc atc tac gcc ttc ccg aac tat gct gcc atg aag ctg gtg       6601
Ala Ile Phe Ile Tyr Ala Phe Pro Asn Tyr Ala Ala Met Lys Leu Val
            2065                2070                2075 aag ccc ttc agc tgaggactct cctgccctgt agaaggggcc gtggggtccc           6653
Lys Pro Phe Ser
        2080 ctccagcatg ggactggcct gcctcctccg cccagctcgg cgagctcctc cagacctcct     6713 aggcctgatt gtcctgccag ggtgggcaga cagacagatg gaccggccca cactcccaga     6773 gttgctaaca tggagctctg agatcacccc acttccatca tttccttctc ccccaaccca     6833 acgctttttt ggatcagctc agacatattt cagtataaaa cagttggaac cacaaaaaaa     6893 aaaaaaaaaa aaaaaaaa                                                    6911

<210> SEQ ID NO 2
<211> LENGTH: 2080
<212> TYPE: PRT
<213> ORGANISM: Homo sapiens

<400> SEQUENCE: 2

Met Leu Arg Val Phe Ile Leu Tyr Ala Glu Asn Val His Thr Pro Asp
  1               5                  10                  15

Thr Asp Ile Ser Asp Ala Tyr Cys Ser Ala Val Phe Ala Gly Val Lys
             20                  25                  30

Lys Arg Thr Lys Val Ile Lys Asn Ser Val Asn Pro Val Trp Asn Glu
         35                  40                  45

Gly Phe Glu Trp Asp Leu Lys Gly Ile Pro Leu Asp Gln Gly Ser Glu
     50                  55                  60

Leu His Val Val Lys Asp His Glu Thr Met Gly Arg Asn Arg Phe
 65                  70                  75                  80

Leu Gly Glu Ala Lys Val Pro Leu Arg Glu Val Leu Ala Thr Pro Ser
                 85                  90                  95

Leu Ser Ala Ser Phe Asn Ala Pro Leu Leu Asp Thr Lys Lys Gln Pro
            100                 105                 110

Thr Gly Ala Ser Leu Val Leu Gln Val Ser Tyr Thr Pro Leu Pro Gly
        115                 120                 125

Ala Val Pro Leu Phe Pro Pro Thr Pro Leu Glu Pro Ser Pro Thr
    130                 135                 140

Leu Pro Asp Leu Asp Val Val Ala Asp Thr Gly Gly Glu Glu Asp Thr
145                 150                 155                 160
```

-continued

```
Glu Asp Gln Gly Leu Thr Gly Asp Glu Ala Glu Pro Phe Leu Asp Gln
                165                 170                 175

Ser Gly Gly Pro Gly Ala Pro Thr Thr Pro Arg Lys Leu Pro Ser Arg
            180                 185                 190

Pro Pro Pro His Tyr Pro Gly Ile Lys Arg Lys Arg Ser Ala Pro Thr
        195                 200                 205

Ser Arg Lys Leu Leu Ser Asp Lys Pro Gln Asp Phe Gln Ile Arg Val
    210                 215                 220

Gln Val Ile Glu Gly Arg Gln Leu Pro Gly Val Asn Ile Lys Pro Val
225                 230                 235                 240

Val Lys Val Thr Ala Ala Gly Gln Thr Lys Arg Thr Arg Ile His Lys
                245                 250                 255

Gly Asn Ser Pro Leu Phe Asn Glu Thr Leu Phe Phe Asn Leu Phe Asp
            260                 265                 270

Ser Pro Gly Glu Leu Phe Asp Glu Pro Ile Phe Ile Thr Val Val Asp
        275                 280                 285

Ser Arg Ser Leu Arg Thr Asp Ala Leu Leu Gly Glu Phe Arg Met Asp
    290                 295                 300

Val Gly Thr Ile Tyr Arg Glu Pro Arg His Ala Tyr Leu Arg Lys Trp
305                 310                 315                 320

Leu Leu Leu Ser Asp Pro Asp Asp Phe Ser Ala Gly Ala Arg Gly Tyr
                325                 330                 335

Leu Lys Thr Ser Leu Cys Val Leu Gly Pro Gly Asp Glu Ala Pro Leu
            340                 345                 350

Glu Arg Lys Asp Pro Ser Glu Asp Lys Glu Asp Ile Glu Ser Asn Leu
        355                 360                 365

Leu Arg Pro Thr Gly Val Ala Leu Arg Gly Ala His Phe Cys Leu Lys
    370                 375                 380

Val Phe Arg Ala Glu Asp Leu Pro Gln Met Asp Asp Ala Val Met Asp
385                 390                 395                 400

Asn Val Lys Gln Ile Phe Gly Phe Glu Ser Asn Lys Lys Asn Leu Val
                405                 410                 415

Asp Pro Phe Val Glu Val Ser Phe Ala Gly Lys Met Leu Cys Ser Lys
            420                 425                 430

Ile Leu Glu Lys Thr Ala Asn Pro Gln Trp Asn Gln Asn Ile Thr Leu
        435                 440                 445

Pro Ala Met Phe Pro Ser Met Cys Glu Lys Met Arg Ile Arg Ile Ile
    450                 455                 460

Asp Trp Asp Arg Leu Thr His Asn Asp Ile Val Ala Thr Thr Tyr Leu
465                 470                 475                 480

Ser Met Ser Lys Ile Ser Ala Pro Gly Gly Glu Ile Glu Glu Glu Pro
                485                 490                 495

Ala Gly Ala Val Lys Pro Ser Lys Ala Ser Asp Leu Asp Asp Tyr Leu
            500                 505                 510

Gly Phe Leu Pro Thr Phe Gly Pro Cys Tyr Ile Asn Leu Tyr Gly Ser
        515                 520                 525

Pro Arg Glu Phe Thr Gly Phe Pro Asp Pro Tyr Thr Glu Leu Asn Thr
    530                 535                 540

Gly Lys Gly Glu Gly Val Ala Tyr Arg Gly Arg Leu Leu Leu Ser Leu
545                 550                 555                 560

Glu Thr Lys Leu Val Glu His Ser Glu Gln Lys Val Glu Asp Leu Pro
                565                 570                 575
```

```
Ala Asp Asp Ile Leu Arg Val Glu Lys Tyr Leu Arg Arg Lys Tyr
            580                 585                 590

Ser Leu Phe Ala Ala Phe Tyr Ser Ala Thr Met Leu Gln Asp Val Asp
            595                 600                 605

Asp Ala Ile Gln Phe Glu Val Ser Ile Gly Asn Tyr Gly Asn Lys Phe
            610                 615                 620

Asp Met Thr Cys Leu Pro Leu Ala Ser Thr Thr Gln Tyr Ser Arg Ala
625                 630                 635                 640

Val Phe Asp Gly Cys His Tyr Tyr Leu Pro Trp Gly Asn Val Lys
                645                 650                 655

Pro Val Val Val Leu Ser Ser Tyr Trp Glu Asp Ile Ser His Arg Ile
                660                 665                 670

Glu Thr Gln Asn Gln Leu Leu Gly Ile Ala Asp Arg Leu Glu Ala Gly
            675                 680                 685

Leu Glu Gln Val His Leu Ala Leu Lys Ala Gln Cys Ser Thr Glu Asp
            690                 695                 700

Val Asp Ser Leu Val Ala Gln Leu Thr Asp Glu Leu Ile Ala Gly Cys
705                 710                 715                 720

Ser Gln Pro Leu Gly Asp Ile His Glu Thr Pro Ser Ala Thr His Leu
                725                 730                 735

Asp Gln Tyr Leu Tyr Gln Leu Arg Thr His His Leu Ser Gln Ile Thr
                740                 745                 750

Glu Ala Ala Leu Ala Leu Lys Leu Gly His Ser Glu Leu Pro Ala Ala
            755                 760                 765

Leu Glu Gln Ala Glu Asp Trp Leu Leu Arg Leu Arg Ala Leu Ala Glu
            770                 775                 780

Glu Pro Gln Asn Ser Leu Pro Asp Ile Val Ile Trp Met Leu Gln Gly
785                 790                 795                 800

Asp Lys Arg Val Ala Tyr Gln Arg Val Pro Ala His Gln Val Leu Phe
                805                 810                 815

Ser Arg Arg Gly Ala Asn Tyr Cys Gly Lys Asn Cys Gly Lys Leu Gln
                820                 825                 830

Thr Ile Phe Leu Lys Tyr Pro Met Glu Lys Val Pro Gly Ala Arg Met
            835                 840                 845

Pro Val Gln Ile Arg Val Lys Leu Trp Phe Gly Leu Ser Val Asp Glu
850                 855                 860

Lys Glu Phe Asn Gln Phe Ala Glu Gly Lys Leu Ser Val Phe Ala Glu
865                 870                 875                 880

Thr Tyr Glu Asn Glu Thr Lys Leu Ala Leu Val Gly Asn Trp Gly Thr
                885                 890                 895

Thr Gly Leu Thr Tyr Pro Lys Phe Ser Asp Val Thr Gly Lys Ile Lys
                900                 905                 910

Leu Pro Lys Asp Ser Phe Arg Pro Ser Ala Gly Trp Thr Trp Ala Gly
            915                 920                 925

Asp Trp Phe Val Cys Pro Glu Lys Thr Leu His Asp Met Asp Ala
            930                 935                 940

Gly His Leu Ser Phe Val Glu Glu Val Phe Glu Asn Gln Thr Arg Leu
945                 950                 955                 960

Pro Gly Gly Gln Trp Ile Tyr Met Ser Asp Asn Tyr Thr Asp Val Asn
                965                 970                 975

Gly Glu Lys Val Leu Pro Lys Asp Asp Ile Glu Cys Pro Leu Gly Trp
                980                 985                 990
```

-continued

```
Lys Trp Glu Asp Glu Trp Ser Thr Asp Leu Asn Arg Ala Val Asp
    995                 1000                1005

Glu Gln Gly Trp Glu Tyr Ser Ile Thr Ile Pro Pro Glu Arg Lys Pro
    1010                1015                1020

Lys His Trp Val Pro Ala Glu Lys Met Tyr Tyr Thr His Arg Arg Arg
1025                1030                1035                1040

Arg Trp Val Arg Leu Arg Arg Arg Asp Leu Ser Gln Met Glu Ala Leu
                1045                1050                1055

Lys Arg His Arg Gln Ala Glu Ala Glu Gly Glu Gly Trp Glu Tyr Ala
                1060                1065                1070

Ser Leu Phe Gly Trp Lys Phe His Leu Glu Tyr Arg Lys Thr Asp Ala
                1075                1080                1085

Phe Arg Arg Arg Arg Trp Arg Arg Arg Met Glu Pro Leu Glu Lys Thr
                1090                1095                1100

Gly Pro Ala Ala Val Phe Ala Leu Glu Gly Ala Leu Gly Gly Val Met
1105                1110                1115                1120

Asp Asp Lys Ser Glu Asp Ser Met Ser Val Ser Thr Leu Ser Phe Gly
                1125                1130                1135

Val Asn Arg Pro Thr Ile Ser Cys Ile Phe Asp Tyr Gly Asn Arg Tyr
                1140                1145                1150

His Leu Arg Cys Tyr Met Tyr Gln Ala Arg Asp Leu Ala Ala Met Asp
                1155                1160                1165

Lys Asp Ser Phe Ser Asp Pro Tyr Ala Ile Val Ser Phe Leu His Gln
                1170                1175                1180

Ser Gln Lys Thr Val Val Val Lys Asn Thr Leu Asn Pro Thr Trp Asp
1185                1190                1195                1200

Gln Thr Leu Ile Phe Tyr Glu Ile Glu Ile Phe Gly Glu Pro Ala Thr
                1205                1210                1215

Val Ala Glu Gln Pro Pro Ser Ile Val Val Glu Leu Tyr Asp His Asp
                1220                1225                1230

Thr Tyr Gly Ala Asp Glu Phe Met Gly Arg Cys Ile Cys Gln Pro Ser
                1235                1240                1245

Leu Glu Arg Met Pro Arg Leu Ala Trp Phe Pro Leu Thr Arg Gly Ser
                1250                1255                1260

Gln Pro Ser Gly Glu Leu Leu Ala Ser Phe Glu Leu Ile Gln Arg Glu
1265                1270                1275                1280

Lys Pro Ala Ile His His Ile Pro Gly Phe Glu Val Gln Glu Thr Ser
                1285                1290                1295

Arg Ile Leu Asp Glu Ser Glu Asp Thr Asp Leu Pro Tyr Pro Pro Pro
                1300                1305                1310

Gln Arg Glu Ala Asn Ile Tyr Met Val Pro Gln Asn Ile Lys Pro Ala
                1315                1320                1325

Leu Gln Arg Thr Ala Ile Glu Ile Leu Ala Trp Gly Leu Arg Asn Met
                1330                1335                1340

Lys Ser Tyr Gln Leu Ala Asn Ile Ser Ser Pro Ser Leu Val Val Glu
1345                1350                1355                1360

Cys Gly Gly Gln Thr Val Gln Ser Cys Val Ile Arg Asn Leu Arg Lys
                1365                1370                1375

Asn Pro Asn Phe Asp Ile Cys Thr Leu Phe Met Glu Val Met Leu Pro
                1380                1385                1390

Arg Glu Glu Leu Tyr Cys Pro Pro Ile Thr Val Lys Val Ile Asp Asn
                1395                1400                1405
```

-continued

```
Arg Gln Phe Gly Arg Arg Pro Val Val Gly Gln Cys Thr Ile Arg Ser
    1410                1415                1420

Leu Glu Ser Phe Leu Cys Asp Pro Tyr Ser Ala Glu Ser Pro Ser Pro
1425                1430                1435                1440

Gln Gly Gly Pro Asp Asp Val Ser Leu Leu Ser Pro Gly Glu Asp Val
                1445                1450                1455

Leu Ile Asp Ile Asp Asp Lys Glu Pro Leu Ile Pro Ile Gln Glu Glu
            1460                1465                1470

Glu Phe Ile Asp Trp Trp Ser Lys Phe Phe Ala Ser Ile Gly Glu Arg
        1475                1480                1485

Glu Lys Cys Gly Ser Tyr Leu Glu Lys Asp Phe Asp Thr Leu Lys Val
    1490                1495                1500

Tyr Asp Thr Gln Leu Glu Asn Val Glu Ala Phe Gly Leu Ser Asp
1505                1510                1515                1520

Phe Cys Asn Thr Phe Lys Leu Tyr Arg Gly Lys Thr Gln Glu Glu Thr
                1525                1530                1535

Glu Asp Pro Ser Val Ile Gly Glu Phe Lys Gly Leu Phe Lys Ile Tyr
            1540                1545                1550

Pro Leu Pro Glu Asp Pro Ala Ile Pro Met Pro Pro Arg Gln Phe His
        1555                1560                1565

Gln Leu Ala Ala Gln Gly Pro Gln Glu Cys Leu Val Arg Ile Tyr Ile
    1570                1575                1580

Val Arg Ala Phe Gly Leu Gln Pro Lys Asp Pro Asn Gly Lys Cys Asp
1585                1590                1595                1600

Pro Tyr Ile Lys Ile Ser Ile Gly Lys Lys Ser Val Ser Asp Gln Asp
                1605                1610                1615

Asn Tyr Ile Pro Cys Thr Leu Glu Pro Val Phe Gly Lys Met Phe Glu
            1620                1625                1630

Leu Thr Cys Thr Leu Pro Leu Glu Lys Asp Leu Lys Ile Thr Leu Tyr
        1635                1640                1645

Asp Tyr Asp Leu Leu Ser Lys Asp Glu Lys Ile Gly Glu Thr Val Val
    1650                1655                1660

Asp Leu Glu Asn Arg Leu Leu Ser Lys Phe Gly Ala Arg Cys Gly Leu
1665                1670                1675                1680

Pro Gln Thr Tyr Cys Val Ser Gly Pro Asn Gln Trp Arg Asp Gln Leu
                1685                1690                1695

Arg Pro Ser Gln Leu Leu His Leu Phe Cys Gln Gln His Arg Val Lys
            1700                1705                1710

Ala Pro Val Tyr Arg Thr Asp Arg Val Met Phe Gln Asp Lys Glu Tyr
        1715                1720                1725

Ser Ile Glu Glu Ile Glu Ala Gly Arg Ile Pro Asn Pro His Leu Gly
    1730                1735                1740

Pro Val Glu Glu Arg Leu Ala Leu His Val Leu Gln Gln Gln Gly Leu
1745                1750                1755                1760

Val Pro Glu His Val Glu Ser Arg Pro Leu Tyr Ser Pro Leu Gln Pro
                1765                1770                1775

Asp Ile Glu Gln Gly Lys Leu Gln Met Trp Val Asp Leu Phe Pro Lys
            1780                1785                1790

Ala Leu Gly Arg Pro Gly Pro Pro Phe Asn Ile Thr Pro Arg Arg Ala
        1795                1800                1805

Arg Arg Phe Phe Leu Arg Cys Ile Ile Trp Asn Thr Arg Asp Val Ile
    1810                1815                1820
```

Leu Asp Asp Leu Ser Leu Thr Gly Glu Lys Met Ser Asp Ile Tyr Val
1825                1830                1835                1840

Lys Gly Trp Met Ile Gly Phe Glu Glu His Lys Gln Lys Thr Asp Val
            1845                1850                1855

His Tyr Arg Ser Leu Gly Gly Glu Gly Asn Phe Asn Trp Arg Phe Ile
        1860                1865                1870

Phe Pro Phe Asp Tyr Leu Pro Ala Glu Gln Val Cys Thr Ile Ala Lys
    1875                1880                1885

Lys Asp Ala Phe Trp Arg Leu Asp Lys Thr Glu Ser Lys Ile Pro Ala
1890                1895                1900

Arg Val Val Phe Gln Ile Trp Asp Asn Asp Lys Phe Ser Phe Asp Asp
1905                1910                1915                1920

Phe Leu Gly Ser Leu Gln Leu Asp Leu Asn Arg Met Pro Lys Pro Ala
                1925                1930                1935

Lys Thr Ala Lys Lys Cys Ser Leu Asp Gln Leu Asp Asp Ala Phe His
            1940                1945                1950

Pro Glu Trp Phe Val Ser Leu Phe Glu Gln Lys Thr Val Lys Gly Trp
        1955                1960                1965

Trp Pro Cys Val Ala Glu Gly Glu Lys Lys Ile Leu Ala Gly Lys
    1970                1975                1980

Leu Glu Met Thr Leu Glu Ile Val Ala Glu Ser Glu His Glu Glu Arg
1985                1990                1995                2000

Pro Ala Gly Gln Gly Arg Asp Glu Pro Asn Met Asn Pro Lys Leu Glu
                2005                2010                2015

Asp Pro Arg Arg Pro Asp Thr Ser Phe Leu Trp Phe Thr Ser Pro Tyr
            2020                2025                2030

Lys Thr Met Lys Phe Ile Leu Trp Arg Arg Phe Arg Trp Ala Ile Ile
        2035                2040                2045

Leu Phe Ile Ile Leu Phe Ile Leu Leu Phe Leu Ala Ile Phe Ile
    2050                2055                2060

Tyr Ala Phe Pro Asn Tyr Ala Ala Met Lys Leu Val Lys Pro Phe Ser
2065                2070                2075                2080

<210> SEQ ID NO 3
<211> LENGTH: 5915
<212> TYPE: DNA
<213> ORGANISM: Homo sapiens

<400> SEQUENCE: 3
tcgaccgccc agccaggtgc aaaatgccgt gtcattggga gactccgcag ccggagcatt     60
agattacagc tcgacggagc tcgggaaggg cggcggggt ggaagatgag cagaagcccc    120
tgttctcgga acgccggctg acaagcgggg tgagcgcagg cggggcgggg acccagccta   180
gcccactgga gcagccgggg gtggcccgtt ccccttttaag agcaactgct ctaagccagg   240
agccagagat tcgagccggc ctcgcccagc cagccctctc cagcgagggg acccacaagc   300
ggcgcctcgg ccctcccgac ctttccgagc cctcctttgcg ccctgggcgc acggggcccc   360
acacgcgcca agcatgctga gggtcttcat cctctatgcc gagaacgtcc acacacccga   420
caccgacatc agcgatgcct actgctccgc ggtgtttgca ggggtgaaga agagaaccaa   480
agtcatcaag aacagcgtga accctgtatg gaatgaggga tttgaatggg acctcaaggg   540 catcccctg gaccagggct ctgagcttca tgtggtggtc aaagaccatg agacgatggg   600
gaggaacagg ttcctggggg aagccaaggt cccactccga gaggtcctcg ccaccctag   660 tctgtccgcc agcttcaatg ccccctgct ggacaccaag aagcagccca caggggcctc   720

-continued

| | |
|---|---|
| gctggtcctg caggtgtcct acacaccgct gcctggagct gtgccctgt tcccgccccc | 780 |
| tactcctctg gagccctccc cgactctgcc tgacctggat gtagtggcag acacaggagg | 840 |
| agaggaagac acagaggacc agggactcac tggagatgag gcggagccat tcctggatca | 900 |
| aagcggaggc ccgggggctc ccaccacccc aaggaaacta ccttcacgtc ctccgcccca | 960 |
| ctaccccggg atcaaaagaa agcgaagtgc gcctacatct agaaagctgc tgtcagacaa | 1020 |
| accgcaggat ttccagatca gggtccaggt gatcgagggg cgccagctgc cggggtgaa | 1080 |
| catcaagcct gtggtcaagg ttaccgctgc agggcagacc aagcggacgc ggatccacaa | 1140 |
| gggaaacagc ccactcttca atgagactct tttcttcaac ttgtttgact ctcctgggga | 1200 |
| gctgtttgat gagcccatct ttatcacggt ggtagactct cgttctctca ggacagatgc | 1260 |
| tctcctcggg gagttccgga tggacgtggg caccatttac agagagcccc ggcacgccta | 1320 |
| tctcaggaag tggctgctgc tctcagaccc tgatgacttc tctgctgggg ccagaggcta | 1380 |
| cctgaaaaca agcctttgtg tgctggggcc tggggacgaa gcgcctctgg agagaaaga | 1440 |
| cccctctgaa gacaaggagg acattgaaag caacctgctc cggcccacag gcgtagccct | 1500 |
| gcgaggagcc cacttctgcc tgaaggtctt ccgggccgag gacttgccgc agatggacga | 1560 |
| tgccgtgatg gacaacgtga aacagatctt tggcttcgag agtaacaaga gaacttggt | 1620 |
| ggacccctt gtggaggtca gctttgcggg gaaaatgctg tgcagcaaga tcttggagaa | 1680 |
| gacggccaac cctcagtgga accagaacat cacactgcct gccatgtttc cctccatgtg | 1740 |
| cgaaaaaatg aggattcgta tcatagactg ggaccgcctg actcacaatg acatcgtggc | 1800 |
| taccacctac ctgagtatgt cgaaaatctc tgcccctgga ggagaaatag aagaggagcc | 1860 |
| tgcaggtgct gtcaagcctt cgaaagcctc agacttggat gactacctgg gcttcctccc | 1920 |
| cacttttggg ccctgctaca tcaacctcta tggcagtccc agagagttca caggcttccc | 1980 |
| agaccctac acagagctca acacaggcaa ggggaaggt gtggcttatc gtggccggct | 2040 |
| tctgctctcc ctggagacca agctggtgga gcacagtgaa cagaaggtgg aggaccttcc | 2100 |
| tgcggatgac atcctccggg tggagaagta ccttaggagg cgcaagtact ccctgttgc | 2160 |
| ggccttctac tcagccacca tgctgcagga tgtggatgat gccatccagt ttgaggtcag | 2220 |
| catcgggaac tacgggaaca agttcgacat gacctgcctg ccgctggcct ccaccactca | 2280 |
| gtacagccgt gcagtctttg acgggtgcca ctactactac ctaccctggg gtaacgtgaa | 2340 |
| acctgtggtg gtgctgtcat cctactggga ggacatcagc catagaatcg agactcagaa | 2400 |
| ccagctgctt gggattgctg accggctgga agctggcctg gagcaggtcc acctggccct | 2460 |
| gaaggcgcag tgctccacgg aggacgtgga ctcgctggtg gctcagctga cggatgagct | 2520 |
| catcgcaggc tgcagccagc ctctgggtga catccatgag acaccctctg ccacccacct | 2580 |
| ggaccagtac ctgtaccagc tgcgcaccca tcacctgagc caaatcactg aggctgccct | 2640 |
| ggccctgaag ctcggccaca gtgagctccc tgcagctctg agcaggcgg aggactggct | 2700 |
| cctgcgtctg cgtgccctgg cagaggagcc ccagaacagc ctgccggaca tcgtcatctg | 2760 |
| gatgctgcag ggagacaagc gtgtggcata ccagcgggtg cccgcccacc aagtcctctt | 2820 |
| ctcccggcgg ggtgccaact actgtggcaa gaattgtggg aagctacaga caatcttct | 2880 |
| gaaatatccg atggagaagg tgcctggcgc ccggatgcca gtgcagatac gggtcaagct | 2940 |
| gtggtttggg ctctctgtgg atgagaagga gttcaaccag tttgctgagg ggaagctgtc | 3000 |
| tgtcttgct gaaacctatg agaacgagac taagttggcc cttgttggga actggggcac | 3060 |
| aacgggcctc acctaccccca gtttttctga cgtcacgggc aagatcaagc tacccaagga | 3120 |

-continued

```
cagcttccgc ccctcggccg gctggacctg ggctggagat tggttcgtgt gtccggagaa    3180
gactctgctc catgacatgg acgccggtca cctgagcttc gtggaagagg tgtttgagaa    3240
ccagacccgg cttcccggag gccagtggat ctacatgagt gacaactaca ccgatgtgaa    3300
cggggagaag gtgcttccca aggatgacat tgagtgccca ctgggctgga gtgggaaga    3360 tgaggaatgg tccacagacc tcaaccgggc tgtcgatgag caaggctggg agtatagcat    3420
caccatcccc ccggagcgga agccgaagca ctgggtccct gctgagaaga tgtactacac    3480
acaccgacgg cggcgctggg tgcgcctgcg caggagggga ctcagccaaa tggaagcact    3540
gaaaaggcac aggcaggcgg aggcggaggg cgagggctgg gagtacgcct ctcttttggg    3600
ctggaagttc cacctcgagt accgcaagac agatgccttc cgccgccgcc gctggcgccg    3660
tcgcatggag ccactggaga agacggggcc tgcagctgtg tttgcccttg agggggccct    3720
gggcggcgtg atgatgaca agagtgaaga ttccatgtcc gtctccacct tgagcttcgg    3780
tgtgaacaga cccacgattt cctgcatatt cgactatggg aaccgctacc atctacgctg    3840
ctacatgtac caggcccggg acctggctgc gatggacaag gactcttttt ctgatcccta    3900
tgccatcgtc tccttcctgc accagagcca gaagacggtg gtggtgaaga caccccttaa    3960
ccccacctgg gaccagacgc tcatcttcta cgagatcgag atctttggcg agccggccac    4020
agttgctgag caaccgccca gcattgtggt ggagctgtac gaccatgaca cttatggtgc    4080
agacgagttt atgggtcgct gcatctgtca accgagtctg gaacggatgc cacggctggc    4140
ctggttccca ctgacgaggg gcagccagcc gtcggggag ctgctggcct cttttgagct    4200
catccagaga gagaagccgg ccatccacca tattcctggt tttgaggtgc aggagacatc    4260
aaggatcctg gatgagtctg aggacacaga cctgccctac ccaccacccc agagggaggc    4320
caacatctac atggttcctc agaacatcaa gccagcgctc cagcgtaccg ccatcgagat    4380
cctggcatgg ggcctgcgga acatgaagag ttaccagctg ccaacatct cctcccccag    4440 cctcgtggta gagtgtgggg ccagacggt gcagtcctgt gtcatcagga acctccggaa    4500
gaaccccaac tttgacatct gcaccctctt catggaagtg atgctgccca gggaggagct    4560
ctactgcccc cccatcaccg tcaaggtcat cgataaccgc cagtttggcc gccggcctgt    4620
ggtgggccag tgtaccatcc gctccctgga gagcttcctg tgtgaccct actcggcgga    4680 gagtccatcc ccacagggtg gcccagacga tgtgagccta ctcagtcctg ggaagacgt    4740 gctcatcgac attgatgaca aggagcccct catcccatc caggaggaag agttcatcga    4800
ttggtggagc aaattctttg cctccatagg ggagagggaa aagtgcggct cctacctgga    4860
gaaggatttt gacaccctga aggtctatga cacacagctg gagaatgtgg aggcctttga    4920
gggcctgtct gacttttgta acaccttcaa gctgtaccgg gcaagacgc aggaggagac    4980 agaagatcca tctgtgattg gtgaatttaa gggcctcttc aaaatttatc ccctcccaga    5040
agacccagcc atccccatgc ccccaagaca gttccaccag ctggccgccc agggacccca    5100
ggagtgcttg gtccgtatct acattgtccg agcatttggc ctgcagccca aggaccccaa    5160
tggaaagtgt gatccttaca tcaagatctc catagggaag aaatcagtga gtgaccagga    5220
taactacatc ccctgcacgc tggagcccgt atttggaaag atgttcgagc tgacctgcac    5280
tctgcctctg gagaaggacc taaagatcac tctctatgac tatgacctcc tctccaagga    5340
cgaaaagatc ggtgagacgg tcgtcgacct ggagaacagg ctgctgtcca gtttggggc    5400 tcgctgtgga ctcccacaga cctactgtgt ctctggaccg aaccagtggc gggaccagct    5460
ccgcccctcc cagctcctcc acctcttctg ccagcagcat agagtcaagg cacctgtgta    5520
```

```
ccggacagac cgtgtaatgt ttcaggataa agaatattcc attgaagaga tagaggctgg    5580
caggatccca aacccacacc tgggcccagt ggaggagcgt ctggctctgc atgtgcttca    5640
gcagcagggc ctggtccgg agcacgtgga gtcacggccc ctctacagcc ccctgcagcc     5700
agacatcgag caggggaagc tgcagatgtg ggtcgaccta tttccgaagg ccctggggcg    5760
gcctggacct cccttcaaca tcaccccacg gagagccaga aggttttcc tgcgttgtat     5820 tatctggaat accagagatg tgatcctgga tgacctgagc ctcacggggg agaagatgag    5880
cgacatttat gtgaaaggtt ggatgattgg ctttg                               5915
```

<210> SEQ ID NO 4
<211> LENGTH: 20
<212> TYPE: DNA
<213> ORGANISM: Homo sapiens

<400> SEQUENCE: 4

```
tgggacctca aagggcatcc                                                  20
```

<210> SEQ ID NO 5
<211> LENGTH: 20
<212> TYPE: DNA
<213> ORGANISM: Homo sapiens

<400> SEQUENCE: 5

```
accatgctgt aggatgtgga                                                  20
```

<210> SEQ ID NO 6
<211> LENGTH: 20
<212> TYPE: DNA
<213> ORGANISM: Homo sapiens

<400> SEQUENCE: 6

```
gggaggtgaa gcaacttcaa                                                  20
```

<210> SEQ ID NO 7
<211> LENGTH: 20
<212> TYPE: DNA
<213> ORGANISM: Homo sapiens

<400> SEQUENCE: 7

```
ctcacggggt agaagatgag                                                  20
```

<210> SEQ ID NO 8
<211> LENGTH: 20
<212> TYPE: DNA
<213> ORGANISM: Homo sapiens

<400> SEQUENCE: 8

```
cagggccgag atgagcccaa                                                  20
```

<210> SEQ ID NO 9
<211> LENGTH: 20
<212> TYPE: DNA
<213> ORGANISM: Homo sapiens

<400> SEQUENCE: 9

```
acatcaaggg tcctggatga                                                  20
```

<210> SEQ ID NO 10
<211> LENGTH: 20
<212> TYPE: DNA
<213> ORGANISM: Homo sapiens -continued

```
<400> SEQUENCE: 10
ctgtggcggt gtttccggtg                                              20

<210> SEQ ID NO 11
<211> LENGTH: 20
<212> TYPE: DNA
<213> ORGANISM: Homo sapiens

<400> SEQUENCE: 11
acagacgtgc gttatcgttc                                              20

<210> SEQ ID NO 12
<211> LENGTH: 20
<212> TYPE: DNA
<213> ORGANISM: Homo sapiens

<400> SEQUENCE: 12
aagactgagc aaaatcccag                                              20

<210> SEQ ID NO 13
<211> LENGTH: 6912
<212> TYPE: DNA
<213> ORGANISM: Homo sapiens

<400> SEQUENCE: 13
tcgaccgccc agccaggtgc aaaatgccgt gtcattggga gactccgcag ccggagcatt    60
agattacagc tcgacggagc tcgggaaggg cggcgggggt ggaagatgag cagaagcccc   120
tgttctcgga acgccggctg acaagcgggg tgagcgcagg cggggcgggg acccagccta   180
gcccactgga gcagccgggg gtggcccgtt cccctttaag agcaactgct ctaagccagg   240
agccagagat tcgagccggc ctcgcccagc cagccctctc cagcgagggg acccacaagc   300
ggcgcctcgg ccctcccgac cttttccgagc cctctttgcg ccctgggcgc acggggccct   360
acacgcgcca agcatgctga gggtcttcat cctctatgcc gagaacgtcc acacacccga   420
caccgacatc agcgatgcct actgctccgc ggtgtttgca ggggtgaaga agagaaccaa   480
agtcatcaag aacagcgtga accctgtatg gaatgaggga tttgaatggg acctcaaagg   540 gcatcccccct ggaccagggc tctgagcttc atgtggtggt caaagaccat gagacgatgg   600
ggaggaacag gttcctgggg gaagccaagg tcccactccg agaggtcctc gccacccta   660 gtctgtccgc cagcttcaat gcccccctgc tggacaccaa gaagcagccc acaggggcct   720
cgctggtcct gcaggtgtcc tacacaccgc tgcctggagc tgtgcccctg ttcccgcccc   780
ctactcctct ggagccctcc ccgactctgc ctgacctgga tgtagtggca gacacaggag   840
gagaggaaga cacagaggac cagggactca ctggagatga ggcggagcca ttcctggatc   900
aaagcggagg cccgggggct cccaccaccc caaggaaact accttcacgt cctccgcccc   960
actacccggg gatcaaaaga aagcgaagtg cgcctacatc tagaaagctg ctgtcagaca  1020
aaccgcagga tttccagatc agggtccagg tgatcgaggg gcgccagctg ccggggggtga  1080 acatcaagcc tgtggtcaag gttaccgctg cagggcagac caagcggacg cggatccaca  1140
agggaaacag cccactcttc aatgagactc ttttcttcaa cttgtttgac tctcctgggg  1200
agctgtttga tgagcccatc tttatcacgg tggtagactc tcgttctctc aggacagatg  1260
ctctcctcgg ggagttccgg atggacgtgg caccattta cagagagccc ggcacgcct   1320 atctcaggaa gtggctgctg ctctcagacc ctgatgactt ctctgctggg ccagaggct   1380 acctgaaaac aagcctttgt gtgctggggc ctgggacga agcgcctctg gagagaaaag  1440
```

-continued

| | | | | | |
|---|---|---|---|---|---|
| accccctctga | agacaaggag | gacattgaaa | gcaacctgct | ccggcccaca | ggcgtagccc | 1500 |
| tgcgaggagc | ccacttctgc | ctgaaggtct | tccgggccga | ggacttgccg | cagatggacg | 1560 |
| atgccgtgat | ggacaacgtg | aaacagatct | ttggcttcga | gagtaacaag | aagaacttgg | 1620 |
| tggacccctt | tgtggaggtc | agctttgcgg | ggaaaatgct | gtgcagcaag | atcttggaga | 1680 |
| agacggccaa | ccctcagtgg | aaccagaaca | tcacactgcc | tgccatgttt | ccctccatgt | 1740 |
| gcgaaaaaat | gaggattcgt | atcatagact | gggaccgcct | gactcacaat | gacatcgtgg | 1800 |
| ctaccaccta | cctgagtatg | tcgaaaatct | ctgcccctgg | aggagaaata | aagaggagc | 1860 |
| ctgcaggtgc | tgtcaagcct | tcgaaagcct | cagacttgga | tgactacctg | ggcttcctcc | 1920 |
| ccactttttgg | gccctgctac | atcaacctct | atggcagtcc | cagagagttc | acaggcttcc | 1980 |
| cagaccccta | cacagagctc | aacacaggca | aggggggaagg | tgtggcttat | cgtggccggc | 2040 |
| ttctgctctc | cctggagacc | aagctggtgg | agcacagtga | acagaaggtg | gaggaccttc | 2100 |
| ctgcggatga | catcctccgg | gtggagaagt | accttaggag | gcgcaagtac | tccctgtttg | 2160 |
| cggccttcta | ctcagccacc | atgctgtagg | atgtggatga | tgccatccag | tttgaggtca | 2220 |
| gcatcgggaa | ctacgggaac | aagttcgaca | tgacctgcct | gccgctggcc | tccaccactc | 2280 |
| agtacagccg | tgcagtcttt | gacgggtgcc | actactacta | cctaccctgg | ggtaacgtga | 2340 |
| aacctgtggt | ggtgctgtca | tcctactggg | aggacatcag | ccatagaatc | gagactcaga | 2400 |
| accagctgct | tgggattgct | gaccggctgg | aagctggcct | ggagcaggtc | cacctggccc | 2460 |
| tgaaggcgca | gtgctccacg | gaggacgtgg | actcgctggt | ggctcagctg | acggatgagc | 2520 |
| tcatcgcagg | ctgcagccag | cctctgggtg | acatccatga | gacaccctct | gccacccacc | 2580 |
| tggaccagta | cctgtaccag | ctgcgcaccc | atcacctgag | ccaaatcact | gaggctgccc | 2640 |
| tggccctgaa | gctcggccac | agtgagctcc | ctgcagctct | ggagcaggcg | gaggactggc | 2700 |
| tcctgcgtct | gcgtgccctg | gcagaggagc | cccagaacag | cctgccggac | atcgtcatct | 2760 |
| ggatgctgca | gggagacaag | cgtgtggcat | accagcgggt | gcccgcccac | caagtcctct | 2820 |
| tctcccggcg | gggtgccaac | tactgtgcca | agaattgtgg | gaagctacag | acaatctttc | 2880 |
| tgaaatatcc | gatggagaag | gtgcctggcg | cccggatgcc | agtgcagata | cgggtcaagc | 2940 |
| tgtggtttgg | gctctctgtg | gatgagaagg | agttcaacca | gtttgctgag | gggaagctgt | 3000 |
| ctgtctttgc | tgaaacctat | gagaacgaga | ctaagttggc | ccttgttggg | aactggggca | 3060 |
| caacgggcct | cacctacccc | aagttttctg | acgtcacggg | caagatcaag | ctacccaagg | 3120 |
| acagcttccg | cccctcggcc | ggctggacct | gggctggaga | ttggttcgtg | tgtccggaga | 3180 |
| agactctgct | ccatgacatg | gacgccggtc | acctgagctt | cgtggaagag | gtgtttgaga | 3240 |
| accagacccg | gcttcccgga | ggccagtgga | tctacatgag | tgacaactac | accgatgtga | 3300 |
| acggggagaa | ggtgcttccc | aaggatgaca | ttgagtgccc | actgggctgg | aagtgggaag | 3360 |
| atgaggaatg | gtccacagac | ctcaaccggg | ctgtcgatga | gcaaggctgg | gagtatagca | 3420 |
| tcaccatccc | cccggagcgg | aagccgaagc | actgggtccc | tgctgagaag | atgtactaca | 3480 |
| cacaccgacg | gcggcgctgg | gtgcgcctgc | gcaggaggga | tctcagccaa | atggaagcac | 3540 |
| tgaaaaggca | caggcaggcg | gaggcggagg | gcgaggctg | ggagtacgcc | tctctttttg | 3600 |
| gctggaagtt | ccacctcgag | taccgcaaga | cagatgcctt | ccgccgccgc | cgctggcgcc | 3660 |
| gtcgcatgga | gccactggag | aagacggggc | ctgcagctgt | gtttgccctt | gagggggccc | 3720 |
| tgggcggcgt | gatggatgac | aagagtgaag | attccatgtc | cgtctccacc | ttgagcttcg | 3780 |
| gtgtgaacag | acccacgatt | tcctgcatat | tcgactatgg | gaaccgctac | catctacgct | 3840 |

-continued

```
gctacatgta ccaggcccgg gacctggctg cgatggacaa ggactctttt tctgatccct      3900
atgccatcgt ctccttcctg caccagagcc agaagacggt ggtggtgaag aacacccTta      3960
accccacctg ggaccagacg ctcatcttct acgagatcga gatctttggc gagccggcca      4020
cagttgctga gcaaccgccc agcattgtgg tggagctgta cgaccatgac acttatggtg      4080
cagacgagtt tatgggtcgc tgcatctgtc aaccgagtct ggaacggatg ccacggctgg      4140
cctggttccc actgacgagg ggcagccagc cgtcggggga gctgctggcc tcttttgagc      4200
tcatccagag agagaagccg gccatccacc atattcctgg ttttgaggtg caggagacat      4260
caaggatcct ggatgagtct gaggacacag acctgcccta cccaccaccc cagagggagg      4320
ccaacatcta catggttcct cagaacatca agccagcgct ccagcgtacc gccatcgaga      4380
tcctggcatg gggcctgcgg aacatgaaga gttaccagct ggccaacatc tcctccccca      4440
gcctcgtggt agagtgtggg ggccagacgt gcagtcctg tgtcatcagg aacctccgga      4500
agaaccccaa ctttgacatc tgcaccctct tcatggaagt gatgctgccc agggaggagc      4560
tctactgccc ccccatcacc gtcaaggtca tcgataaccg ccagtttggc cgccggcctg      4620
tggtgggcca gtgtaccatc cgctccctgg agagcttcct gtgtgacccc tactcggcgg      4680
agagtccatc cccacaggt ggcccagacg atgtgagcct actcagtcct ggggaagacg      4740
tgctcatcga cattgatgac aaggagcccc tcatccccat ccaggaggaa gagttcatcg      4800
attggtggag caaattcttt gcctccatag gggagaggga aaagtgcggc tcctacctgg      4860
agaaggattt tgacaccctg aaggtctatg acacacagct ggagaatgtg gaggcctttg      4920
agggcctgtc tgacttttgt aacaccttca agctgtaccg gggcaagacg caggaggaga      4980
cagaagatcc atctgtgatt ggtgaattta agggcctctt caaatttat ccctcccag       5040
aagacccagc catccccatg cccccaagac agttccacca gctggccgcc cagggacccc      5100
aggagtgctt ggtccgtatc tacattgtcc gagcatttgg cctgcagccc aaggacccca      5160
atggaaagtg tgatccttac atcaagatct ccatagggaa gaaatcagtg agtgaccagg      5220
ataactacat cccctgcacg ctggagcccg tatttggaaa gatgttcgag ctgacctgca      5280
ctctgcctct ggagaaggac ctaaagatca ctctctatga ctatgacctc ctctccaagg      5340
acgaaaagat cggtgagacg gtcgtcgacc tggagaacag gctgctgtcc aagtttgggg      5400
ctcgctgtgg actcccacag acctactgtg tctctggacc gaaccagtgg cgggaccagc      5460
tccgcccctc ccagctcctc cacctcttct gccagcagca tagagtcaag gcacctgtgt      5520
accggacaga ccgtgtaatg tttcaggata agaatattc cattgaagag atagaggctg      5580
gcaggatccc aaacccacac ctgggcccag tggaggagcg tctggctctg catgtgcttc      5640
agcagcaggg cctggtcccg gagcacgtgg agtcacggcc cctctacagc cccctgcagc      5700
cagacatcga gcaggggaag ctgcagatgt gggtcgacct atttccgaag gccctggggc      5760
ggcctggacc tcccttcaac atcaccccac ggagagccag aaggtttttc ctgcgttgta      5820
ttatctggaa taccagagat gtgatcctgg atgacctgag cctcacgggg gagaagatga      5880
gcgacattta tgtgaaaggt tggatgattg ctttgaaga acacaagcaa aagacagacg      5940
tgcattatcg ttccctggga ggtgaaggca cttcaactg gaggttcatt ttccccttcg      6000
actacctgcc agctgagcaa gtctgtacca ttgccaagaa ggatgccttc tggaggctgg      6060
acaagactga gagcaaaatc ccagcacgag tggtgttcca gatctgggac aatgacaagt      6120
ctccctttga tgatttttctg ggctccctgc agctcgatct caaccgcatg cccaagccag      6180
ccaagacagc caagaagtgc tccttggacc agctggatga tgctttccac ccagaatggt      6240
```

-continued

```
ttgtgtccct ttttgagcag aaaacagtga agggctggtg gccctgtgta gcagaagagg    6300
gtgagaagaa aatactggcg ggcaagctgg aaatgacctt ggagattgta gcagagagtg    6360
agcatgagga gcggcctgct ggccagggcc gggatgagcc caacatgaac cctaagcttg    6420
aggacccaag gcgccccgac acctccttcc tgtggtttac ctccccatac aagaccatga    6480
agttcatcct gtggcggcgt ttccggtggg ccatcatcct cttcatcatc ctcttcatcc    6540
tgctgctgtt cctggccatc ttcatctacg ccttcccgaa ctatgctgcc atgaagctgg    6600
tgaagccctt cagctgagga ctctcctgcc ctgtagaagg ggccgtgggg tcccctccag    6660
catgggactg gcctgcctcc tccgcccagc tcggcgagct cctccagacc tcctaggcct    6720
gattgtcctg ccagggtggg cagacagaca gatggaccgg cccacactcc cagagttgct    6780
aacatggagc tctgagatca ccccacttcc atcatttcct tctcccccaa cccaacgctt    6840
ttttggatca gctcagacat atttcagtat aaaacagttg gaaccacaaa aaaaaaaaaa    6900
aaaaaaaaaa aa                                                       6912
```

<210> SEQ ID NO 14
<211> LENGTH: 6911
<212> TYPE: DNA
<213> ORGANISM: Homo sapiens

<400> SEQUENCE: 14

```
tcgaccgccc agccaggtgc aaaatgccgt gtcattggga gactccgcag ccggagcatt      60
agattacagc tcgacggagc tcgggaaggg cggcgggggt ggaagatgag cagaagcccc     120
tgttctcgga acgccggctg acaagcgggg tgagcgcagg cggggcgggg acccagccta     180
gcccactgga gcagccgggg gtggcccgtt ccccttaag agcaactgct ctaagccagg      240
agccagagat tcgagccggc ctcgcccagc cagccctctc cagcgagggg acccacaagc     300
ggcgcctcgg ccctcccgac ctttccgagc cctctttgcg ccctgggcgc acggggccct     360
acacgcgcca agcatgctga gggtcttcat cctctatgcc gagaacgtcc acacacccga     420
caccgacatc agcgatgcct actgctccgc ggtgtttgca ggggtgaaga agagaaccaa     480
agtcatcaag aacagcgtga accctgtatg gaatgaggga tttgaatggg acctcaaggg     540 catcccctg gaccagggct ctgagcttca tgtggtggtc aaagaccatg agacgatggg      600
gaggaacagg ttcctggggg aagccaaggt cccactccga gaggtcctcg ccaccctag      660 tctgtccgcc agcttcaatg cccccctgct ggacaccaag aagcagccca caggggcctc     720
gctggtcctg caggtgtcct acacaccgct gcctggagct gtgcccctgt tcccgccccc     780
tactcctctg gagccctccc cgactctgcc tgacctggat gtagtggcag acacaggagg     840
agaggaagac acagaggacc agggactcac tggagatgag gcggagccat tcctggatca     900
aagcggaggc ccgggggctc ccaccacccc aaggaaacta ccttcacgtc ctccgcccca     960
ctaccccggg atcaaaagaa agcgaagtgc gcctacatct agaaagctgc tgtcagacaa    1020
accgcaggat ttccagatca gggtccaggt gatcgagggg cgccagctgc gggggtgaa     1080 catcaagcct gtggtcaagg ttaccgctgc agggcagacc aagcggacgc ggatccacaa    1140
gggaaacagc ccactcttca atgagactct tttcttcaac ttgtttgact ctcctgggga    1200
gctgtttgat gagcccatct ttatcacggt ggtagactct cgttctctca ggacagatgc    1260
tctcctcggg gagttccgga tggacgtggg caccatttac agagagcccc ggcacgccta    1320
tctcaggaag tggctgctgc tctcagaccc tgatgacttc tctgctgggg ccagaggcta    1380
cctgaaaaca agccttttgtg tgctggggcc tggggacgaa gcgcctctgg agagaaaaga    1440
```

-continued

```
cccctctgaa gacaaggagg acattgaaag caacctgctc cggcccacag gcgtagccct    1500
gcgaggagcc cacttctgcc tgaaggtctt ccgggccgag gacttgccgc agatggacga    1560
tgccgtgatg gacaacgtga aacagatctt tggcttcgag agtaacaaga gaacttggt    1620 ggaccccttt gtggaggtca gctttgcggg gaaaatgctg tgcagcaaga tcttggagaa    1680
gacggccaac cctcagtgga accagaacat cacactgcct gccatgtttc cctccatgtg    1740
cgaaaaaatg aggattcgta tcatagactg ggaccgcctg actcacaatg acatcgtggc    1800
taccacctac ctgagtatgt cgaaaatctc tgccctggga ggagaaatag aagaggagcc    1860
tgcaggtgct gtcaagcctt cgaaagcctc agacttggat gactacctgg gcttcctccc    1920
cacttttggg ccctgctaca tcaacctcta tggcagtccc agagagttca caggcttccc    1980 agaccctac acagagctca acacaggcaa gggggaaggt gtggcttatc gtggccggct    2040
tctgctctcc ctggagacca agctggtgga gcacagtgaa cagaaggtgg aggaccttcc    2100 tgccggatgac atcctccggg tggagaagta ccttaggagg cgcaagtact ccctgtttgc    2160
ggccttctac tcagccacca tgctgtagga tgtggatgat gccatccagt ttgaggtcag    2220
catcgggaac tacgggaaca agttcgacat gacctgcctg ccgctggcct ccaccactca    2280
gtacagccgt gcagtcttg acgggtgcca ctactactac ctaccctggg gtaacgtgaa    2340
acctgtggtg gtgctgtcat cctactggga ggacatcagc catagaatcg agactcagaa    2400
ccagctgctt gggattgctg accggctgga agctggcctg gagcaggtcc acctggccct    2460
gaaggcgcag tgctccacgg aggacgtgga ctcgctggtg gctcagctga cggatgagct    2520
catcgcaggc tgcagccagc ctctgggtga catccatgag acaccctctg ccacccacct    2580
ggaccagtac ctgtaccagc tgcgcaccca tcacctgagc caaatcactg aggctgccct    2640
ggccctgaag ctcggccaca gtgagctccc tgcagctctg gagcaggcgg aggactggct    2700
cctgcgtctg cgtgccctgg cagaggagcc ccagaacagc ctgccggaca tcgtcatctg    2760
gatgctgcag ggagacaagc gtgtggcata ccagcgggtg cccgcccacc aagtcctctt    2820
ctcccggcgg ggtgccaact actgtggcaa gaattgtggg aagctacaga caatctttct    2880
gaaatatccg atggagaagg tgcctggcgc ccggatgcca gtgcagatac gggtcaagct    2940
gtggtttggg ctctctgtgg atgagaagga gttcaaccag tttgctgagg ggaagctgtc    3000
tgtctttgct gaaacctatg agaacgagac taagttggcc cttgttggga actggggcac    3060
aacgggcctc acctacccca gttttctga cgtcacgggc aagatcaagc tacccaagga    3120
cagcttccgc ccctcggccg gctggacctg gctggagat tggttcgtgt gtccggagaa    3180
gactctgctc catgacatgg acgccggtca cctgagcttc gtggaagagg tgtttgagaa    3240
ccagacccgg cttcccggag gccagtggat ctacatgagt gacaactaca ccgatgtgaa    3300
cggggagaag gtgcttccca aggatgacat tgagtgccca ctgggctgga gtgggaaga    3360 tgaggaatgg tccacagacc tcaaccgggc tgtcgatgag caaggctggg agtatagcat    3420
caccatcccc ccgagcgga agccgaagca ctgggtccct gctgagaaga tgtactacac    3480
acaccgacgg cggcgctggg tgcgcctgcg caggagggat ctcagccaaa tggaagcact    3540
gaaaaggcac aggcaggcgg aggcggaggg cgagggctgg gagtacgcct ctctttttgg    3600
ctggaagttc cacctcgagt accgcaagac agatgccttc cgccgccgcc gctggcgccg    3660
tcgcatggag ccactggaga agacggggcc tgcagctgtg tttgcccttg agggggccct    3720
gggcggcgtg atggatgaca agagtgaaga ttccatgtcc gtctccacct tgagcttcgg    3780
tgtgaacaga cccacgattt cctgcatatt cgactatggg aaccgctacc atctacgctg    3840
```

```
ctacatgtac caggcccggg acctggctgc gatggacaag gactcttttt ctgatccta    3900
tgccatcgtc tccttcctgc accagagcca gaagacggtg gtggtgaaga acacccttaa    3960
ccccacctgg gaccagacgc tcatcttcta cgagatcgag atctttggcg agccggccac    4020
agttgctgag caaccgccca gcattgtggt ggagctgtac gaccatgaca cttatggtgc    4080
agacgagttt atgggtcgct gcatctgtca accgagtctg gaacgatgc cacggctggc    4140
ctggttccca ctgacgaggg gcagccagcc gtcggggag ctgctggcct cttttgagct    4200
catccagaga gagaagccgg ccatccacca tattcctggt tttgaggtgc aggagacatc    4260
aaggatcctg gatgagtctg aggacacaga cctgccctac ccaccacccc agagggaggc    4320
caacatctac atggttcctc agaacatcaa gccagcgctc cagcgtaccg ccatcgagat    4380
cctggcatgg ggcctgcgga acatgaagag ttaccagctg gccaacatct cctcccccag    4440
cctcgtggta gagtgtgggg ccagacggt gcagtcctgt gtcatcagga acctccggaa    4500
gaaccccaac tttgacatct gcaccctctt catggaagtg atgctgccca gggaggagct    4560
ctactgcccc cccatcaccg tcaaggtcat cgataaccgc cagtttggcc gccggcctgt    4620
ggtgggccag tgtaccatcc gctccctgga gagcttcctg tgtgacccct actcggcgga    4680
gagtccatcc ccacagggtg gcccagacga tgtgagccta ctcagtcctg ggaagacgt    4740
gctcatcgac attgatgaca ggagcccct catccccatc caggaggaag agttcatcga    4800
ttggtggagc aaattctttg cctccatagg ggagagggaa aagtgcggct cctacctgga    4860
gaaggatttt gacaccctga aggtctatga cacacagctg gagaatgtgg aggcctttga    4920
gggcctgtct gacttttgta acaccttcaa gctgtaccgg ggcaagacgc aggaggagac    4980
agaagatcca tctgtgattg gtgaatttaa gggcctcttc aaaattatc ccctccaga    5040
agacccagcc atccccatgc ccccaagaca gttccaccag ctggccgccc agggaccccca    5100
ggagtgcttg gtccgtatct acattgtccg agcatttggc ctgcagccca aggacccaa    5160
tggaaagtgt gatccttaca tcaagatctc catagggaag aaatcagtga gtgaccagga    5220
taactacatc ccctgcacgc tggagcccgt atttggaaag atgttcgagc tgacctgcac    5280
tctgcctctg gagaaggacc taaagatcac tctctatgac tatgacctcc tctccaagga    5340
cgaaaagatc ggtgagacgg tcgtcgacct ggagaacagg ctgctgtcca gtttggggc    5400
tcgctgtgga ctcccacaga cctactgtgt ctctggaccg aaccagtggc gggaccagct    5460
ccgcccctcc cagctcctcc acctcttctg ccagcagcat agagtcaagg cacctgtgta    5520
ccggacagac cgtgtaatgt ttcaggataa agaatattcc attgaagaga tagaggctgg    5580
caggatccca aacccacacc tgggcccagt ggaggagcgt ctggctctgc atgtgcttca    5640
gcagcagggc ctggtcccgg agcacgtgga gtcacggccc ctctacagcc cctgcagcc    5700
agacatcgag caggggaagc tgcagatgtg ggtcgaccta tttccgaagg ccctgggggcg    5760
gcctggacct cccttcaaca tcaccccacg gagagccaga aggttttcc tgcgttgtat    5820
tatctggaat accagagatg tgatcctgga tgacctgagc ctcacggggg agaagatgag    5880
cgacatttat gtgaaaggtt ggatgattgg ctttgaagaa cacaagcaaa agacagacgt    5940
gcattatcgt tccctgggag gtgaaggcaa cttcaactgg aggttcattt ccccttcga    6000
ctacctgcca gctgagcaag tctgtaccat tgccaagaag gatgccttct ggaggctgga    6060
caagactgag agcaaaatcc cagcacgagt ggtgttccag atctgggaca atgacaagtt    6120
ctccttgat gattttctgg ctccctgca gctcgatctc aaccgcatgc ccaagccagc    6180
caagacagcc aagaagtgct ccttggacca gctggatgat gctttccacc cagaatggtt    6240
```

```
tgtgtccctt tttgagcaga aaacagtgaa gggctggtgg ccctgtgtag cagaagaggg    6300
tgagaagaaa atactggcgg gcaagctgga aatgaccttg gagattgtag cagagagtga    6360
gcatgaggag cggcctgctg gccagggccg ggatgagccc aacatgaacc ctaagcttga    6420
ggacccaagg cgccccgaca cctccttcct gtggtttacc tccccataca agaccatgaa    6480
gttcatcctg tggcggcgtt ccggtgggc catcatcctc ttcatcatcc tcttcatcct    6540
gctgctgttc ctggccatct tcatctacgc cttcccgaac tatgctgcca tgaagctggt    6600
gaagcccttc agctgaggac tctcctgccc tgtagaaggg gccgtggggt ccctccagc    6660 atgggactgg cctgcctcct ccgcccagct cggcgagctc ctccagacct cctaggcctg    6720
attgtcctgc cagggtgggc agacagacag atggaccggc ccacactccc agagttgcta    6780
acatggagct ctgagatcac cccacttcca tcatttcctt ctcccccaac ccaacgcttt    6840
tttggatcag ctcagacata tttcagtata aacagttgg aaccacaaaa aaaaaaaaa    6900 aaaaaaaaa a                                                          6911

<210> SEQ ID NO 15
<211> LENGTH: 6910
<212> TYPE: DNA
<213> ORGANISM: Homo sapiens

<400> SEQUENCE: 15
tcgaccgccc agccaggtgc aaaatgccgt gtcattggga gactccgcag ccggagcatt      60
agattacagc tcgacggagc tcgggaaggg cggcggggg ggaagatgag cagaagcccc     120
tgttctcgga acgccggctg acaagcgggg tgagcgcagg cggggcgggg acccagccta    180
gcccactgga gcagccgggg gtggcccgtt ccccttaag agcaactgct ctaagccagg    240
agccagagat tcgagccggc ctcgcccagc cagccctctc cagcgagggg acccacaagc    300
ggcgcctcgg ccctcccgac cttccgagc cctctttgcg ccctgggcgc acggggccct    360
acacgcgcca agcatgctga gggtcttcat cctctatgcc gagaacgtcc acacacccga    420
caccgacatc agcgatgcct actgctccgc ggtgtttgca ggggtgaaga agagaaccaa    480
agtcatcaag aacagcgtga accctgtatg gaatgaggga tttgaatggg acctcaaggg    540
catccccctg gaccagggct ctgagcttca tgtggtggtc aaagaccatg agacgatggg    600
gaggaacagg ttcctggggg aagccaaggt cccactccga gaggtcctcg ccacccctag    660
tctgtccgcc agcttcaatg cccccctgct ggacaccaag aagcagccca gggggcctc    720 gctggtcctg caggtgtcct acacaccgct gcctggagct gtgcccctgt cccgccccc    780 tactcctctg gagccctccc cgactctgcc tgacctggat gtagtggcag acacaggagg    840
agaggaagac acagaggacc agggactcac tggagatgag gcggagccat tcctggatca    900
aagcggaggc ccgggggctc ccaccaccc aaggaaacta ccttcacgtc ctccgcccca    960
ctaccccggg atcaaaagaa agcgaagtgc gcctacatct agaaagctgc tgtcagacaa    1020
accgcaggat ttccagatca gggtccaggt gatcgagggg cgccagctgc cggggtgaa    1080 catcaagcct gtggtcaagg ttaccgctgc agggcagacc aagcggacgc ggatccacaa    1140
gggaaacagc ccactcttca atgagactct tttcttcaac ttgtttgact ctcctgggga    1200
gctgtttgat gagcccatct ttatcacggt ggtagactct cgttctctca ggacagatgc    1260
tctcctcggg gagttccgga tggacgtggg caccatttac agagagcccc ggcacgccta    1320
tctcaggaag tggctgctgc tctcagaccc tgatgacttc tctgctgggg ccagaggcta    1380
cctgaaaaca agccctttgt tgctggggcc tggggacgaa gcgcctctgg agagaaaaga    1440
```

-continued

```
cccctctgaa gacaaggagg acattgaaag caacctgctc cggcccacag gcgtagccct      1500
gcgaggagcc cacttctgcc tgaaggtctt ccgggccgag gacttgccgc agatggacga      1560
tgccgtgatg gacaacgtga aacagatctt tggcttcgag agtaacaaga gaacttggt      1620 ggaccccttt gtggaggtca gctttgcggg gaaaatgctg tgcagcaaga tcttggagaa      1680
gacggccaac cctcagtgga accagaacat cacactgcct gccatgtttc cctccatgtg      1740
cgaaaaaatg aggattcgta tcatagactg ggaccgcctg actcacaatg acatcgtggc      1800
taccacctac ctgagtatgt cgaaaatctc tgcccctgga ggagaaatag aagaggagcc      1860
tgcaggtgct gtcaagcctt cgaaagcctc agacttggat gactacctgg gcttcctccc      1920
cacttttggg ccctgctaca tcaacctcta tggcagtccc agagagttca caggcttccc      1980
agacccctac acagagctca acacaggcaa gggggaaggt gtggcttatc gtggccggct      2040
tctgctctcc ctggagacca agctggtgga gcacagtgaa cagaaggtgg aggaccttcc      2100
tgcggatgac atcctccggg tggagaagta ccttaggagg cgcaagtact ccctgtttgc      2160
ggccttctac tcagccacca tgctgcagga tgtggatgat gccatccagt ttgaggtcag      2220
catcgggaac tacgggaaca agttcgacat gacctgcctg ccgctggcct ccaccactca      2280
gtacagccgt gcagtctttg acgggtgcca ctactactac ctaccctggg gtaacgtgaa      2340
acctgtggtg gtgctgtcat cctactggga ggacatcagc catagaatcg agactcagaa      2400
ccagctgctt gggattgctg accggctgga agctggcctg gagcaggtcc acctggccct      2460
gaaggcgcag tgctccacgg aggacgtgga ctcgctggtg gctcagctga cggatgagct      2520
catcgcaggc tgcagccagc ctctgggtga catccatgag acaccctctg ccacccacct      2580
ggaccagtac ctgtaccagc tgcgcaccca tcacctgagc caaatcactg aggctgccct      2640
ggccctgaag ctcggccaca gtgagctccc tgcagctctg gagcaggcgg aggactggct      2700
cctgcgtctg cgtgccctgg cagaggagcc ccagaacagc ctgccggaca tcgtcatctg      2760
gatgctgcag ggagacaagc gtgtggcata ccagcgggtg cccgcccacc aagtcctctt      2820
ctcccggcgg ggtgccaact actgtggcaa gaattgtggg aagctacaga caatctttct      2880
gaaatatccg atggagaagg tgcctggcgc ccggatgcca gtgcagatac gggtcaagct      2940
gtggtttggg ctctctgtgg atgagaagga gttcaaccag tttgctgagg ggaagctgtc      3000
tgtctttgct gaaacctatg agaacgagac taagttggcc cttgttggga actggggcac      3060
aacgggcctc acctacccca gttttctga cgtcacgggc aagatcaagc tacccaagga      3120
cagcttccgc ccctcggccg gctggacctg gctggagat tggttcgtgt gtccggagaa      3180
gactctgctc catgacatgg acgccggtca cctgagcttc gtggaagagg tgtttgagaa      3240
ccagacccgg cttcccggag gccagtggat ctacatgagt gacaactaca ccgatgtgaa      3300
cggggagaag gtgcttccca aggatgacat tgagtgccca ctgggctgga gtgggaaga      3360 tgaggaatgg tccacagacc tcaaccgggc tgtcgatgag caaggctggg agtatagcat      3420
caccatcccc ccggagcgga agccgaagca ctgggtccct gctgagaaga tgtactacac      3480
acaccgacgg cggcgctggg tgcgcctgcg caggaggat ctcagccaaa tggaagcact      3540
gaaaaggcac aggcaggcgg aggcggaggg cgagggctgg gagtacgcct ctcttttgg      3600 ctggaagttc cacctcgagt accgcaagac agatgccttc cgccgccgcc gctggcgccg      3660
tcgcatggag ccactggaga agacgggggcc tgcagctgtg tttgcccttg agggggcccct      3720 gggcggcgtg atggatgaca agagtgaaga ttccatgtcc gtctccacct tgagcttcgg      3780
tgtgaacaga cccacgattt cctgcatatt cgactatggg aaccgctacc atctacgctg      3840
```

```
ctacatgtac caggcccggg acctggctgc gatggacaag gactcttttt ctgatcccta    3900
tgccatcgtc tccttcctgc accagagcca gaagacggtg gtggtgaaga cacccttaa    3960
ccccacctgg gaccagacgc tcatcttcta cgagatcgag atctttggcg agccggccac    4020
agttgctgag caaccgccca gcattgtggt ggagctgtac gaccatgaca cttatggtgc    4080
agacgagttt atgggtcgct gcatctgtca accgagtctg gaacggatgc cacggctggc    4140
ctggttccca ctgacgaggg gcagccagcc gtcgggggag ctgctggcct cttttgagct    4200
catccagaga gagaagccgg ccatccacca tattcctggt tttgaggtgc aggagacatc    4260
aaggatcctg gatgagtctg aggacacaga cctgccctac ccaccacccc agagggaggc    4320
caacatctac atggttcctc agaacatcaa gccagcgctc cagcgtaccg ccatcgagat    4380
cctggcatgg ggcctgcgga acatgaagag ttaccagctg gccaacatct cctccccag    4440
cctcgtggta gagtgtgggg ccagacggt gcagtcctgt gtcatcagga acctccggaa     4500
gaaccccaac tttgacatct gcaccctctt catggaagtg atgctgccca gggaggagct    4560
ctactgcccc cccatcaccg tcaaggtcat cgataaccgc cagtttggcc gccggcctgt    4620
ggtgggccag tgtaccatcc gctccctgga gagcttcctg tgtgacccct actcggcgga    4680
gagtccatcc ccacagggtg gcccagacga tgtgagccta ctcagtcctg ggaagacgt    4740
gctcatcgac attgatgaca aggagcccct catccccatc caggaggaag agttcatcga    4800
ttggtggagc aaattctttg cctccatagg ggagagggaa aagtgcggct cctacctgga    4860
gaaggatttt gacaccctga aggtctatga cacacagctg gagaatgtgg aggcctttga    4920
gggcctgtct gacttttgta acaccttcaa gctgtaccgg ggcaagacgc aggaggagac    4980
agaagatcca tctgtgattg gtgaatttaa gggcctcttc aaaatttatc ccctcccaga    5040
agacccagcc atccccatgc ccccaagaca gttccaccag ctggccgccc agggacccca    5100
ggagtgcttg gtccgtatct acattgtccg agcatttggc ctgcagccca aggacccaa    5160
tggaaagtgt gatccttaca tcaagatctc cataggggaag aaatcagtga gtgaccagga    5220
taactacatc ccctgcacgc tggagcccgt atttggaaag atgttcgagc tgacctgcac    5280
tctgcctctg gagaaggacc taaagatcac tctctatgac tatgacctcc tctccaagga    5340
cgaaaagatc ggtgagacgg tcgtcgacct ggagaacagg ctgctgtcca gtttggggc    5400
tcgctgtgga ctcccacaga cctactgtgt ctctggaccg aaccagtggc gggaccagct    5460
ccgcccctcc cagctcctcc acctcttctg ccagcagcat agagtcaagg cacctgtgta    5520
ccggacagac cgtgtaatgt tcaggataa agaatattcc attgaagaga tagaggctgg    5580
caggatccca aacccacacc tgggcccagt ggaggagcgt ctggctctgc atgtgcttca    5640
gcagcagggc ctggtcccgg agcacgtgga gtcacggccc ctctacagcc cctgcagcc    5700
agacatcgag caggggaagc tgcagatgtg ggtcgaccta tttccgaagg ccctgggcg    5760
gcctggacct cccttcaaca tcaccccacg gagagccaga aggttttttcc tgcgttgtat    5820
tatctggaat accagagatg tgatcctgga tgacctgagc ctcacggggg agaagatgag    5880
cgacatttat gtgaaaggtt ggatgattgg cttttgaagaa cacaagcaaa agacagacgt    5940
gcattatcgt tccctgggag gtgaagcaac ttcaactgga ggttcatttt ccccttcgac    6000
tacctgccag ctgagcaagt ctgtaccatt gccaagaagg atgccttctg gaggctggac    6060
aagactgaga gcaaaatccc agcacgagtg gtgttccaga tctgggacaa tgacaagttc    6120
tcctttgatg attttctggg ctccctgcag ctcgatctca accgcatgcc caagccagcc    6180
aagacagcca agaagtgctc cttggaccag ctggatgatg cttccacccc agaatggttt    6240
```

| | |
|---|---:|
| gtgtccctttt ttgagcagaa aacagtgaag ggctggtggc cctgtgtagc agaagagggt | 6300 |
| gagaagaaaa tactggcggg caagctggaa atgaccttgg agattgtagc agagagtgag | 6360 |
| catgaggagc ggcctgctgg ccagggccgg gatgagccca acatgaaccc taagcttgag | 6420 |
| gacccaaggc gccccgacac ctccttcctg tggtttacct ccccatacaa gaccatgaag | 6480 |
| ttcatcctgt ggcggcgttt ccgtgggcc atcatcctct tcatcatcct cttcatcctg | 6540 |
| ctgctgttcc tggccatctt catctacgcc ttcccgaact atgctgccat gaagctggtg | 6600 |
| aagcccttca gctgaggact ctcctgccct gtagaagggg ccgtgggtc ccctccagca | 6660 |
| tgggactggc ctgcctcctc cgcccagctc ggcgagctcc tccagacctc ctaggcctga | 6720 |
| ttgtcctgcc agggtgggca gacagacaga tggaccggcc cacactccca gagttgctaa | 6780 |
| catggagctc tgagatcacc ccacttccat catttccttc tcccccaacc caacgctttt | 6840 |
| ttggatcagc tcagacatat ttcagtataa aacagttgga accacaaaaa aaaaaaaaaa | 6900 |
| aaaaaaaaaa | 6910 |

<210> SEQ ID NO 16
<211> LENGTH: 6911
<212> TYPE: DNA
<213> ORGANISM: Homo sapiens

<400> SEQUENCE: 16

| | |
|---|---:|
| tcgaccgccc agccaggtgc aaaatgccgt gtcattggga gactccgcag ccggagcatt | 60 |
| agattacagc tcgacggagc tcgggaaggg cggcgggggt ggaagatgag cagaagcccc | 120 |
| tgttctcgga acgccggctg acaagcgggg tgagcgcagg cggggcgggg acccagccta | 180 |
| gcccactgga gcagccgggg gtggcccgtt cccctttaag agcaactgct ctaagccagg | 240 |
| agccagagat tcgagccggc ctcgcccagc cagccctctc cagcgagggg acccacaagc | 300 |
| ggcgcctcgg ccctcccgac cttttccgagc cctctttgcg ccctgggcgc acggggccct | 360 |
| acacgcgcca agcatgctga gggtcttcat cctctatgcc gagaacgtcc acacacccga | 420 |
| caccgacatc agcgatgcct actgctccgc ggtgtttgca ggggtgaaga agagaaccaa | 480 |
| agtcatcaag aacagcgtga accctgtatg gaatgaggga tttgaatggg acctcaaggg | 540 |
| catccccctg gaccagggct ctgagcttca tgtggtggtc aaagaccatg agacgatggg | 600 |
| gaggaacagg ttcctggggg aagccaaggt cccactccga gaggtcctcg ccacccctag | 660 |
| tctgtccgcc agcttcaatg ccccccctgct ggacaccaag aagcagccca ggggcctc | 720 |
| gctggtcctg caggtgtcct acacaccgct gcctggagct gtgcccctgt tcccgcccccc | 780 |
| tactcctctg gagccctccc cgactctgcc tgacctggat gtagtggcag acacaggagg | 840 |
| agaggaagac acagaggacc agggactcac tggagatgag gcggagccat tcctggatca | 900 |
| aagcggaggc ccggggctc ccaccacccc aaggaaacta ccttcacgtc ctccgcccca | 960 |
| ctaccccggg atcaaaagaa agcgaagtgc gcctacatct agaaagctgc tgtcagacaa | 1020 |
| accgcaggat ttccagatca gggtccaggt gatcgagggg cgccagctgc cggggtgaa | 1080 |
| catcaagcct gtggtcaagg ttaccgctgc agggcagacc aagcggacgc ggatccacaa | 1140 |
| gggaaacagc ccactcttca atgagactct tttcttcaac ttgtttgact ctcctgggga | 1200 |
| gctgtttgat gagcccatct ttatcacggt ggtagactct cgttctctca ggacagatgc | 1260 |
| tctcctcggg gagttccgga tggacgtgg caccatttac agagagcccc ggcacgccta | 1320 |
| tctcaggaag tggctgctgc tctcagaccc tgatgacttc tctgctgggg ccagaggcta | 1380 |
| cctgaaaaca agccctttgtg tgctggggcc tggggacgaa gcgcctctgg agagaaaga | 1440 |

-continued

```
cccctctgaa gacaaggagg acattgaaag caacctgctc cggcccacag gcgtagccct      1500
gcgaggagcc cacttctgcc tgaaggtctt ccgggccgag gacttgccgc agatggacga      1560
tgccgtgatg gacaacgtga aacagatctt tggcttcgag agtaacaaga gaacttggt      1620 ggacccettt gtggaggtca gctttgcggg gaaaatgctg tgcagcaaga tcttggagaa      1680
gacggccaac cctcagtgga accagaacat cacactgcct gccatgtttc cctccatgtg      1740
cgaaaaaatg aggattcgta tcatagactg ggaccgcctg actcacaatg acatcgtggc      1800
taccacctac ctgagtatgt cgaaaatctc tgccctgga ggagaaatag aagaggagcc       1860
tgcaggtgct gtcaagcctt cgaaagcctc agacttggat gactacctgg gcttcctccc      1920
cacttttggg ccctgctaca tcaacctcta tggcagtccc agagagttca caggcttccc      1980 agaccectac acagagctca acacaggcaa gggggaaggt gtggcttatc gtggccggct      2040
tctgctctcc ctggagacca agctggtgga gcacagtgaa cagaaggtgg aggaccttcc      2100 tgccggatgac atcctccggg tggagaagta ccttaggagg cgcaagtact ccctgtttgc      2160
ggccttctac tcagccacca tgctgcagga tgtggatgat gccatccagt ttgaggtcag      2220
catcgggaac tacgggaaca agttcgacat gacctgcctg ccgctggcct ccaccactca      2280
gtacagccgt gcagtctttg acgggtgcca ctactactac ctaccctggg gtaacgtgaa      2340
acctgtggtg gtgctgtcat cctactggga ggacatcagc catagaatcg agactcagaa      2400
ccagctgctt gggattgctg accggctgga agctggcctg gagcaggtcc acctggccct      2460
gaaggcgcag tgctccacgg aggacgtgga ctcgctggtg gctcagctga cggatgagct      2520
catcgcaggc tgcagccagc ctctgggtga catccatgag acaccctctg ccacccacct      2580
ggaccagtac ctgtaccagc tgcgcaccca tcacctgagc caaatcactg aggctgccct      2640
ggccctgaag ctcggccaca gtgagctccc tgcagctctg gagcaggcgg aggactggct      2700
cctgcgtctg cgtgccctgg cagaggagcc ccagaacagc ctgccggaca tcgtcatctg      2760
gatgctgcag ggagacaagc gtgtggcata ccagcgggtg cccgcccacc aagtcctctt      2820
ctcccggcgg ggtgccaact actgtggcaa gaattgtggg aagctacaga caatctttct      2880
gaaatatccg atggagaagg tgcctggcgc ccggatgcca gtgcagatac gggtcaagct      2940
gtggtttggg ctctctgtgg atgagaagga gttcaaccag tttgctgagg ggaagctgtc      3000
tgtctttgct gaaacctatg agaacgagac taagttggcc cttgttggga actggggcac      3060
aacgggcctc acctacccca gttttctga cgtcacgggc aagatcaagc tacccaagga      3120
cagcttccgc ccctcggccg gctggacctg gctggagat tggttcgtgt gtccggagaa      3180
gactctgctc catgacatgg acgccggtca cctgagcttc gtggaagagg tgtttgagaa      3240
ccagacccgg cttccggag gccagtggat ctacatgagt gacaactaca ccgatgtgaa      3300
cggggagaag gtgcttccca aggatgacat tgagtgccca ctgggctgga gtgggaaga      3360 tgaggaatgg tccacagacc tcaaccgggc tgtcgatgag caaggctggg agtatagcat      3420
caccatcccc ccggagcgga agccgaagca ctgggtccct gctgagaaga tgtactacac      3480
acaccgacgg cggcgctggg tgcgcctgcg caggagggat ctcagccaaa tggaagcact      3540
gaaaaggcac aggcaggcgg aggcggaggg cgagggctgg gagtacgcct ctctttttgg      3600
ctggaagttc cacctcgagt accgcaagac agatgccttc cgccgccgcc gctggcgccg      3660
tcgcatggag ccactggaga agacggggcc tgcagctgtg tttgcccttg agggggccct      3720
gggcggcgtg atggatgaca agagtgaaga ttccatgtcc gtctccacct tgagcttcgg      3780
tgtgaacaga cccacgattt cctgcatatt cgactatggg aaccgctacc atctacgctg      3840
```

```
ctacatgtac caggcccggg acctggctgc gatggacaag gactcttttt ctgatcccta    3900
tgccatcgtc tccttcctgc accagagcca gaagacggtg gtggtgaaga caccccttaa    3960
ccccacctgg gaccagacgc tcatcttcta cgagatcgag atctttggcg agccggccac    4020
agttgctgag caaccgccca gcattgtggt ggagctgtac gaccatgaca cttatggtgc    4080
agacgagttt atgggtcgct gcatctgtca accgagtctg gaacggatgc cacggctggc    4140
ctggttccca ctgacgaggg gcagccagcc gtcggggag ctgctggcct cttttgagct    4200
catccagaga gagaagccgg ccatccacca tattcctggt tttgaggtgc aggagacatc    4260
aaggatcctg gatgagtctg aggacacaga cctgccctac ccaccacccc agagggaggc    4320
caacatctac atggttcctc agaacatcaa gccagcgctc cagcgtaccg ccatcgagat    4380
cctggcatgg ggcctgcgga acatgaagag ttaccagctg gccaacatct cctccccag    4440
cctcgtggta gagtgtgggg gccagacggt gcagtcctgt gtcatcagga acctccggaa    4500
gaaccccaac tttgacatct gcaccctctt catggaagtg atgctgccca gggaggagct    4560
ctactgcccc cccatcaccg tcaaggtcat cgataaccgc cagtttggcc gccggcctgt    4620
ggtgggccag tgtaccatcc gctccctgga gagcttcctg tgtgaccct actcggcgga    4680
gagtccatcc ccacagggtg gcccagacga tgtgagccta ctcagtcctg ggaagacgt    4740
gctcatcgac attgatgaca aggagcccct catccccatc caggaggaag agttcatcga    4800
ttggtggagc aaattctttg cctccatagg ggagagggaa aagtgcggct cctacctgga    4860
gaaggatttt gacacccctga aggtctatga cacacagctg gagaatgtgg aggcctttga    4920
gggcctgtct gacttttgta acaccttcaa gctgtaccgg gcaagacgc aggaggagac    4980
agaagatcca tctgtgattg gtgaatttaa gggcctcttc aaaatttatc ccctcccaga    5040
agacccagcc atccccatgc ccccaagaca gttccaccag ctggccgccc agggacccca    5100
ggagtgcttg gtccgtatct acattgtccg agcatttggc ctgcagccca aggaccccaa    5160
tggaaagtgt gatccttaca tcaagatctc catagggaag aaatcagtga gtgaccagga    5220
taactacatc ccctgcacgc tggagcccgt atttggaaag atgttcgagc tgacctgcac    5280
tctgcctctg gagaaggacc taaagatcac tctctatgac tatgacctcc tctccaagga    5340
cgaaaagatc ggtgagacgg tcgtcgacct ggagaacagg ctgctgtcca gtttggggc    5400
tcgctgtgga ctcccacaga cctactgtgt ctctggaccg aaccagtggc gggaccagct    5460
ccgcccctcc cagctcctcc acctcttctg ccagcagcat agagtcaagg cacctgtgta    5520
ccggacagac cgtgtaatgt tcaggataa agaatattcc attgaagaga tagaggctgg    5580
caggatccca aacccacacc tgggcccagt ggaggagcgt ctggctctgc atgtgcttca    5640
gcagcagggc ctggtcccgg agcacgtgga gtcacggccc ctctacagcc cctgcagcc    5700
agacatcgag caggggaagc tgcagatgtg ggtcgaccta tttccgaagg ccctgggcg    5760
gcctggacct cccttcaaca tcaccccacg gagagccaga aggttttttcc tgcgttgtat    5820
tatctggaat accagagatg tgatcctgga tgacctgagc ctcacggggt agaagatgag    5880
cgacatttat gtgaaaggtt ggatgattgg cttttgaagaa cacaagcaaa agacagacgt    5940
gcattatcgt tccctgggag gtgaaggcaa cttcaactgg aggttcattt tcccccttcga    6000
ctacctgcca gctgagcaag tctgtaccat tgccaagaag gatgccttct ggaggctgga    6060
caagactgag agcaaaatcc cagcacgagt ggtgttccag atctgggaca atgacaagtt    6120
ctccttttgat gattttctgg gctccctgca gctcgatctc aaccgcatgc ccaagccagc    6180
caagacagcc aagaagtgct ccttggacca gctggatgat gctttccacc agaatggtt    6240
```

-continued

```
tgtgtccctt tttgagcaga aaacagtgaa gggctggtgg ccctgtgtag cagaagaggg      6300
tgagaagaaa atactggcgg gcaagctgga aatgaccttg gagattgtag cagagagtga      6360
gcatgaggag cggcctgctg gccagggccg ggatgagccc aacatgaacc ctaagcttga      6420
ggacccaagg cgccccgaca cctccttcct gtggtttacc tccccataca agaccatgaa      6480
gttcatcctg tggcggcgtt ccggtgggc catcatcctc ttcatcatcc tcttcatcct       6540
gctgctgttc ctggccatct tcatctacgc cttcccgaac tatgctgcca tgaagctggt      6600
gaagcccttc agctgaggac tctcctgccc tgtagaaggg gccgtggggt ccctccagc       6660 atgggactgg cctgcctcct ccgcccagct cggcgagctc ctccagacct cctaggcctg      6720
attgtcctgc cagggtgggc agacagacag atggaccggc ccacactccc agagttgcta      6780
acatggagct ctgagatcac cccacttcca tcatttcctt ctcccccaac ccaacgcttt      6840
tttggatcag ctcagacata tttcagtata aacagttgg aaccacaaaa aaaaaaaaa       6900 aaaaaaaaaa a                                                          6911
```

<210> SEQ ID NO 17
<211> LENGTH: 6911
<212> TYPE: DNA
<213> ORGANISM: Homo sapiens

<400> SEQUENCE: 17

```
tcgaccgccc agccaggtgc aaaatgccgt gtcattggga gactccgcag ccggagcatt       60
agattacagc tcgacggagc tcgggaaggg cggcggggt ggaagatgag cagaagcccc       120
tgttctcgga acgccggctg acaagcgggg tgagcgcagg cggggcgggg acccagccta      180
gcccactgga gcagccgggg gtggcccgtt cccctttaag agcaactgct ctaagccagg      240
agccagagat tcgagccggc ctcgcccagc cagccctctc cagcgagggg acccacaagc      300
ggcgcctcgg ccctcccgac cttccgagc cctctttgcg ccctgggcgc acggggccct      360
acacgcgcca agcatgctga gggtcttcat cctctatgcc gagaacgtcc acacacccga      420
caccgacatc agcgatgcct actgctccgc ggtgtttgca ggggtgaaga agagaaccaa      480
agtcatcaag aacagcgtga accctgtatg gaatgaggga tttgaatggg accttcaaggg      540 catccccctg gaccagggct ctgagcttca tgtggtggtc aaagaccatg agacgatggg      600
gaggaacagg ttcctgggggg aagccaaggt cccactccga gaggtcctcg ccacccctag      660
tctgtccgcc agcttcaatg ccccctgct ggacaccaag aagcagccca caggggcctc       720
gctggtcctg caggtgtcct acacaccgct gcctggagct gtgcccctgt cccgcccccc      780
tactcctctg gagccctccc cgactctgcc tgacctggat gtagtggcag acacaggagg      840
agaggaagac acagaggacc agggactcac tggagatgag gcggagccat tcctggatca      900
aagcggaggc ccgggggctc ccaccacccc aaggaaacta ccttcacgtc ctccgcccca      960
ctaccccggg atcaaaagaa agcgaagtgc gcctacatct agaaagctgc tgtcagacaa      1020
accgcaggat ttccagatca gggtccaggt gatcgagggg cgccagctgc cggggtgaa       1080 catcaagcct gtggtcaagg ttaccgctgc agggcagacc aagcggacgc ggatccacaa      1140
gggaaacagc ccactcttca atgagactct tttcttcaac ttgtttgact ctcctgggga      1200
gctgtttgat gagcccatct ttatcacggt ggtagactct cgttctctca ggacagatgc      1260
tctcctcggg gagttccga tggacgtggg caccatttac agagagcccc ggcacgccta      1320
tctcaggaag tggctgctgc tctcagaccc tgatgacttc tctgctgggg ccagaggcta      1380
cctgaaaaca agccttttgtg tgctggggcc tggggacgaa gcgcctctgg agagaaaaga      1440
```

-continued

| | | | | |
|---|---|---|---|---|
| cccctctgaa | gacaaggagg | acattgaaag | caacctgctc | cggcccacag gcgtagccct | 1500 |
| gcgaggagcc | cacttctgcc | tgaaggtctt | ccgggccgag | gacttgccgc agatggacga | 1560 |
| tgccgtgatg | gacaacgtga | aacagatctt | tggcttcgag | agtaacaaga gaacttggt | 1620 |
| ggacccettt | gtggaggtca | gctttgcggg | gaaaatgctg | tgcagcaaga tcttggagaa | 1680 |
| gacggccaac | cctcagtgga | accagaacat | cacactgcct | gccatgtttc cctccatgtg | 1740 |
| cgaaaaaatg | aggattcgta | tcatagactg | ggaccgcctg | actcacaatg acatcgtggc | 1800 |
| taccacctac | ctgagtatgt | cgaaaatctc | tgccectgga | ggagaaatag aagaggagcc | 1860 |
| tgcaggtgct | gtcaagcctt | cgaaagcctc | agacttggat | gactacctgg gcttcctccc | 1920 |
| cacttttggg | ccctgctaca | tcaacctcta | tggcagtccc | agagagttca caggcttccc | 1980 |
| agacccctac | acagagctca | acacaggcaa | gggggaaggt | gtggcttatc gtggccggct | 2040 |
| tctgctctcc | ctggagacca | gctggtggga | gcacagtgaa | cagaaggtgg aggacctccc | 2100 |
| tgccggatgac | atcctccggg | tggagaagta | ccttaggagg | cgcaagtact ccctgtttgc | 2160 |
| ggccttctac | tcagccacca | tgctgcagga | tgtggatgat | gccatccagt ttgaggtcag | 2220 |
| catcgggaac | tacgggaaca | agttcgacat | gacctgcctg | ccgctggcct ccaccactca | 2280 |
| gtacagccgt | gcagtctttg | acgggtgcca | ctactactac | ctaccctggg gtaacgtgaa | 2340 |
| acctgtggtg | gtgctgtcat | cctactggga | ggacatcagc | catagaatcg agactcagaa | 2400 |
| ccagctgctt | gggattgctg | accggctgga | agctggcctg | gagcaggtcc acctggccct | 2460 |
| gaaggcgcag | tgctccacgg | aggacgtgga | ctcgctggtg | gctcagctga cggatgagct | 2520 |
| catcgcaggc | tgcagccagc | ctctgggtga | catccatgag | acaccctctg ccacccacct | 2580 |
| ggaccagtac | ctgtaccagc | tgcgcaccca | tcacctgagc | caaatcactg aggctgccc | 2640 |
| ggccctgaag | ctcggccaca | gtgagctccc | tgcagctctg | gagcaggcgg aggactggct | 2700 |
| cctgcgtctg | cgtgccctgg | cagaggagcc | ccagaacagc | ctgccggaca tcgtcatctg | 2760 |
| gatgctgcag | ggagacaagc | gtgtggcata | ccagcgggtg | cccgcccacc aagtcctctt | 2820 |
| ctcccggcgg | ggtgccaact | actgtggcaa | gaattgtggg | aagctacaga caatcttttct | 2880 |
| gaaatatccg | atggagaagg | tgcctggcgc | ccggatgcca | gtgcagatac gggtcaagct | 2940 |
| gtggtttggg | ctctctgtgg | atgagaagga | gttcaaccag | tttgctgagg ggaagctgtc | 3000 |
| tgtctttgct | gaaacctatg | agaacgagac | taagttggcc | cttgttggga actggggcac | 3060 |
| aacgggcctc | acctaccccca | agtttctga | cgtcacgggc | aagatcaagc tacccaagga | 3120 |
| cagcttccgc | ccctcggccg | gctggacctg | ggctggagat | tggttcgtgt gtccggagaa | 3180 |
| gactctgctc | catgacatgg | acgccggtca | cctgagcttc | gtggaagagg tgtttgagaa | 3240 |
| ccagacccgg | cttcccggag | gccagtggat | ctacatgagt | gacaactaca ccgatgtgaa | 3300 |
| cggggagaag | gtgcttccca | aggatgacat | tgagtgccca | ctgggctgga gtgggaaga | 3360 |
| tgaggaatgg | tccacagacc | tcaaccgggc | tgtcgatgag | caaggctggg agtatagcat | 3420 |
| caccatcccc | ccgagcgga | agccgaagca | ctgggtccct | gctgagaaga tgtactacac | 3480 |
| acaccgacgg | cggcgctggg | tgcgcctgcg | caggaggat | ctcagccaaa tggaagcact | 3540 |
| gaaaaggcac | aggcaggcgg | aggcggaggg | cgagggctgg | gagtacgcct ctcttttggg | 3600 |
| ctggaagttc | cacctcgagt | accgcaagac | agatgccttc | cgccgccgcc gctggcgccg | 3660 |
| tcgcatggag | ccactggaga | agacggggcc | tgcagctgtg | tttgcccttg agggggccct | 3720 |
| gggcggcgtg | atggatgaca | agagtgaaga | ttccatgtcc | gtctccacct tgagcttcgg | 3780 |
| tgtgaacaga | cccacgattt | cctgcatatt | cgactatggg | aaccgctacc atctacgctg | 3840 |

```
ctacatgtac caggcccggg acctggctgc gatggacaag gactcttttt ctgatccctc    3900
tgccatcgtc tccttcctgc accagagcca gaagacggtg gtggtgaaga acacccttaa    3960
ccccacctgg gaccagacgc tcatcttcta cgagatcgag atctttggcg agccggccac    4020
agttgctgag caaccgccca gcattgtggt ggagctgtac gaccatgaca cttatggtgc    4080
agacgagttt atgggtcgct gcatctgtca accgagtctg gaacgatgc cacggctggc     4140
ctggttccca ctgacgaggg gcagccagcc gtcggggag ctgctggcct cttttgagct     4200
catccagaga gagaagccgg ccatccacca tattcctggt tttgaggtgc aggagacatc    4260
aaggatcctg gatgagtctg aggacacaga cctgccctac ccaccacccc agagggaggc    4320
caacatctac atggttcctc agaacatcaa gccagcgctc cagcgtaccg ccatcgagat    4380
cctggcatgg ggcctgcgga acatgaagag ttaccagctg gccaacatct cctccccag     4440
cctcgtggta gagtgtgggg gccagacggt gcagtcctgt gtcatcagga acctccggaa    4500
gaaccccaac tttgacatct gcaccctctt catggaagtg atgctgccca gggaggagct    4560
ctactgcccc cccatcaccg tcaaggtcat cgataaccgc cagtttggcc gccggcctgt    4620
ggtgggccag tgtaccatcc gctccctgga gagcttcctg tgtgaccct actcggcgga     4680
gagtccatcc ccacagggtg gcccagacga tgtgagccta ctcagtcctg ggaagacgt     4740
gctcatcgac attgatgaca ggagcccct catccccatc caggaggaag agttcatcga     4800
ttggtggagc aaattctttg cctccatagg ggagagggaa aagtgcggct cctacctgga    4860
gaaggatttt gacaccctga aggtctatga cacacagctg gagaatgtgg aggcctttga    4920
gggcctgtct gacttttgta acaccttcaa gctgtaccgg gcaagacgc aggaggagac     4980
agaagatcca tctgtgattg gtgaatttaa gggcctcttc aaaatttatc ccctcccaga    5040
agacccagcc atccccatgc ccccaagaca gttccaccag ctggccgccc agggaccccc    5100
ggagtgcttg gtccgtatct acattgtccg agcatttggc ctgcagccca aggacccca     5160
tggaaagtgt gatccttaca tcaagatctc catagggaag aaatcagtga gtgaccagga    5220
taactacatc ccctgcacgc tggagcccgt atttggaaag atgttcgagc tgacctgcac    5280
tctgcctctg gagaaggacc taaagatcac tctctatgac tatgacctcc tctccaagga    5340
cgaaaagatc ggtgagacgg tcgtcgacct ggagaacagg ctgctgtcca gtttggggc     5400
tcgctgtgga ctcccacaga cctactgtgt ctctggaccg aaccagtggc gggaccagct    5460
ccgcccctcc cagctcctcc acctcttctg ccagcagcat agagtcaagg cacctgtgta    5520
ccggacagac cgtgtaatgt tcaggataa agaatattcc attgaagaga tagaggctgg     5580
caggatccca aacccacacc tgggcccagt ggaggagcgt ctggctctgc atgtgcttca    5640
gcagcagggc ctggtcccgg agcacgtgga gtcacggccc ctctacagcc cctgcagcc     5700
agacatcgag caggggaagc tgcagatgtg ggtcgaccta tttccgaagg ccctggggcg    5760
gcctggacct cccttcaaca tcaccccacg gagagccaga aggttttcc tgcgttgtat     5820
tatctggaat accagagatg tgatcctgga tgacctgagc ctcacggggg agaagatgag    5880
cgacatttat gtgaaaggtt ggatgattgg ctttgaagaa cacaagcaaa agacagacgt    5940
gcattatcgt tccctgggag gtgaaggcaa cttcaactgg aggttcattt tcccctcga     6000
ctacctgcca gctgagcaag tctgtaccat tgccaagaag gatgccttct ggaggctgga    6060
caagactgag agcaaaatcc cagcacgagt ggtgttccag atctgggaca atgacaagtt    6120
ctccttgat gattttctgg ctccctgca gctcgatctc aaccgcatgc ccaagccagc      6180
caagacagcc aagaagtgct ccttggacca gctggatgat gctttccacc agaatggtt     6240
```

```
tgtgtcccett tttgagcaga aaacagtgaa gggctggtgg ccctgtgtag cagaagaggg      6300
tgagaagaaa atactggcgg gcaagctgga aatgaccttg gagattgtag cagagagtga      6360
gcatgaggag cggcctgctg gccagggccg agatgagccc aacatgaacc ctaagcttga      6420
ggacccaagg cgccccgaca cctccttcct gtggtttacc tccccataca agaccatgaa      6480
gttcatcctg tggcggcgtt ccggtgggc catcatcctc ttcatcatcc tcttcatcct      6540
gctgctgttc ctggccatct tcatctacgc cttcccgaac tatgctgcca tgaagctggt      6600
gaagcccttc agctgaggac tctcctgccc tgtagaaggg gccgtggggt ccctccagc      6660
atgggactgg cctgcctcct ccgcccagct cggcgagctc ctccagacct cctaggcctg      6720
attgtcctgc cagggtgggc agacagacag atggaccggc ccacactccc agagttgcta      6780
acatggagct ctgagatcac cccacttcca tcatttcctt ctcccccaac ccaacgcttt      6840
tttggatcag ctcagacata tttcagtata aacagttgg aaccacaaaa aaaaaaaaaa      6900
aaaaaaaaa a                                                             6911

<210> SEQ ID NO 18
<211> LENGTH: 6911
<212> TYPE: DNA
<213> ORGANISM: Homo sapiens

<400> SEQUENCE: 18
tcgaccgccc agccaggtgc aaaatgccgt gtcattggga gactccgcag ccggagcatt       60
agattacagc tcgacggagc tcgggaaggg cggcgggggt ggaagatgag cagaagcccc      120
tgttctcgga acgccggctg acaagcgggg tgagcgcagg cggggcgggg acccagccta      180
gcccactgga gcagccgggg gtggcccgtt cccctttaag agcaactgct ctaagccagg      240
agccagagat tcgagccggc ctcgcccagc cagccctctc cagcgagggg acccacaagc      300
ggcgcctcgg ccctcccgac cttccgagc cctctttgcg ccctgggcgc acggggccct      360
acacgcgcca gcatgctga gggtcttcat cctctatgcc gagaacgtcc acacacccga      420
caccgacatc agcgatgcct actgctccgc ggtgtttgca ggggtgaaga agagaaccaa      480
agtcatcaag aacagcgtga accctgtatg gaatgaggga tttgaatggg acctcaaggg      540
catcccctg gaccagggct ctgagcttca tgtggtggtc aaagaccatg agacgatggg      600
gaggaacagg ttcctggggg aagccaaggt cccactccga gaggtcctcg ccacccctag      660
tctgtccgcc agcttcaatg ccccctgct ggacaccaag aagcagccca gggggcctc      720
gctggtcctg caggtgtcct acacaccgct gcctggagct gtgcccctgt cccgccccc      780
tactcctctg gagccctccc cgactctgcc tgacctggat gtagtggcag acacaggagg      840
agaggaagac acagaggacc agggactcac tggagatgag gcggagccat tcctggatca      900
aagcggaggc ccggggggctc ccaccacccc aaggaaacta ccttcacgtc ctccgcccca      960
ctaccccggg atcaaaagaa agcgaagtgc gcctacatct agaaagctgc tgtcagacaa     1020
accgcaggat ttccagatca gggtccaggt gatcgagggg cgccagctgc gggggtgaa     1080
catcaagcct gtggtcaagg ttaccgctgc agggcagacc aagcggacgc ggatccacaa     1140
gggaaacagc ccactcttca atgagactct tttcttcaac ttgtttgact ctcctgggga     1200
gctgtttgat gagcccatct ttatcacggt ggtagactct cgttctctca ggacagatgc     1260
tctcctcggg gagttccgga tggacgtggg caccatttac agagagcccc ggcacgccta     1320
tctcaggaag tggctgctgc tctcagaccc tgatgacttc tctgctgggg ccagaggcta     1380
cctgaaaaca agccttttgtg tgctggggcc tggggacgaa gcgcctctgg agagaaaaga     1440
```

-continued

| | | | | |
|---|---|---|---|---|
| cccctctgaa | gacaaggagg | acattgaaag | caacctgctc | cggcccacag gcgtagccct | 1500 |
| gcgaggagcc | cacttctgcc | tgaaggtctt | ccgggccgag | gacttgccgc agatggacga | 1560 |
| tgccgtgatg | gacaacgtga | aacagatctt | tggcttcgag | agtaacaaga gaacttggt | 1620 |
| ggaccccttt | gtggaggtca | gctttgcggg | gaaaatgctg | tgcagcaaga tcttggagaa | 1680 |
| gacggccaac | cctcagtgga | accagaacat | cacactgcct | gccatgtttc cctccatgtg | 1740 |
| cgaaaaaatg | aggattcgta | tcatagactg | ggaccgcctg | actcacaatg acatcgtggc | 1800 |
| taccacctac | ctgagtatgt | cgaaaatctc | tgcccctgga | ggagaaatag aagaggagcc | 1860 |
| tgcaggtgct | gtcaagcctt | cgaaagcctc | agacttggat | gactacctgg gcttcctccc | 1920 |
| cactttggg | ccctgctaca | tcaacctcta | tggcagtccc | agagagttca caggcttccc | 1980 |
| agacccctac | acagagctca | acacaggcaa | gggggaaggt | gtggcttatc gtggccggct | 2040 |
| tctgctctcc | ctggagacca | agctggtgga | gcacagtgaa | cagaaggtgg aggaccttcc | 2100 |
| tgccggatgac | atcctccggg | tggagaagta | ccttaggagg | cgcaagtact ccctgtttgc | 2160 |
| ggccttctac | tcagccacca | tgctgcagga | tgtggatgat | gccatccagt ttgaggtcag | 2220 |
| catcgggaac | tacgggaaca | agttcgacat | gacctgcctg | ccgctggcct ccaccactca | 2280 |
| gtacagccgt | gcagtctttg | acgggtgcca | ctactactac | ctaccctggg gtaacgtgaa | 2340 |
| acctgtggtg | gtgctgtcat | cctactggga | ggacatcagc | catagaatcg agactcagaa | 2400 |
| ccagctgctt | gggattgctg | accggctgga | agctggcctg | gagcaggtcc acctggccct | 2460 |
| gaaggcgcag | tgctccacgg | aggacgtgga | ctcgctggtg | gctcagctga cggatgagct | 2520 |
| catcgcaggc | tgcagccagc | ctctgggtga | catccatgag | acaccctctg ccacccacct | 2580 |
| ggaccagtac | ctgtaccagc | tgcgcaccca | tcacctgagc | caaatcactg aggctgccct | 2640 |
| ggccctgaag | ctcggccaca | gtgagctccc | tgcagctctg | gagcaggcgg aggactggct | 2700 |
| cctgcgtctg | cgtgccctgg | cagaggagcc | ccagaacagc | ctgccggaca tcgtcatctg | 2760 |
| gatgctgcag | ggagacaagc | gtgtggcata | ccagcgggtg | cccgcccacc aagtcctctt | 2820 |
| ctcccggcgg | ggtgccaact | actgtggcaa | gaattgtggg | aagctacaga caatcttttct | 2880 |
| gaaatatccg | atggagaagg | tgcctggcgc | ccggatgcca | gtgcagatac gggtcaagct | 2940 |
| gtggtttggg | ctctctgtgg | atgagaagga | gttcaaccag | tttgctgagg ggaagctgtc | 3000 |
| tgtctttgct | gaaacctatg | agaacgagac | taagttggcc | cttgttggga actggggcac | 3060 |
| aacgggcctc | acctacccca | gttttctga | cgtcacgggc | aagatcaagc tacccaagga | 3120 |
| cagcttccgc | ccctcggccg | gctggacctg | ggctggagat | tggttcgtgt gtccggagaa | 3180 |
| gactctgctc | catgacatgg | acgccggtca | cctgagcttc | gtggaagagg tgtttgagaa | 3240 |
| ccagacccgg | cttcccggag | gccagtggat | ctacatgagt | gacaactaca ccgatgtgaa | 3300 |
| cggggagaag | gtgcttccca | aggatgacat | tgagtgccca | ctgggctgga gtgggaaga | 3360 |
| tgaggaatgg | tccacagacc | tcaaccgggc | tgtcgatgag | caaggctggg agtatagcat | 3420 |
| caccatcccc | ccggagcgga | agccgaagca | ctgggtccct | gctgagaaga tgtactacac | 3480 |
| acaccgacgg | cggcgctggg | tgcgcctgcg | caggagggat | ctcagccaaa tggaagcact | 3540 |
| gaaaggcac | aggcaggcgg | aggcggaggg | cgagggctgg | gagtacgcct ctcttttggg | 3600 |
| ctggaagttc | cacctcgagt | accgcaagac | agatgccttc | cgccgccgcc gctggcgccg | 3660 |
| tcgcatggag | ccactggaga | agacggggcc | tgcagctgtg | tttgcccttg aggggcccct | 3720 |
| gggcggcgtg | atggatgaca | agagtgaaga | ttccatgtcc | gtctccacct tgagcttcgg | 3780 |
| tgtgaacaga | cccacgattt | cctgcatatt | cgactatggg | aaccgctacc atctacgctg | 3840 |

```
ctacatgtac caggcccggg acctggctgc gatggacaag gactcttttt ctgatcccta    3900
tgccatcgtc tccttcctgc accagagcca gaagacggtg gtggtgaaga cacccttaa    3960
ccccacctgg gaccagacgc tcatcttcta cgagatcgag atctttggcg agccggccac    4020
agttgctgag caaccgccca gcattgtggt ggagctgtac gaccatgaca cttatggtgc    4080
agacgagttt atgggtcgct gcatctgtca accgagtctg gaacggatgc cacggctggc    4140
ctggttccca ctgacgaggg gcagccagcc gtcggggag ctgctggcct cttttgagct    4200
catccagaga gagaagccgg ccatccacca tattcctggt tttgaggtgc aggagacatc    4260
aagggtcctg gatgagtctg aggacacaga cctgccctac ccaccacccc agagggaggc    4320
caacatctac atggttcctc agaacatcaa gccagcgctc cagcgtaccg ccatcgagat    4380
cctggcatgg ggcctgcgga acatgaagag ttaccagctg gccaacatct cctccccag    4440
cctcgtggta gagtgtgggg gccagacggt gcagtcctgt gtcatcagga acctccggaa    4500
gaaccccaac tttgacatct gcaccctctt catggaagtg atgctgccca gggaggagct    4560
ctactgcccc cccatcaccg tcaaggtcat cgataaccgc cagtttggcc gccggcctgt    4620
ggtgggccag tgtaccatcc gctccctgga gagcttcctg tgtgacccct actcggcgga    4680
gagtccatcc ccacagggtg gcccagacga tgtgagccta ctcagtcctg ggaagacgt    4740
gctcatcgac attgatgaca aggagcccct catccccatc caggaggaag agttcatcga    4800
ttggtggagc aaattctttg cctccatagg ggagagggaa aagtgcggct cctacctgga    4860
gaaggatttt gacaccctga aggtctatga cacacagctg gagaatgtgg aggcctttga    4920
gggcctgtct gacttttgta acaccttcaa gctgtaccgg gcaagacgc aggaggagac    4980
agaagatcca tctgtgattg gtgaatttaa gggcctcttc aaaatttatc ccctcccaga    5040
agacccagcc atccccatgc ccccaagaca gttccaccag ctggccgccc agggaccca    5100
ggagtgcttg gtccgtatct acattgtccg agcatttggc ctgcagccca aggaccccaa    5160
tggaaagtgt gatccttaca tcaagatctc cataggggaag aaatcagtga gtgaccagga    5220
taactacatc ccctgcacgc tggagcccgt atttggaaag atgttcgagc tgacctgcac    5280
tctgcctctg gagaaggacc taaagatcac tctctatgac tatgacctcc tctccaagga    5340
cgaaaagatc ggtgagacgg tcgtcgacct ggagaacagg ctgctgtcca gtttggggc    5400
tcgctgtgga ctcccacaga cctactgtgt ctctggaccg aaccagtggc gggaccagct    5460
ccgcccctcc cagctcctcc acctcttctg ccagcagcat agagtcaagg cacctgtgta    5520
ccggacagac cgtgtaatgt ttcaggataa agaatattcc attgaagaga tagaggctgg    5580
caggatccca aacccacacc tgggcccagt ggaggagcgt ctggctctgc atgtgcttca    5640
gcagcagggc ctggtcccgg agcacgtgga gtcacggccc ctctacagcc ccctgcagcc    5700
agacatcgag caggggaagc tgcagatgtg ggtcgaccta tttccgaagg ccctgggcg    5760
gcctggacct cccttcaaca tcaccccacg gagagccaga aggttttcc tgcgttgtat    5820
tatctggaat accagagatg tgatcctgga tgacctgagc ctcacggggg agaagatgag    5880
cgacatttat gtgaaaggtt ggatgattgg cttttgaagaa cacaagcaaa agacagacgt    5940
gcattatcgt tccctgggag gtgaaggcaa cttcaactgg aggttcattt tcccttcga    6000
ctacctgcca gctgagcaag tctgtaccat tgccaagaag gatgccttct ggaggctgga    6060
caagactgag agcaaaatcc cagcacgagt ggtgttccag atctgggaca atgacaagtt    6120
ctccttttgat gattttctgg ctccctgca gctcgatctc aaccgcatgc ccaagccagc    6180
caagacagcc aagaagtgct ccttggacca gctggatgat gctttccacc agaatggtt    6240
```

-continued

| | |
|---|---|
| tgtgtccctt tttgagcaga aaacagtgaa gggctggtgg ccctgtgtag cagaagaggg | 6300 |
| tgagaagaaa atactggcgg gcaagctgga aatgaccttg gagattgtag cagagagtga | 6360 |
| gcatgaggag cggcctgctg gccagggccg ggatgagccc aacatgaacc ctaagcttga | 6420 |
| ggacccaagg cgcccccgaca cctccttcct gtggtttacc tccccataca agaccatgaa | 6480 |
| gttcatcctg tggcggcgtt tccggtgggc catcatcctc ttcatcatcc tcttcatcct | 6540 |
| gctgctgttc ctggccatct tcatctacgc cttcccgaac tatgctgcca tgaagctggt | 6600 |
| gaagcccttc agctgaggac tctcctgccc tgtagaaggg gccgtggggt ccctccagc | 6660 |
| atgggactgg cctgcctcct ccgcccagct cggcgagctc ctccagacct cctaggcctg | 6720 |
| attgtcctgc cagggtgggc agacagacag atggaccggc ccacactccc agagttgcta | 6780 |
| acatggagct ctgagatcac cccacttcca tcatttcctt ctcccccaac ccaacgcttt | 6840 |
| tttggatcag ctcagacata tttcagtata aacagttgg aaccacaaaa aaaaaaaaa | 6900 |
| aaaaaaaaaa a | 6911 |

<210> SEQ ID NO 19
<211> LENGTH: 6911
<212> TYPE: DNA
<213> ORGANISM: Homo sapiens

<400> SEQUENCE: 19

| | |
|---|---|
| tcgaccgccc agccaggtgc aaaatgccgt gtcattggga gactccgcag ccggagcatt | 60 |
| agattacagc tcgacggagc tcgggaaggg cggcgggggt ggaagatgag cagaagcccc | 120 |
| tgttctcgga acgccggctg acaagcgggg tgagcgcagg cggggcgggg acccagccta | 180 |
| gcccactgga gcagccgggg gtggcccgtt ccccttaag agcaactgct ctaagccagg | 240 |
| agccagagat tcgagccggc ctcgcccagc cagccctctc cagcgagggg acccacaagc | 300 |
| ggcgcctcgg ccctcccgac cttccgagc cctcttgcg ccctgggcgc acggggccct | 360 |
| acacgcgcca agcatgctga gggtcttcat cctctatgcc gagaacgtcc acacacccga | 420 |
| caccgacatc agcgatgcct actgctccgc ggtgtttgca ggggtgaaga agagaaccaa | 480 |
| agtcatcaag aacagcgtga accctgtatg gaatgaggga tttgaatggg acctcaaggg | 540 |
| catccccctg gaccagggct ctgagcttca tgtggtggtc aaagaccatg agacgatggg | 600 |
| gaggaacagg ttcctggggg aagccaaggt cccactccga gaggtcctcg ccaccccta g | 660 |
| tctgtccgcc agcttcaatg cccccctgct ggacaccaag aagcagccca caggggcctc | 720 |
| gctggtcctg caggtgtcct acacaccgct gcctggagct gtgcccctgt tcccgccccc | 780 |
| tactcctctg gagccctccc cgactctgcc tgacctggat gtagtggcag acacaggagg | 840 |
| agaggaagac acagaggacc agggactcac tggagatgag gcggagccat tcctggatca | 900 |
| aagcggaggc ccggggggctc ccaccacccc aaggaaacta ccttcacgtc ctccgcccca | 960 |
| ctaccccggg atcaaaagaa agcgaagtgc gcctacatct agaaagctgc tgtcagacaa | 1020 |
| accgcaggat ttccagatca gggtccaggt gatcgagggg cgccagctgc cggggtgaa | 1080 |
| catcaagcct gtggtcaagg ttaccgctgc agggcagacc aagcggacgc ggatccacaa | 1140 |
| gggaaacagc ccactcttca atgagactct tttcttcaac ttgtttgact ctcctgggga | 1200 |
| gctgtttgat gagcccatct ttatcacggt ggtagactct cgttctctca ggacagatgc | 1260 |
| tctcctcggg gagttccgga tggacgtggg caccatttac agagagcccc ggcacgccta | 1320 |
| tctcaggaag tggctgctgc tctcagaccc tgatgacttc tctgctgggg ccagaggcta | 1380 |
| cctgaaaaca agcctttgtg tgctggggcc tgggacgaa cgcctctgg agagaaaaga | 1440 |

```
cccctctgaa gacaaggagg acattgaaag caacctgctc cggcccacag gcgtagccct    1500
gcgaggagcc cacttctgcc tgaaggtctt ccgggccgag gacttgccgc agatggacga    1560
tgccgtgatg gacaacgtga aacagatctt tggcttcgag agtaacaaga gaacttggt     1620
ggacccettt gtggaggtca gctttgcggg gaaaatgctg tgcagcaaga tcttggagaa    1680
gacggccaac cctcagtgga accagaacat cacactgcct gccatgtttc cctccatgtg    1740
cgaaaaaatg aggattcgta tcatagactg ggaccgcctg actcacaatg acatcgtggc    1800
taccacctac ctgagtatgt cgaaaatctc tgccccctgga ggagaaatag aagaggagcc    1860
tgcaggtgct gtcaagcctt cgaaagcctc agacttggat gactacctgg gcttcctccc    1920
cactttggg ccctgctaca tcaacctcta tggcagtccc agagagttca caggcttccc      1980
agaccctac acagagctca acacaggcaa gggggaaggt gtggcttatc gtggccggct     2040
tctgctctcc ctggagacca agctggtgga gcacagtgaa cagaaggtgg aggaccttcc    2100
tgcggatgac atcctccggg tggagaagta ccttaggagg cgcaagtact ccctgtttgc    2160
ggccttctac tcagccacca tgctgcagga tgtggatgat gccatccagt ttgaggtcag    2220
catcgggaac tacgggaaca agttcgacat gacctgcctg ccgctggcct ccaccactca    2280
gtacagccgt gcagtctttg acgggtgcca ctactactac ctaccctggg gtaacgtgaa    2340
acctgtggtg gtgctgtcat cctactggga ggacatcagc catagaatcg agactcagaa    2400
ccagctgctt gggattgctg accggctgga agctggcctg gagcaggtcc acctggccct    2460
gaaggcgcag tgctccacgg aggacgtgga ctcgctggtg gctcagctga cggatgagct    2520
catcgcaggc tgcagccagc ctctgggtga catccatgag acaccctctg ccacccacct    2580
ggaccagtac ctgtaccagc tgcgcaccca tcacctgagc caaatcactg aggctgccct    2640
ggccctgaag ctcggccaca gtgagctccc tgcagctctg gagcaggcgg aggactggct    2700
cctgcgtctg cgtgccctgg cagaggagcc ccagaacagc ctgccggaca tcgtcatctg    2760
gatgctgcag ggagacaagc gtgtggcata ccagcgggtg cccgcccacc aagtcctctt    2820
ctcccggcgg ggtgccaact actgtggcaa gaattgtggg aagctacaga caatctttct    2880
gaaatatccg atggagaagg tgcctggcgc ccggatgcca gtgcagatac gggtcaagct    2940
gtggtttggg ctctctgtgg atgagaagga gttcaaccag tttgctgagg ggaagctgtc    3000
tgtctttgct gaaacctatg agaacgagac taagttggcc cttgttggga actggggcac    3060
aacgggcctc acctaccca agttttctga cgtcacgggc aagatcaagc tacccaagga    3120
cagcttccgc ccctcggccg gctggacctg gctggagat tggttcgtgt gtccggagaa    3180
gactctgctc catgacatgg acgccggtca cctgagcttc gtggaagagg tgtttgagaa    3240
ccagacccgg cttcccggag gccagtggat ctacatgagt gacaactaca ccgatgtgaa    3300
cgggagaag gtgcttccca aggatgacat tgagtgccca ctgggctgga gtgggaaga     3360
tgaggaatgg tccacagacc tcaaccgggc tgtcgatgag caaggctggg agtatagcat    3420
caccatcccc ccggagcgga agccgaagca ctgggtccct gctgagaaga tgtactacac    3480
acaccgacgg cggcgctggg tgcgcctgcg caggagggat ctcagccaaa tggaagcact    3540
gaaaaggcac aggcaggcgg aggcggaggg cgagggctgg gagtacgcct ctcttttggg    3600
ctggaagttc cacctcgagt accgcaagac agatgccttc cgccgccgcc gctggcgccg    3660
tcgcatggag ccactggaga agacggggcc tgcagctgtg tttgcccttg aggggccct    3720
gggcggcgtg atggatgaca agagtgaaga ttccatgtcc gtctccacct tgagcttcgg    3780
tgtgaacaga cccacgattt cctgcatatt cgactatggg aaccgctacc atctacgctg    3840
```

-continued

| | |
|---|---|
| ctacatgtac caggcccggg acctggctgc gatggacaag gactctttt ctgatccta | 3900 |
| tgccatcgtc tccttcctgc accagagcca gaagacggtg gtggtgaaga caccccttaa | 3960 |
| ccccacctgg gaccagacgc tcatcttcta cgagatcgag atctttggcg agccggccac | 4020 |
| agttgctgag caaccgccca gcattgtggt ggagctgtac gaccatgaca cttatggtgc | 4080 |
| agacgagttt atgggtcgct gcatctgtca accgagtctg gaacggatgc cacggctggc | 4140 |
| ctggttccca ctgacgaggg gcagccagcc gtcggggag ctgctggcct cttttgagct | 4200 |
| catccagaga gagaagccgg ccatccacca tattcctggt tttgaggtgc aggagacatc | 4260 |
| aaggatcctg gatgagtctg aggacacaga cctgccctac ccaccacccc agagggaggc | 4320 |
| caacatctac atggttcctc agaacatcaa gccagcgctc cagcgtaccg ccatcgagat | 4380 |
| cctggcatgg ggcctgcgga acatgaagag ttaccagctg gccaacatct cctcccccag | 4440 |
| cctcgtggta gagtgtgggg ccagacggt gcagtcctgt gtcatcagga acctccggaa | 4500 |
| gaaccccaac tttgacatct gcaccctctt catggaagtg atgctgccca gggaggagct | 4560 |
| ctactgcccc cccatcaccg tcaaggtcat cgataaccgc cagtttggcc gccggcctgt | 4620 |
| ggtgggccag tgtaccatcc gctccctgga gagcttcctg tgtgaccct actcggcgga | 4680 |
| gagtccatcc ccacagggtg gcccagacga tgtgagccta tcagtcctg gggaagacgt | 4740 |
| gctcatcgac attgatgaca ggagcccct catccccatc caggaggaag agttcatcga | 4800 |
| ttggtggagc aaattctttg cctccatagg ggagagggaa aagtgcggct cctacctgga | 4860 |
| gaaggatttt gacaccctga aggtctatga cacacagctg gagaatgtgg aggcctttga | 4920 |
| gggcctgtct gacttttgta acaccttcaa gctgtaccgg ggcaagacgc aggaggagac | 4980 |
| agaagatcca tctgtgattg gtgaatttaa gggcctcttc aaaatttatc ccctcccaga | 5040 |
| agacccagcc atccccatgc ccccaagaca gttccaccag ctggccgccc agggacccca | 5100 |
| ggagtgcttg gtccgtatct acattgtccg agcatttggc ctgcagccca aggaccccaa | 5160 |
| tggaaagtgt gatccttaca tcaagatctc cataggaag aaatcagtga gtgaccagga | 5220 |
| taactacatc ccctgcacgc tggagcccgt atttggaaag atgttcgagc tgacctgcac | 5280 |
| tctgcctctg gagaaggacc taaagatcac tctctatgac tatgacctcc tctccaagga | 5340 |
| cgaaaagatc ggtgagacgg tcgtcgacct ggagaacagg ctgctgtcca gtttggggc | 5400 |
| tcgctgtgga ctcccacaga cctactgtgt ctctggaccg aaccagtggc gggaccagct | 5460 |
| ccgcccctcc cagctcctcc acctcttctg ccagcagcat agagtcaagg cacctgtgta | 5520 |
| ccggacagac cgtgtaatgt tcaggataa agaatattcc attgaagaga tagaggctgg | 5580 |
| caggatccca aacccacacc tgggcccagt ggaggagcgt ctggctctgc atgtgcttca | 5640 |
| gcagcagggc ctggtcccgg agcacgtgga gtcacggccc ctctacagcc cctgcagcc | 5700 |
| agacatcgag caggggaagc tgcagatgtg ggtcgaccta tttccgaagg ccctggggcg | 5760 |
| gcctggacct cccttcaaca tcaccccacg gagagccaga aggtttttcc tgcgttgtat | 5820 |
| tatctggaat accagagatg tgatcctgga tgacctgagc ctcacggggg agaagatgag | 5880 |
| cgacatttat gtgaaaggtt ggatgattgg cttttgaagaa cacaagcaaa agacagacgt | 5940 |
| gcattatcgt tccctgggag gtgaaggcaa cttcaactgg aggttcattt tccccttcga | 6000 |
| ctacctgcca gctgagcaag tctgtaccat tgccaagaag gatgccttct ggaggctgga | 6060 |
| caagactgag agcaaaatcc cagcacgagt ggtgttccag atctgggaca atgacaagtt | 6120 |
| ctccttgat gattttctgg ctccctgca gctcgatctc aaccgcatgc ccaagccagc | 6180 |
| caagacagcc aagaagtgct ccttggacca gctggatgat gctttccacc agaatggtt | 6240 |

-continued

```
tgtgtccctt tttgagcaga aaacagtgaa gggctggtgg ccctgtgtag cagaagaggg      6300
tgagaagaaa atactggcgg gcaagctgga aatgaccttg gagattgtag cagagagtga      6360
gcatgaggag cggcctgctg gccagggccg ggatgagccc aacatgaacc ctaagcttga      6420
ggacccaagg cgccccgaca cctccttcct gtggtttacc tccccataca agaccatgaa      6480
gttcatcctg tggcggtgtt tccggtgggc catcatcctc ttcatcatcc tcttcatcct      6540
gctgctgttc ctggccatct tcatctacgc cttcccgaac tatgctgcca tgaagctggt      6600
gaagcccttc agctgaggac tctcctgccc tgtagaaggg gccgtggggt ccctccagc      6660 atgggactgg cctgcctcct ccgcccagct cggcgagctc ctccagacct cctaggcctg      6720
attgtcctgc cagggtgggc agacagacag atggaccggc ccacactccc agagttgcta      6780
acatggagct ctgagatcac cccacttcca tcatttcctt ctcccccaac ccaacgcttt      6840
tttggatcag ctcagacata tttcagtata aaacagttgg aaccacaaaa aaaaaaaaaa      6900
aaaaaaaaaa a                                                           6911
```

<210> SEQ ID NO 20
<211> LENGTH: 6911
<212> TYPE: DNA
<213> ORGANISM: Homo sapiens

<400> SEQUENCE: 20

```
tcgaccgccc agccaggtgc aaaatgccgt gtcattggga gactccgcag ccggagcatt        60
agattacagc tcgacggagc tcgggaaggg cggcgggggt ggaagatgag cagaagcccc       120
tgttctcgga acgccggctg acaagcgggg tgagcgcagg cggggcgggg acccagccta       180
gcccactgga gcagccgggg gtggcccgtt ccccttttaag agcaactgct ctaagccagg      240
agccagagat tcgagccggc ctcgcccagc cagccctctc cagcgagggg acccacaagc       300
ggcgcctcgg ccctcccgac cttccgagc cctctttgcg ccctgggcgc acggggccct        360
acacgcgcca agcatgctga gggtcttcat cctctatgcc gagaacgtcc acacacccga       420
caccgacatc agcgatgcct actgctccgc ggtgtttgca ggggtgaaga agagaaccaa       480
agtcatcaag aacagcgtga accctgtatg gaatgaggga tttgaatggg acctcaaggg      540 catcccctg gaccagggct ctgagcttca tgtggtggtc aaagaccatg agacgatggg       600
gaggaacagg ttcctggggg aagccaaggt cccactccga gaggtcctcg ccacccctag      660
tctgtccgcc agcttcaatg ccccctgct ggacaccaag aagcagccca caggggcctc      720
gctggtcctg caggtgtcct acacaccgct gcctggagct gtgcccctgt tcccgccccc       780
tactcctctg gagccctccc cgactctgcc tgacctggat gtagtggcag acacaggagg      840
agaggaagac acagaggacc agggactcac tggagatgag gcggagccat tcctggatca      900
aagcggaggc ccggggctc ccaccacccc aaggaaacta ccttcacgtc ctccgcccca       960
ctacccgggg atcaaaagaa agcgaagtgc gcctacatct agaaagctgc tgtcagacaa      1020
accgcaggat ttccagatca gggtccaggt gatcgagggg cgccagctgc cgggggtgaa       1080
catcaagcct gtggtcaagg ttaccgctgc agggcagacc aagcggacgc ggatccacaa      1140
gggaaacagc ccactcttca atgagactct tttcttcaac ttgtttgact ctcctgggga      1200
gctgtttgat gagcccatct ttatcacggt ggtagactct cgttctctca ggacagatgc      1260
tctcctcggg gagttccgga tggacgtggg caccatttac agagagcccc ggcacgccta      1320
tctcaggaag tggctgctgc tctcagaccc tgatgacttc tctgctgggg ccagaggcta      1380
cctgaaaaca agcctttgtg tgctggggcc tggggacgaa gcgcctctgg agagaaaga       1440
```

-continued

```
cccctctgaa gacaaggagg acattgaaag caacctgctc cggcccacag gcgtagccct   1500
gcgaggagcc cacttctgcc tgaaggtctt ccgggccgag gacttgccgc agatggacga   1560
tgccgtgatg gacaacgtga aacagatctt tggcttcgag agtaacaaga gaacttggt    1620 ggaccccttt gtggaggtca gctttgcggg gaaaatgctg tgcagcaaga tcttggagaa   1680
gacggccaac cctcagtgga accagaacat cacactgcct gccatgtttc cctccatgtg   1740
cgaaaaaatg aggattcgta tcatagactg ggaccgcctg actcacaatg acatcgtggc   1800
taccacctac ctgagtatgt cgaaaatctc tgccccctgga ggagaaatag aagaggagcc   1860
tgcaggtgct gtcaagcctt cgaaagcctc agacttggat gactacctgg gcttcctccc   1920
cacttttggg ccctgctaca tcaacctcta tggcagtccc agagagttca caggcttccc   1980 agaccctac acagagctca acacaggcaa gggggaaggt gtggcttatc gtggccggct    2040
tctgctctcc ctggagacca gctggtgga gcacagtgaa cagaaggtgg aggaccttcc    2100
tgcggatgac atcctccggg tggagaagta ccttaggagg cgcaagtact ccctgtttgc   2160
ggccttctac tcagccacca tgctgcagga tgtggatgat gccatccagt ttgaggtcag   2220
catcgggaac tacgggaaca agttcgacat gacctgcctg ccgctggcct ccaccactca   2280
gtacagccgt gcagtctttg acgggtgcca ctactactac ctaccctggg gtaacgtgaa   2340
acctgtggtg gtgctgtcat cctactggga ggacatcagc catagaatcg agactcagaa   2400
ccagctgctt gggattgctg accggctgga agctggcctg gagcaggtcc acctggccct   2460
gaaggcgcag tgctccacgg aggacgtgga ctcgctggtg gctcagctga cggatgagct   2520
catcgcaggc tgcagccagc ctctgggtga catccatgag acaccctctg ccacccacct   2580
ggaccagtac ctgtaccagc tgcgcaccca tcacctgagc caaatcactg aggctgccct   2640
ggccctgaag ctcggccaca gtgagctccc tgcagctctg gagcaggcgg aggactggct   2700
cctgcgtctg cgtgccctgg cagaggagcc ccagaacagc ctgccggaca tcgtcatctg   2760
gatgctgcag ggagacaagc gtgtggcata ccagcgggtg cccgcccacc aagtcctctt   2820
ctcccggcgg ggtgccaact actgtggcaa gaattgtggg aagctacaga caatctttct   2880
gaaatatccg atggagaagg tgcctggcgc ccggatgcca gtgcagatac gggtcaagct   2940
gtggtttggg ctctctgtgg atgagaagga gttcaaccag tttgctgagg ggaagctgtc   3000
tgtctttgct gaaacctatg agaacgagac taagttggcc cttgttggga actggggcac   3060
aacgggcctc acctaccccca gttttctga cgtcacgggc aagatcaagc tacccaagga   3120
cagcttccgc ccctcggccg gctggacctg gctggagat tggttcgtgt gtccggagaa    3180
gactctgctc catgacatgg acgccggtca cctgagcttc gtggaagagg tgtttgagaa   3240
ccagacccgg cttcccggag gccagtggat ctacatgagt gacaactaca ccgatgtgaa   3300
cggggagaag gtgcttccca aggatgacat tgagtgccca ctgggctgga gtgggaaga    3360 tgaggaatgg tccacagacc tcaaccgggc tgtcgatgag caaggctggg agtatagcat   3420
caccatcccc ccggagcgga agccgaagca ctgggtccct gctgagaaga tgtactacac   3480
acaccgacgg cggcgctggg tgcgcctgcg caggagggat ctcagccaaa tggaagcact   3540
gaaaaggcac aggcaggcgg aggcggaggg cgagggctgg gagtacgcct ctctttttgg   3600
ctggaagttc cacctcgagt accgcaagac agatgccttc cgccgccgcc gctggcgccg   3660
tcgcatggag ccactggaga agacggggcc tgcagctgtg tttgcccttg agggggccct   3720
gggcggcgtg atggatgaca agagtgaaga ttccatgtcc gtctccacct tgagcttcgg   3780
tgtgaacaga cccacgattt cctgcatatt cgactatggg aaccgctacc atctacgctg   3840
```

-continued

| | |
|---|---|
| ctacatgtac caggcccggg acctggctgc gatggacaag gactctttt ctgatccta | 3900 |
| tgccatcgtc tccttcctgc accagagcca gaagacggtg gtggtgaaga cacccttaa | 3960 |
| ccccacctgg gaccagacgc tcatcttcta cgagatcgag atctttggcg agccggccac | 4020 |
| agttgctgag caaccgccca gcattgtggt ggagctgtac gaccatgaca cttatggtgc | 4080 |
| agacgagttt atgggtcgct gcatctgtca accgagtctg gaacggatgc cacggctggc | 4140 |
| ctggttccca ctgacgaggg gcagccagcc gtcggggag ctgctggcct cttttgagct | 4200 |
| catccagaga gagaagccgg ccatccacca tattcctggt tttgaggtgc aggagacatc | 4260 |
| aaggatcctg gatgagtctg aggacacaga cctgccctac ccaccacccc agagggaggc | 4320 |
| caacatctac atggttcctc agaacatcaa gccagcgctc cagcgtaccg ccatcgagat | 4380 |
| cctggcatgg ggcctgcgga acatgaagag ttaccagctg gccaacatct cctccccag | 4440 |
| cctcgtggta gagtgtgggg ccagacggt gcagtcctgt gtcatcagga acctccggaa | 4500 |
| gaaccccaac tttgacatct gcaccctctt catggaagtg atgctgccca gggaggagct | 4560 |
| ctactgcccc cccatcaccg tcaaggtcat cgataaccgc cagtttggcc gccggcctgt | 4620 |
| ggtgggccag tgtaccatcc gctccctgga gagcttcctg tgtgacccct actcggcgga | 4680 |
| gagtccatcc ccacagggtg gcccagacga tgtgagccta tcagtcctg gggaagacgt | 4740 |
| gctcatcgac attgatgaca aggagcccct catccccatc caggaggaag agttcatcga | 4800 |
| ttggtggagc aaattctttg cctccatagg ggagagggaa aagtgcggct cctacctgga | 4860 |
| gaaggatttt gacaccctga aggtctatga cacacagctg gagaatgtgg aggcctttga | 4920 |
| gggcctgtct gacttttgta acaccttcaa gctgtaccgg ggcaagacgc aggaggagac | 4980 |
| agaagatcca tctgtgattg gtgaatttaa gggcctcttc aaaatttatc ccctcccaga | 5040 |
| agacccagcc atccccatgc ccccaagaca gttccaccag ctggccgccc agggacccca | 5100 |
| ggagtgcttg gtccgtatct acattgtccg agcatttggc ctgcagccca aggaccccaa | 5160 |
| tggaaagtgt gatccttaca tcaagatctc cataggggaag aaatcagtga gtgaccagga | 5220 |
| taactacatc ccctgcacgc tggagcccgt atttggaaag atgttcgagc tgacctgcac | 5280 |
| tctgcctctg gagaaggacc taaagatcac tctctatgac tatgacctcc tctccaagga | 5340 |
| cgaaaagatc ggtgagacgg tcgtcgacct ggagaacagg ctgctgtcca gtttggggc | 5400 |
| tcgctgtgga ctcccacaga cctactgtgt ctctggaccg aaccagtggc gggaccagct | 5460 |
| ccgcccctcc cagctcctcc acctcttctg ccagcagcat agagtcaagg cacctgtgta | 5520 |
| ccggacagac cgtgtaatgt tcaggataaa agaatattcc attgaagaga tagaggctgg | 5580 |
| caggatccca aacccacacc tgggcccagt ggaggagcgt ctggctctgc atgtgcttca | 5640 |
| gcagcagggc ctggtcccgg agcacgtgga gtcacggccc ctctacagcc cctgcagcc | 5700 |
| agacatcgag caggggaagc tgcagatgtg ggtcgaccta tttccgaagg ccctgggcg | 5760 |
| gcctggacct cccttcaaca tcaccccacg gagagccaga aggttttcc tgcgttgtat | 5820 |
| tatctggaat accagagatg tgatcctgga tgacctgagc ctcacggggg agaagatgag | 5880 |
| cgacatttat gtgaaaggtt ggatgattgg cttttgaagaa cacaagcaaa agacagacgt | 5940 |
| gcgttatcgt tccctgggag gtgaaggcaa cttcaactgg aggttcattt tcccttcga | 6000 |
| ctacctgcca gctgagcaag tctgtaccat tgccaagaag gatgccttct ggaggctgga | 6060 |
| caagactgag agcaaaatcc agcacgagt ggtgttccag atctgggaca atgacaagtt | 6120 |
| ctcctttgat gattttctgg ctccctgca gctcgatctc aaccgcatgc ccaagccagc | 6180 |
| caagacagcc aagaagtgct ccttggacca gctggatgat gctttccacc agaatggtt | 6240 |

-continued

```
tgtgtccctt tttgagcaga aaacagtgaa gggctggtgg ccctgtgtag cagaagaggg      6300
tgagaagaaa atactggcgg gcaagctgga aatgaccttg agattgtag cagagagtga       6360 gcatgaggag cggcctgctg gccagggccg ggatgagccc aacatgaacc ctaagcttga     6420
ggacccaagg cgccccgaca cctccttcct gtggtttacc tccccataca agaccatgaa     6480
gttcatcctg tggcggcgtt ccggtgggc catcatcctc ttcatcatcc tcttcatcct      6540
gctgctgttc ctggccatct tcatctacgc cttcccgaac tatgctgcca tgaagctggt    6600
gaagcccttc agctgaggac tctcctgccc tgtagaaggg gccgtgggt cccctccagc     6660 atgggactgg cctgcctcct ccgcccagct cggcgagctc ctccagacct cctaggcctg   6720
attgtcctgc cagggtgggc agacagacag atggaccggc ccacactccc agagttgcta   6780
acatggagct ctgagatcac cccacttcca tcatttcctt ctcccccaac ccaacgcttt   6840
tttggatcag ctcagacata tttcagtata aacagttgg aaccacaaaa aaaaaaaaaa     6900 aaaaaaaaa a                                                            6911
```

<210> SEQ ID NO 21
<211> LENGTH: 6909
<212> TYPE: DNA
<213> ORGANISM: Homo sapiens

<400> SEQUENCE: 21

```
tcgaccgccc agccaggtgc aaaatgccgt gtcattggga gactccgcag ccggagcatt       60
agattacagc tcgacggagc tcgggaaggg cggcgggggt ggaagatgag cagaagcccc     120
tgttctcgga acgccggctg acaagcgggg tgagcgcagg cggggcgggg acccagccta    180
gcccactgga gcagccgggg gtggcccgtt cccctttaag agcaactgct ctaagccagg    240
agccagagat tcgagccggc ctcgcccagc cagccctctc cagcgagggg acccacaagc    300
ggcgcctcgg ccctcccgac cttccgagc cctctttgcg ccctgggcgc acggggccct      360
acacgcgcca agcatgctga gggtcttcat cctctatgcc gagaacgtcc acacacccga     420
caccgacatc agcgatgcct actgctccgc ggtgtttgca ggggtgaaga agagaaccaa    480
agtcatcaag aacagcgtga accctgtatg gaatgaggga tttgaatggg acctcaaggg    540
catccccctg gaccagggct ctgagcttca tgtggtggtc aaagaccatg agacgatggg     600
gaggaacagg ttcctggggg aagccaaggt cccactccga gaggtcctcg ccacccctag   660
tctgtccgcc agcttcaatg ccccccctgct ggacaccaag aagcagccca caggggcctc     720
gctggtcctg caggtgtcct acacaccgct gcctggagct gtgcccctgt tcccgccccc    780
tactcctctg gagccctccc cgactctgcc tgacctggat gtagtggcag acacaggagg     840
agaggaagac acagaggacc agggactcac tggagatgag gcggagccat tcctggatca    900
aagcggaggc ccgggggctc ccaccacccc aaggaaacta ccttcacgtc ctccgcccca   960
ctaccccggg atcaaaagaa agcgaagtgc gcctacatct agaaagctgc tgtcagacaa   1020
accgcaggat ttccagatca gggtccaggt gatcagggg cgccagctgc cggggtgaa     1080 catcaagcct gtggtcaagg ttaccgctgc agggcagacc aagcggacgc ggatccacaa    1140
gggaaacagc ccactcttca atgagactct tttcttcaac ttgtttgact ctcctgggga    1200
gctgtttgat gagcccatct ttatcacggt ggtagactct cgttctctca ggacagatgc    1260
tctcctcggg gagttccgga tggacgtggg caccatttac agagagccc ggcacgccta     1320 tctcaggaag tggctgctgc tctcagaccc tgatgacttc tctgctgggg ccagaggcta    1380
cctgaaaaca agcctttgtg tgctggggcc tggggacgaa gcgcctctgg agagaaaaga    1440
```

-continued

```
cccctctgaa gacaaggagg acattgaaag caacctgctc cggcccacag gcgtagccct    1500
gcgaggagcc cacttctgcc tgaaggtctt ccgggccgag gacttgccgc agatggacga    1560
tgccgtgatg gacaacgtga aacagatctt tggcttcgag agtaacaaga gaacttggt     1620
ggaccccttt gtggaggtca gctttgcggg gaaaatgctg tgcagcaaga tcttggagaa    1680
gacggccaac cctcagtgga accagaacat cacactgcct gccatgtttc cctccatgtg    1740
cgaaaaaatg aggattcgta tcatagactg ggaccgcctg actcacaatg acatcgtggc    1800
taccacctac ctgagtatgt cgaaaatctc tgcccctgga ggagaaatag aagaggagcc    1860
tgcaggtgct gtcaagcctt cgaaagcctc agacttggat gactacctgg gcttcctccc    1920
cacttttggg ccctgctaca tcaacctcta tggcagtccc agagagttca caggcttccc    1980
agacccctac acagagctca acacaggcaa gggggaaggt gtggcttatc gtggccggct    2040
tctgctctcc ctggagacca agctggtgga gcacagtgaa cagaaggtgg aggaccttcc    2100
tgccggatgac atcctccggg tggagaagta ccttaggagg cgcaagtact ccctgtttgc    2160
ggccttctac tcagccacca tgctgcagga tgtggatgat gccatccagt ttgaggtcag    2220
catcgggaac tacgggaaca agttcgacat gacctgcctg ccgctggcct ccaccactca    2280
gtacagccgt gcagtctttg acgggtgcca ctactactac ctaccctggg gtaacgtgaa    2340
acctgtggtg gtgctgtcat cctactggga ggacatcagc catagaatcg agactcagaa    2400
ccagctgctt gggattgctg accggctgga agctggcctg gagcaggtcc acctggccct    2460
gaaggcgcag tgctccacgg aggacgtgga ctcgctggtg gctcagctga cggatgagct    2520
catcgcaggc tgcagccagc ctctgggtga catccatgag acaccctctg ccacccacct    2580
ggaccagtac ctgtaccagc tgcgcaccca tcacctgagc caaatcactg aggctgccct    2640
ggccctgaag ctcggccaca gtgagctccc tgcagctctg gagcaggcgg aggactggct    2700
cctgcgtctg cgtgccctgg cagaggagcc ccagaacagc ctgccggaca tcgtcatctg    2760
gatgctgcag ggagacaagc gtgtggcata ccagcgggtg cccgcccacc aagtcctctt    2820
ctcccggcgg ggtgccaact actgtggcaa gaattgtggg aagctacaga caatcttttct    2880
gaaatatccg atggagaagg tgcctggcgc ccggatgcca gtgcagatac gggtcaagct    2940
gtggtttggg ctctctgtgg atgagaagga gttcaaccag tttgctgagg ggaagctgtc    3000
tgtctttgct gaaacctatg agaacgagac taagttggcc cttgttggga actggggcac    3060
aacgggcctc acctacccca gttttctga cgtcacgggc aagatcaagc tacccaagga    3120
cagcttccgc ccctcggccg gctggacctg gctggagat tggttcgtgt gtccggagaa    3180
gactctgctc catgacatgg acgccggtca cctgagcttc gtggaagagg tgtttgagaa    3240
ccagacccgg cttcccggag gccagtggat ctacatgagt gacaactaca ccgatgtgaa    3300
cggggagaag gtgcttccca aggatgacat tgagtgccca ctgggctgga gtgggaaga    3360
tgaggaatgg tccacagacc tcaaccgggc tgtcgatgag caaggctggg agtatagcat    3420
caccatcccc ccggagcgga agccgaagca ctgggtccct gctgagaaga tgtactacac    3480
acaccgacgg cggcgctggg tgcgcctgcg caggagggat ctcagccaaa tggaagcact    3540
gaaaaggcac aggcaggcgg aggcggaggg cgagggctgg gagtacgcct ctctttttgg    3600
ctggaagttc cacctcgagt accgcaagac agatgccttc cgccgccgcc gctggcgccg    3660
tcgcatggag ccactggaga agacggggcc tgcagctgtg tttgcccttg aggggcccct    3720
gggcggcgtg atggatgaca agagtgaaga ttccatgtcc gtctccacct tgagcttcgg    3780
tgtgaacaga cccacgattt cctgcatatt cgactatggg aaccgctacc atctacgctg    3840
```

-continued

| | |
|---|---|
| ctacatgtac caggcccggg acctggctgc gatggacaag gactcttttt ctgatcccta | 3900 |
| tgccatcgtc tccttcctgc accagagcca gaagacggtg gtggtgaaga acacccttaa | 3960 |
| ccccacctgg gaccagacgc tcatcttcta cgagatcgag atctttggcg agccggccac | 4020 |
| agttgctgag caaccgccca gcattgtggt ggagctgtac gaccatgaca cttatggtgc | 4080 |
| agacgagttt atgggtcgct gcatctgtca accgagtctg gaacggatgc cacggctggc | 4140 |
| ctggttccca ctgacgaggg gcagccagcc gtcggggag ctgctggcct cttttgagct | 4200 |
| catccagaga gagaagccgg ccatccacca tattcctggt tttgaggtgc aggagacatc | 4260 |
| aaggatcctg gatgagtctg aggacacaga cctgccctac ccaccacccc agagggaggc | 4320 |
| caacatctac atggttcctc agaacatcaa gccagcgctc cagcgtaccg ccatcgagat | 4380 |
| cctggcatgg ggcctgcgga acatgaagag ttaccagctg gccaacatct cctcccccag | 4440 |
| cctcgtggta gagtgtgggg gccagacggt gcagtcctgt gtcatcagga acctccggaa | 4500 |
| gaaccccaac tttgacatct gcaccctctt catggaagtg atgctgccca gggaggagct | 4560 |
| ctactgcccc cccatcaccg tcaaggtcat cgataaccgc cagtttggcc gccggcctgt | 4620 |
| ggtgggccag tgtaccatcc gctccctgga gagcttcctg tgtgaccct actcggcgga | 4680 |
| gagtccatcc ccacagggtg gcccagacga tgtgagccta ctcagtcctg gggaagacgt | 4740 |
| gctcatcgac attgatgaca aggagcccct catccccatc caggaggaag agttcatcga | 4800 |
| ttggtggagc aaattctttg cctccatagg ggagagggaa aagtgcggct cctacctgga | 4860 |
| gaaggatttt gacaccctga aggtctatga cacacagctg gagaatgtgg aggcctttga | 4920 |
| gggcctgtct gacttttgta acaccttcaa gctgtaccgg ggcaagacgc aggaggagac | 4980 |
| agaagatcca tctgtgattg gtgaatttaa gggcctcttc aaaatttatc ccctcccaga | 5040 |
| agacccagcc atccccatgc ccccaagaca gttccaccag ctggccgccc agggacccca | 5100 |
| ggagtgcttg gtccgtatct acattgtccg agcatttggc ctgcagccca aggacccaa | 5160 |
| tggaaagtgt gatccttaca tcaagatctc catagggaag aaatcagtga gtgaccagga | 5220 |
| taactacatc ccctgcacgc tggagcccgt atttggaaag atgttcgagc tgacctgcac | 5280 |
| tctgcctctg gagaaggacc taaagatcac tctctatgac tatgacctcc tctccaagga | 5340 |
| cgaaaagatc ggtgagacgg tcgtcgacct ggagaacagg ctgctgtcca gtttggggc | 5400 |
| tcgctgtgga ctcccacaga cctactgtgt ctctggaccg aaccagtggc gggaccagct | 5460 |
| ccgccctcc cagctcctcc acctcttctg ccagcagcat agagtcaagg cacctgtgta | 5520 |
| ccggacagac cgtgtaatgt tcaggataa agaatattcc attgaagaga tagaggctgg | 5580 |
| caggatccca aacccacacc tgggcccagt ggaggagcgt ctggctctgc atgtgcttca | 5640 |
| gcagcagggc ctggtcccgg agcacgtgga gtcacggccc ctctacagcc cctgcagcc | 5700 |
| agacatcgag caggggaagc tgcagatgtg ggtcgaccta tttccgaagg ccctggggcg | 5760 |
| gcctggacct cccttcaaca tcaccccacg gagagccaga aggttttcc tgcgttgtat | 5820 |
| tatctggaat accagagatg tgatcctgga tgacctgagc ctcacggggg agaagatgag | 5880 |
| cgacatttat gtgaaaggtt ggatgattgg ctttgaagaa cacaagcaaa agacagacgt | 5940 |
| gcattatcgt tccctgggag gtgaaggcaa cttcaactgg aggttcattt tccccttcga | 6000 |
| ctacctgcca gctgagcaag tctgtaccat tgccaagaag gatgccttct ggaggctgga | 6060 |
| caagactgag caaaatccca gcacgagtgg tgttccagat ctgggacaat gacaagttct | 6120 |
| cctttgatga ttttctgggc tccctgcagc tcgatctcaa ccgcatgccc aagccagcca | 6180 |
| agacagccaa gaagtgctcc ttggaccagc tggatgatgc tttccaccca gaatggtttg | 6240 |

```
tgtcccttttt tgagcagaaa acagtgaagg gctggtggcc ctgtgtagca gaagagggtg   6300
agaagaaaat actggcgggc aagctggaaa tgaccttgga gattgtagca gagagtgagc   6360
atgaggagcg gcctgctggc cagggccggg atgagcccaa catgaaccct aagcttgagg   6420
acccaaggcg ccccgacacc tccttcctgt ggtttacctc cccatacaag accatgaagt   6480
tcatcctgtg gcggcgtttc cggtgggcca tcatcctctt catcatcctc ttcatcctgc   6540
tgctgttcct ggccatcttc atctacgcct cccgaactga tgctgccatg aagctggtga   6600
agcccttcag ctgaggactc tcctgccctg tagaagggc cgtggggtcc cctccagcat   6660
gggactggcc tgcctcctcc gcccagctcg gcgagctcct ccagacctcc taggcctgat   6720
tgtcctgcca gggtgggcag acagacagat ggaccggccc acactcccag agttgctaac   6780
atggagctct gagatcaccc cacttccatc atttccttct cccccaaccc aacgcttttt   6840
tggatcagct cagacatatt tcagtataaa acagttggaa ccacaaaaaa aaaaaaaaaa   6900
aaaaaaaaa                                                           6909

<210> SEQ ID NO 22
<211> LENGTH: 20
<212> TYPE: DNA
<213> ORGANISM: Homo sapiens

<400> SEQUENCE: 22
tgggacctca agggcatccc                                               20

<210> SEQ ID NO 23
<211> LENGTH: 20
<212> TYPE: DNA
<213> ORGANISM: Homo sapiens

<400> SEQUENCE: 23
accatgctgc aggatgtgga                                               20

<210> SEQ ID NO 24
<211> LENGTH: 20
<212> TYPE: DNA
<213> ORGANISM: Homo sapiens

<400> SEQUENCE: 24
gggaggtgaa ggcaacttca                                               20

<210> SEQ ID NO 25
<211> LENGTH: 20
<212> TYPE: DNA
<213> ORGANISM: Homo sapiens

<400> SEQUENCE: 25
ctcacggggg agaagatgag                                               20

<210> SEQ ID NO 26
<211> LENGTH: 20
<212> TYPE: DNA
<213> ORGANISM: Homo sapiens

<400> SEQUENCE: 26
ctgtggcggc gtttccggtg                                               20

<210> SEQ ID NO 27
<211> LENGTH: 20
<212> TYPE: DNA
<213> ORGANISM: Homo sapiens
```

```
<400> SEQUENCE: 27
acatcaagga tcctggatga                                                    20

<210> SEQ ID NO 28
<211> LENGTH: 20
<212> TYPE: DNA
<213> ORGANISM: Homo sapiens

<400> SEQUENCE: 28
ctgtggcggc gtttccggtg                                                    20

<210> SEQ ID NO 29
<211> LENGTH: 20
<212> TYPE: DNA
<213> ORGANISM: Homo sapiens

<400> SEQUENCE: 29
acagacgtgc attatcgttc                                                    20

<210> SEQ ID NO 30
<211> LENGTH: 20
<212> TYPE: DNA
<213> ORGANISM: Homo sapiens

<400> SEQUENCE: 30
aagactgaga gcaaaatccc                                                    20

<210> SEQ ID NO 31
<211> LENGTH: 507
<212> TYPE: DNA
<213> ORGANISM: Homo sapiens

<400> SEQUENCE: 31
tcgaccgccc agccaggtgc aaaatgccgt gtcattggga gactccgcag ccggagcatt        60
agattacagc tcgacggagc tcgggaaggg cggcggggt ggaagatgag cagaagcccc        120
tgttctcgga acgccggctg acaagcgggg tgagcgcagg cggggcgggg acccagccta       180
gcccactgga gcagccgggg gtggcccgtt cccctttaag agcaactgct ctaagccagg       240
agccagagat tcgagccggc ctcgcccagc cagccctctc cagcgagggg acccacaagc       300
ggcgcctcgg ccctcccgac ctttccgagc cctcttttgcg ccctgggcgc acggggccct     360
acacgcgcca agcatgctga gggtcttcat cctctatgcc gagaacgtcc acacacccga       420
caccgacatc agcgatgcct actgctccgc ggtgtttgca ggtaggaggg gccgaccacc       480
ctcgccgggg tcggggtggg gtagagg                                           507

<210> SEQ ID NO 32
<211> LENGTH: 183
<212> TYPE: DNA
<213> ORGANISM: Homo sapiens

<400> SEQUENCE: 32
aaaggcggga tgtgtctctc cattctccct tttgtgtctc ttgtagggt gaagaagaga         60 accaaagtca tcaagaacag cgtgaaccct gtatggaatg aggtatgtga gtttttctcc      120
ttccttttct ctctgtctgc tgcaggggc ttgggaggag gtgccttctc agcagtgtcc       180
ttg                                                                     183

<210> SEQ ID NO 33
<211> LENGTH: 264
```

```
<212> TYPE: DNA
<213> ORGANISM: Homo sapiens

<400> SEQUENCE: 33
cattcatgaa tgcctactca gtgccctggt ggcacgaagg tgaaccagac acagtctctt      60
ctcctagagg gccataggtt aagatgcctt ttctcttttt cttccaggga tttgaatggg     120
acctcaaggg catcccctg gaccagggct ctgagcttca tgtggtggtc aaagaccatg      180
agacgatggg gaggaacagg taaggtggcc agagggggt gctccatggc ttgaaggtgc      240
aggtaggatt gtggagtata caga                                            264

<210> SEQ ID NO 34
<211> LENGTH: 223
<212> TYPE: DNA
<213> ORGANISM: Homo sapiens

<400> SEQUENCE: 34
cagaagagcc aggtgcctt aggctagttt tctacatttg acttctctct cctctcaggt      60 tcctgggga agccaaggtc ccactccgag aggtcctcgc caccctagt ctgtccgcca      120 gcttcaatgc cccctgctg gacaccaaga agcagcccac agggtaagt gcccatcagc      180 ctctgccagg ttaaggtcca aggcattgcc agtggcttc ctc                        223

<210> SEQ ID NO 35
<211> LENGTH: 224
<212> TYPE: DNA
<213> ORGANISM: Homo sapiens

<400> SEQUENCE: 35
cagtggtccg aggccagcgc accaacctgt cccccacgtc tcatctcttc caggcctcgc      60
tggtcctgca ggtgtcctac acccgctgc ctggagctgt gccccctgttc ccgcccccta     120 ctcctctgga gccctccccg actctgcctg acctggatgt agtggcaggt gggtagccca     180
cgttggcctg gctgggcccc agcaagaatg gccggcagtg gcac                      224

<210> SEQ ID NO 36
<211> LENGTH: 315
<212> TYPE: DNA
<213> ORGANISM: Homo sapiens

<400> SEQUENCE: 36
aggggcaggg gcagggccag agggccaggc ctcattaggg ccctctcctc ttagacacag      60
gaggagagga agacacagag gaccagggac tcactggaga tgaggcggag ccattcctgg     120
atcaaagcgg aggcccgggg gctcccacca ccccaaggaa actaccttca cgtcctccgc     180
cccactaccc cgggatcaaa agaaagcgaa gtgcgcctac atctagaaag ctgctgtcag     240
acaaaccgca ggatttccag gtgatgaacg ggctttctct gaccccaggc tcctcttcag     300
ccatcagctg cgggt                                                      315

<210> SEQ ID NO 37
<211> LENGTH: 249
<212> TYPE: DNA
<213> ORGANISM: Homo sapiens

<400> SEQUENCE: 37
ccagtggtga gatggtccct gagatttctg actcttgggg tggatggtgg gtggtcctta      60
actcttcccc cttctggctt tcagatcagg gtccaggtga tcgaggggcg ccagctgccg     120
```

```
ggggtgaaca tcaagcctgt ggtcaaggtt accgctgcag ggcagaccaa gcggacgcgg    180
atccacaagg gaaacagccc actcttcaat gaggtgggag acatgggca tgagggcaga    240 accttgtgg                                                            249

<210> SEQ ID NO 38
<211> LENGTH: 185
<212> TYPE: DNA
<213> ORGANISM: Homo sapiens

<400> SEQUENCE: 38
ccctggcctg agggatcagc aggcactgat atgtctctct ttgctctgaa ccaacagact     60
cttttcttca acttgtttga ctctcctggg gagctgtttg atgagcccat ctttatcacg    120
gtatgtctca gcagtcaaag tgttctccgt gggctgtatg tatgcacata ggtgtcagtg    180
cacac                                                                185

<210> SEQ ID NO 39
<211> LENGTH: 196
<212> TYPE: DNA
<213> ORGANISM: Homo sapiens

<400> SEQUENCE: 39
aagagctatt ggggttggccg tgtgggccac atgtccctgt gaatgtgagc catgatcttt    60
ctctgcaggt ggtagactct cgttctctca ggacagatgc tctcctcggg gagttccggg   120
taattgctta ttttctaaaa gcagtcagtt ctcacttctc cgtgttggtg gagcctctgt   180
ggaccatggg cagggg                                                    196

<210> SEQ ID NO 40
<211> LENGTH: 178
<212> TYPE: DNA
<213> ORGANISM: Homo sapiens

<400> SEQUENCE: 40
tggaatcgta taatgcacca cactttattt aacgctttgg cggcaagagt ttgatttgtg     60
tctcctctct tgattgcaga tggacgtggg caccatttac agagagcccc gtgagttctc   120
accactttgg ccgtatcctt gcattttggt tctggaggct gattggggac actcattt     178

<210> SEQ ID NO 41
<211> LENGTH: 231
<212> TYPE: DNA
<213> ORGANISM: Homo sapiens

<400> SEQUENCE: 41
ggggtcttct gattctggga tcaccaaagg atgttgtctc tcttagggca cgcctatctc     60
aggaagtggc tgctgctctc agaccctgat gacttctctg ctggggccag aggctacctg   120
aaaacaagcc tttgtgtgct ggggcctggg gacgaagcgc ctgtgagtac atttccctgg   180
gtcttcctta cggtcccccca cgcggcactt ggttgcggag gcaccaaacc a            231

<210> SEQ ID NO 42
<211> LENGTH: 247
<212> TYPE: DNA
<213> ORGANISM: Homo sapiens

<400> SEQUENCE: 42
gtcaaaaccc tgtgctcagg agcgcatgaa ggaacgtatt tggttttctt tgtagctgga    60
gagaaaagac ccctctgaag acaaggagga cattgaaagc aacctgctcc ggcccacagg   120
```

```
cgtagccctg cgaggagccc acttctgcct gaaggtcttc cgggccgagg acttgccgca      180
gagtgcgtgg ggcgcgccct tgggtgggag gtctgcagga ggctggaggc gcagggctgg      240
tgggggt                                                                247

<210> SEQ ID NO 43
<211> LENGTH: 179
<212> TYPE: DNA
<213> ORGANISM: Homo sapiens

<400> SEQUENCE: 43
caggcagtga ctggtgtgtc cctcttccca gtggacgatg ccgtgatgga caacgtgaaa      60
cagatctttg gcttcgagag taacaagaag aacttggtgg accccttgt ggaggtcagc      120 tttgcgggga aaatggtaag gagcaaggga gcaggagggt tctctcggga ggggacggg      179

<210> SEQ ID NO 44
<211> LENGTH: 202
<212> TYPE: DNA
<213> ORGANISM: Homo sapiens

<400> SEQUENCE: 44
ccccggggga gcccagagtc cccatggagc tgatcaactt gtcccctccc tgtgtcttct      60
agctgtgcag caagatcttg gagaagacgg ccaaccctca gtggaaccag aacatcacac      120
tgcctgccat ggtgagcctc ctgtccccag caaacccaag gaggcccctg ggctctggg      180 cttcgggagg tccagggctc ct                                              202

<210> SEQ ID NO 45
<211> LENGTH: 167
<212> TYPE: DNA
<213> ORGANISM: Homo sapiens

<400> SEQUENCE: 45 gggagggct gttctatctt caaaaggact cttctcccaa cacgcctcta ttccttcctc      60
agtttccctc catgtgcgaa aaatgagga ttcgtatcat agactggtga gttctgagtc      120
ttggagtctt tagggcgggc tgtcctgagg gggcgctccc tcagttt                   167

<210> SEQ ID NO 46
<211> LENGTH: 220
<212> TYPE: DNA
<213> ORGANISM: Homo sapiens

<400> SEQUENCE: 46
tgtggcctga gttcctttcc tgtgtcaggc cctctctgct cccttgctct ctagggaccg      60
cctgactcac aatgacatcg tggctaccac ctacctgagt atgtcgaaaa tctctgcccc      120
tggaggagaa atagaaggta tgttccctct tcgttctgcc ctttgacccc ctgtgctctc      180 ccccctcta tccagcttac acttctagtt ttgagagttt                            220

<210> SEQ ID NO 47
<211> LENGTH: 172
<212> TYPE: DNA
<213> ORGANISM: Homo sapiens

<400> SEQUENCE: 47
acagcctgtt catgtaaccc gtccttctcc cagccatgcc caccctaacc cctttttccat    60 ttctttacgc ttcagaggag cctgcaggtg ctgtcaagcc ttcgaaagcc tcagactgta    120
cgttgctgtc accttgggga caaccagggg agtgggcct tgggtttttg ct              172
```

<210> SEQ ID NO 48
<211> LENGTH: 200
<212> TYPE: DNA
<213> ORGANISM: Homo sapiens

<400> SEQUENCE: 48

| ccgacccctc | tgattgccac | ttgtgtctcc | cagtggatga | ctacctgggc | ttcctcccca | 60 |
| cttttgggcc | ctgctacatc | aacctctatg | gcagtcccag | agagttcaca | ggcttcccag | 120 |
| acccctacac | agagctcaac | acaggcaagg | taagccggct | ggagccctgg | caagggcagg | 180 |
| atgccacatg | cccaggtggg | | | | | 200 |

<210> SEQ ID NO 49
<211> LENGTH: 217
<212> TYPE: DNA
<213> ORGANISM: Homo sapiens

<400> SEQUENCE: 49

| cctccctct | gtctcccctg | ctccttgtga | cctgacctcc | ctggcagggg | gaaggtgtgg | 60 |
| cttatcgtgg | ccggcttctg | ctctcccctgg | agaccaagct | ggtggagcac | agtgaacaga | 120 |
| aggtggagga | ccttcctgcg | gatgacatcc | tccgggtgga | ggtgaggggt | gtggctctgg | 180 |
| gtgggagctg | ggcgtcgggg | cagggaaggg | atggcca | | | 217 |

<210> SEQ ID NO 50
<211> LENGTH: 269
<212> TYPE: DNA
<213> ORGANISM: Homo sapiens

<400> SEQUENCE: 50

| agcctgggtg | cctttctttg | ctcctcccgt | gaccctctgg | tctactctct | gctctcagaa | 60 |
| gtaccttagg | aggcgcaagt | actccctgtt | tgcggccttc | tactcagcca | ccatgctgca | 120 |
| ggatgtggat | gatgccatcc | agtttgaggt | cagcatcggg | aactacggga | acaagttcga | 180 |
| catgacctgc | ctgccgctgg | cctccaccac | tcagtacagc | cgtgcagtct | ttgacggtga | 240 |
| ggcagtgctc | ctggctggga | ccccgatca | | | | 269 |

<210> SEQ ID NO 51
<211> LENGTH: 225
<212> TYPE: DNA
<213> ORGANISM: Homo sapiens

<400> SEQUENCE: 51

| actcctggca | cagcgctcag | gcccgtctct | ccattccagg | gtgccactac | tactacctac | 60 |
| cctgggtaa | cgtgaaacct | gtggtggtgc | tgtcatccta | ctgggaggac | atcagccata | 120 |
| gaatcgagac | tcagaaccag | ctgcttggga | ttgctgaccg | gctggtgagt | gaaaacttgc | 180 |
| ccaaagctgc | acatgcctat | gcatgcacct | gctaccccg | ctgca | | 225 |

<210> SEQ ID NO 52
<211> LENGTH: 227
<212> TYPE: DNA
<213> ORGANISM: Homo sapiens

<400> SEQUENCE: 52

| gggtccagca | tgcaccctct | gccctgtggt | gacacacctg | accccttgcct | gcccattcca | 60 |
| caggaagctg | gcctggagca | ggtccacctg | gccctgaagg | cgcagtgctc | cacggaggac | 120 |

```
gtggactcgc tggtggctca gctgacggat gagctcatcg caggctgcag gtagggggga    180
cctggcgccc ctggtgccca cctctcctgg ctcaactggg cctgttt                  227

<210> SEQ ID NO 53
<211> LENGTH: 303
<212> TYPE: DNA
<213> ORGANISM: Homo sapiens

<400> SEQUENCE: 53
tgggagaccc tgggctcatc aggcgcattc catctgtccg tccctcacag ccagcctctg    60
ggtgacatcc atgagacacc ctctgccacc cacctggacc agtacctgta ccagctgcgc   120
acccatcacc tgagccaaat cactgaggct gccctggccc tgaagctcgg ccacagtgag   180
ctccctgcag ctctggagca ggcggaggac tggctcctgc gtctgcgtgc cctggcagag   240
gaggtaatta agcctggggg tgcctttctt cttctgctct cctgctgcct ggaacatcag   300
aac                                                                 303

<210> SEQ ID NO 54
<211> LENGTH: 272
<212> TYPE: DNA
<213> ORGANISM: Homo sapiens

<400> SEQUENCE: 54
cgtgggcctg gtgtgtcacc atccccaccc cgaccaccac cctctgttca gccccagaac    60
agcctgccgg acatcgtcat ctggatgctg cagggagaca agcgtgtggc ataccagcgg   120
gtgcccgccc accaagtcct cttctcccgg cggggtgcca actactgtgg caagaattgt   180
gggaagctac agacaatctt tctgaaagtg agttttctttt tccaagtca tgatcgtatt   240 tccaacataa ggcctttctc ccatctcttg ct                                 272

<210> SEQ ID NO 55
<211> LENGTH: 219
<212> TYPE: DNA
<213> ORGANISM: Homo sapiens

<400> SEQUENCE: 55
tgtgggtttc tgtccttctt cggtacccag tatccgatgg agaaggtgcc tggcgcccgg    60
atgccagtgc agatacgggt caagctgtgg tttgggctct ctgtggatga aaggagttc   120 aaccagtttg ctgaggggaa gctgtctgtc tttgctgaaa ccgtgagtac ctgccagccc   180
ccacctctgc ctcccactac ctggagctgc cttggcccc                          219

<210> SEQ ID NO 56
<211> LENGTH: 292
<212> TYPE: DNA
<213> ORGANISM: Homo sapiens

<400> SEQUENCE: 56
tgcctcccac tacctggagc tgccttggcc cccttcacgc ctcattcttc ctggccctcc    60
agtatgagaa cgagactaag ttggcccttg ttgggaactg gggcacaacg ggcctcacct   120
accccaagtt ttctgacgtc acgggcaaga tcaagctacc caaggacagc ttccgccct   180 cggccggctg gacctgggct ggagattggt tcgtgtgtcc ggagaagacg tgagtcgtgg   240
gcagggaggg ctggggagag ccaggccagg ctgcccacca tggactgcac cc           292
```

```
<210> SEQ ID NO 57
<211> LENGTH: 242
<212> TYPE: DNA
<213> ORGANISM: Homo sapiens

<400> SEQUENCE: 57
tggatggggg cctctccagc agagcagcag agactctgac cagccctcct ccacagtctg      60
ctccatgaca tggacgccgg tcacctgagc ttcgtggaag aggtgtttga gaaccagacc     120
cggcttcccg gaggccagtg gatctacatg agtgacaact acaccgatgt ggtaaagcag     180
gcactcaggg gcaggtgggg tctagacatt tggtctctgg aggcacctgg tgctcaggga     240
ca                                                                   242

<210> SEQ ID NO 58
<211> LENGTH: 215
<212> TYPE: DNA
<213> ORGANISM: Homo sapiens

<400> SEQUENCE: 58
tcacatctgt ctgtctcctc tcattgcttg cctgttcggt tttgtcctta gaacggggag      60
aaggtgcttc ccaaggatga cattgagtgc ccactgggct ggaagtggga agatgaggaa     120
tggtccacag acctcaaccg ggctgtcgat gagcaaggtg ggcagcatgt ggaacctggc     180
gagccccatc cccggcaagc tctcaagcca tgcat                                215

<210> SEQ ID NO 59
<211> LENGTH: 246
<212> TYPE: DNA
<213> ORGANISM: Homo sapiens

<400> SEQUENCE: 59
agagatggtc ccaggagaga tgggggggaag tgccaagcaa tgagtgaccg gttccccctc     60
ccccaggctg ggagtatagc atcaccatcc ccccggagcg gaagccgaag cactgggtcc    120
ctgctgagaa gatgtactac acacaccgac ggcggcgctg ggtgcgcctg cgcaggaggg    180
atctcagcca aatggaagca ctgaaaaagg gtgagccagc aggtggtggg tgggagtgag    240
gcctgt                                                              246

<210> SEQ ID NO 60
<211> LENGTH: 253
<212> TYPE: DNA
<213> ORGANISM: Homo sapiens

<400> SEQUENCE: 60
cttcccaccg gcctctgagt ctgccccttc ttgtgcagca caggcaggcg gaggcggagg      60
gcgagggctg ggagtacgcc tctcttttg gctggaagtt ccacctcgag taccgcaaga    120
cagatgcctt ccgccgccgc cgctggcgcc gtcgcatgga ccactggag aagacggggc    180 ctgcagctgt gtttgccctt gagggggccc tggtatgtgg ggctgcactt gtcctggctt    240
gggtagggta tat                                                      253

<210> SEQ ID NO 61
<211> LENGTH: 177
<212> TYPE: DNA
<213> ORGANISM: Homo sapiens
```

-continued

<400> SEQUENCE: 61
gaatctgcca taaccagctt cgtgtctcca gggcggcgtg atggatgaca agagtgaaga    60
ttccatgtcc gtctccacct tgagcttcgg tgtgaacaga cccacgattt cctgcatatt   120
cgactgtaag taggcttcga ggcctctatg gggtgataag ggtgtgtcac cttatgc      177

<210> SEQ ID NO 62
<211> LENGTH: 181
<212> TYPE: DNA
<213> ORGANISM: Homo sapiens

<400> SEQUENCE: 62
aaccactcca gccactcact ctggcacctc tgttttttcc cttggtgaag atgggaaccg    60
ctaccatcta cgctgctaca tgtaccaggc ccgggacctg gctgcgatgg acaaggactc   120
tttttctggt aggtgggaga gaggcaggag agtcagagac tgtgggctga gatctgggaa   180
t                                                                  181

<210> SEQ ID NO 63
<211> LENGTH: 319
<212> TYPE: DNA
<213> ORGANISM: Homo sapiens

<400> SEQUENCE: 63
ccccacatgg ctctggagaa gacatctctc agggtccctg ctgtgtaatg tctccctcc     60 ccctctggcc atgcagatcc ctatgccatc gtctccttcc tgcaccagag ccagaagacg   120
gtggtggtga agaacaccct taaccccacc tgggaccaga cgctcatctt ctacgagatc   180
gagatctttg gcgagccggc cacagttgct gagcaaccgc cagcattgt ggtggagctg    240 tacgaccatg acacttatgt gagtctgccc agctcctgcc tcgtcccctc acagggaggg   300
accatgtgca aggtgggg                                                319

<210> SEQ ID NO 64
<211> LENGTH: 249
<212> TYPE: DNA
<213> ORGANISM: Homo sapiens

<400> SEQUENCE: 64
gccctgggta agggatgctg attcttgtct ctctacgctt ggtctagggt gcagacgagt    60
ttatgggtcg ctgcatctgt caaccgagtc tggaacggat gccacggctg gcctggttcc   120
cactgacgag gggcagccag ccgtcggggg agctgctggc ctcttttgag ctcatccaga   180
gagagaaggt gaggctggtc tatatccaga tccaggaggc ccaggcagga gtggggtggg   240
ggccaaccc                                                          249

<210> SEQ ID NO 65
<211> LENGTH: 158
<212> TYPE: DNA
<213> ORGANISM: Homo sapiens

<400> SEQUENCE: 65
cactgacata gtccatgagt gtcatgaggg tgatgggggc cttaggtgac aagcacatga    60
ccagagctct cttttcttca ctccagccgg ccatccacca tattcctggt tttgaggtaa   120
gtcttgctct gacctttcct tcttcaaact gattgcca                          158

<210> SEQ ID NO 66
<211> LENGTH: 132

```
<212> TYPE: DNA
<213> ORGANISM: Homo sapiens

<400> SEQUENCE: 66 cttttcccc ttccaacccc tctcaccatc tcctgatgtg cacatcccat ggctgtgggc      60
caggtgcagg agacatcaag gatcctggat gaggtgagct ggcggggccg aggtagaggg     120
aaggtgaagc ca                                                         132

<210> SEQ ID NO 67
<211> LENGTH: 216
<212> TYPE: DNA
<213> ORGANISM: Homo sapiens

<400> SEQUENCE: 67
tcttccttcc acctttgtct ccattctacc tgctgtccac tgcagtctga ggacacagac     60
ctgccctacc caccacccca gagggaggcc aacatctaca tggttcctca gaacatcaag    120
ccagcgctcc agcgtaccgc catcgaggtg agccgtccgg gcctgggcgt gggggctggg    180
agcagcctgc cttcccctt cctggcccca gccttt                                216

<210> SEQ ID NO 68
<211> LENGTH: 263
<212> TYPE: DNA
<213> ORGANISM: Homo sapiens

<400> SEQUENCE: 68
cccgggcctt ctgagccact ctcctcattc tgtgtgctta gaatcctggc atggggcctg     60
cggaacatga agagttacca gctggccaac atctcctccc ccagcctcgt ggtagagtgt    120
gggggccaga cggtgcagtc ctgtgtcatc aggaacctcc ggaagaaccc caactttgac    180
atctgcaccc tcttcatgga agtggtgagc cccacctccc tactgtcccc ttccagagtc    240
ctggggctag aagttctaca tgt                                             263

<210> SEQ ID NO 69
<211> LENGTH: 249
<212> TYPE: DNA
<213> ORGANISM: Homo sapiens

<400> SEQUENCE: 69
caggccagtg cgttcttcct cctccaccca gatgctgccc agggaggagc tctactgccc     60
ccccatcacc gtcaaggtca tcgataaccg ccagtttggc cgccggcctg tggtgggcca    120
gtgtaccatc cgctccctgg agagcttcct gtgtgacccc tactcggcgg agagtccatc    180
cccacagggt ggcccaggta ggggaagggg agatgatggg caggtcaggg aaggggagc     240 ctagggcaa                                                             249

<210> SEQ ID NO 70
<211> LENGTH: 180
<212> TYPE: DNA
<213> ORGANISM: Homo sapiens

<400> SEQUENCE: 70
aggggcgagc cttttgagag agccctgtc aggcctggat ggctccctcc cctgcagacg      60
atgtgagcct actcagtcct ggggaagacg tgctcatcga cattgatgac aaggagcccc    120
tcatccccat ccaggtagga tgggcatcct ccagggaggc ctgggtcacc tttcccctcc    180
```

<210> SEQ ID NO 71
<211> LENGTH: 211
<212> TYPE: DNA
<213> ORGANISM: Homo sapiens

<400> SEQUENCE: 71

```
tgctgcttgg cgagtcctgt ttctgaaatg gtctctttct ttctacccac tcaggaggaa      60
gagttcatcg attggtggag caaattcttt gcctccatag gggagaggga aaagtgcggc     120
tcctacctgg agaaggattt tgacaccctg aaggtaaggc ctctcttcag tctgacagtc     180
ggtgtgtgtg tgcgtgctgg gcagtgggag a                                    211
```

<210> SEQ ID NO 72
<211> LENGTH: 235
<212> TYPE: DNA
<213> ORGANISM: Homo sapiens

<400> SEQUENCE: 72

```
gttctacttt ctttctgtct cttgtcccct cctctaatcc ccatgtgtgg caggtctatg      60
acacacagct ggagaatgtg gaggcctttg agggcctgtc tgactttgt aacaccttca     120
agctgtaccg gggcaagacg caggaggaga cagaagatcc atctgtgatt ggtgaattta     180
aggtaaatcc tcgaagacgt ccctaaccca ggtgggccta agactgtggt gttgg          235
```

<210> SEQ ID NO 73
<211> LENGTH: 268
<212> TYPE: DNA
<213> ORGANISM: Homo sapiens

<400> SEQUENCE: 73

```
ggggacacag ccaaaccata tcaacaatga tgataaaata aaattaaccc ttccttcttt      60
tcagggcctc ttcaaaattt atccctccc agaagaccca gccatcccca tgccccaag      120
acagttccac cagctggccg cccagggacc ccaggagtgc ttggtccgta tctacattgt     180
ccgagcattt ggcctgcagc ccaaggaccc caatggaaag gtaactttct agagccctca     240
cctccccaga gtagcaggct caggtaca                                        268
```

<210> SEQ ID NO 74
<211> LENGTH: 200
<212> TYPE: DNA
<213> ORGANISM: Homo sapiens

<400> SEQUENCE: 74

```
tttggaaagt gttttcacag aagtgttttg tctcctcctc cagtgtgatc cttacatcaa      60
gatctccata gggaagaaat cagtgagtga ccaggataac tacatcccct gcacgctgga     120
gcccgtattt ggaaagtaaa ttggggcatc ttgggtcttg gggtggagga gccagacagg     180
ataacccaca gtctagtggg                                                 200
```

<210> SEQ ID NO 75
<211> LENGTH: 263
<212> TYPE: DNA
<213> ORGANISM: Homo sapiens

<400> SEQUENCE: 75

```
cctgttccct tgggtgccct gtgttggctg acattcggga atctgcccct tcctgcagga      60
tgttcgagct gacctgcact ctgcctctgg agaaggacct aaagatcact ctctatgact     120
atgacctcct ctccaaggac gaaaagatcg gtgagacggt cgtcgacctg gagaacaggc     180
```

-continued

| | |
|---|---|
| tgctgtccaa gtttgggget cgctgtggac tcccacagac ctactgtgtg tacgtggatg | 240 |
| ggggctggct gcctgcttct ctg | 263 |

<210> SEQ ID NO 76
<211> LENGTH: 237
<212> TYPE: DNA
<213> ORGANISM: Homo sapiens

<400> SEQUENCE: 76

| | |
|---|---|
| aagcatctcg tctatgtctt gtgcttgctc ctcagctctg gaccgaacca gtggcgggac | 60 |
| cagctccgcc cctcccagct cctccacctc ttctgccagc agcatagagt caaggcacct | 120 |
| gtgtaccgga cagaccgtgt aatgtttcag gataaagaat attccattga agagataggt | 180 |
| gagctgccac atgaccccaa accatggtgg gctctcgctg tatccctccc tctctca | 237 |

<210> SEQ ID NO 77
<211> LENGTH: 245
<212> TYPE: DNA
<213> ORGANISM: Homo sapiens

<400> SEQUENCE: 77

| | |
|---|---|
| tctctcgctt ccccagctcc tgcaactttt ttgtgttctc tctggggcag aggctggcag | 60 |
| gatcccaaac ccacacctgg gcccagtgga ggagcgtctg gctctgcatg tgcttcagca | 120 |
| gcagggcctg gtcccggagc acgtggagtc acggcccctc tacagccccc tgcagccaga | 180 |
| catcgagcag gtaggacctt accttggtc ccagagtcct cgaactccag aagcccaacc | 240 |
| ccagg | 245 |

<210> SEQ ID NO 78
<211> LENGTH: 214
<212> TYPE: DNA
<213> ORGANISM: Homo sapiens

<400> SEQUENCE: 78

| | |
|---|---|
| ggtgcttggt aacagctggt taaatgagaa gggtggggag agaacggacc tgtctccgca | 60 |
| ggggaagctg gggaagctgc agatgtgggt cgacctattt ccgaaggccc tggggcggcc | 120 |
| tggacctccc ttcaacatca ccccacggag agccagaagg tgacttccca gccacaggct | 180 |
| ctgagctggg ctgaggggtg gggcgttgca gcct | 214 |

<210> SEQ ID NO 79
<211> LENGTH: 229
<212> TYPE: DNA
<213> ORGANISM: Homo sapiens

<400> SEQUENCE: 79

| | |
|---|---|
| ttcttaaggc cttcccatcc tttggtagga aatctaggtg gattagagtg atacctttcc | 60 |
| ccaggttttt cctgcgttgt attatctgga ataccagaga tgtgatcctg gatgacctga | 120 |
| gcctcacggg ggagaagatg agcgacattt atgtgaaagg gtagggagcc agcgtcctct | 180 |
| tgcctgtcca gcttcccgca gctcccgtgc tccctctggg ttgtgcaca | 229 |

<210> SEQ ID NO 80
<211> LENGTH: 261
<212> TYPE: DNA
<213> ORGANISM: Homo sapiens -continued

```
<400> SEQUENCE: 80
acgatgtata tactgtgttg gaaatcttaa tgagaactat tctctaaaaa catgtatgtc      60
tagttggatg attggctttg aagaacacaa gcaaaagaca gacgtgcatt atcgttccct     120
gggaggtgaa ggcaacttca actggaggtt cattttcccc ttcgactacc tgccagctga    180
gcaagtctgt accattgcca agaaggtcag tgtccttccg attccctgtg gtgccagcac    240
cagggcttct aaagttagcc t                                              261

<210> SEQ ID NO 81
<211> LENGTH: 234
<212> TYPE: DNA
<213> ORGANISM: Homo sapiens

<400> SEQUENCE: 81
tgcctctctc taactttgct tccttgcatc cttctctgtt cctcttccgg gtcaggatgc      60
cttctggagg ctggacaaga ctgagagcaa aatcccagca cgagtggtgt tccagatctg    120
ggacaatgac aagttctcct ttgatgattt tctggtgatt ttctgggtaa gcgctattgc    180
tagaatccca ttctgcacat gggggctgcc ccagaaccca cactgtgtgt ttat          234

<210> SEQ ID NO 82
<211> LENGTH: 297
<212> TYPE: DNA
<213> ORGANISM: Homo sapiens

<400> SEQUENCE: 82
ggctacaggc tggcagtgat cgagaaaccc ggccaaaaac cacctctctg ttgcaggctc      60
cctgcagctc gatctcaacc gcatgcccaa gccagccaag acagccaaga agtgctcctt    120
ggaccagctg gatgatgctt tccacccaga atggtttgtg tcccttttg agcagaaaac     180 agtgaagggc tggtggccct gtgtagcaga agagggtgag aagaaaatac tggcggtaag    240
tctacttcct ccagccccag tggagggcat ggggaagct tcttccatag aaattgt        297

<210> SEQ ID NO 83
<211> LENGTH: 237
<212> TYPE: DNA
<213> ORGANISM: Homo sapiens

<400> SEQUENCE: 83
cctggttact ctccaggcca ctgagcagag ccttcgtgcc cctaaccaag tgctctctgt      60
cccctcaggg caagctggaa atgaccttgg agattgtagc agagagtgag catgaggagc    120
ggcctgctgg ccagggccgg gatgagccca acatgaaccc taagcttgag acccaaggt     180 cagtgcccag cccctgagcc ccaatgccca caggtctggg ggtataggca cagtcca       237

<210> SEQ ID NO 84
<211> LENGTH: 252
<212> TYPE: DNA
<213> ORGANISM: Homo sapiens

<400> SEQUENCE: 84
ccctagtaaa ggatgcccag ttgactccgg gatctcgctt ccaggcgccc cgacacctcc      60
ttcctgtggt ttacctcccc atacaagacc atgaagttca tcctgtggcg gcgtttccgg    120
tgggccatca tcctcttcat catcctcttc atcctgctgc tgttcctggc catcttcatc    180
tacgccttcc cggtgagcag gcctgacgac actgtggtgg gggaactctg ggtctaatgg    240
gggagttcat ca                                                        252
```

-continued

<210> SEQ ID NO 85
<211> LENGTH: 391
<212> TYPE: DNA
<213> ORGANISM: Homo sapiens

<400> SEQUENCE: 85

| tggctgtgcc tgccccagtg ggatcaccat gggtccctgt ctcctccctc cctccagaac | 60 |
| tatgctgcca tgaagctggt gaagcccttc agctgaggac tctcctgccc tgtagaaggg | 120 |
| gccgtggggt ccctccagc atgggactgg cctgcctcct ccgcccagct cggcgagctc | 180 |
| ctccagacct cctaggcctg attgtcctgc agggtgggga agacagacag atggaccggc | 240 |
| ccacactccc agagttgcta acatggagct ctgagatcac cccacttcca tcatttcctt | 300 |
| ctcccccaac ccaacgcttt tttggatcag ctcagacata tttcagtata aaacagttgg | 360 |
| aaccacaaaa aaaaaaaaaa aaaaaaaaaa a | 391 |

<210> SEQ ID NO 86
<211> LENGTH: 51
<212> TYPE: PRT
<213> ORGANISM: Homo sapiens

<400> SEQUENCE: 86

Lys Lys Arg Thr Lys Val Ile Lys Asn Ser Val Asn Pro Val Trp Asn
 1               5                  10                  15

Glu Gly Phe Glu Trp Asp Leu Lys Gly Ile Pro Leu Asp Gln Gly Ser
            20                  25                  30

Glu Leu His Val Val Lys Asp His Glu Thr Met Gly Arg Asn Arg
        35                  40                  45

Phe Leu Gly
    50

<210> SEQ ID NO 87
<211> LENGTH: 45
<212> TYPE: PRT
<213> ORGANISM: Homo sapiens

<400> SEQUENCE: 87

Ser Lys Ile Leu Glu Lys Thr Ala Asn Pro Gln Trp Asn Gln Asn Ile
 1               5                  10                  15

Thr Leu Pro Ala Met Phe Pro Ser Met Cys Glu Lys Met Arg Ile Arg
            20                  25                  30

Ile Ile Asp Trp Asp Arg Leu Thr His Asn Asp Ile Val
        35                  40                  45

<210> SEQ ID NO 88
<211> LENGTH: 82
<212> TYPE: PRT
<213> ORGANISM: Homo sapiens

<400> SEQUENCE: 88

Gln Ala Arg Asp Leu Ala Ala Met Asp Lys Asp Ser Phe Ser Asp Pro
 1               5                  10                  15

Tyr Ala Ile Val Ser Phe Leu His Gln Ser Gln Lys Thr Val Val Val
            20                  25                  30

Lys Asn Thr Leu Asn Pro Thr Trp Asp Gln Thr Leu Ile Phe Tyr Glu
        35                  40                  45

Ile Glu Ile Phe Gly Glu Pro Ala Thr Val Ala Glu Gln Pro Pro Ser
    50                  55                  60

```
Ile Val Val Glu Leu Tyr Asp His Asp Thr Tyr Gly Ala Asp Glu Phe
 65                  70                  75                  80

Met Gly
```

<210> SEQ ID NO 89
<211> LENGTH: 79
<212> TYPE: PRT
<213> ORGANISM: Homo sapiens

<400> SEQUENCE: 89

```
Ile Tyr Ile Val Arg Ala Phe Gly Leu Gln Pro Lys Asp Pro Asn Gly
 1               5                  10                  15

Lys Cys Asp Pro Tyr Ile Lys Ile Ser Ile Gly Lys Lys Ser Val Ser
             20                  25                  30

Asp Gln Asp Asn Tyr Ile Pro Cys Thr Leu Glu Pro Val Phe Gly Lys
         35                  40                  45

Met Phe Glu Leu Thr Cys Thr Leu Pro Leu Glu Lys Asp Leu Lys Ile
     50                  55                  60

Thr Leu Tyr Asp Tyr Asp Leu Leu Ser Lys Asp Glu Lys Ile Gly
 65                  70                  75
```

<210> SEQ ID NO 90
<211> LENGTH: 152
<212> TYPE: DNA
<213> ORGANISM: Homo sapiens

<400> SEQUENCE: 90

```
acgatgtata tactgtgttg gaaatcttaa tgagaactat tctctaaaaa catgtatgtc     60
tagttggatg attggctttg aagaacacaa gcaaaagaca gacgtgcatt atcgttccct    120
gggaggtgaa ggcaacttca actggaggtt ca                                  152
```

<210> SEQ ID NO 91
<211> LENGTH: 56
<212> TYPE: DNA
<213> ORGANISM: Homo sapiens

<400> SEQUENCE: 91

```
gtcagtgtcc ttccgattcc ctgtggtgcc agcaccaggg cttctaaagt tagcct         56
```

<210> SEQ ID NO 92
<211> LENGTH: 55
<212> TYPE: DNA
<213> ORGANISM: Homo sapiens

<400> SEQUENCE: 92

```
tgcctctctc taactttgct tccttgcatc cttctctgtt cctcttccgg gtcag          55
```

<210> SEQ ID NO 93
<211> LENGTH: 68
<212> TYPE: DNA
<213> ORGANISM: Homo sapiens

<400> SEQUENCE: 93

```
gtaagcgcta ttgctagaat cccattctgc acatggggc tgccccagaa cccacactgt     60
gtgtttat                                                             68
```

<210> SEQ ID NO 94
<211> LENGTH: 56
<212> TYPE: DNA
<213> ORGANISM: Homo sapiens

```
<400> SEQUENCE: 94
ggctacaggc tggcagtgat cgagaaaccc ggccaaaaac cacctctctg ttgcag        56

<210> SEQ ID NO 95
<211> LENGTH: 62
<212> TYPE: DNA
<213> ORGANISM: Homo sapiens

<400> SEQUENCE: 95
gtaagtctac ttcctccagc cccagtggag ggcatggggg aagcttcttc catagaaatt   60
gt                                                                 62

<210> SEQ ID NO 96
<211> LENGTH: 68
<212> TYPE: DNA
<213> ORGANISM: Homo sapiens

<400> SEQUENCE: 96
cctggttact ctccaggcca ctgagcagag ccttcgtgcc cctaaccaag tgctctctgt   60
cccctcag                                                           68

<210> SEQ ID NO 97
<211> LENGTH: 59
<212> TYPE: DNA
<213> ORGANISM: Homo sapiens

<400> SEQUENCE: 97
gtcagtgccc agcccctgag ccccaatgcc cacaggtctg ggggtatagg cacagtcca    59

<210> SEQ ID NO 98
<211> LENGTH: 44
<212> TYPE: DNA
<213> ORGANISM: Homo sapiens

<400> SEQUENCE: 98
ccctagtaaa ggatgcccag ttgactccgg gatctcgctt ccag                   44

<210> SEQ ID NO 99
<211> LENGTH: 60
<212> TYPE: DNA
<213> ORGANISM: Homo sapiens

<400> SEQUENCE: 99
gtgagcaggc ctgacgacac tgtggtgggg gaactctggg tctaatgggg gagttcatca   60

<210> SEQ ID NO 100
<211> LENGTH: 57
<212> TYPE: DNA
<213> ORGANISM: Homo sapiens

<400> SEQUENCE: 100
tggctgtgcc tgccccagtg ggatcaccat gggtccctgt ctcctccctc cctccag      57

<210> SEQ ID NO 101
<211> LENGTH: 23
<212> TYPE: DNA
<213> ORGANISM: Homo sapiens

<400> SEQUENCE: 101
tctcttctcc tagagggcca tag                                          23
```

-continued

```
<210> SEQ ID NO 102
<211> LENGTH: 24
<212> TYPE: DNA
<213> ORGANISM: Homo sapiens

<400> SEQUENCE: 102
ctgttcctcc ccatcgtctc atgg                                          24

<210> SEQ ID NO 103
<211> LENGTH: 20
<212> TYPE: DNA
<213> ORGANISM: Homo sapiens

<400> SEQUENCE: 103
gctcctcccg tgaccctctg                                               20

<210> SEQ ID NO 104
<211> LENGTH: 21
<212> TYPE: DNA
<213> ORGANISM: Homo sapiens

<400> SEQUENCE: 104
gggtcccagc caggagcact g                                             21

<210> SEQ ID NO 105
<211> LENGTH: 24
<212> TYPE: DNA
<213> ORGANISM: Homo sapiens

<400> SEQUENCE: 105
cccctctcac catctcctga tgtg                                          24

<210> SEQ ID NO 106
<211> LENGTH: 25
<212> TYPE: DNA
<213> ORGANISM: Homo sapiens

<400> SEQUENCE: 106
tggcttcacc ttccctctac ctcgg                                         25

<210> SEQ ID NO 107
<211> LENGTH: 24
<212> TYPE: DNA
<213> ORGANISM: Homo sapiens

<400> SEQUENCE: 107
tcctttggta ggaaatctag gtgg                                          24

<210> SEQ ID NO 108
<211> LENGTH: 21
<212> TYPE: DNA
<213> ORGANISM: Homo sapiens

<400> SEQUENCE: 108
ggaagctgga caggcaagag g                                             21

<210> SEQ ID NO 109
<211> LENGTH: 27
<212> TYPE: DNA
<213> ORGANISM: Homo sapiens

<400> SEQUENCE: 109
atatactgtg ttggaaatct taatgag                                       27
```

<210> SEQ ID NO 110
<211> LENGTH: 21
<212> TYPE: DNA
<213> ORGANISM: Homo sapiens

<400> SEQUENCE: 110
gctggcacca cagggaatcg g                                              21

<210> SEQ ID NO 111
<211> LENGTH: 25
<212> TYPE: DNA
<213> ORGANISM: Homo sapiens

<400> SEQUENCE: 111
ctttgcttcc ttgcatcctt ctctg                                          25

<210> SEQ ID NO 112
<211> LENGTH: 21
<212> TYPE: DNA
<213> ORGANISM: Homo sapiens

<400> SEQUENCE: 112
agcccccatg tgcagaatgg g                                              21

<210> SEQ ID NO 113
<211> LENGTH: 21
<212> TYPE: DNA
<213> ORGANISM: Homo sapiens

<400> SEQUENCE: 113
ggcagtgatc gagaaacccg g                                              21

<210> SEQ ID NO 114
<211> LENGTH: 21
<212> TYPE: DNA
<213> ORGANISM: Homo sapiens

<400> SEQUENCE: 114
catgccctcc actggggctg g                                              21

<210> SEQ ID NO 115
<211> LENGTH: 21
<212> TYPE: DNA
<213> ORGANISM: Homo sapiens

<400> SEQUENCE: 115
ggatgcccag ttgactccgg g                                              21

<210> SEQ ID NO 116
<211> LENGTH: 21
<212> TYPE: DNA
<213> ORGANISM: Homo sapiens

<400> SEQUENCE: 116
ccccaccaca gtgtcgtcag g                                              21

<210> SEQ ID NO 117
<211> LENGTH: 6240
<212> TYPE: DNA
<213> ORGANISM: Homo sapiens

```
<400> SEQUENCE: 117
atgctgaggg tcttcatcct ctatgccgag aacgtccaca caccccgacac cgacatcagc      60
gatgcctact gctccgcggt gtttgcaggg gtgaagaaga gaaccaaagt catcaagaac     120
agcgtgaacc ctgtatggaa tgagggattt gaatgggacc tcaagggcat ccccctggac     180
cagggctctg agcttcatgt ggtggtcaaa gaccatgaga cgatggggag gaacaggttc     240
ctggggggaag ccaaggtccc actccgagag gtcctcgcca ccctagtct gtccgccagc     300
ttcaatgccc cctgctgga caccaagaag cagcccacag gggcctcgct ggtcctgcag     360
gtgtcctaca caccgctgcc tggagctgtg cccctgttcc cgcccctac tcctctggag     420
ccctccccga ctctgcctga cctggatgta gtggcagaca caggaggaga ggaagacaca     480
gaggaccagg gactcactgg agatgaggcg gagccattcc tggatcaaag cggaggcccg     540
ggggctccca ccaccccaag gaaactacct tcacgtcctc cgccccacta ccccgggatc     600
aaaagaaagc gaagtgcgcc tacatctaga aagctgctgt cagacaaacc gcaggatttc     660
cagatcaggg tccaggtgat cgaggggcgc cagctgccgg gggtgaacat caagcctgtg     720
gtcaaggtta ccgctgcagg gcagaccaag cggacgcgga tccacaaggg aaacagccca     780
ctcttcaatg agactctttt cttcaacttg tttgactctc ctggggagct gtttgatgag     840
cccatctta tcacggtggt agactctcgt tctctcagga cagatgctct cctcggggag     900
ttccggatgg acgtgggcac catttacaga gagccccggc acgcctatct caggaagtgg     960
ctgctgctct cagaccctga tgacttctct gctggggcca gaggctacct gaaaacaagc    1020
ctttgtgtgc tggggcctgg ggacgaagcg cctctggaga gaaaagaccc ctctgaagac    1080
aaggaggaca ttgaaagcaa cctgctccgg cccacaggcg tagccctgcg aggagcccac    1140
ttctgcctga aggtcttccg ggccgaggac ttgccgcaga tggacgatgc cgtgatggac    1200
aacgtgaaac agatctttgg cttcgagagt aacaagaaga acttggtgga cccctttgtg    1260
gaggtcagct ttgcggggaa aatgctgtgc agcaagatct tggagaagac ggccaaccct    1320
cagtggaacc agaacatcac actgcctgcc atgtttccct ccatgtgcga aaaaatgagg    1380
attcgtatca tagactggga ccgcctgact cacaatgaca tcgtggctac cacctacctg    1440
agtatgtcga aaatctctgc ccctggagga gaaatagaag aggagcctgc aggtgctgtc    1500
aagccttcga agcctcaga cttggatgac tacctgggct tcctccccac ttttgggccc    1560
tgctacatca acctctatgg cagtcccaga gagttcacag gcttcccaga ccctacaca    1620
gagctcaaca caggcaaggg ggaaggtgtg gcttatcgtg gccggcttct gctctccctg    1680
gagaccaagc tggtggagca cagtgaacag aaggtggagg accttcctgc ggatgacatc    1740
ctccgggtgg agaagtacct taggaggcgc aagtactccc tgtttgcggc cttctactca    1800
gccaccatgc tgcaggatgt ggatgatgcc atccagtttg aggtcagcat cgggaactac    1860
gggaacaagt tcgacatgac ctgcctgccg ctggcctcca ccactcagta cagccgtgca    1920
gtctttgacg ggtgccacta ctactaccta ccctgggta acgtgaaacc tgtggtggtg    1980
ctgtcatcct actgggagga catcagccat agaatcgaga ctcagaacca gctgcttggg    2040
attgctgacc ggctggaagc tggcctggag caggtccacc tggccctgaa ggcgcagtgc    2100
tccacggagg acgtggactc gctggtggct cagctgacgg atgagctcat cgcaggctgc    2160
agccagcctc tgggtgacat ccatgagaca ccctctgcca cccacctgga ccagtacctg    2220
taccagctgc gcacccatca cctgagccaa atcactgagg ctgccctggc cctgaagctc    2280
ggccacagtg agctccctgc agctctggag caggcggagg actggctcct gcgtctgcgt    2340
```

-continued

| | | | | |
|---|---|---|---|---|
| gccctggcag | aggagcccca | gaacagcctg | ccggacatcg | tcatctggat gctgcaggga | 2400 |
| gacaagcgtg | tggcatacca | gcgggtgccc | gcccaccaag | tcctcttctc ccggcgggt | 2460 |
| gccaactact | gtggcaagaa | ttgtgggaag | ctacagacaa | tctttctgaa atatccgatg | 2520 |
| gagaaggtgc | ctggcgcccg | gatgccagtg | cagatacggg | tcaagctgtg gtttgggctc | 2580 |
| tctgtggatg | agaaggagtt | caaccagttt | gctgagggga | agctgtctgt ctttgctgaa | 2640 |
| acctatgaga | acgagactaa | gttggccctt | gttgggaact | ggggcacaac gggcctcacc | 2700 |
| taccccaagt | tttctgacgt | cacgggcaag | atcaagctac | caaggacag cttccgcccc | 2760 |
| tcggccggct | ggacctgggc | tggagattgg | ttcgtgtgtc | cggagaagac tctgctccat | 2820 |
| gacatggacg | ccggtcacct | gagcttcgtg | aagaggtgt | ttgagaacca gacccggctt | 2880 |
| cccggaggcc | agtggatcta | catgagtgac | aactacaccg | atgtgaacgg ggagaaggtg | 2940 |
| cttcccaagg | atgacattga | gtgcccactg | ggctggaagt | gggaagatga ggaatggtcc | 3000 |
| acagacctca | accgggctgt | cgatgagcaa | ggctgggagt | atagcatcac catcccccccg | 3060 |
| gagcggaagc | cgaagcactg | ggtccctgct | gagaagatgt | actacacaca ccgacggcgg | 3120 |
| cgctgggtgc | gcctgcgcag | gagggatctc | agccaaatgg | aagcactgaa aaggcacagg | 3180 |
| caggcggagg | cggagggcga | gggctgggag | tacgcctctc | tttttggctg aagttccac | 3240 |
| ctcgagtacc | gcaagacaga | tgccttccgc | cgccgccgct | ggcgccgtcg catggagcca | 3300 |
| ctggagaaga | cggggcctgc | agctgtgttt | gcccttgagg | gggccctggg cggcgtgatg | 3360 |
| gatgacaaga | gtgaagattc | catgtccgtc | tccaccttga | gcttcggtgt gaacagaccc | 3420 |
| acgatttcct | gcatattcga | ctatgggaac | cgctaccatc | tacgctgcta catgtaccag | 3480 |
| gcccgggacc | tggctgcgat | ggacaaggac | tcttttcctg | atccctatgc catcgtctcc | 3540 |
| ttcctgcacc | agagccagaa | gacggtggtg | gtgaagaaca | cccttaaccc cacctgggac | 3600 |
| cagacgctca | tcttctacga | gatcgagatc | tttggcgagc | cggccacagt tgctgagcaa | 3660 |
| ccgcccagca | ttgtggtgga | gctgtacgac | catgacactt | atggtgcaga cgagtttatg | 3720 |
| ggtcgctgca | tctgtcaacc | gagtctggaa | cggatgccac | ggctggcctg gttcccactg | 3780 |
| acgaggggca | gccagccgtc | gggggagctg | ctggcctctt | ttgagctcat ccagagagag | 3840 |
| aagccggcca | tccaccatat | tcctggtttt | gaggtgcagg | agacatcaag gatcctggat | 3900 |
| gagtctgagg | acacagacct | gccctaccca | ccaccccaga | gggaggccaa catctacatg | 3960 |
| gttcctcaga | acatcaagcc | agcgctccag | cgtaccgcca | tcgagatcct ggcatggggc | 4020 |
| ctgcggaaca | tgaagagtta | ccagctggcc | aacatctcct | ccccagcct cgtggtagag | 4080 |
| tgtgggggcc | agacggtgca | gtcctgtgtc | atcaggaacc | tccggaagaa ccccaacttt | 4140 |
| gacatctgca | ccctcttcat | ggaagtgatg | ctgcccaggg | aggagctcta ctgccccccc | 4200 |
| atcaccgtca | aggtcatcga | taaccgccag | tttggccgcc | ggcctgtggt gggccagtgt | 4260 |
| accatccgct | ccctggagag | cttcctgtgt | gaccccttact | cggcggagag tccatcccca | 4320 |
| cagggtggcc | cagacgatgt | gagcctactc | agtcctgggg | aagacgtgct catcgacatt | 4380 |
| gatgacaagg | agcccctcat | ccccatccag | gaggaagagt | tcatcgattg gtggagcaaa | 4440 |
| ttctttgcct | ccatagggga | gagggaaaag | tgcggctcct | acctggagaa ggattttgac | 4500 |
| acccctgaagg | tctatgacac | acagctggag | aatgtggagg | cctttgaggg cctgtctgac | 4560 |
| ttttgtaaca | ccttcaagct | gtaccggggc | aagacgcagg | aggagacaga agatccatct | 4620 |
| gtgattggtg | aatttaaggg | cctcttcaaa | atttatcccc | tcccagaaga cccagccatc | 4680 |
| cccatgcccc | caagacagtt | ccaccagctg | ccgcccagg | accccagga gtgcttggtc | 4740 |

```
cgtatctaca ttgtccgagc atttggcctg cagcccaagg accccaatgg aaagtgtgat    4800
ccttacatca agatctccat agggaagaaa tcagtgagtg accaggataa ctacatcccc    4860
tgcacgctgg agcccgtatt tggaaagatg ttcgagctga cctgcactct gcctctggag    4920
aaggacctaa agatcactct ctatgactat gacctcctct ccaaggacga aagatcggt     4980 gagacggtcg tcgacctgga acaggctg ctgtccaagt ttggggctcg ctgtggactc      5040
ccacagacct actgtgtctc tggaccgaac cagtggcggg accagctccg cccctcccag    5100
ctcctccacc tcttctgcca gcagcataga gtcaaggcac ctgtgtaccg gacagaccgt    5160
gtaatgtttc aggataaaga atattccatt gaagagatag aggctggcag gatcccaaac    5220
ccacacctgg gcccagtgga ggagcgtctg gctctgcatg tgcttcagca gcagggcctg    5280
gtcccggagc acgtggagtc acggcccctc tacagccccc tgcagccaga catcgagcag    5340
gggaagctgc agatgtgggt cgacctattt ccgaaggccc tggggcggcc tggacctccc    5400
ttcaacatca ccccacggag agccagaagg ttttttcctgc gttgtattat ctggaatacc    5460
agagatgtga tcctggatga cctgagcctc acgggggaga agatgagcga catttatgtg    5520
aaaggttgga tgattggctt tgaagaacac aagcaaaaga cagacgtgca ttatcgttcc    5580
ctgggaggtg aaggcaactt caactggagg ttcatttttcc ccttcgacta cctgccagct    5640
gagcaagtct gtaccattgc caagaaggat gccttctgga ggctggacaa gactgagagc    5700
aaaatcccag cacgagtggt gttccagatc tgggacaatg acaagttctc ctttgatgat    5760
tttctgggct ccctgcagct cgatctcaac cgcatgccca gccagccaa gacagccaag    5820 aagtgctcct tggaccagct ggatgatgct ttccacccag aatggtttgt gtccctttttt    5880 gagcagaaaa cagtgaaggg ctggtggccc tgtgtagcag aagagggtga aagaaaata    5940 ctggcgggca agctggaaat gaccttggag attgtagcag agagtgagca tgaggagcgg    6000
cctgctggcc agggccggga tgagcccaac atgaaccta agcttgagga cccaaggcgc    6060
cccgacacct ccttcctgtg gtttacctcc ccatacaaga ccatgaagtt catcctgtgg    6120
cggcgtttcc ggtgggccat catcctcttc atcatcctct tcatcctgct gctgttcctg    6180
gccatcttca tctacgcctt cccgaactat gctgccatga agctggtgaa gcccttcagc    6240
```

<210> SEQ ID NO 118
<211> LENGTH: 13
<212> TYPE: DNA
<213> ORGANISM: Homo sapiens

<400> SEQUENCE: 118
cgcaagcatg ctg                                                       13

<210> SEQ ID NO 119
<211> LENGTH: 12
<212> TYPE: DNA
<213> ORGANISM: Homo sapiens

<400> SEQUENCE: 119
gagacgatgg gg                                                        12

<210> SEQ ID NO 120
<211> LENGTH: 21
<212> TYPE: DNA
<213> ORGANISM: Homo sapiens

<400> SEQUENCE: 120
gatctaaccc tgctgctcac c                                              21

-continued

```
<210> SEQ ID NO 121
<211> LENGTH: 21
<212> TYPE: DNA
<213> ORGANISM: Homo sapiens

<400> SEQUENCE: 121
ctggtgtgtt gcagagcgct g                                              21

<210> SEQ ID NO 122
<211> LENGTH: 21
<212> TYPE: DNA
<213> ORGANISM: Homo sapiens

<400> SEQUENCE: 122
cctctcttct gctgtcttca g                                              21

<210> SEQ ID NO 123
<211> LENGTH: 21
<212> TYPE: DNA
<213> ORGANISM: Homo sapiens

<400> SEQUENCE: 123
tgtgtctggt tcaccttcgt g                                              21

<210> SEQ ID NO 124
<211> LENGTH: 21
<212> TYPE: DNA
<213> ORGANISM: Homo sapiens

<400> SEQUENCE: 124
tccaaataga aatgcctgaa c                                              21

<210> SEQ ID NO 125
<211> LENGTH: 21
<212> TYPE: DNA
<213> ORGANISM: Homo sapiens

<400> SEQUENCE: 125
aggtatcacc tccaagtgtt g                                              21

<210> SEQ ID NO 126
<211> LENGTH: 21
<212> TYPE: DNA
<213> ORGANISM: Homo sapiens

<400> SEQUENCE: 126
taccagcttc agagctccct g                                              21

<210> SEQ ID NO 127
<211> LENGTH: 19
<212> TYPE: DNA
<213> ORGANISM: Homo sapiens

<400> SEQUENCE: 127
ttgatcaggg tgctcttgg                                                 19

<210> SEQ ID NO 128
<211> LENGTH: 20
<212> TYPE: DNA
<213> ORGANISM: Homo sapiens

<400> SEQUENCE: 128
ggagaattgc ttgaacccag                                                20
```

```
<210> SEQ ID NO 129
<211> LENGTH: 22
<212> TYPE: DNA
<213> ORGANISM: Homo sapiens

<400> SEQUENCE: 129
tggctaatga tgttgaacat tt                                          22

<210> SEQ ID NO 130
<211> LENGTH: 21
<212> TYPE: DNA
<213> ORGANISM: Homo sapiens

<400> SEQUENCE: 130
gacccacaag cggcgcctcg g                                           21

<210> SEQ ID NO 131
<211> LENGTH: 21
<212> TYPE: DNA
<213> ORGANISM: Homo sapiens

<400> SEQUENCE: 131
gaccccggcg agggtggtcg g                                           21

<210> SEQ ID NO 132
<211> LENGTH: 24
<212> TYPE: DNA
<213> ORGANISM: Homo sapiens

<400> SEQUENCE: 132
tgtctctcca ttctcccttt tgtg                                        24

<210> SEQ ID NO 133
<211> LENGTH: 24
<212> TYPE: DNA
<213> ORGANISM: Homo sapiens

<400> SEQUENCE: 133
aggacactgc tgagaaggca cctc                                        24

<210> SEQ ID NO 134
<211> LENGTH: 21
<212> TYPE: DNA
<213> ORGANISM: Homo sapiens

<400> SEQUENCE: 134
agtgccctgg tggcacgaag g                                           21

<210> SEQ ID NO 135
<211> LENGTH: 24
<212> TYPE: DNA
<213> ORGANISM: Homo sapiens

<400> SEQUENCE: 135
cctacctgca ccttcaagcc atgg                                        24

<210> SEQ ID NO 136
<211> LENGTH: 23
<212> TYPE: DNA
<213> ORGANISM: Homo sapiens

<400> SEQUENCE: 136
cagaagagcc agggtgcctt agg                                         23
```

```
<210> SEQ ID NO 137
<211> LENGTH: 24
<212> TYPE: DNA
<213> ORGANISM: Homo sapiens

<400> SEQUENCE: 137
ccttggacct taacctggca gagg                                              24

<210> SEQ ID NO 138
<211> LENGTH: 21
<212> TYPE: DNA
<213> ORGANISM: Homo sapiens

<400> SEQUENCE: 138
cgaggccagc gcaccaacct g                                                 21

<210> SEQ ID NO 139
<211> LENGTH: 22
<212> TYPE: DNA
<213> ORGANISM: Homo sapiens

<400> SEQUENCE: 139
actgccggcc attcttgctg gg                                                22

<210> SEQ ID NO 140
<211> LENGTH: 21
<212> TYPE: DNA
<213> ORGANISM: Homo sapiens

<400> SEQUENCE: 140
ccaggcctca ttagggccct c                                                 21

<210> SEQ ID NO 141
<211> LENGTH: 22
<212> TYPE: DNA
<213> ORGANISM: Homo sapiens

<400> SEQUENCE: 141
ctgaagagga gcctggggtc ag                                                22

<210> SEQ ID NO 142
<211> LENGTH: 24
<212> TYPE: DNA
<213> ORGANISM: Homo sapiens

<400> SEQUENCE: 142
ctgagatttc tgactcttgg ggtg                                              24

<210> SEQ ID NO 143
<211> LENGTH: 24
<212> TYPE: DNA
<213> ORGANISM: Homo sapiens

<400> SEQUENCE: 143
aaggttctgc cctcatgccc catg                                              24

<210> SEQ ID NO 144
<211> LENGTH: 21
<212> TYPE: DNA
<213> ORGANISM: Homo sapiens

<400> SEQUENCE: 144
ctggcctgag ggatcagcag g                                                 21
```

```
<210> SEQ ID NO 145
<211> LENGTH: 23
<212> TYPE: DNA
<213> ORGANISM: Homo sapiens

<400> SEQUENCE: 145
gtgcatacat acagcccacg gag                                              23

<210> SEQ ID NO 146
<211> LENGTH: 24
<212> TYPE: DNA
<213> ORGANISM: Homo sapiens

<400> SEQUENCE: 146
gagctattgg gttggccgtg tggg                                             24

<210> SEQ ID NO 147
<211> LENGTH: 24
<212> TYPE: DNA
<213> ORGANISM: Homo sapiens

<400> SEQUENCE: 147
accaacacgg agaagtgaga actg                                             24

<210> SEQ ID NO 148
<211> LENGTH: 26
<212> TYPE: DNA
<213> ORGANISM: Homo sapiens

<400> SEQUENCE: 148
ccacacttta tttaacgctt tggcgg                                           26

<210> SEQ ID NO 149
<211> LENGTH: 24
<212> TYPE: DNA
<213> ORGANISM: Homo sapiens

<400> SEQUENCE: 149
cagaaccaaa atgcaaggat acgg                                             24

<210> SEQ ID NO 150
<211> LENGTH: 25
<212> TYPE: DNA
<213> ORGANISM: Homo sapiens

<400> SEQUENCE: 150
cttctgattc tgggatcacc aaagg                                            25

<210> SEQ ID NO 151
<211> LENGTH: 22
<212> TYPE: DNA
<213> ORGANISM: Homo sapiens

<400> SEQUENCE: 151
ggaccgtaag gaagacccag gg                                               22

<210> SEQ ID NO 152
<211> LENGTH: 24
<212> TYPE: DNA
<213> ORGANISM: Homo sapiens

<400> SEQUENCE: 152
cctgtgctca ggagcgcatg aagg                                             24
```

```
<210> SEQ ID NO 153
<211> LENGTH: 22
<212> TYPE: DNA
<213> ORGANISM: Homo sapiens

<400> SEQUENCE: 153
gcagacctcc cacccaaggg cg                                            22

<210> SEQ ID NO 154
<211> LENGTH: 24
<212> TYPE: DNA
<213> ORGANISM: Homo sapiens

<400> SEQUENCE: 154
gagacagatg ggggacagtc aggg                                          24

<210> SEQ ID NO 155
<211> LENGTH: 21
<212> TYPE: DNA
<213> ORGANISM: Homo sapiens

<400> SEQUENCE: 155
cctcccgaga gaaccctcct g                                             21

<210> SEQ ID NO 156
<211> LENGTH: 21
<212> TYPE: DNA
<213> ORGANISM: Homo sapiens

<400> SEQUENCE: 156
gggagcccag agtccccatg g                                             21

<210> SEQ ID NO 157
<211> LENGTH: 21
<212> TYPE: DNA
<213> ORGANISM: Homo sapiens

<400> SEQUENCE: 157
gggcctcctt gggtttgctg g                                             21

<210> SEQ ID NO 158
<211> LENGTH: 21
<212> TYPE: DNA
<213> ORGANISM: Homo sapiens

<400> SEQUENCE: 158
gcctccccag catcctgccg g                                             21

<210> SEQ ID NO 159
<211> LENGTH: 24
<212> TYPE: DNA
<213> ORGANISM: Homo sapiens

<400> SEQUENCE: 159
tcactgagcc gaatgaaact gagg                                          24

<210> SEQ ID NO 160
<211> LENGTH: 24
<212> TYPE: DNA
<213> ORGANISM: Homo sapiens

<400> SEQUENCE: 160
tgtggcctga gttcctttcc tgtg                                          24
```

-continued

```
<210> SEQ ID NO 161
<211> LENGTH: 24
<212> TYPE: DNA
<213> ORGANISM: Homo sapiens

<400> SEQUENCE: 161
ggtcaaaggg cagaacgaag aggg                                          24

<210> SEQ ID NO 162
<211> LENGTH: 21
<212> TYPE: DNA
<213> ORGANISM: Homo sapiens

<400> SEQUENCE: 162
cccgtccttc tcccagccat g                                             21

<210> SEQ ID NO 163
<211> LENGTH: 21
<212> TYPE: DNA
<213> ORGANISM: Homo sapiens

<400> SEQUENCE: 163
ctcccctggt tgtccccaag g                                             21

<210> SEQ ID NO 164
<211> LENGTH: 24
<212> TYPE: DNA
<213> ORGANISM: Homo sapiens

<400> SEQUENCE: 164
cgacccctct gattgccact tgtg                                          24

<210> SEQ ID NO 165
<211> LENGTH: 21
<212> TYPE: DNA
<213> ORGANISM: Homo sapiens

<400> SEQUENCE: 165
ggcatcctgc ccttgccagg g                                             21

<210> SEQ ID NO 166
<211> LENGTH: 20
<212> TYPE: DNA
<213> ORGANISM: Homo sapiens

<400> SEQUENCE: 166
tctgtctccc ctgctccttg                                               20

<210> SEQ ID NO 167
<211> LENGTH: 21
<212> TYPE: DNA
<213> ORGANISM: Homo sapiens

<400> SEQUENCE: 167
cttccctgcc ccgacgccca g                                             21

<210> SEQ ID NO 168
<211> LENGTH: 21
<212> TYPE: DNA
<213> ORGANISM: Homo sapiens

<400> SEQUENCE: 168
cagcgctcag gcccgtctct c                                             21
```

```
<210> SEQ ID NO 169
<211> LENGTH: 24
<212> TYPE: DNA
<213> ORGANISM: Homo sapiens

<400> SEQUENCE: 169
tgcataggca tgtgcagctt tggg                                           24

<210> SEQ ID NO 170
<211> LENGTH: 21
<212> TYPE: DNA
<213> ORGANISM: Homo sapiens

<400> SEQUENCE: 170
catgcaccct ctgccctgtg g                                              21

<210> SEQ ID NO 171
<211> LENGTH: 21
<212> TYPE: DNA
<213> ORGANISM: Homo sapiens

<400> SEQUENCE: 171
agttgagcca ggagaggtgg g                                              21

<210> SEQ ID NO 172
<211> LENGTH: 24
<212> TYPE: DNA
<213> ORGANISM: Homo sapiens

<400> SEQUENCE: 172
catcaggcgc attccatctg tccg                                           24

<210> SEQ ID NO 173
<211> LENGTH: 24
<212> TYPE: DNA
<213> ORGANISM: Homo sapiens

<400> SEQUENCE: 173
agcaggagag cagaagaaga aagg                                           24

<210> SEQ ID NO 174
<211> LENGTH: 22
<212> TYPE: DNA
<213> ORGANISM: Homo sapiens

<400> SEQUENCE: 174
gtgtgtcacc atccccaccc cg                                             22

<210> SEQ ID NO 175
<211> LENGTH: 25
<212> TYPE: DNA
<213> ORGANISM: Homo sapiens

<400> SEQUENCE: 175
caagagatgg gagaaaggcc ttatg                                          25

<210> SEQ ID NO 176
<211> LENGTH: 23
<212> TYPE: DNA
<213> ORGANISM: Homo sapiens

<400> SEQUENCE: 176
ctgggacatc cggatcctga agg                                            23
```

-continued

```
<210> SEQ ID NO 177
<211> LENGTH: 22
<212> TYPE: DNA
<213> ORGANISM: Homo sapiens

<400> SEQUENCE: 177
tccaggtagt gggaggcaga gg                                            22

<210> SEQ ID NO 178
<211> LENGTH: 24
<212> TYPE: DNA
<213> ORGANISM: Homo sapiens

<400> SEQUENCE: 178
tcccactacc tggagctgcc ttgg                                          24

<210> SEQ ID NO 179
<211> LENGTH: 21
<212> TYPE: DNA
<213> ORGANISM: Homo sapiens

<400> SEQUENCE: 179
ggctctcccc agccctccct g                                             21

<210> SEQ ID NO 180
<211> LENGTH: 24
<212> TYPE: DNA
<213> ORGANISM: Homo sapiens

<400> SEQUENCE: 180
cagagcagca gagactctga ccag                                          24

<210> SEQ ID NO 181
<211> LENGTH: 21
<212> TYPE: DNA
<213> ORGANISM: Homo sapiens

<400> SEQUENCE: 181
tagaccccac ctgcccctga g                                             21

<210> SEQ ID NO 182
<211> LENGTH: 24
<212> TYPE: DNA
<213> ORGANISM: Homo sapiens

<400> SEQUENCE: 182
tcctctcatt gcttgcctgt tcgg                                          24

<210> SEQ ID NO 183
<211> LENGTH: 21
<212> TYPE: DNA
<213> ORGANISM: Homo sapiens

<400> SEQUENCE: 183
ttgagagctt gccggggatg g                                             21

<210> SEQ ID NO 184
<211> LENGTH: 24
<212> TYPE: DNA
<213> ORGANISM: Homo sapiens

<400> SEQUENCE: 184
aagtgccaag caatgagtga ccgg                                          24
```

-continued

```
<210> SEQ ID NO 185
<211> LENGTH: 21
<212> TYPE: DNA
<213> ORGANISM: Homo sapiens

<400> SEQUENCE: 185
ctcactccca cccaccacct g                                           21

<210> SEQ ID NO 186
<211> LENGTH: 21
<212> TYPE: DNA
<213> ORGANISM: Homo sapiens

<400> SEQUENCE: 186
cccaccggcc tctgagtctg c                                           21

<210> SEQ ID NO 187
<211> LENGTH: 24
<212> TYPE: DNA
<213> ORGANISM: Homo sapiens

<400> SEQUENCE: 187
accctaccca agccaggaca agtg                                        24

<210> SEQ ID NO 188
<211> LENGTH: 24
<212> TYPE: DNA
<213> ORGANISM: Homo sapiens

<400> SEQUENCE: 188
gaatctgcca taaccagctt cgtg                                        24

<210> SEQ ID NO 189
<211> LENGTH: 24
<212> TYPE: DNA
<213> ORGANISM: Homo sapiens

<400> SEQUENCE: 189
tatcacccca tagaggcctc gaag                                        24

<210> SEQ ID NO 190
<211> LENGTH: 24
<212> TYPE: DNA
<213> ORGANISM: Homo sapiens

<400> SEQUENCE: 190
cagccactca ctctggcacc tctg                                        24

<210> SEQ ID NO 191
<211> LENGTH: 24
<212> TYPE: DNA
<213> ORGANISM: Homo sapiens

<400> SEQUENCE: 191
agcccacagt ctctgactct cctg                                        24

<210> SEQ ID NO 192
<211> LENGTH: 24
<212> TYPE: DNA
<213> ORGANISM: Homo sapiens

<400> SEQUENCE: 192
acatctctca gggtccctgc tgtg                                        24
```

```
<210> SEQ ID NO 193
<211> LENGTH: 21
<212> TYPE: DNA
<213> ORGANISM: Homo sapiens

<400> SEQUENCE: 193
cctgtgaggg gacgaggcag g                                              21

<210> SEQ ID NO 194
<211> LENGTH: 24
<212> TYPE: DNA
<213> ORGANISM: Homo sapiens

<400> SEQUENCE: 194
gccctgggta agggatgctg attc                                           24

<210> SEQ ID NO 195
<211> LENGTH: 21
<212> TYPE: DNA
<213> ORGANISM: Homo sapiens

<400> SEQUENCE: 195
cctgcctggg cctcctggat c                                              21

<210> SEQ ID NO 196
<211> LENGTH: 21
<212> TYPE: DNA
<213> ORGANISM: Homo sapiens

<400> SEQUENCE: 196
gagggtgatg ggggccttag g                                              21

<210> SEQ ID NO 197
<211> LENGTH: 24
<212> TYPE: DNA
<213> ORGANISM: Homo sapiens

<400> SEQUENCE: 197
gcaatcagtt tgaagaagga aagg                                           24

<210> SEQ ID NO 198
<211> LENGTH: 24
<212> TYPE: DNA
<213> ORGANISM: Homo sapiens

<400> SEQUENCE: 198
cacctttgtc tccattctac ctgc                                           24

<210> SEQ ID NO 199
<211> LENGTH: 21
<212> TYPE: DNA
<213> ORGANISM: Homo sapiens

<400> SEQUENCE: 199
ctcccagccc ccacgcccag g                                              21

<210> SEQ ID NO 200
<211> LENGTH: 24
<212> TYPE: DNA
<213> ORGANISM: Homo sapiens

<400> SEQUENCE: 200
ctgagccact ctcctcattc tgtg                                           24
```

-continued

```
<210> SEQ ID NO 201
<211> LENGTH: 21
<212> TYPE: DNA
<213> ORGANISM: Homo sapiens

<400> SEQUENCE: 201
tggaagggga cagtagggag g                                              21

<210> SEQ ID NO 202
<211> LENGTH: 22
<212> TYPE: DNA
<213> ORGANISM: Homo sapiens

<400> SEQUENCE: 202
ggccagtgcg ttcttcctcc tc                                             22

<210> SEQ ID NO 203
<211> LENGTH: 22
<212> TYPE: DNA
<213> ORGANISM: Homo sapiens

<400> SEQUENCE: 203
tccctgacct gcccatcatc tc                                             22

<210> SEQ ID NO 204
<211> LENGTH: 21
<212> TYPE: DNA
<213> ORGANISM: Homo sapiens

<400> SEQUENCE: 204
gcccctgtca ggcctggatg g                                              21

<210> SEQ ID NO 205
<211> LENGTH: 21
<212> TYPE: DNA
<213> ORGANISM: Homo sapiens

<400> SEQUENCE: 205
tgacccaggc ctccctggag g                                              21

<210> SEQ ID NO 206
<211> LENGTH: 24
<212> TYPE: DNA
<213> ORGANISM: Homo sapiens

<400> SEQUENCE: 206
ctgaaatggt ctctttcttt ctac                                           24

<210> SEQ ID NO 207
<211> LENGTH: 24
<212> TYPE: DNA
<213> ORGANISM: Homo sapiens

<400> SEQUENCE: 207
cacaccgact gtcagactga agag                                           24

<210> SEQ ID NO 208
<211> LENGTH: 24
<212> TYPE: DNA
<213> ORGANISM: Homo sapiens

<400> SEQUENCE: 208
ttgtcccctc ctctaatccc catg                                           24
```

-continued

```
<210> SEQ ID NO 209
<211> LENGTH: 21
<212> TYPE: DNA
<213> ORGANISM: Homo sapiens

<400> SEQUENCE: 209
gggttaggga cgtcttcgag g                                            21

<210> SEQ ID NO 210
<211> LENGTH: 22
<212> TYPE: DNA
<213> ORGANISM: Homo sapiens

<400> SEQUENCE: 210
cagccaaacc atatcaacaa tg                                           22

<210> SEQ ID NO 211
<211> LENGTH: 21
<212> TYPE: DNA
<213> ORGANISM: Homo sapiens

<400> SEQUENCE: 211
ctggggaggt gagggctcta g                                            21

<210> SEQ ID NO 212
<211> LENGTH: 21
<212> TYPE: DNA
<213> ORGANISM: Homo sapiens

<400> SEQUENCE: 212
gaagtgtttt gtctcctcct c                                            21

<210> SEQ ID NO 213
<211> LENGTH: 20
<212> TYPE: DNA
<213> ORGANISM: Homo sapiens

<400> SEQUENCE: 213
gcaggcagcc agcccccatc                                              20

<210> SEQ ID NO 214
<211> LENGTH: 21
<212> TYPE: DNA
<213> ORGANISM: Homo sapiens

<400> SEQUENCE: 214
gggtgccctg tgttggctga c                                            21

<210> SEQ ID NO 215
<211> LENGTH: 20
<212> TYPE: DNA
<213> ORGANISM: Homo sapiens

<400> SEQUENCE: 215
gcaggcagcc agcccccatc                                              20

<210> SEQ ID NO 216
<211> LENGTH: 24
<212> TYPE: DNA
<213> ORGANISM: Homo sapiens

<400> SEQUENCE: 216
ctcgtctatg tcttgtgctt gctc                                         24
```

-continued

```
<210> SEQ ID NO 217
<211> LENGTH: 23
<212> TYPE: DNA
<213> ORGANISM: Homo sapiens

<400> SEQUENCE: 217
caccatggtt tggggtcatg tgg                                              23

<210> SEQ ID NO 218
<211> LENGTH: 21
<212> TYPE: DNA
<213> ORGANISM: Homo sapiens

<400> SEQUENCE: 218
tctcgcttcc ccagctcctg c                                                21

<210> SEQ ID NO 219
<211> LENGTH: 22
<212> TYPE: DNA
<213> ORGANISM: Homo sapiens

<400> SEQUENCE: 219
tctggagttc gaggactctg gg                                               22

<210> SEQ ID NO 220
<211> LENGTH: 21
<212> TYPE: DNA
<213> ORGANISM: Homo sapiens

<400> SEQUENCE: 220
agaagggtgg ggagagaacg g                                                21

<210> SEQ ID NO 221
<211> LENGTH: 21
<212> TYPE: DNA
<213> ORGANISM: Homo sapiens

<400> SEQUENCE: 221
cagctcagag cctgtggctg g                                                21

<210> SEQ ID NO 222
<211> LENGTH: 24
<212> TYPE: DNA
<213> ORGANISM: Homo sapiens

<400> SEQUENCE: 222
aaggccttcc catcctttgg tagg                                             24

<210> SEQ ID NO 223
<211> LENGTH: 21
<212> TYPE: DNA
<213> ORGANISM: Homo sapiens

<400> SEQUENCE: 223
acaacccaga gggagcacgg g                                                21

<210> SEQ ID NO 224
<211> LENGTH: 25
<212> TYPE: DNA
<213> ORGANISM: Homo sapiens

<400> SEQUENCE: 224
gttgacgatg tatatactgt gttgg                                            25
```

```
<210> SEQ ID NO 225
<211> LENGTH: 25
<212> TYPE: DNA
<213> ORGANISM: Homo sapiens

<400> SEQUENCE: 225
gcctctctct aactttgctt ccttg                                          25

<210> SEQ ID NO 226
<211> LENGTH: 24
<212> TYPE: DNA
<213> ORGANISM: Homo sapiens

<400> SEQUENCE: 226
ggctacaggc tggcagtgat cgag                                           24

<210> SEQ ID NO 227
<211> LENGTH: 21
<212> TYPE: DNA
<213> ORGANISM: Homo sapiens

<400> SEQUENCE: 227
ttcccccatg ccctccactg g                                              21

<210> SEQ ID NO 228
<211> LENGTH: 24
<212> TYPE: DNA
<213> ORGANISM: Homo sapiens

<400> SEQUENCE: 228
agccttcgtg cccctaacca agtg                                           24

<210> SEQ ID NO 229
<211> LENGTH: 21
<212> TYPE: DNA
<213> ORGANISM: Homo sapiens

<400> SEQUENCE: 229
ctgtgggcat tggggctcag g                                              21

<210> SEQ ID NO 230
<211> LENGTH: 20
<212> TYPE: DNA
<213> ORGANISM: Homo sapiens

<400> SEQUENCE: 230
gccccagtgg gatcaccatg                                                20

<210> SEQ ID NO 231
<211> LENGTH: 21
<212> TYPE: DNA
<213> ORGANISM: Homo sapiens

<400> SEQUENCE: 231
atgctggagg ggaccccacg g                                              21

<210> SEQ ID NO 232
<211> LENGTH: 3671
<212> TYPE: DNA
<213> ORGANISM: Homo sapiens
<220> FEATURE:
<221> NAME/KEY: CDS
<222> LOCATION: (418)...(3381)
```

<400> SEQUENCE: 232

```
tcctggttca agcgattctc tggcctcagc ctcccgagta gctgggatta caggcatgct     60
ccaccaagcc cgggtaattt tgtatttta atagagacgg ggttttgcca tgttggtcag    120
gctggtctcg aactcctgac ctcaggtgat ctgcccacct tggcctccca acgtgctgag    180
attacaggca tgagtcactg tgcccggcag agatggtcta attcatatga aagaactctg    240
aaaaaagtag aaagtgattt tctaaaataa ggtacaaata attaatgtaa gcataatcac    300
ctaaccttgt ggaattttt ttttttgaga agcaaattgc aaatttgtga tagatctaaa    360
ggagattgac taagagggtg accatctgga aatgacgtca tgtgagaatg gttaaag atg    420
                                                                Met
                                                                  1
```

| | | | | | | | | | | | | | | | |
|---|---|---|---|---|---|---|---|---|---|---|---|---|---|---|---|
| ctc | ggg | aga | ttg | agc | cta | gag | aaa | gga | aga | ttt | gtg | aac | cca | gga | ggc | 468 |
| Leu | Gly | Arg | Leu | Ser | Leu | Glu | Lys | Gly | Arg | Phe | Val | Asn | Pro | Gly | Gly | |
| | | | 5 | | | | 10 | | | | | 15 | | | | |

```
aga ggt aga gat cca gga gag ggc ggc gtg atg gat gac aag agt gaa   516
Arg Gly Arg Asp Pro Gly Glu Gly Gly Val Met Asp Asp Lys Ser Glu
         20              25                  30 gat tcc atg tcc gtc tcc acc ttg agc ttc ggt gtg aac aga ccc acg   564
Asp Ser Met Ser Val Ser Thr Leu Ser Phe Gly Val Asn Arg Pro Thr
 35              40                  45 att tcc tgc ata ttc gac tat ggg aac cgc tac cat cta cgc tgc tac   612
Ile Ser Cys Ile Phe Asp Tyr Gly Asn Arg Tyr His Leu Arg Cys Tyr
 50                  55                  60                  65 atg tac cag gcc cgg gac ctg gct gcg atg gac aag gac tct ttt tct   660
Met Tyr Gln Ala Arg Asp Leu Ala Ala Met Asp Lys Asp Ser Phe Ser
             70                  75                  80 gat ccc tat gcc atc gtc tcc ttc ctg cac cag agc cag aag acg gtg   708
Asp Pro Tyr Ala Ile Val Ser Phe Leu His Gln Ser Gln Lys Thr Val
                 85                  90                  95 gtg gtg aag aac acc ctt aac ccc acc tgg gac cag acg ctc atc ttc   756
Val Val Lys Asn Thr Leu Asn Pro Thr Trp Asp Gln Thr Leu Ile Phe
                100                 105                 110 tac gag atc gag atc ttt ggc gag ccg gcc aca gtt gct gag caa ccg   804
Tyr Glu Ile Glu Ile Phe Gly Glu Pro Ala Thr Val Ala Glu Gln Pro
            115                 120                 125 ccc agc att gtg gtg gag ctg tac gac cat gac act tat ggt gca gac   852
Pro Ser Ile Val Val Glu Leu Tyr Asp His Asp Thr Tyr Gly Ala Asp
130                 135                 140                 145 gag ttt atg ggt cgc tgc atc tgt caa ccg agt ctg gaa cgg atg cca   900
Glu Phe Met Gly Arg Cys Ile Cys Gln Pro Ser Leu Glu Arg Met Pro
                150                 155                 160 cgg ctg gcc tgg ttc cca ctg acg agg ggc agc cag ccg tcg ggg gag   948
Arg Leu Ala Trp Phe Pro Leu Thr Arg Gly Ser Gln Pro Ser Gly Glu
            165                 170                 175 ctg ctg gcc tct ttt gag ctc atc cag aga gag aag ccg gcc atc cac   996
Leu Leu Ala Ser Phe Glu Leu Ile Gln Arg Glu Lys Pro Ala Ile His
        180                 185                 190 cat att cct ggt ttt gag gtg cag gag aca tca agg atc ctg gat gag   1044
His Ile Pro Gly Phe Glu Val Gln Glu Thr Ser Arg Ile Leu Asp Glu
    195                 200                 205 tct gag gac aca gac ctg ccc tac cca cca ccc cag agg gag gcc aac   1092
Ser Glu Asp Thr Asp Leu Pro Tyr Pro Pro Pro Gln Arg Glu Ala Asn
210                 215                 220                 225 atc tac atg gtt cct cag aac atc aag cca gcg ctc cag cgt acc gcc   1140
Ile Tyr Met Val Pro Gln Asn Ile Lys Pro Ala Leu Gln Arg Thr Ala
                230                 235                 240
```

-continued

| | |
|---|---|
| atc gag atc ctg gca tgg ggc ctg cgg aac atg aag agt tac cag ctg<br>Ile Glu Ile Leu Ala Trp Gly Leu Arg Asn Met Lys Ser Tyr Gln Leu<br>245                    250                    255 | 1188 |
| gcc aac atc tcc tcc ccc agc ctc gtg gta gag tgt ggg ggc cag acg<br>Ala Asn Ile Ser Ser Pro Ser Leu Val Val Glu Cys Gly Gly Gln Thr<br>260                    265                    270 | 1236 |
| gtg cag tcc tgt gtc atc agg aac ctc cgg aag aac ccc aac ttt gac<br>Val Gln Ser Cys Val Ile Arg Asn Leu Arg Lys Asn Pro Asn Phe Asp<br>275                    280                    285 | 1284 |
| atc tgc acc ctc ttc atg gaa gtg atg ctg ccc agg gag gag ctc tac<br>Ile Cys Thr Leu Phe Met Glu Val Met Leu Pro Arg Glu Glu Leu Tyr<br>290                    295                    300                    305 | 1332 |
| tgc ccc ccc atc acc gtc aag gtc atc gat aac cgc cag ttt ggc cgc<br>Cys Pro Pro Ile Thr Val Lys Val Ile Asp Asn Arg Gln Phe Gly Arg<br>310                    315                    320 | 1380 |
| cgg cct gtg gtg ggc cag tgt acc atc cgc tcc ctg gag agc ttc ctg<br>Arg Pro Val Val Gly Gln Cys Thr Ile Arg Ser Leu Glu Ser Phe Leu<br>325                    330                    335 | 1428 |
| tgt gac ccc tac tcg gcg gag agt cca tcc cca cag ggt ggc cca gac<br>Cys Asp Pro Tyr Ser Ala Glu Ser Pro Ser Pro Gln Gly Gly Pro Asp<br>340                    345                    350 | 1476 |
| gat gtg agc cta ctc agt cct ggg gaa gac gtg ctc atc gac att gat<br>Asp Val Ser Leu Leu Ser Pro Gly Glu Asp Val Leu Ile Asp Ile Asp<br>355                    360                    365 | 1524 |
| gac aag gag ccc ctc atc ccc atc cag gag gaa gag ttc atc gat tgg<br>Asp Lys Glu Pro Leu Ile Pro Ile Gln Glu Glu Glu Phe Ile Asp Trp<br>370                    375                    380                    385 | 1572 |
| tgg agc aaa ttc ttt gcc tcc ata ggg gag agg gaa aag tgc ggc tcc<br>Trp Ser Lys Phe Phe Ala Ser Ile Gly Glu Arg Glu Lys Cys Gly Ser<br>390                    395                    400 | 1620 |
| tac ctg gag aag gat ttt gac acc ctg aag gtc tat gac aca cag ctg<br>Tyr Leu Glu Lys Asp Phe Asp Thr Leu Lys Val Tyr Asp Thr Gln Leu<br>405                    410                    415 | 1668 |
| gag aat gtg gag gcc ttt gag ggc ctg tct gac ttt tgt aac acc ttc<br>Glu Asn Val Glu Ala Phe Glu Gly Leu Ser Asp Phe Cys Asn Thr Phe<br>420                    425                    430 | 1716 |
| aag ctg tac cgg ggc aag acg cag gag gag aca gaa gat cca tct gtg<br>Lys Leu Tyr Arg Gly Lys Thr Gln Glu Glu Thr Glu Asp Pro Ser Val<br>435                    440                    445 | 1764 |
| att ggt gaa ttt aag ggc ctc ttc aaa att tat ccc ctc cca gaa gac<br>Ile Gly Glu Phe Lys Gly Leu Phe Lys Ile Tyr Pro Leu Pro Glu Asp<br>450                    455                    460                    465 | 1812 |
| cca gcc atc ccc atg ccc cca aga cag ttc cac cag ctg gcc gcc cag<br>Pro Ala Ile Pro Met Pro Pro Arg Gln Phe His Gln Leu Ala Ala Gln<br>470                    475                    480 | 1860 |
| gga ccc cag gag tgc ttg gtc cgt atc tac att gtc cga gca ttt ggc<br>Gly Pro Gln Glu Cys Leu Val Arg Ile Tyr Ile Val Arg Ala Phe Gly<br>485                    490                    495 | 1908 |
| ctg cag ccc aag gac ccc aat gga aag tgt gat cct tac atc aag atc<br>Leu Gln Pro Lys Asp Pro Asn Gly Lys Cys Asp Pro Tyr Ile Lys Ile<br>500                    505                    510 | 1956 |
| tcc ata ggg aag aaa tca gtg agt gac cag gat aac tac atc ccc tgc<br>Ser Ile Gly Lys Lys Ser Val Ser Asp Gln Asp Asn Tyr Ile Pro Cys<br>515                    520                    525 | 2004 |
| acg ctg gag ccc gta ttt gga aag atg ttc gag ctg acc tgc act ctg<br>Thr Leu Glu Pro Val Phe Gly Lys Met Phe Glu Leu Thr Cys Thr Leu<br>530                    535                    540                    545 | 2052 |
| cct ctg gag aag gac cta aag atc act ctc tat gac tat gac ctc ctc<br>Pro Leu Glu Lys Asp Leu Lys Ile Thr Leu Tyr Asp Tyr Asp Leu Leu<br>550                    555                    560 | 2100 |

```
                                                     -continued tcc aag gac gaa aag atc ggt gag acg gtc gtc gac ctg gag aac agg        2148
Ser Lys Asp Glu Lys Ile Gly Glu Thr Val Val Asp Leu Glu Asn Arg
            565                 570                 575 ctg ctg tcc aag ttt ggg gct cgc tgt gga ctc cca cag acc tac tgt        2196
Leu Leu Ser Lys Phe Gly Ala Arg Cys Gly Leu Pro Gln Thr Tyr Cys
        580                 585                 590 gtc tct gga ccg aac cag tgg cgg gac cag ctc cgc ccc tcc cag ctc        2244
Val Ser Gly Pro Asn Gln Trp Arg Asp Gln Leu Arg Pro Ser Gln Leu
    595                 600                 605 ctc cac ctc ttc tgc cag cag cat aga gtc aag gca cct gtg tac cgg        2292
Leu His Leu Phe Cys Gln Gln His Arg Val Lys Ala Pro Val Tyr Arg
610                 615                 620                 625 aca gac cgt gta atg ttt cag gat aaa gaa tat tcc att gaa gag ata        2340
Thr Asp Arg Val Met Phe Gln Asp Lys Glu Tyr Ser Ile Glu Glu Ile
                630                 635                 640 gag gct ggc agg atc cca aac cca cac ctg ggc cca gtg gag gag cgt        2388
Glu Ala Gly Arg Ile Pro Asn Pro His Leu Gly Pro Val Glu Glu Arg
            645                 650                 655 ctg gct ctg cat gtg ctt cag cag cag ggc ctg gtc ccg gag cac gtg        2436
Leu Ala Leu His Val Leu Gln Gln Gln Gly Leu Val Pro Glu His Val
        660                 665                 670 gag tca cgg ccc ctc tac agc ccc ctg cag cca gac atc gag cag ggg        2484
Glu Ser Arg Pro Leu Tyr Ser Pro Leu Gln Pro Asp Ile Glu Gln Gly
    675                 680                 685 aag ctg cag atg tgg gtc gac cta ttt ccg aag gcc ctg ggg cgg cct        2532
Lys Leu Gln Met Trp Val Asp Leu Phe Pro Lys Ala Leu Gly Arg Pro
690                 695                 700                 705 gga cct ccc ttc aac atc acc cca cgg aga gcc aga agg ttt ttc ctg        2580
Gly Pro Pro Phe Asn Ile Thr Pro Arg Arg Ala Arg Arg Phe Phe Leu
                710                 715                 720 cgt tgt att atc tgg aat acc aga gat gtg atc ctg gat gac ctg agc        2628
Arg Cys Ile Ile Trp Asn Thr Arg Asp Val Ile Leu Asp Asp Leu Ser
            725                 730                 735 ctc acg ggg gag aag atg agc gac att tat gtg aaa ggt tgg atg att        2676
Leu Thr Gly Glu Lys Met Ser Asp Ile Tyr Val Lys Gly Trp Met Ile
        740                 745                 750 ggc ttt gaa gaa cac aag caa aag aca gac gtg cat tat cgt tcc ctg        2724
Gly Phe Glu Glu His Lys Gln Lys Thr Asp Val His Tyr Arg Ser Leu
    755                 760                 765 gga ggt gaa ggc aac ttc aac tgg agg ttc att ttc ccc ttc gac tac        2772
Gly Gly Glu Gly Asn Phe Asn Trp Arg Phe Ile Phe Pro Phe Asp Tyr
770                 775                 780                 785 ctg cca gct gag caa gtc tgt acc att gcc aag aag gat gcc ttc tgg        2820
Leu Pro Ala Glu Gln Val Cys Thr Ile Ala Lys Lys Asp Ala Phe Trp
                790                 795                 800 agg ctg gac aag act gag agc aaa atc cca gca cga gtg gtg ttc cag        2868
Arg Leu Asp Lys Thr Glu Ser Lys Ile Pro Ala Arg Val Val Phe Gln
            805                 810                 815 atc tgg gac aat gac aag ttc tcc ttt gat gat ttt ctg ggc tcc ctg        2916
Ile Trp Asp Asn Asp Lys Phe Ser Phe Asp Asp Phe Leu Gly Ser Leu
        820                 825                 830 cag ctc gat ctc aac cgc atg ccc aag cca gcc aag aca gcc aag aag        2964
Gln Leu Asp Leu Asn Arg Met Pro Lys Pro Ala Lys Thr Ala Lys Lys
    835                 840                 845 tgc tcc ttg gac cag ctg gat gat gct ttc cac cca gaa tgg ttt gtg        3012
Cys Ser Leu Asp Gln Leu Asp Asp Ala Phe His Pro Glu Trp Phe Val
850                 855                 860                 865 tcc ctt ttt gag cag aaa aca gtg aag ggc tgg tgg ccc tgt gta gca        3060
Ser Leu Phe Glu Gln Lys Thr Val Lys Gly Trp Trp Pro Cys Val Ala
                870                 875                 880
```

```
gaa gag ggt gag aag aaa ata ctg gcg ggc aag ctg gaa atg acc ttg    3108
Glu Glu Gly Glu Lys Lys Ile Leu Ala Gly Lys Leu Glu Met Thr Leu
            885                 890                 895 gag att gta gca gag agt gag cat gag gag cgg cct gct ggc cag ggc    3156
Glu Ile Val Ala Glu Ser Glu His Glu Glu Arg Pro Ala Gly Gln Gly
        900                 905                 910 cgg gat gag ccc aac atg aac cct aag ctt gag gac cca agg cgc ccc    3204
Arg Asp Glu Pro Asn Met Asn Pro Lys Leu Glu Asp Pro Arg Arg Pro
    915                 920                 925 gac acc tcc ttc ctg tgg ttt acc tcc cca tac aag acc atg aag ttc    3252
Asp Thr Ser Phe Leu Trp Phe Thr Ser Pro Tyr Lys Thr Met Lys Phe
930                 935                 940                 945 atc ctg tgg cgg cgt ttc cgg tgg gcc atc atc ctc ttc atc atc ctc    3300
Ile Leu Trp Arg Arg Phe Arg Trp Ala Ile Ile Leu Phe Ile Ile Leu
                950                 955                 960 ttc atc ctg ctg ctg ttc ctg gcc atc ttc atc tac gcc ttc ccg aac    3348
Phe Ile Leu Leu Leu Phe Leu Ala Ile Phe Ile Tyr Ala Phe Pro Asn
            965                 970                 975 tat gct gcc atg aag ctg gtg aag ccc ttc agc tgaggactct cctgccctgt   3401
Tyr Ala Ala Met Lys Leu Val Lys Pro Phe Ser
        980                 985 agaaggggcc gtggggtccc ctccagcatg ggactggcct gcctcctccg cccagctcgg   3461
cgagctcctc cagacctcct aggcctgatt gtcctgccag ggtgggcaga cagacagatg   3521
gaccggccca cactcccaga gttgctaaca tggagctctg agatcacccc acttccatca   3581
tttccttctc ccccaaccca acgcttttt ggatcagctc agacatattt cagtataaaa    3641
cagttggaac acaaaaaaa aaaaaaaaaa                                     3671

<210> SEQ ID NO 233
<211> LENGTH: 988
<212> TYPE: PRT
<213> ORGANISM: Homo sapiens

<400> SEQUENCE: 233

Met Leu Gly Arg Leu Ser Leu Glu Lys Gly Arg Phe Val Asn Pro Gly
 1               5                  10                  15

Gly Arg Gly Arg Asp Pro Gly Glu Gly Gly Val Met Asp Asp Lys Ser
            20                  25                  30

Glu Asp Ser Met Ser Val Ser Thr Leu Ser Phe Gly Val Asn Arg Pro
        35                  40                  45

Thr Ile Ser Cys Ile Phe Asp Tyr Gly Asn Arg Tyr His Leu Arg Cys
    50                  55                  60

Tyr Met Tyr Gln Ala Arg Asp Leu Ala Ala Met Asp Lys Asp Ser Phe
65                  70                  75                  80

Ser Asp Pro Tyr Ala Ile Val Ser Phe Leu His Gln Ser Gln Lys Thr
                85                  90                  95

Val Val Val Lys Asn Thr Leu Asn Pro Thr Trp Asp Gln Thr Leu Ile
            100                 105                 110

Phe Tyr Glu Ile Glu Ile Phe Gly Glu Pro Ala Thr Val Ala Glu Gln
        115                 120                 125

Pro Pro Ser Ile Val Val Glu Leu Tyr Asp His Asp Thr Tyr Gly Ala
    130                 135                 140

Asp Glu Phe Met Gly Arg Cys Ile Cys Gln Pro Ser Leu Glu Arg Met
145                 150                 155                 160

Pro Arg Leu Ala Trp Phe Pro Leu Thr Arg Gly Ser Gln Pro Ser Gly
                165                 170                 175
```

-continued

```
Glu Leu Leu Ala Ser Phe Glu Leu Ile Gln Arg Glu Lys Pro Ala Ile
            180                 185                 190

His His Ile Pro Gly Phe Glu Val Gln Glu Thr Ser Arg Ile Leu Asp
            195                 200                 205

Glu Ser Glu Asp Thr Asp Leu Pro Tyr Pro Pro Gln Arg Glu Ala
    210                 215                 220

Asn Ile Tyr Met Val Pro Gln Asn Ile Lys Pro Ala Leu Gln Arg Thr
225                 230                 235                 240

Ala Ile Glu Ile Leu Ala Trp Gly Leu Arg Asn Met Lys Ser Tyr Gln
            245                 250                 255

Leu Ala Asn Ile Ser Ser Pro Ser Leu Val Val Glu Cys Gly Gly Gln
            260                 265                 270

Thr Val Gln Ser Cys Val Ile Arg Asn Leu Arg Lys Asn Pro Asn Phe
            275                 280                 285

Asp Ile Cys Thr Leu Phe Met Glu Val Met Leu Pro Arg Glu Glu Leu
            290                 295                 300

Tyr Cys Pro Pro Ile Thr Val Lys Val Ile Asp Asn Arg Gln Phe Gly
305                 310                 315                 320

Arg Arg Pro Val Val Gly Gln Cys Thr Ile Arg Ser Leu Glu Ser Phe
            325                 330                 335

Leu Cys Asp Pro Tyr Ser Ala Glu Ser Pro Ser Pro Gln Gly Gly Pro
            340                 345                 350

Asp Asp Val Ser Leu Leu Ser Pro Gly Glu Asp Val Leu Ile Asp Ile
            355                 360                 365

Asp Asp Lys Glu Pro Leu Ile Pro Ile Gln Glu Glu Phe Ile Asp
            370                 375                 380

Trp Trp Ser Lys Phe Phe Ala Ser Ile Gly Glu Arg Glu Lys Cys Gly
385                 390                 395                 400

Ser Tyr Leu Glu Lys Asp Phe Asp Thr Leu Lys Val Tyr Asp Thr Gln
            405                 410                 415

Leu Glu Asn Val Glu Ala Phe Glu Gly Leu Ser Asp Phe Cys Asn Thr
            420                 425                 430

Phe Lys Leu Tyr Arg Gly Lys Thr Gln Glu Glu Thr Glu Asp Pro Ser
            435                 440                 445

Val Ile Gly Glu Phe Lys Gly Leu Phe Lys Ile Tyr Pro Leu Pro Glu
    450                 455                 460

Asp Pro Ala Ile Pro Met Pro Pro Arg Gln Phe His Gln Leu Ala Ala
465                 470                 475                 480

Gln Gly Pro Gln Glu Cys Leu Val Arg Ile Tyr Ile Val Arg Ala Phe
            485                 490                 495

Gly Leu Gln Pro Lys Asp Pro Asn Gly Lys Cys Asp Pro Tyr Ile Lys
            500                 505                 510

Ile Ser Ile Gly Lys Lys Ser Val Ser Asp Gln Asp Asn Tyr Ile Pro
            515                 520                 525

Cys Thr Leu Glu Pro Val Phe Gly Lys Met Phe Glu Leu Thr Cys Thr
            530                 535                 540

Leu Pro Leu Glu Lys Asp Leu Lys Ile Thr Leu Tyr Asp Tyr Asp Leu
545                 550                 555                 560

Leu Ser Lys Asp Glu Lys Ile Gly Glu Thr Val Val Asp Leu Glu Asn
            565                 570                 575

Arg Leu Leu Ser Lys Phe Gly Ala Arg Cys Gly Leu Pro Gln Thr Tyr
            580                 585                 590
```

-continued

```
Cys Val Ser Gly Pro Asn Gln Trp Arg Asp Gln Leu Arg Pro Ser Gln
            595                 600                 605

Leu Leu His Leu Phe Cys Gln Gln His Arg Val Lys Ala Pro Val Tyr
        610                 615                 620

Arg Thr Asp Arg Val Met Phe Gln Asp Lys Glu Tyr Ser Ile Glu Glu
625                 630                 635                 640

Ile Glu Ala Gly Arg Ile Pro Asn Pro His Leu Gly Pro Val Glu Glu
                645                 650                 655

Arg Leu Ala Leu His Val Leu Gln Gln Gln Gly Leu Val Pro Glu His
            660                 665                 670

Val Glu Ser Arg Pro Leu Tyr Ser Pro Leu Gln Pro Asp Ile Glu Gln
        675                 680                 685

Gly Lys Leu Gln Met Trp Val Asp Leu Phe Pro Lys Ala Leu Gly Arg
    690                 695                 700

Pro Gly Pro Pro Phe Asn Ile Thr Pro Arg Arg Ala Arg Arg Phe Phe
705                 710                 715                 720

Leu Arg Cys Ile Ile Trp Asn Thr Arg Asp Val Ile Leu Asp Asp Leu
                725                 730                 735

Ser Leu Thr Gly Glu Lys Met Ser Asp Ile Tyr Val Lys Gly Trp Met
            740                 745                 750

Ile Gly Phe Glu Glu His Lys Gln Lys Thr Asp Val His Tyr Arg Ser
        755                 760                 765

Leu Gly Gly Glu Gly Asn Phe Asn Trp Arg Phe Ile Phe Pro Phe Asp
    770                 775                 780

Tyr Leu Pro Ala Glu Gln Val Cys Thr Ile Ala Lys Lys Asp Ala Phe
785                 790                 795                 800

Trp Arg Leu Asp Lys Thr Glu Ser Lys Ile Pro Ala Arg Val Val Phe
                805                 810                 815

Gln Ile Trp Asp Asn Asp Lys Phe Ser Phe Asp Phe Leu Gly Ser
            820                 825                 830

Leu Gln Leu Asp Leu Asn Arg Met Pro Lys Pro Ala Lys Thr Ala Lys
        835                 840                 845

Lys Cys Ser Leu Asp Gln Leu Asp Asp Ala Phe His Pro Glu Trp Phe
    850                 855                 860

Val Ser Leu Phe Glu Gln Lys Thr Val Lys Gly Trp Trp Pro Cys Val
865                 870                 875                 880

Ala Glu Glu Gly Glu Lys Lys Ile Leu Ala Gly Lys Leu Glu Met Thr
                885                 890                 895

Leu Glu Ile Val Ala Glu Ser Glu His Glu Glu Arg Pro Ala Gly Gln
            900                 905                 910

Gly Arg Asp Glu Pro Asn Met Asn Pro Lys Leu Glu Asp Pro Arg Arg
        915                 920                 925

Pro Asp Thr Ser Phe Leu Trp Phe Thr Ser Pro Tyr Lys Thr Met Lys
    930                 935                 940

Phe Ile Leu Trp Arg Arg Phe Arg Trp Ala Ile Ile Leu Phe Ile Ile
945                 950                 955                 960

Leu Phe Ile Leu Leu Leu Phe Leu Ala Ile Phe Ile Tyr Ala Phe Pro
                965                 970                 975

Asn Tyr Ala Ala Met Lys Leu Val Lys Pro Phe Ser
            980                 985
```

US 6,673,909 B1

OLIGONUCLEOTIDES FOR DYSFERLIN, A GENE MUTATED IN DISTAL MYOPATHY AND LIMB GIRDLE MUSCULAR DYSTROPHY

RELATED APPLICATION INFORMATION

This application claims priority from provisional application serial No. 60/097,927, filed Aug. 25, 1998.

STATEMENT AS TO FEDERALLY SPONSORED RESEARCH

The work described herein was supported in part by NIH grants 5P01AG12992, 5R01N834913A, and 5P01NS31248. The Federal Government therefore may have certain rights in the invention.

BACKGROUND OF THE INVENTION

The invention relates to genes involved in the onset of muscular dystrophy.

Muscular dystrophies constitute a heterogeneous group of disorders. Most are characterized by weakness and atrophy of the proximal muscles, although in rare myopathies such as "Miyoshi myopathy" symptoms may first arise in distal muscles. Of the various hereditary types of muscular dystrophy, several are caused by mutations or deletions in genes encoding individual components of the dystrophin-associated protein (DAP) complex. It is this DAP complex that links the cytoskeletal protein dystrophin to the extracellular matrix protein, laminin-2.

Muscular dystrophies may be classified according to the gene mutations that are associated with specific clinical syndromes. For example, mutations in the gene encoding the cytoskeletal protein dystrophin result in either Duchenne's Muscular Dystrophy or Becker's Muscular Dystrophy, whereas mutations in the gene encoding the extracellular matrix protein merosin produce Congenital Muscular Dystrophy. Muscular dystrophies with an autosomal recessive mode of inheritance include "Miyoshi myopathy" and the several limb-girdle muscular dystrophies (LGMD2). Of the limb-girdle muscular dystrophies, the deficiencies resulting in LGMD2C, D, E, and F result from mutations in genes encoding the membrane-associated sarcoglycan components of the DAP complex.

SUMMARY OF THE INVENTION

A novel protein, designated dysferlin, is identified and characterized. The dysferlin gene is normally expressed in skeletal muscle cells and is selectively mutated in several families with the hereditary muscular dystrophies, e.g., Miyoshi myopathy (MM) and limb girdle muscular dystrophy-2B (LGMD2B). These characteristics of dysferlin render it a candidate disease gene for both MM and LGMD2B. An additional novel protein, brain-specific dysferlin, has also been identified. Defects in brain-specific dysferlin may predispose to selected disorders of the central nervous system. Moreover, the expression of brain-specific dysferlin may be important as a marker for normal neural development (e.g., in vivo or in neural cells in culture). Manipulation of levels of expression of brain-specific dysferlin, and of the type of expressed brain-specific dysferlin is of use for analyzing the function of brain-specific dysferlin and related dysferlin-associated molecules.

The invention features an isolated DNA which includes a nucleotide sequence hybridizing under stringent hybridization conditions to a strand of SEQ ID NO:3 or SEQ ID NO:117. SEQ ID NO:117 corresponds to nucleotides 374–6613 of wild type dysferlin.

The invention also features an isolated DNA including a nucleotide sequence selected from SEQ ID NOs:4–12. SEQ ID NOs:4–12 are oligonucleotides that span the mutations of 537insA, Q605X, 5966delG, E1883X, 6391+1G to A, I1298V, R2042C, H1857R, and 6071/2delAG, respectively (Table 2).

Also within the invention is an isolated DNA comprising a nucleotide sequence selected from the group consisting of SEQ ID NOs:22–30.

Also within the invention is an isolated DNA comprising a nucleotide sequence selected from the group consisting of SEQ ID NOs:22–30. SEQ ID NOs:22–30 are oligonucleotides with wild type sequences that span the mutant regions identified in the mutants 537inSA, Q605X, 5966delG, E1883X, 6391+1G to A, I1298V, R2042C, H1857R, and 6071/2delAG, respectively (Table 2).

Also within the invention is a pair of PCR primers consisting of:
(a) a first single stranded oligonucleotide consisting of 14–50 contiguous nucleotides of the sense strand of SEQ ID NO:117; and
(b) a second single stranded oligonucleotide consisting of 14–50 contiguous nucleotides of the antisense strand of SEQ ID NO:117, wherein the sequence of at least one of the oligonucleotides is identical to a portion of a strand of SEQ ID NO:3, and the first oligonucleotide is not complementary to the second oligonucleotide.

Also within the invention is a pair of single stranded oligonucleotides selected from of SEQ ID NOs 130–231, SEQ ID NO:110, and SEQ ID NO:112.

Also within the invention is an isolated DNA including a nucleotide sequence that encodes a protein that shares at least 70% sequence identity with SEQ ID NO:2, or a complement of the nucleotide sequence.

Also within the invention is an isolated DNA including a nucleotide sequence which hybridizes under stringent hybridization conditions to a strand of a nucleic acid, the nucleic acid having a sequence selected from SEQ ID NOs:31–79 and 90–100. SEQ ID NOs:90–100 are intron sequences from a dysferlin gene. Specifically, SEQ ID NOs:90–100 are intron sequence 5' of exon 50, intron sequence 3' of exon 50, intron sequence 5' of exon 51, intron sequence 3' of exon 51, intron sequence 5' of exon 52, intron sequence 3' of exon 52, intron sequence 5' of exon 53, intron sequence 3' of exon 53, intron sequence 5' of exon 54, intron sequence 3' of exon 54, and intron sequence 5' of exon 55.

Also within the invention is a single stranded oligonucleotide of 14–50 nucleotides in length having a nucleotide sequence which is identical to a portion of a strand of a nucleic acid selected from SEQ ID NOs:31–79 and 90–100.

Also within the invention is a pair of PCR primers consisting of:
(a) a first single stranded oligonucleotide consisting of 14–50 contiguous nucleotides of the sense strand of a nucleic acid selected from SEQ ID NOs:31–85; and
(b) a second single stranded oligonucleotide consisting of 14–50 contiguous nucleotides of the antisense strand of a nucleic acid selected from SEQ ID NOs:31–85, wherein the sequence of at least one of the oligonucleotides includes a sequence identical to a portion of a strand of a nucleic acid selected from SEQ ID NOs: 31–79 and 90–100, and the first oligonucleotide is not complementary to the second oligonucleotide.

Also within the invention is a pair of single stranded oligonucleotides selected from SEQ ID NOs 101–116, SEQ ID NOs 184–185, SEQ ID NOs 188–191, SEQ ID NOs 210–213, and SEQ ID NOs 216–217.

Also within the invention is a substantially pure protein that has an amino acid sequence sharing at least 70% sequence identity with SEQ ID NO:2.

Also within the invention is a substantially pure protein the sequence of which includes amino acid residues 1–500, 501–1000, 1001–1500, or 1501–2080 of SEQ ID NO:2.

Also within the invention is a substantially pure protein including the amino acid sequence of SEQ ID NO:86, SEQ ID NO:87, SEQ ID NO:88, or SEQ ID NO:89.

In another aspect, the invention features a transgenic non-human mammal having a transgene disrupting or interfering with the expression of a dysferlin gene, the transgene being chromosomally integrated into the germ cells of the animal.

Another embodiment of the invention features a method of decreasing the symptoms of muscular dystrophy in a mammal by introducing into a cell of the mammal (e.g., a muscle cell or a muscle precursor cell) an isolated DNA which hybridizes under stringent hybridization conditions to a strand of SEQ ID NO:3.

Another aspect of the invention provides a method for identifying a patient, a fetus, or a pre-embryo at risk for having a dysferlin-related disorder by (a) providing a sample of genomic DNA from the patient, fetus, or pre-embryo; and (b) determining whether the sample contains a mutation in a dysferlin gene.

In another aspect, the invention provides a method for identifying a patient, a fetus, or a pre-embryo at risk for having a dysferlin-related disorder by (a) providing a sample including dysferlin mRNA from the patient, fetus, or pre-embryo; and (b) determining whether the dysferlin mRNA contains a mutation.

Methods of identifying mutations in a dysferlin sequence are useful for predicting (e.g., predicting whether an individual is at risk for developing a dysferlin-related disorder) or diagnosing disorders associated with dysferlin, e.g., MM and LGMD2B. Such methods can also be used to determine if an individual, fetus, or a pre-embryo is a carrier of a dysferlin mutation, for example in screening procedures. Methods which distinguish between different dysferlin alleles (e.g., a mutant dysferlin allele and a normal dysferlin allele) can be used to determine carrier status.

The invention also features an isolated nucleic acid comprising a nucleotide sequence which hybridizes under stringent hybridization conditions to nucleic acids 3284–3720 of SEQ ID NO:232, or the complement of the nucleotide sequence. An isolated nucleic acid including a nucleotide sequence identical to the sequence of nucleotides 3284–3720 of SEQ ID NO:232, or a complement of the nucleotide sequence is also a feature of the invention. The isolated nucleic acid can include the entire sequence of SEQ ID NO:232 or the complement of SEQ ID NO:232.

Another aspect of the invention features an isolated polypeptide that includes: a) at least 15 contiguous amino acids of the polypeptide comprising amino acids 1–24 of SEQ ID NO:233, b) a naturally occuring allelic variant of a polypeptide comprising amino acids 1–24 of SEQ ID NO:233, or c) an amino acid sequence which is encoded by a nucleic acid molecule which hybridizes under stringent conditions to nucleotides 3284–3720 of SEQ ID NO:232. The polypeptide of this aspect can include the entire sequence of SEQ ID NO:233.

Also included in the invention is a vector comprising the nucleic acid of claim 44 and a cell that contains the vector. Another aspect of the invention features a method of making a polypeptide by culturing the cell which contains the vector.

The invention also features an antibody which specifically binds to a polypeptide of such as those described above. The antibody can bind to a polypeptide selected from amino acids 253–403 of SEQ ID NO:233, amino acids 624–865 of SEQ ID NO:233, and amino acids 1664–1786 of SEQ ID NO:233. Antibodies of the invention can be monclonal or polyclonal antibodies.

An "isolated DNA" is DNA which has a naturally occurring sequence corresponding to part or all of a given gene but is free of the two genes that normally flank the given gene in the genome of the organism in which the given gene naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment, as well as a recombinant nucleotide sequence that is part of a hybrid gene, i.e., a gene encoding a fusion protein. The term excludes intact chromosomes and large genomic segments containing multiple genes contained in vectors or constructs such as cosmids, yeast artificial chromosomes (YACs), and P1-derived artificial chromosome (PAC) contigs.

A "noncoding sequence" is a sequence which corresponds to part or all of an intron of a gene, or to a sequence which is 5' or 3' to a coding sequence and so is not normally translated.

An expression control sequence is "operably linked" to a coding sequence when it is within the same nucleic acid and can control expression of the coding sequence.

A "protein" or "polypeptide" is any chain of amino acids linked by peptide bonds, regardless of length or post-translational modification, e.g., glycosylation or phosphorylation.

As used herein, the term "percent sequence identity" means the percentage of identical subunits at corresponding positions in two sequences when the two sequences are aligned to maximize subunit matching, i.e., taking into account gaps and insertions. For purposes of the present invention, percent sequence identity between two polypeptides is to be determined using the Gap program and the default parameters as specified therein. The Gap program is part of the Sequence Analysis Software Package of the Genetics Computer Group, University of Wisconsin Biotechnology Center, 1710 University Avenue, Madison, Wis. 53705.

The algorithm of Myers and Miller, CABIOS (1989) can also be used to determine whether two sequences are similar or identical. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

As used herein, the term "stringent hybridization conditions" means the following DNA hybridization and wash conditions: hybridization at 60° C. in the presence of 6×SSC, 0.5% SDS, 5×Denhardt's Reagent, and 100 $\mu$g/ml denatured salmon sperm DNA; followed by a first wash at room temperature for 20 minutes in 0.5×SSC and 0.1% SDS and a second wash at 55° C. for 30 minutes in 0.2×SSC and 0.1% SDS.

A "substantially pure protein" is a protein separated from components that naturally accompany it. The protein is considered to be substantially pure when it is at least 60%, by dry weight, free from the proteins and other naturally-occurring organic molecules with which it is naturally associated. Preferably, the purity of the preparation is at least 75%, more preferably at least 90%, and most preferably at least 99%, by weight. A substantially pure dysferlin protein can be obtained, for example, by extraction from a natural source, by expression of a recombinant nucleic acid encoding a dysferlin polypeptide, or by chemical synthesis. Purity can be measured by any appropriate method, e.g., column chromatography, polyacrylamide gel electrophoresis, or HPLC analysis. A chemically synthesized protein or a recombinant protein produced in a cell type other than the cell type in which it naturally occurs is, by definition, substantially free from components that naturally accompany it. Accordingly, substantially pure proteins include those having sequences derived from eukaryotic organisms but which have been recombinantly produced in *E. coli* or other prokaryotes.

An antibody that "specifically binds" to an antigen is an antibody that recognizes and binds to the antigen, e.g., a dysferlin polypeptide, but which does not substantially recognize and bind to other molecules in a sample (e.g., a biological sample) which naturally includes the antigen, e.g., a dysferlin polypeptide. An antibody that "specifically binds" to dysferlin is sufficient to detect a dysferlin polypeptide in a biological sample using one or more standard immunological techniques (for example, Western blotting or immunoprecipitation).

A "transgene" is any piece of DNA, other than an intact chromosome, which is inserted by artifice into a cell, and becomes part of the genome of the organism which develops from that cell. Such a transgene may include a gene which is partly or entirely heterologous (i.e., foreign) to the host organism, or may represent a gene homologous to an endogenous gene of the organism.

Unless otherwise defined, all technical and scientific terms used herein have the same meaning as commonly understood by one of ordinary skill in the art to which this invention belongs. Methods and materials similar or equivalent to those described herein can be used in the practice or testing of the present invention. The present materials, methods, and examples are illustrative only and not intended to be limiting. All publications, patent applications, patents, and other references mentioned herein are incorporated by reference in their entirety. In case of conflict, the present specification, including definitions, will control. All the sequences disclosed in the sequence listing are meant to be double-stranded except the sequences of oligonucleotides.

Other features and advantages of the invention will be apparent from the following detailed description, and from the claims.

DESCRIPTION OF THE DRAWINGS

FIG. 1B is a representation of the dysferlin cDNA clones. The probes used in the three successive screens are shown in bold (130347, cDNA10, A27-F2R2). The two most 5' cDNA clones are also shown (B22, B33). The 6.9 kb cDNA for dysferlin (SEQ ID NO:1) is illustrated at the bottom with start and stop codons as shown.

FIG. 1C is a representation of the predicted dysferlin protein. The locations of four C2 domains (SEQ ID NOS: 86–89) are indicated by stippled boxes, while the putative transmembrane region is hatched. Vertical lines above the cDNA denote the positions of the mutations in Table 2; the associated labels indicate the phenotypes (MM—Miyoshi myopathy; LGMD—limb girdle muscular dystrophy; DMAT—distal myopathy with anterior tibial onset).

FIG. 2 is the sequence of the predicted 2,080 amino acids of dysferlin (SEQ ID NO:2). The predicted membrane spanning residues are in bold at the carboxy terminus (residues 2047–2063). Partial C2 domains are underlined. Bold, underlined sequences are putative nuclear targeting residues. Possible membrane retention sequences are enclosed within a box.

FIG. 5 is a representation of the genomic structure of dysferlin. The 55 exons of the dysferlin gene and their corresponding SEQ ID NOs are indicated below the 6911 bp cDNA (solid line). The cDNA sequences corresponding to SEQ ID NO:1 and SEQ ID NO:3 are shown relative to the 6911 bp cDNA.

FIGS. 6A–D are the cDNA sequence of brain-specific dysferlin (SEQ ID NO:232) and the predicted amino acid sequence (in single-letter code) of brain-specific dysferlin (SEQ ID NO:233).

DETAILED DESCRIPTION

Figure 1A:
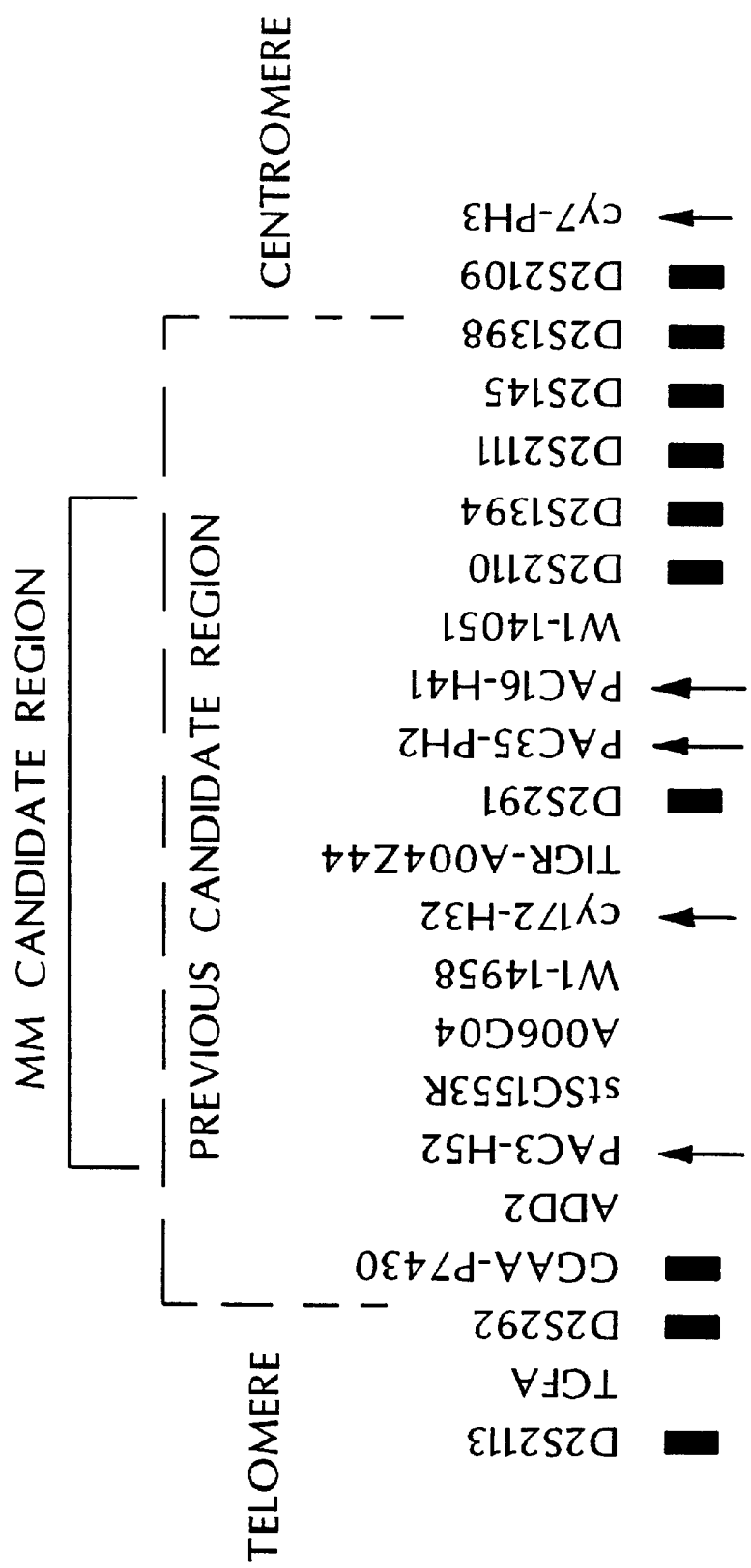
FIG. 1A is a physical map of the MM locus. Arrows indicate the five new polymorphic markers and filled, vertical rectangular boxes indicate the previously known polymorphic markers. The five ESTs that are expressed in skeletal muscle are highlighted in bold. Detailed information on the minimal tiling path of the PAC contig spanning the MM/LGMD2B region is provided in Liu et al., 1998, *Genomics* 49:23–29. The minimal candidate MM region is designated by the solid bracket (top) and compared to the previous candidate region (dashed bracket). TGFA and ADD2 are transforming growth factor alpha and β-adducin 2.

The Miyoshi myopathy (MM) locus maps to human chromosome 2p12-14 between the genetic markers D2S292 and D2S286 (Bejaoui et al., 1995, *Neurology* 45:768–72). Further refined genetic mapping in MM families placed the MM locus between markers GGAA-P7430 and D2S2109 (Bejaoui et al., 1998, *Neurogenetics* 1:189–96). Independent investigation has localized the limb-girdle muscular dystrophy (LGMD-2B) to the same genetic interval (Bashir et al., 1994, *Hum. Molec. Genetics* 3:455–57; Bashir et al., 1996, *Genomics* 33:46–52; Passos-Bueno et al., 1995, *Genomics* 27:192–95). Furthermore, two large, inbred kindreds have been described whose members include both MM and LGMD2B patients (Weiler et al., 1996, *Am. J. Hum. Genet.* 59:872–78; Illarioshkin et al., 1997, *Genomics* 42:345–48). In these familial studies, the disease gene(s) for both MM and LGMD2B mapped to essentially the same genetic interval. Moreover, in both pedigrees, individuals with MM or LGMD2B phenotypes share the same haplotypes. This raises the intriguing possibility that the two diseases may arise from the same gene defect and that a particular disease phenotype is the result of modification by additional factors.

A 3-Mb PAC contig spanning the entire MM/LGMD2B candidate region was recently constructed to facilitate the cloning of the MM/LGMD2B gene(s) (Liu et al., 1998, *Genomics* 49:23–29). This high resolution PAC contig resolved the discrepancies of the order of markers in previous studies (Bejaoui et al., 1998, *Neurogenetics* 1:189–96; Bashir et al., 1996, *Genomics* 33:46–52; Hudson et al., 1995, Science 270:1945–54). The physical size of the PAC contig also indicated that the previous minimal size estimation based on YAC mapping data was significantly underestimated.

Identification of Repeat Sequences and Repeat Typing

The PAC contig spanning the MM/LGMD2B region (Liu et al., 1998, *Genomics* 49:23–29) was used as a source for the isolation of new informative markers to narrow the genetic interval of the disease gene(s). DNA from the PAC clones spanning the MM/LGMD2B region was spotted onto Hybond N+™ membrane filters (Amersham, Arlington Heights, Ill.). The filters were hybridized independently with the following $\gamma$-$^{32}$P (Du Pont, Wilmington, Del.) labeled repeat sequences: (1) $(CA)_{15}$; (2) pool of $(ATT)_{10}$, $(GATA)_8$ and $(GGAA)_8$; (3) pool of $(GAAT)_8$, $(GGAT)_8$ and $(GTAT)_8$; and (4) pool of $(AAG)_{10}$ and $(ATC)_{10}$. Hybridization and washing of the filters were carried out at 55° C. following standard protocols (Sambrook et al., 1989, *Molecular Cloning: A Laboratory Manual* (2nd Edition), Cold Spring Harbor Press, N.Y.).

Miniprep DNAs of PAC clones containing repeat sequences were digested with restriction enzymes HindIII and PstI and ligated into pBluescript II (KS+) vector which is (Stratagene, La Jolla, Calif.) digested with the same enzymes. Filters of the PAC subclones were hybridized to the $\gamma$-$^{32}$P labeled repeats that detected the respective PACs. For clones with an insert size greater than 1 kb the repeat sequences of which could not be identified by a single round of sequencing, the inserts were further subcloned by digestion with HaeIII and ligation in EcoRV-digested pZero-2.1 vector (Invitrogen, Inc., Carlsbad, Calif.). Miniprep DNAs of the positive subclones were subjected to manual dideoxy sequencing with Sequenase™ enzyme (US Biochemicals, Inc., Cleveland, Ohio). Primer pairs for amplifying the repeat sequences were selected using the computer program Oligo (Version 4.0, National Biosciences, Inc., Plymouth, Minn.). Primer sequences are shown in Table 1.

Identification of Repeat Markers and Haplotype Analysis

After hybridization with labeled repeat oligos, 17 different groups of overlapping PACs were identified that contained repeat sequences. Some groups contained previously identified repeat markers. For example, five groups of PACs were positively identified by a pool of repeat probes including $(ATT)_{10}$, $(GATA)_8$, and $(GGAA)_8$. Of these, three groups contained known markers GGAA-P7430 (GGAA repeat), D2S1394 (GATA repeat) and D2S1398 (GGAA repeat) (Hudson et al., 1992, *Nature* 13:622–29; Gastier et al., 1995, *Hum. Molecular Genetics* 4:1829–36). No attempt was made to isolate new repeat markers from these PACs and they were not further analyzed. Similarly, seven groups of PACs that contained known CA repeat markerswere excluded. Seven groups of PACs that contained unidentified repeats were retained for further analysis. For each group, the PAC containing the smallest insert was selected for subcloning. Subclones were re-screened and positive clones were sequenced to identify repeats. In total, seven new repeat sequences were identified within the MM/LGMD2B PAC contig. Of these, five are polymorphic within the population that was tested. The information for these five markers is summarized in Table 1. Based on the PAC contig constructed previously across the MM candidate locus (Liu et al., 1998, *Genomics* 48:23–29), the five new markers and ten previously published polymorphic markers were placed in an unambiguous order (FIG. 1).

These markers were analyzed in a large, consanguineous MM family (Bejaoui et al., 1995, *Neurology* 45: 768–72; Bejaoui et al., 1998, *Neurogenetics* 1:189–96). Because MM is a recessive condition, the locus can be defined by identifying regions of the genome that show homozygosity in affected individuals. Conversely, because of the high penetrance of this adult-onset condition, unaffected adult individuals are not expected to be homozygous by descent across the region. Analysis of haplotype homozygosity in this pedigree indicates that the disease gene lies between

TABLE 1

New Polymorphic Markers Mapped to the MM/LGMD2B Region

| Marker | Repeat | Primers (5' to 3') | Annealing Tm (° C.) | Size in PAC (bp) | No. of alleles[1] | Het[2] |
|---|---|---|---|---|---|---|
| PAC3-H52 | CA | GATCTAACCCTGCTGCTCACC (SEQ ID NO: 120) CTGGTGTGTTGCAGAGCGCTG (SEQ ID NO: 121) | 57 | 138 | 10 | 0.82 |
| Cy172-H32[3] | CCAT | CCTCTCTTCTGCTGTCTTCAG (SEQ ID NO: 122) TGTGTCTGGTTCCACCTTCGT (SEQ ID NO: 123) | 56 | 199 | 7 | 0.72 |
| PAC35-PH2 | CAT | TCCAAATAGAAATGCCTGAAC (SEQ ID NO: 124) AGGTATCACCTCCAAGTGTTG (SEQ ID NO: 125) | 56 | 161 | 5 | 0.30 |
| PAC16-H41 | Complex | TACCAGCTTCAGAGCTCCCTG (SEQ ID NO: 126) TTGATCAGGGTGCTCTTGG (SEQ ID NO: 127) | 58 | 280 | 4 | 0.41 |
| Cy7-PH3 | AAGG | GGAGAATTGCTTGAACCCAG (SEQ ID NO: 128) TGGCTAATGATGTTGAACATTT (SEQ ID NO: 129) | 56 | 211 | 4 | 0.32 |

[1]Observed in 50 unrelated caucasians.
[2]Heterozygosity index.
[3]Located within intron 2 of the dysferlin gene.
All oligonucleotides were synthesized by Integrated DNA Technologies, Inc. (Coralville, IA). PCR typing of the repeat markers followed previously described protocols (Bejaoui et al., 1995, Neurology 45: 768–772).

markers D2S2111 and PAC3-H52. Based on the PAC mapping data, the physical distance for this interval is approximately 2.0 Mb. No recombination events were detected between four informative markers (markers cy172-H32 to PAC16-H41) and the disease locus in family MM-21 (FIG. 1A).

Identification of Five Muscle-Expressed ESTs

Twenty-two ESTs and two genes (transforming growth factor alpha [TGFα] and beta-adducin [ADD2]) were previously mapped to the MM/LGMD2B PAC contig (FIG. 1A) (Liu et al., 1998, *Genomics* 48:23–29). Two µl (approximately 0.1 ng/µl) of Marathon-ready™ skeletal muscle cDNA (Clontech, Palo Alto, Calif.) were used as template in a 10 µl PCR reaction for analysis of muscle expression of ESTs. The PCR conditions were the same as for the PCR typing of repeat markers. PCR analysis of skeletal muscle cDNA indicated that five of these ESTs (A006G04, stSG1553R, WI-14958, TIGR-A004Z44 and WI-14051) map within the minimal genetic MM interval of MM and are expressed in skeletal muscle.

Probes were selected corresponding to each of these five ESTs for Northern blot analysis. cDNA clones (130347, 48106, 172575, 184080, and 510138) corresponding to the five ESTs that are expressed in muscle (respectively TIGR-A004Z44, WI-14051, WI-14958, stSG1553R and A006G04) were selected from the UniGene database (http://www.ncbi.nlm.nih.gov/UniGene/) and obtained from Genome Systems, Inc. (St. Louis, Mo.). The cDNA probes were first used to screen the MM/LGMD2B PAC filters to confirm that they mapped to the expected position in the MM/LGMD2B contig.

A Northern blot (Clontech) of multiple human tissues was sequentially hybridized to the five cDNA probes and a control β-actin cDNA at 65° C. following standard hybridization and washing protocols (Sambrook et al., supra). Between hybridizations, probes were removed by boiling the blot at 95–100° C. for 4–10 min with 0.5% SDS. The blot was then re-exposed for 24 h to confirm the absence of previous hybridization signals before proceeding with the next round of hybridization.

The tissue distribution, intensity of the signals and size of transcripts detected by the five cDNA probes varied. Probes corresponding to ESTs stSG1553R, TIGR-A004Z44 and WI-14958 detected strong signals in skeletal muscle. In addition, the cDNA corresponding to TIGR-A004Z44 detected a 3.6–3.8 kb brain-specific transcript instead of the 8.5 kb message that was present in other tissues. It is likely that these five ESTs correspond to different genes since the corresponding cDNA probes used for Northern analysis derive from the 3' end of messages, map to different positions in the MM/LGMD2B contig (FIG. 1A), and differ in their expression patterns.

Current database analysis suggests that three of these ESTs (stSG1553R, WI-14958 and WI-14051) do not match any known proteins (Schuler et al., 1996, *Science* 274:540–46). A006G04 has weak homology with a protein sequence of unknown function that derives from *C. elegans*. TIGR-A004Z44 has homology only to subdomains present within protein kinase C. Because the five genes corresponding to the ESTs are expressed in skeletal muscle and map within the minimal genetic interval of the MM/LGMD2B gene(s), they are candidate MM/LGMD2B gene(s).

Cloning of Dysferlin cDNA

EST TIGR-A004Z44 gave a particularly strong skeletal muscle signal on the Northern blot. Moreover, it is bracketed by genetic markers that show no recombination with the disease phenotype in family MM-21 (FIG. 1). The corresponding transcript was therefore cloned and analyzed as a candidate MM gene. From the Unigene database, a cDNA IMAGE clone (130347, 979 bp) was identified that contained the 483 bp EST TIGR-A004Z44.

Approximately 1×10$^6$ recombinant clones of a λgt11 human skeletal muscle cDNA library (Clontech) were plated and screened following standard techniques (Sambrook et al., supra). The initial library screening was performed using the insert released from the clone 130347 that contains EST TIGR-A0044Z44, corresponding to the 3' end of the gene. Positive phages were plaque purified and phage DNA was isolated according to standard procedures (Sambrook et al., supra). The inserts of the positive clones were released by EcoRI digestion of phage DNA and subsequently subcloned into the EcoRI site of pBluescript II (KS+) vector (Stratagene).

Fifty cDNA clones were identified when a human skeletal muscle cDNA library was screened with the 130347 cDNA. Clone cDNA10 with the largest insert (~6.5 kb) (FIG. 1B) was digested independently with BamHI and PstI and further subcloned into pBluescript vector. Miniprep DNA of cDNA clones and subclones of cDNA10 was prepared using the Qiagen plasmid Miniprep kit (Valencia, Calif.). Sequencing was carried out from both ends of each clone using the SequiTherm EXCEL™ long-read DNA sequencing kit (Epicenter, Madison, Wis.), fluorescent-labeled M13 forward and reverse primers, and a LI-COR sequencer (Lincoln, Nebr.). Assembly of cDNA contigs and sequence analysis were performed using Sequencher software (Gene Codes Corporation, Inc., Ann Arbor, Mich.).

Two additional screens, first with the insert of cDNA10 and then a 683 bp PCR product (A27-F2R2) amplified from the 5' end of the cDNA contig, identified 87 additional cDNA clones. Clones B22 and B33 extended the 5' end by 94 and 20 bp, respectively. The compiled sequence allowed for the generation of a sequence of 6.9 kb (SEQ ID NO:1) (with 10-fold average coverage).

Although the 5' end of the gene has not been further extended to the 8.5 kb predicted by Northern analysis, an open reading frame (ORF) of 6,243 bp has been identified within this 6.9 kb sequence. This ORF is preceded by an in-frame stop codon and begins with the sequence cgcaag-cATGCTG (SEQ ID NO:118); five of the first seven bp are consistent with the Kozak consensus sequence for a start codon (Kozak, 1989, *Nucl. Acids Res.* 15:8125–33; Kozak, 1989, *J. Cell. Biol.* 108:229–41). An alternate start codon, in the same frame, +75 bp downstream, appears less likely as a start site GAGACGATGGGG (SEQ ID NO:119). Thus, the entire coding region of this candidate gene is believed to have been identified, as represented by the 6.9 kb sequence contig.

Isolation of the Brain-Specific Dysferlin Isoform

Identification of the Brain-specific Isoform of Dysferlin

A brain-specific isoform of dysferlin was identified using Northern blot analysis of poly(A+)RNA derived from multiple human adult tissues probed with radiolabeled full-length dysferlin cDNA subclones. A prominent 7.2 kb transcript was detected on Northern blots in skeletal muscle, heart, placenta, lung, and kidney, while a distinct but equally prominent 3.6 kb–3.8 kb transcript was identified exclusively in the brain. Using long exposures, a faint 7.2 kb mRNA was also detected in the brain. This finding suggested that the shorter brain isoform was likely to be a tissue-specific splice variant of the dysferlin gene. To test this hypothesis, a human brain cDNA library (Stratagene) was screened for the dysferlin brain isoform.

Cloning of the Brain-specific Dysferlin Isoform

To identify probes that hybridize to the brain-specific dysferlin sequence and so could be used for library screening, fragments of the full-length dysferlin cDNA clone (derived from a skeletal muscle cDNA library) were generated using restriction enzymes. The fragments were about 1 kb in length and were analyzed by hybridization to a Northern blot that included brain RNA. Sequences suitable for library screening were those that hybridized to the 3.6–3.8 kb brain-specific transcript. A region of the 3' end of the dysferlin cDNA sequence that is approximately 3 kb in length was identified as hybridizing to brain mRNA. DNA containing sequence from this region was used as a probe for hybridization screening of a human brain cDNA library (Stratagene).

The human brain cDNA library was plated out and screened using standard procedures. Of the approximately 720,000 plaques screened, 63 primary positive clones were identified. Of these, 20 clones were selected for further analysis involving standard methods of hybridization, restriction enzyme mapping, and sequencing. The primary positive clones shared regions of overlap with each other.

Figure 6A:
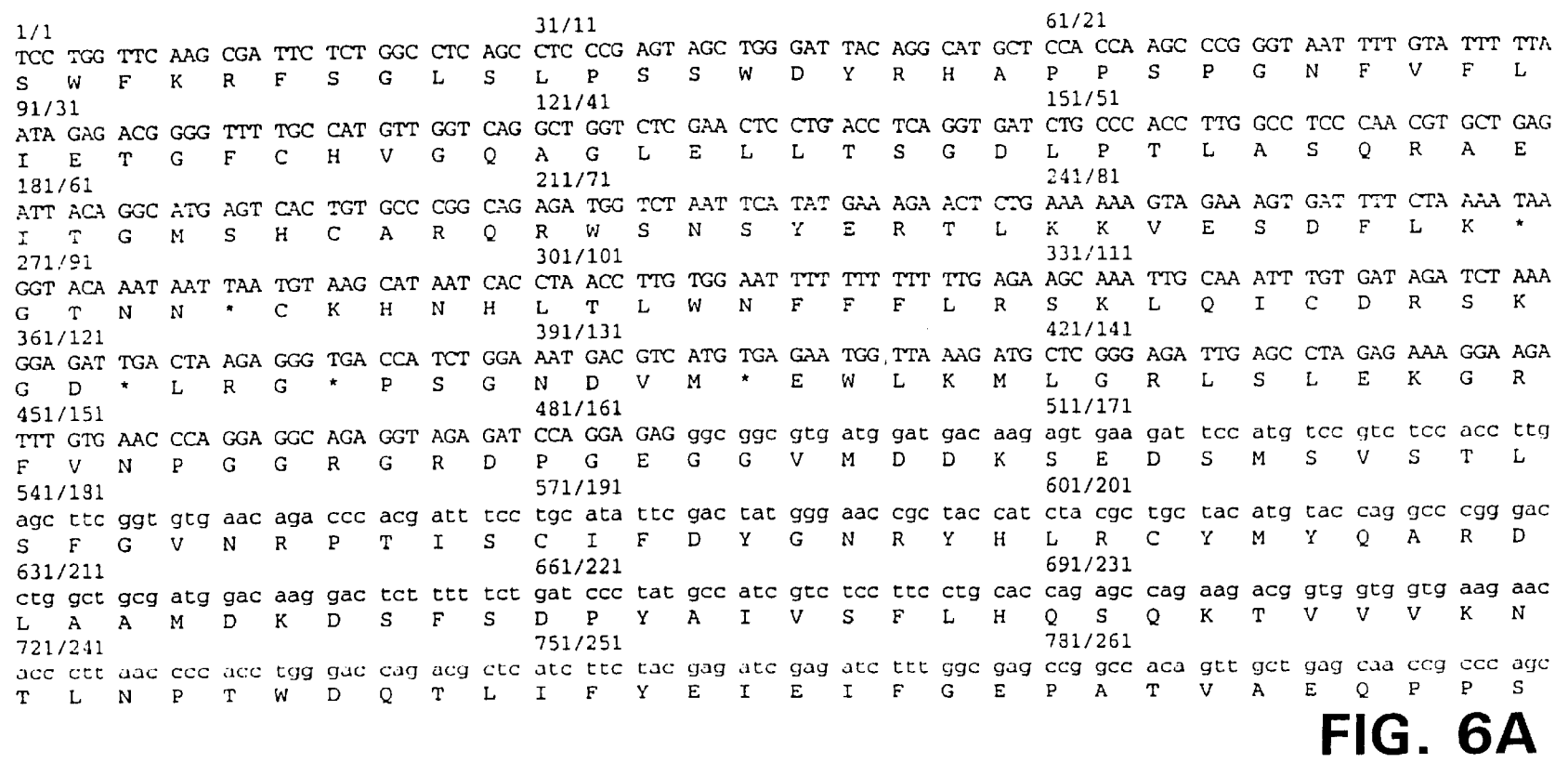

Sequencing of positive clones, provided 3671 nucleotides of the brain-specific dysferlin sequence (SEQ ID NO:232; FIGS. 6A–D). The identified sequence corresponds closely to the size of the brain-specific dysferlin transcript detected on Northern blots. With the exception of the 5' region of the sequence, the brain-specific sequence is identical to about 3.1 kb of the dysferlin sequence (from nucleotide 3722 to 6904 of the dysferlin sequence). In the dysferlin gene, position 3722 corresponds to the start of exon 32. This finding is consistent with the hypothesis that the brain isoform is a splice-variant of the dysferlin gene. At the 5' end of the brain isoform, 489 nucleotides are unique to brain-specific dysferlin. The amino acid sequence encoded by the brain dysferlin nucleic acid sequence (SEQ ID NO:233; FIG. 6) contains a unique sequence with an initiation codon within a Kozak consensus sequence. The nucleic acid sequence unique to brain-specific dysferlin encodes a novel 24 amino acid sequence.

Identification of Mutations in Miyoshi Myopathy

Two strategies were used to determine whether this 6.9 kb cDNA (SEQ ID NO:1) is mutated in MM. First, the genomic organization of the corresponding gene was determined and the adjoining intronic sequence at each of the 55 exons which make up the cDNA was identified. To identify exon-intron boundaries within the gene, PAC DNA was extracted with the standard Qiagen—Mini Prep protocol. Direct sequencing was performed with DNA Sequence System (Promega, Madison, Wis.) using $^{32}$P end-labeled primers (Benes et al., 1997, *Biotechniques* 23:98–100). Exon-intron boundaries were identified as the sites where genomic and cDNA sequences diverged. Second, in patients for whom muscle biopsies were available, RT-PCR was also used to prepare cDNA for the candidate gene from the muscle biopsy specimen.

Single strand conformational polymorphism analysis (SSCP) was used to screen each exon in patients from 12 MM families. Putative mutations identified in this way were confirmed by direct sequencing from genomic DNA using exon-specific intronic primers. Approximately 20 ng of total genomic DNA from immortalized lymphocyte cell lines were used as a template for PCR amplification analysis of each exon using primers (below) located in the adjacent introns. SSCP analysis was performed as previously described (Aoki et al., 1998, *Ann. Neurol.* 43:645–53). In patients for whom muscle biopsies were available, mRNA was isolated using RNA-STAT-60™ (Tel-Test, Friendswood, Tex.) and first-strand cDNA was synthesized from 1–2 µg total RNA with MMLV reverse transcriptase and random hexamer primers (Life Technologies, Gaithersburg, Md.). Three µl of this product were used for PCR amplification. Eight sets of primers were designed for muscle cDNA, and overlapping cDNA fragments suitable for SSCP analysis were amplified. After initial denaturation at 94° C. for 2 min, amplification was performed using 30 cycles at 94° C. for 30 s, 56° C. for 30 s, and 72° C. for 60 s. The sequences of polymorphisms detected by SSCP analysis were determined by the dideoxy termination method using the Sequenase kit (US Biochemicals). In some instances, the base pair changes predicted corresponding changes in restriction enzyme recognition sites. Such alterations in restriction sites were verified by digesting the relevant PCR products with the appropriate restriction enzymes.

Primer pairs used for SSCP screening and exon sequencing are as follows:

(1) exon 3, F3261 5'-tctcttctcctagagggccatag-3' (SEQ ID NO: 101) and R326 5'-ctgttcctccccatcgtctcatgg-3' (SEQ ID NO: 102);

(2) exon 20, F3121 5'-gctcctcccgtgaccctctg-3' (SEQ ID NO: 103) and R3121 5'-gggtcccagccaggagcactg-3' (SEQ ID NO: 104);

(3) exon 36, F2102 5'-cccctctcaccatctcctgatgtg-3' (SEQ ID NO: 105) and R2111 5'-tggcttcaccttccctctacctcgg-3' (SEQ ID NO: 106);

(4) exon 49, F1081 5'-tcctttggtaggaaatctaggtgg-3' (SEQ ID NO: 107) and R1081 5'-ggaagctggacaggcaagagg-3' (SEQ ID NO: 108);

(5) exon 50, F1091 5'-atatactgtgttggaaatcttaatgag-3' (SEQ ID NO: 109) and R1091 5'-gctggcaccacagggaatcgg-3' (SEQ ID NO: 110);

(6) exon 51, F1101 5'-ctttgcttccttgcatccttctctg-3' (SEQ ID NO: 111) and R1101 5'-agcccccatgtgcagaatggg-3' (SEQ ID NO: 112);

(7) exon 52, F1111 5'-ggcagtgatcgagaaacccgg-3' (SEQ ID NO: 113) and R1111 5'-catgccctccactggggctgg-3' (SEQ ID NO: 114);

(8) exon 54, F1141 5'-ggatgcccagttgactccggg-3' (SEQ ID NO: 115) and R1141 5'-ccccaccacagtgtcgtcagg-3' (SEQ ID NO: 116);

(9) exon 29, F3031 5'-aagtgccaagcaatgagtgaccgg-3' (SEQ ID NO: 184) and R3021 5'-ctcactcccacccaccacctg-3' (SEQ ID NO: 185);

(10) exon 31, F2141 5'-gaatctgccataaccagcttcgtg-3' (SEQ ID NO: 188) and R2141 5'-tatcaccccatagaggcctcgaag-3' (SEQ ID NO: 189);

(11) exon 32, F2981 5'-cagccactcactctggcacctctg-3' (SEQ ID NO: 190) and R2981 5'-agcccacagtctctgactctcctg-3' (SEQ ID NO: 191);

(12) exon 43, F2031 5'-cagccaaaccatatcaacaatg-3' (SEQ ID NO: 210) and R2021 5'-ctggggaggtgagggctctag-3' (SEQ ID NO: 211);

(13) exon 44, F2011 5'-gaagtgttttgtctcctcctc-3' (SEQ ID NO: 212) and R2011 5'-gcaggcagccagccccccatc-3' (SEQ ID NO: 213);

(14) exon 46, F1041 5'-ctcgtctatgtcttgtgcttgctc-3' (SEQ ID NO: 216) and R1051 5'-caccatggtttggggtcatgtgg-3' (SEQ ID NO: 217).

These primers were used in SSCP screening and exon sequencing, and identified eighteen different mutations in fifteen families (Table 2).

TABLE 2

Mutations in Dysferlin in Distal Myopathy and LGMD[1]

| Name | Nucleotide Change | Exon | Consequence | Origin | Family name | Allele | Change of restriction site |
|---|---|---|---|---|---|---|---|
| Mutations | | | | | | | |
| 537insA | ins of A at 537 | 3 | Frameshift | Arabic | MM59 | Hom | no change |
| Q605X | CAG to TAG at 2186 | 20 | Stop at 605 | French | MM67 | Hom | −Pst I, −Fnu 4H I[1] |
| I1298V | ATC to GTC at 4265 | 36 | Amino acid change | Italian | MM, LGMD56 | Het | −BamHI, −BStYI; +Ava II |
| E1883X | GAG to TAG at 5870 | 49 | Stop at 1883 | English | MM8 | Het | no change |
| H1857R | CAT to CGT at 5943 | 50 | Amino acid change | English | MM50 | Het | no change |
| 5966delG | del of G at 5966 | 50 | Frameshift | Spanish | DMAT71 | Hom | no change |
| 5966delG | del of G at 5966 | 50 | Frameshift | Spanish | MM75 | Hom | no change |
| 6071/6072delAG | del of AG at 6071/6072 | 51 | Frameshift | English | MM58 | Het | no change |
| 6319+1G to A | Ggt to Gat at 6319+1 | 52 | 5' splice site | English | MM8 | Het | no change |
| R2042C | CGT to TGT at 6497 | 54 | Amino acid change | Italian | MM56 | Het | −Fnu4HI |
| R1046H | CGC to CAG at 3510 | 29 | Amino acid change | Japanese | MM10 | Hom | −HinPI, −Fsp I |
| 3746delG | del of G at 3746 | 31 | Frameshift | Japanese | MM17 | Hom | −MboII |
| Q1160X | CAG to TAG at 3851 | 32 | Stop at 1160 | Mexican | MM46 | Hom | −ScrFI, −BstNI, +MaeI, +BfaI |
| 5122/5123delCA | del of CA at 5122/5123, A to T at 5121 | 43 | Frameshift | Japanese | MM14 | Het | no change |
| R1586X | CGA to TGA at 5129 | 43 | Stop at 1586 | Japanese | MM12 | Hom | +Dde I |
| 5245delG | del of G at 5245 and G to C at 5249, or G to C at 5245 and del G at 5249 | 44 | Frameshift | French | MM63 | Hom | −Bpm I, −BanII, +AvaII, +Sau96I |
| E1732X | GAG to TAG at 5567 | 46 | Stop at 1732 | Spanish | MM73 | Het | −Mbo II |
| 2573-77 del ACCCA | Del of ACCCA at 2573-77 | 23 | Frameshift | Italian | MM69 | Hom | ?Please provide |

[1]MM: Miyoshi myopathy; DMAT: distal myopathy with anterior tibial onset; LGMD: limb girdle muscular dystrophy
[2]+: create a new restriction site, −: eliminate an existing restriction site.

Figure 4:
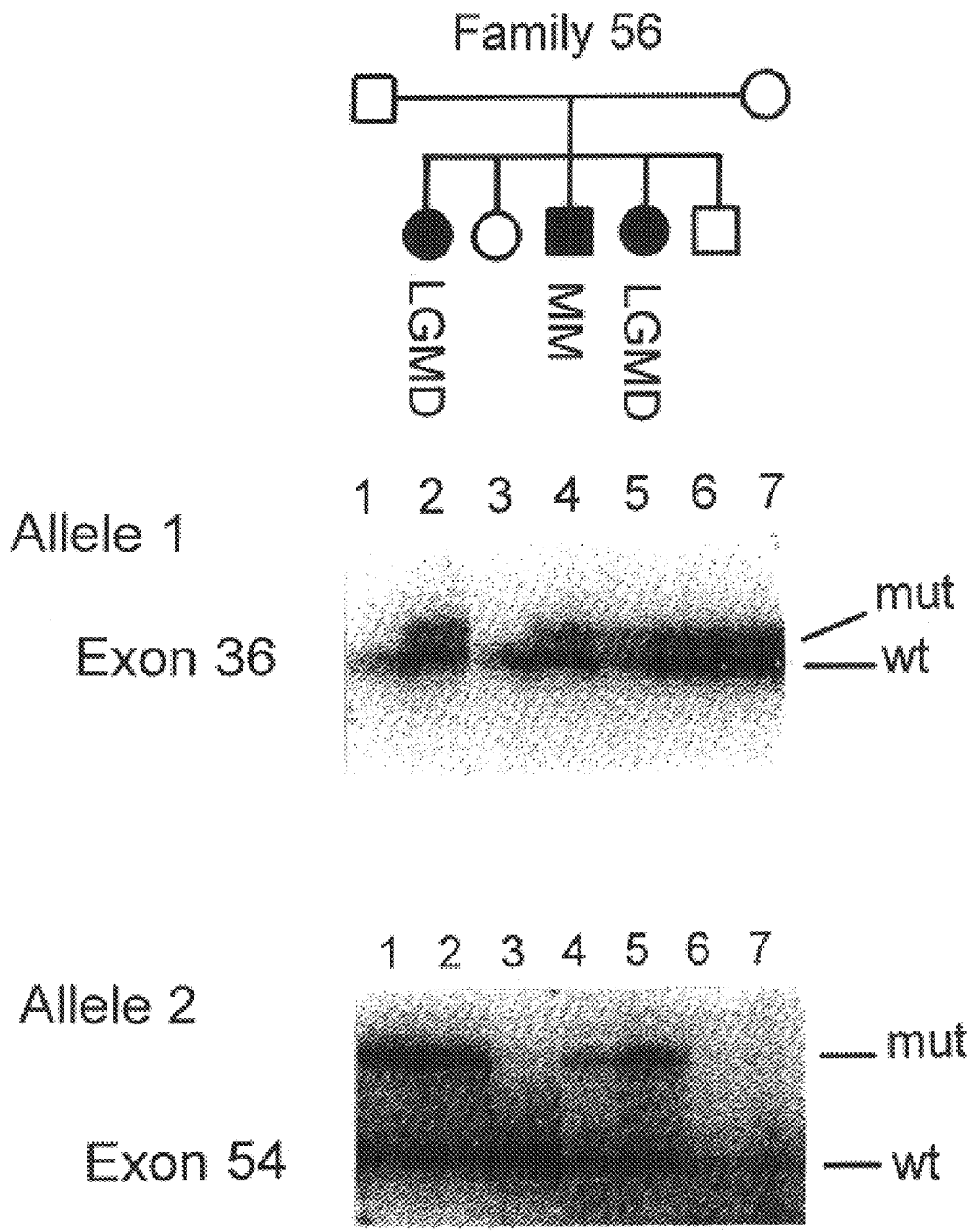
FIG. 4 is a SSCP analysis of a representative pedigree with dysferlin mutations. Each member of the pedigree is illustrated above the corresponding SSCP analysis. For each affected individual (solid symbols) shifts are evident in alleles 1 and 2, corresponding respectively to exons 36 and 54. As indicated, the allele 1 and 2 variants are transmitted respectively from the mother and the father. The two affected daughters in this pedigree have the limb girdle muscular dystrophy (LGMD) phenotype while their affected brother has a pattern of weakness suggestive of Miyoshi myopathy (MM).

Twelve of the eighteen different mutations are predicted to block dysferlin expression, either through nonsense or frameshift changes. Seven of the thirteen samples are homozygous and thus expected to result in complete loss of dysferlin function. For each mutated exon in these patients, at least 50 control DNA samples (100 chromosomes) were screened to determine the frequencies of the sequence variants. When possible, the parents and siblings of affected individuals were also screened to verify that defined mutations were appropriately co-inherited with the disease in each pedigree (FIG. 4). In two families (50, 58 in Table 2) heterozygous mutations were identified in one allele (respectively a missense mutation and a 2 bp deletion). Mutations in the other allele are presumed to have not been detected (or in three of the screened MM families) either because the mutant and normal SSCP products are indistinguishable or because the mutation lies outside of coding sequence (i.e., in the promoter or a regulatory region of an intron). The disease-associated mutations did not appear to arise in the population as common polymorphisms.

More mutations can be identified by using appropriate primer pairs to amplify an exon and analyze its sequence. The following primer pairs are useful for exon amplification.

| Exon | Code | Primer Sequence |
|---|---|---|
| 1 | F408 | 5'-gacccacaagcggcgcctcgg-3' {SEQ ID NO: 130} |
| | F4101 | 5'-gacccggcgagggtggtcgg-3' {SEQ ID NO: 131} |
| 2 | F4111 | 5'-tgtctctccattctcccttttgtg-3' {SEQ ID NO: 132} |
| | R4111 | 5'-aggacactgctgagaaggcacctc-3' {SEQ ID NO: 133} |
| 3 | F3262 | 5-agtgccctggtggcacgaagg-3' {SEQ ID NO: 134} |
| | R3261 | 5-cctacctgcaccttcaagccatgg-3' {SEQ ID NO: 135} |
| 4 | F3251 | 5-cagaagagccagggtgccttagg-3' {SEQ ID NO: 136} |
| | R3251 | 5-ccttggaccttaacctggcagagg-3' {SEQ ID NO: 137} |

-continued

| Exon | Code | Primer Sequence |
|---|---|---|
| 5 | F3242 | 5-cgaggccagcgcaccaacctg-3' {SEQ ID NO: 138} |
|  | R3242 | 5-actgccggccattcttgctggg-3' {SEQ ID NO: 139} |
| 6 | F3231 | 5-ccaggcctcattagggccctc-3' (SEQ ID NO: 140} |
|  | R3231 | 5-ctgaagaggagcctggggtcag-3' {SEQ ID NO: 141} |
| 7 | F3222 | 5-ctgagatttctgactcttggggtg-3' {SEQ ID NO: 142} |
|  | R3211 | 5-aaggttctgccctcatgccccatg-3' {SEQ ID NO: 143} |
| 8 | F3561 | 5-ctggcctgagggatcagcagg-3' {SEQ ID NO: 144} |
|  | R3561 | 5-gtgcatacatacagcccacggag-3' {SEQ ID NO: 145} |
| 9 | F3551 | 5-gagctattgggttggccgtgtggg-3' {SEQ ID NO: 146} |
|  | R3552 | 5-accaacacggagaagtgagaactg-3' {SEQ ID NO: 147} |
| 10 | F3201 | 5-ccacactttatttaacgctttggcgg-3' {SEQ ID NO: 148} |
|  | R3201 | 5-cagaaccaaaatgcaaggatacgg-3' (SEQ ID NO: 149} |
| 11 | F3191 | 5-cttctgattctgggatcaccaaagg-3' {SEQ ID NO: 150} |
|  | F3191 | 5-ggaccgtaaggaagacccaggg-3' {SEQ ID NO: 151} |
| 12 | F3181 | 5-cctgtgctcaggagcgcatgaagg-3' {SEQ ID NO: 152} |
|  | R3181 | 5-gcagacctcccacccaagggcg-3' {SEQ ID NO: 153} |
| 13 | F3171 | 5-gagacagatgggggacagtcaggg-3' {SEQ ID NO: 154} |
|  | R3171 | 5-cctcccgagagaaccctcctg-3' {SEQ ID NO: 155} |
| 14 | F3161 | 5-gggagcccagagtcccccatgg-3' {SEQ ID NO: 156} |
|  | R3161 | 5-gggcctccttgggtttgctgg-3' {SEQ ID NO: 157} |
| 15 | F3541 | 5-gcctccccagcatcctgccgg-3' {SEQ ID NO: 158} |
|  | R3541 | 5-tcactgagccgaatgaaactgagg-3' {SEQ ID NO: 159} |
| 16 | F3531 | 5-tgtggcctgagttccttcctgtg-3' {SEQ ID NO: 160} |
|  | R3531 | 5-ggtcaaagggcagaacgaagaggg-3' {SEQ ID NO: 161} |
| 17 | F3151 | 5-cccgtccttctcccagccatg-3' {SEQ ID NO: 162} |
|  | R3151 | 5-ctcccctggttgtcccaagg-3' {SEQ ID NO: 163} |
| 18 | F3141 | 5-cgaccctctgattgccacttgtg-3' {SEQ ID NO: 164} |
|  | R3141 | 5-ggcatcctgccctgccaggg-3' {SEQ ID NO: 165} |
| 19 | F3522 | 5-tctgtctcccctgctccttg-3' {SEQ ID NO: 166} |
|  | R3522 | 5-cttccctgccccgacgcccag-3' {SEQ ID NO: 167} |
| 20 | F3121 | 5-gctcctcccgtgaccctctgg-3' {SEQ ID NO: 103} |
|  | R3121 | 5-gggtcccagccaggagcactg-3' {SEQ ID NO: 104} |
| 21 | F3111 | 5-cagcgctcaggcccgtctctc-3' {SEQ ID NO: 168} |
|  | R3111 | 5-tgcataggcatgtgcagcttttggg-3' {SEQ ID NO: 169} |
| 22 | F3512 | 5-catgcaccctctgccctgtgg-3' {SEQ ID NO: 170} |
|  | R3512 | 5-agttgagccaggagaggtggg-3' {SEQ ID NO: 171} |
| 23 | F3101 | 5-catcaggcgcattccatctgtccg-3' {SEQ ID NO: 172} |
|  | R3091 | 5-agcaggagagcagaagaagaaagg-3' {SEQ ID NO: 173} |
| 24 | F3082 | 5-gtgtgtcaccatcccaccccg-3' {SEQ ID NO: 174} |
|  | R3082 | 5-caagagatgggagaaaggccttatg-3' {SEQ ID NO: 175} |
| 25 | F3073 | 5-ctgggacatccggatcctgaagg-3' {SEQ ID NO: 176} |
|  | R3073 | 5-tccaggtagtgggaggcagagg-3' {SEQ ID NO: 177} |
| 26 | F3061 | 5-tcccactacctggagctgccttgg-3' {SEQ ID NO: 178} |
|  | R3051 | 5-ggctctccccagcccctccctg-3' {SEQ ID NO: 179} |
| 27 | F3601 | 5-cagagcagcagagactctgaccag-3' {SEQ ID NO: 180} |
|  | R3601 | 5-tagacccacctgccccctgag-3' {SEQ ID NO: 181} |
| 28 | F3501 | 5-tcctctcattgcttgcctgttcgg-3' {SEQ ID NO: 182} |
|  | R3501 | 5-ttgagagcttgccggggatgg-3' {SEQ ID NO: 183} |
| 29 | F3031 | 5-aagtgccaagcaatgagtgaccgg-3' {SEQ ID NO: 184} |
|  | R3021 | 5-ctcactcccacccaccacctg-3' {SEQ ID NO: 185} |
| 30 | F3011 | 5-cccaccggcctctgagtctgc-3' {SEQ ID NO: 186} |
|  | R3001 | 5-accctacccaagccaggacaagtg-3' {SEQ ID NO: 187} |
| 31 | F2141 | 5-gaatctgccataaccagcttcgtg-3' {SEQ ID NO: 188} |
|  | R2141 | 5-tatcacccccatagaggcctcgaag-3' {SEQ ID NO: 189} |
| 32 | F2981 | 5-cagccactcactctggcacctctg-3' {SEQ ID NO: 190} |
|  | R2981 | 5-agcccacagtctctgactctcctg-3' {SEQ ID NO: 191} |
| 33 | F2131 | 5-acatctctcagggtccctgctgtg-3' #SEQ ID NO: 192} |
|  | R2211 | 5-cctgtgagggacgaggcagg-3' {SEQ ID NO: 193} |
| 34 | F2202 | 5-gccctgggtaagggatgctgattc-3' {SEQ ID NO: 194} |
|  | R2202 | 5-cctgcctgggcctcctggatc-3' {SEQ ID NO: 195} |
| 35 | F2111 | 5-gagggtgatggggggccttagg-3' {SEQ ID NO: 196} |
|  | R2112 | 5-gcaatcagtttgaagaaggaaagg-3' {SEQ ID NO: 197} |
| 36 | F2102 | 5-cccctctcaccatctcctgatgtg-3' {SEQ ID NO: 105} |
|  | R2111 | 5-ggcttcaccttccctctacctcgg-3' {SEQ ID NO: 106} |
| 37 | F2101 | 5-caccttttgtctccattctacctgc-3' {SEQ ID NO: 198} |
|  | R2101 | 5-ctcccagccccccacgcccagg-3' {SEQ ID NO: 199} |
| 38 | F2091 | 5-ctgagccactctcctcattctgtg-3' {SEQ ID NO: 200} |
|  | R2091 | 5-tggaaggggacagtagggagg-3' {SEQ ID NO: 201} |
| 39 | F2081 | 5-ggccagtgcgttcttcctcctc-3' {SEQ ID NO: 202} |
|  | R2071 | 5-tccctgacctgcccatcatctc-3' {SEQ ID NO: 203} |
| 40 | F2061 | 5-gcccctgtcaggcctggatgg-3' {SEQ ID NO: 204} |
|  | R2061 | 5-tgacccaggcctccctggagg-3' {SEQ ID NO: 205} |
| 41 | F2051 | 5-ctgaaatggtctctttctttctac-3' {SEQ ID NO: 206} |
|  | R2051 | 5-cacaccgactgtcagactgaagag-3' {SEQ ID NO: 207} |
| 42 | F2041 | 5-ttgtcccctcctctaatccccatg-3' {SEQ ID NO: 208} |
|  | R2041 | 5-gggttagggacgtcttcgagg-3' {SEQ ID NO: 209} |
| 43 | F2031 | 5-cagccaaaccatatcaacaatg-3' {SEQ ID NO: 210} |
|  | R2021 | 5-ctggggaggtgagggctctag-3' {SEQ ID NO: 211} |
| 44 | F2011 | 5-gaagtgttttgtctcctcctc-3' {SEQ ID NO: 212} |
|  | R2011 | 5-gcaggcagccagccccccatc-3' {SEQ ID NO: 213} |
| 45 | F1021 | 5-gggtgccctgtgttggctgac-3' {SEQ ID NO: 214} |
|  | R1031 | 5-gcaggcagccagccccccatc-3' {SEQ ID NO: 215} |
| 46 | F1041 | 5-ctcgtctatgtcttgtgcttgctc-3' {SEQ ID NO: 216} |
|  | R1051 | 5-caccatggtttggggtcatgtgg-3' {SEQ ID NO: 217} |
| 47 | F1061 | 5-tctcgcttccccagctcctgc-3' {SEQ ID NO: 218} |
|  | R1061 | 5-tctggagttcgaggactctggg-3' {SEQ ID NO: 219} |
| 48 | F1071 | 5-agaagggtggggagagaacgg-3' {SEQ ID NO: 220} |
|  | R1071 | 5-cagctcagagcctgtggctgg-3' {SEQ ID NO: 221} |
| 49 | F1082 | 5-aaggccttcccatccttttggtagg-3' {SEQ ID NO: 222} |
|  | R1082 | 5-acaacccagagggagcacggg-3' {SEQ ID NO: 223} |
| 50 | F1092 | 5-gttgacgatgtatatactgtgttgg-3' {SEQ ID NO: 224} |
|  | R1091 | 5-gctggcaccacagggaatcgg-3' {SEQ ID NO: 110} |
| 51 | F1102 | 5-gcctctctctaactttgcttccttg-3' {SEQ ID NO: 225} |
|  | R1101 | 5-agccccccatgtgcagaatggg-3' {SEQ ID NO: 112} |
| 52 | F1112 | 5-ggctacaggctggcagtgatcgag-3' {SEQ ID NO: 226} |
|  | R1112 | 5-ttccccccatgccctccactgg-3' {SEQ ID NO: 227} |
| 53 | F1121 | 5-agccttcgtgcccctaaccaagtg-3' {SEQ ID NO: 228} |
|  | R1121 | 5-ctgtgggcattggggctcagg-3' {SEQ ID NO: 229} |
| 54 | F1141 | 5-ggatgcccagttgactccggg-3' {SEQ ID NO: 115} |
|  | R1141 | 5-ccccaccacagtgtcgtcagg-3' {SEQ ID NO: 116} |
| 55 | F1151 | 5-gccccagtgggatcaccatg-3' {SEQ ID NO: 230} |
|  | R116 | 5-atgctggaggggaccccacgg-3' {SEQ ID NO: 231} |

Comparison of Dysferlin with Other Proteins

Figures 1B, 1C:
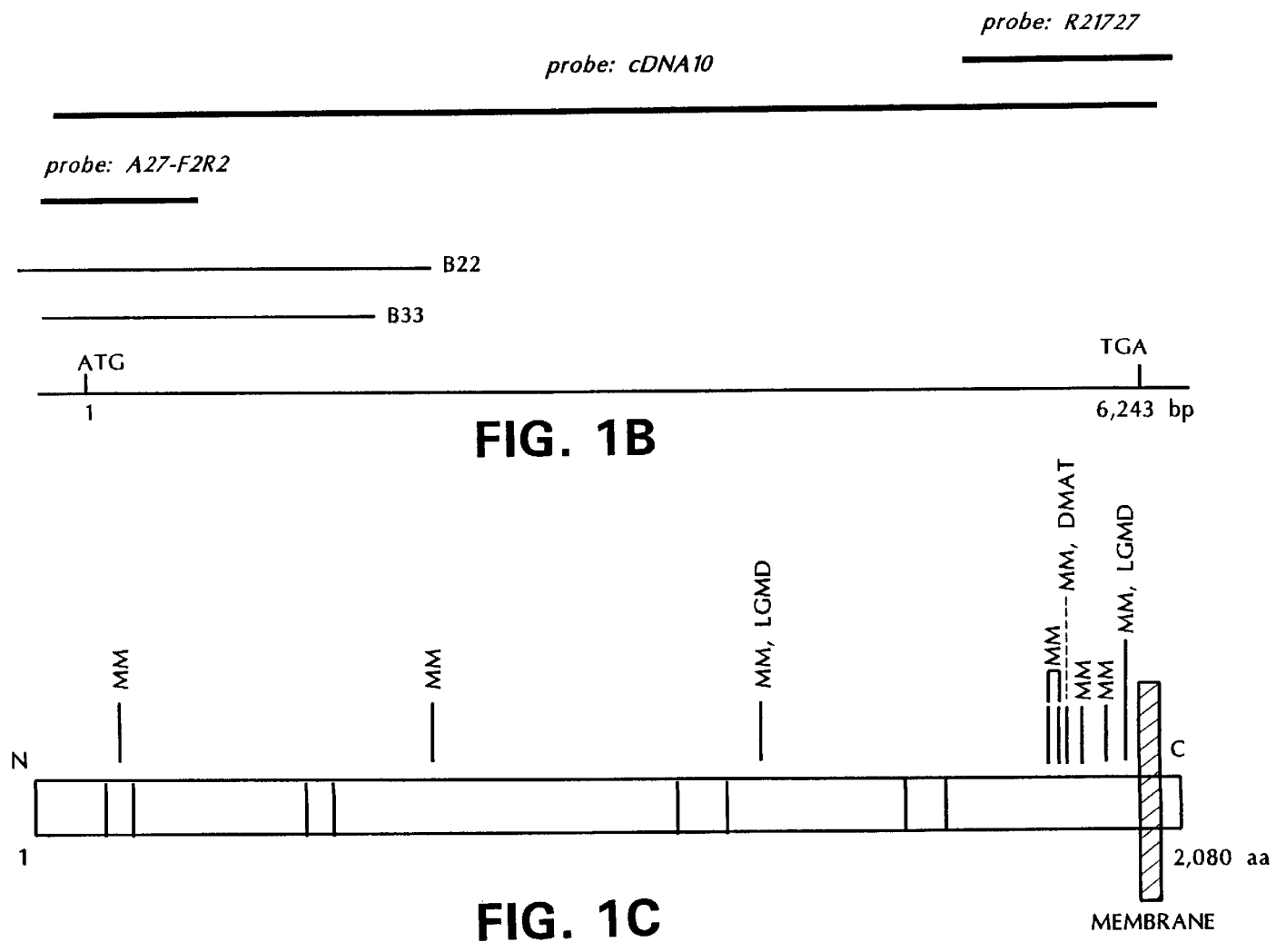

The 6,243 bp ORF of this candidate MM gene is predicted to encode 2,080 amino acids (FIGS. 1C and 2; SEQ ID NO:2). At the amino acid level, this protein is highly homologous to the nematode (*Caenorhabditis elegans*) protein fer-1 (27% identical, 57% identical or similar: the sequence alignment and comparison was performed using http://vega.igh.cnrs.fr/bin/nph-align_query.pl.) (Argon & Ward, 1980, *Genetics* 96:413–33; Achanzar & Ward, 1997, *J. Cell Science* 110:1073–81). This dystrophy-associated, fer-1-like protein has therefore been designated "dysferlin."

Figure 3:
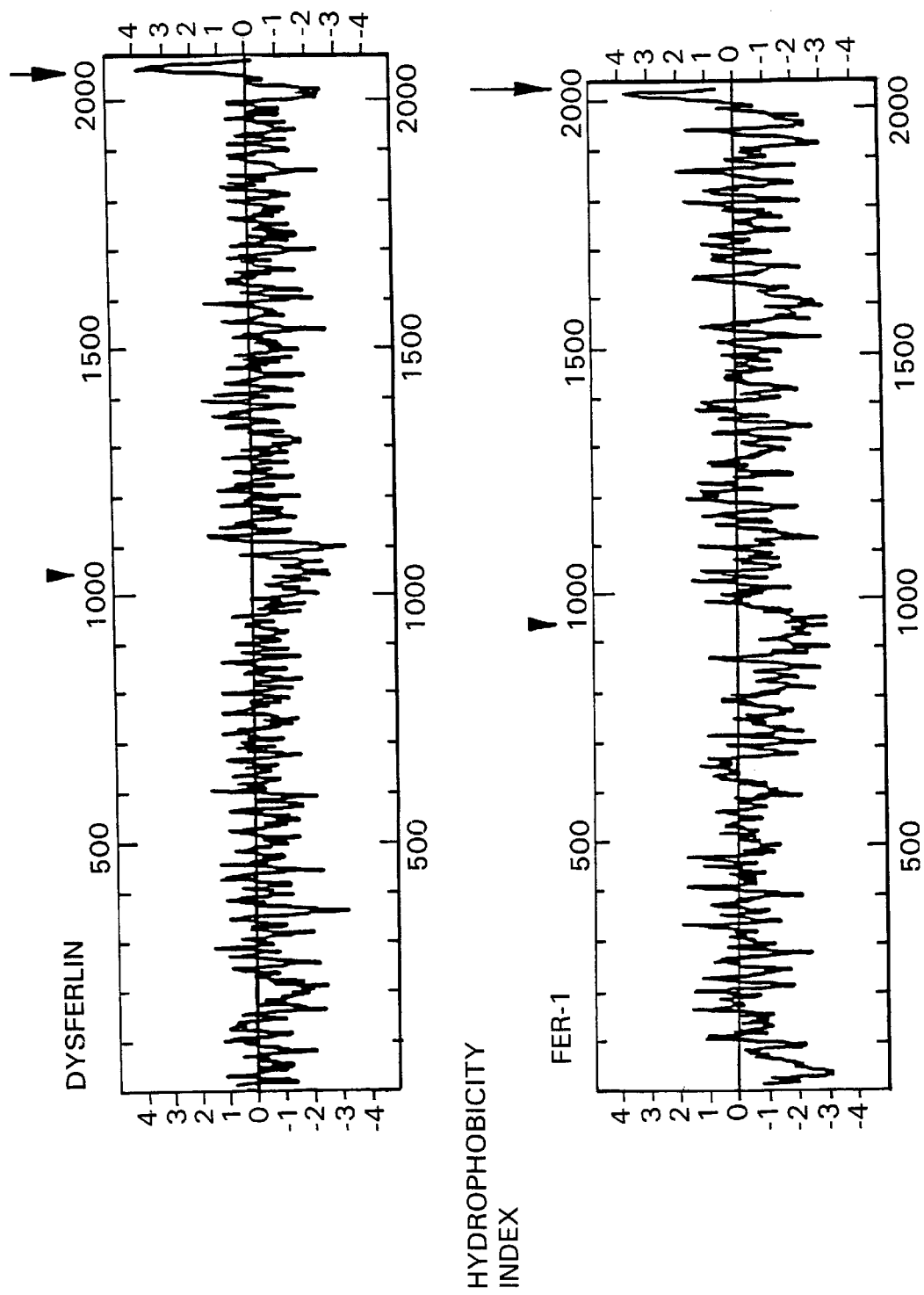
FIG. 3 is a comparison of the Kyle-Doolittle hydrophobicity plots of the dysferlin protein and fer-1. On the Y-axis, increasing positivity corresponds to increasing hydrophobicity. Both proteins have a single, highly hydrophobic stretch at the carboxy terminal end (arrow). Both share regions of relative hydrophilicity approximately at residue 1,000 (arrowhead).

The fer-1 protein was originally identified through molecular genetic analysis of a class of fertilization-defective *C. elegans* mutants in which spermatogenesis is abnormal (Argon & Ward, 1980, *Genetics* 96:413–33). The mutant fer-1 spermatozoa have defective mobility and show imperfect fusion of membranous organelles (Ward et al., 1981, *J. Cell Bio.* 91:26–44). Like fer-1, dysferlin is a large protein with an extensive, highly charged hydrophilic region and a single predicted membrane spanning region at the carboxy terminus (FIG. 3). There is a membrane retention sequence 3' to the membrane spanning stretch, indicating that the protein may be preferentially targeted to either endoplasmic or sarcoplasmic reticulum, probably as a Type II protein (i.e. with the $NH_2$ end and most of the following protein located within the cytoplasm) (FIG. 1C). Several nuclear membrane targeting sequences are predicted within the cytoplasmic domain of the protein (http://psort.nibb.ac.jp/form.html). Immunocytochemical detection of dysferlin suggests that dysferlin is targeted to or anchored within the sarcoplasmic reticulum.

The cytoplasmic component of this protein contains four motifs homologous to C2 domains. C2 domains are intracellular protein modules composed of 80–130 amino acids (Rizo & Sudhof, 1998, *J. Biol. Chem.* 273:15897). Originally identified within a calcium-dependent isoform of protein kinase C (Nishizuka, 1988, *Nature* 334:661–65), C2 domains are present in numerous proteins. These domains often arise in approximately homologous pairs described as double C2 or DOC2 domains. One DOC2 protein, DOC2α, is brain specific and highly concentrated in synaptic vesicles (Orita et al., 1995, *Biochem. Biophys. Res. Comm.* 206:439–48), while another, DOC2β, is ubiquitously expressed (Sakaguchi et al., 1995, *Biochem. Biophys. Res. Comm.* 217:1053–61). Many C2 modules can fold to bind calcium, thereby initiating signaling events such as phospholipid binding. At distal nerve terminals, for example, the synaptic vesicle protein synaptotagmin has two C2 domains that, upon binding calcium, permit this protein to interact with syntaxin, triggering vesicle fusion with the distal membrane and neurotransmitter release (Sudhof & Rizo, 1996, *Neuron* 17:379–88).

The four dysferlin C2 domains are located at amino acid positions 32–82, 431–475, 1160–1241, and 1582–1660 (FIGS. 1C and 3). Indeed, it is almost exclusively through these regions that dysferlin has homology to any proteins other than fer-1. Each of these segments in dysferlin is considerably smaller than a typical C2 domain. Moreover, these segments are more widely separated in comparison with the paired C2 regions in synaptotagmin, DOC2α and β and related C2-positive proteins. For this reason, it is difficult to predict whether the four relatively short C2 domains in dysferlin function analogously to conventional C2 modules. That dysferlin might, by analogy with synaptotagmin, signal events such as membrane fusion is suggested by the fact that fer-1 deficient worms show defective membrane organelle fusion within spermatozoa (Ward et al., 1981, *J. Cell Bio.* 91:26–44).

The invention will be further described in the following examples, which do not limit the scope of the invention described in the claims.

EXAMPLES

Example 1

Production of Dysferlin Protein

Standard methods can be used to synthesize either wild type or mutant dysferlin, or fragments of either. These methods can also be used to synthesize brain-specific dysferlin polypeptides including full-length or fragments (e.g., a polypeptide unique to brain-specific dysferlin). For example, a recombinant expression vector encoding dysferlin (or a fragment thereof: e.g., dysferlin minus its membrane-spanning region) operably linked to appropriate expression control sequences can be used to express dysferlin in a prokaryotic (e.g., *E.coli*) or eukaryotic host (e.g., insect cells, yeast cells, or mammalian cells). The protein is then purified by standard techniques. If desired, DNA encoding part or all of the dysferlin sequence can be joined in-frame to DNA encoding a different polypeptide, to produce a chimeric DNA that encodes a hybrid polypeptide. This can be used, for example, to add a tag that will simplify identification or purification of the expressed protein, or to render the dysferlin (or fragment thereof) more immunogenic.

The preferred means for making short peptide fragments of dysferlin is by chemical synthesis. These fragments, like dysferlin itself, can be used to generate antibodies, or as positive controls for antibody-based assays.

Fusion proteins are useful, e.g., for generating antibodies. Such fusion proteins are generated using known methods. In one example, to construct glutathione S-transferase (GST) :dysferlin fusion proteins, the BLAST program (Altschul et al., 1990, *J. Molec. Biol.* 215:403–410) was used to identify three regions of the dysferlin cDNA that show no homology to any known human proteins (FIG. 1). These were subcloned from the dysferlin cDNA as BstYI (881–1333), XmnI (1990–2718) and SalI (5364–5732) fragments ligated respectively into BamHI, SmaI and SalI sites of pGEX-5X-3 (Pharmacia). The three fragments correspond to amino acid sequences at amino acid locations 253–403, 624–865, and 1664–1786 of SEQ ID NO:2, respectively. The resulting GST fusion proteins of BamHI (43 kDa) and SmaI (53.3 kDa) formed isoluble aggregates that were isolated by SDS-PAGE. The fusion protein of SalI (40.2 kDa) was soluble and thus could be purified using a glutathione Sepharose 4B column; the SalI dysferlin fragment (14.2 kDa) was isolated by cleavage from GST using Factor Xa protease. The eluted protein was concentrated and further purified by SDS-PAGE. For all three of the fusion peptides, the resulting SDS-PAGE bands were excised and used to immunize rabbits.

Example 2

Production and Characterization of Anti-dysferlin Antibodies

Techniques for generating both monoclonal and polyclonal antibodies specific for a particular protein are well known. The antibodies can be raised against a short peptide epitope of dysferlin, an epitope linked to a known immunogen to enhance immunogenicity, a long fragment of dysferlin, or the intact protein. Antibodies can also be raised against brain-specific dysferlin polypeptides, e.g., against amino acids 1–24 of SEQ ID NO:233. Such antibodies raised against dysferlin or brain-specific dysferlin polypeptides are useful for e.g., localizing such polypeptides in tissue sections or fractionated cell preparations and diagnosing dysferlin-related disorders.

An isolated dysferlin protein, or a portion or fragment thereof, can be used as an immunogen to generate antibodies that bind dysferlin using standard techniques for polyclonal and monoclonal antibody preparation. The dysferlin immunogen can also be a mutant dysferlin or a fragment of a mutant dysferlin. A full-length dysferlin protein can be used or, alternatively, antigenic peptide fragments of dysferlin can be used as immunogens. The antigenic peptide of dysferlin comprises at least 8 (preferably 10, 15, 20, or 30) amino acid residues of the amino acid sequence shown in SEQ ID NO:2 and encompasses an epitope of such that an antibody raised against the peptide forms a specific immune complex with dysferlin. Preferred epitopes encompassed by the antigenic peptide are regions of dysferlin that are located on the surface of the protein, e.g., hydrophilic regions.

A dysferlin immunogen typically is used to prepare antibodies by immunizing a suitable subject (e.g., rabbit, goat, mouse or other mammal) with the immunogen. An appropriate immunogenic preparation can contain, for example, recombinantly expressed dysferlin protein or a chemically synthesized dysferlin polypeptide. The preparation can further include an adjuvant, such as Freund's complete or incomplete adjuvant, or similar immunostimulatory agent. Immunization of a suitable subject with an immunogenic dysferlin preparation induces a polyclonal anti-dysferlin antibody response.

Polyclonal anti-dysferlin antibodies ("dysferlin antibodies") can be prepared as described above by immunizing a suitable subject with a dysferlin immunogen. The dysferlin antibody titer in the immunized subject can be monitored over time by standard techniques, such as with an enzyme linked immunosorbent assay (ELISA) using immobilized dysferlin. If desired, the antibody molecules directed against dysferlin can be isolated from the mammal (e.g., from the blood) and further purified by well-known techniques, such as protein A chromatography to obtain the IgG fraction. At an appropriate time after immunization, e.g., when the dysferlin antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985), *Monoclonal Antibodies and Cancer Therapy,* Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with a dysferlin immunogen as described above, and the culture supernatants of the resulting hybridoma cells are screened to identify a hybridoma producing a monoclonal antibody that binds dysferlin.

Any of the many well known protocols used for fusing lymphocytes and immortalized cell lines can be applied for the purpose of generating a monoclonal antibody against dysferlin (see, e.g., *Current Protocols in Immunology,* supra; Galfre et al. (1977) *Nature* 266:55052; R. H. Kenneth, in *Monoclonal Antibodies: A New Dimension In Biological Analyses,* Plenum Publishing Corp., New York, N.Y. (1980); and Lerner (1981) *Yale J. Biol. Med.,* 54:387–402. Moreover, the one in the art will appreciate that there are many variations of such methods which also would be useful. Hybridoma cells producing a monoclonal antibody of the invention are detected by screening the hybridoma culture supernatants for antibodies that bind dysferlin, e.g., using a standard ELISA assay.

Alternative to preparing monoclonal antibody-secreting hybridomas, a monoclonal dysferlin antibody can be identified and isolated by screening a recombinant combinatorial immunoglobulin library (e.g., an antibody phage display library) with dysferlin to thereby isolate immunoglobulin library members that bind dysferlin. Kits for generating and screening phage display libraries are commercially available (e.g., the Pharmacia *Recombinant Phage Antibody System,* Catalog No. 27-9400-01; and the Stratagene SurfZAP™ *Phage Display Kit,* Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

As an example, two polyclonal antisera were raised for each of the fusion peptide antigens described above using New Zealand White rabbits. The rabbits were injected with 0.5 mg of antigen using keyhole limpet hemocyanin (KLH) as the adjuvent. Booster injections of 0.25 mg antigen were administered every three weeks over 12 weeks. Serum was prepared from the rabbits and was purified using affinity column chromatography (HiTrap; Pharmacia) or antigen-blotted polyvinylidene difluoride (PVDF) membrane.

Immunoblotting was used to verify that the affinity-purified antisera recognize the cognate fusion peptides by Western immunoblotting (WIB) and that this reactivity was immunoadsorbed by pre-incubation of the antisera with the peptides. Thus, antiserum raised against the polypeptide encoded by the SalI fragment (encoding amino acids 1664–1786) identified the fragment both as a cleaved, 14.2 kDa fragment and as a component of the 40.2 kDa GST-SalI fusion peptide. No reactivity was evident in the fraction containing only the GST fusion partner. Immunoadsorption entirely abolished this staining. Analogous results were detected with all six antisera (to the three different target fusion peptides).

Preparation of Subcellular Fractions

Frozen human muscle (0.3 g) was homogenized in five volumes of 0.25 M sucrose containing proteinase inhibitor (Complete, Boehringer). Subcellular fractions of nuclei, mitochondria, microsomes, and cytosol were separated by differential centrifugation. The purity of each fraction was evaluated by immunoblotting of fraction-specific proteins with antibodies to histone H1 (Calbiochem), cytochrome c (Santa Cruz), $Na^+$—$K^+$ ATPase $\alpha 1$ subunit (Research Diagnostics) and cytosolic superoxide dismutase (Calbiochem).

Dysferlin in Subcellular Fractions

Immunoblotting was used to analyze dysferlin expression. Twenty $\mu g$ of each subcellular fraction and 40 $\mu g$ of whole homogenate of muscle were separated by SDS-PAGE (4–15% gradient gel) and transferred to a nitrocellulose membrane. Immunoblotting was performed according to standard methods, using chemiluminescence (ECL, Amersham).

Immunoblotting of multi-tissue blots identified prominent dysferlin positively at approximately 230 kDa in heart, placenta, skeletal muscle and kidney. Little or no immuno-positive staining was detected in brain, liver, spleen, ovary, or testis. Lower molecular weight bands (approximately 40 kDa) were also evident. Immunoadsorption with the corresponding fusion peptide abolished both the large and the smaller bands. The 230 kDa band was observed with all of the affinity purified, anti-dysferlin antisera.

Immunoblotting of fractionated human muscle documented distinct 230 kDa bands in the whole muscle homogenate and in microsomal and nuclear fractions. Some immunoreactivity was also evident in the nuclear and mitochondrial fractions. No immunoreactivity was detected in the cytosolic fractions. This pattern was seen with all of the anti-dysferlin antisera, and was eliminated by immunoadsorption. The identity of the assayed fractions was verified by Western blotting using fraction-specific antibodies: histone HI for the nuclear fraction, cytochrome c for the mitochondrial fraction, $Na^+$—$K^+$ ATPase $\alpha 1$-subunit for the microsomal fraction, and SOD1 for the cytosolic fraction.

Example 3

Diagnosis

The discovery of mutations in the dysferlin gene that are associated with the MM and LMGD2B phenotypes means that individuals can be tested for the disease gene before symptoms appear. This will permit genetic testing and counseling of those with a family history of the disease. Additionally, individuals diagnosed with the genetic defect can be closely monitored for the appearance of symptoms, thereby permitting early intervention, including genetic therapy, as appropriate. Individuals with a brain-specific dysferlin-related disorder can be diagnosed using such methods.

Diagnosis can be carried out on any suitable genomic DNA sample from the individual to be tested. Typically, a blood sample from an adult or child, or a sample of placental or umbilical cord cells of a newborn would be used; alternatively, one could utilize a fetal sample obtained by amniocentesis or chorionic villi sampling.

It is expected that standard genetic diagnostic methods can be used. For example, PCR can be utilized to identify the presence of a deletion, addition, or substitution of one or more nucleotides within any one of the exons of dysferlin. Following the PCR reaction, the PCR product can be analyzed by methods such as a heteroduplex detection technique based upon that of White et al. (1992, Genomics 12:301–06), or by techniques such as cleavage of RNA-DNA hybrids using RNase A (Myers et al., 1985, Science 230:1242–46), single-stranded conformation polymorphism (SSCP) analysis (Orita et al., 1989, Genomics 10:298–99), di-deoxy-fingerprinting (DDF) (Blaszyk et al., 1995, Biotechniques 18: 256–260) and denaturing gradient gel electrophoresis (DGGE; Myers et al., 1987, Methods Enzymol. 155:501–27). The PCR may be carried out using a primer which adds a G+C rich sequence (termed a "GC-clamp") to one end of the PCR product, thus improving the sensitivity of the subsequent DGGE procedure (Sheffield et al., 1989, Proc. Natl. Acad. Sci. USA 86:232–36). If the particular mutation present in the patient's family is known to have removed or added a restriction site, or to have significantly increased or decreased the length of a particular restriction fragment, a protocol based upon restriction fragment length polymorphism (RFLP) analysis (perhaps combined with PCR) may be appropriate.

The apparent genetic heterogeneity resulting in the MM/LGMD2B phenotypes means that the nature of the particular mutation carried by affected individuals in the patient's family may have to be ascertained prior to attempting genetic diagnosis of the patient. Alternatively, a battery of tests designed to identify any of several mutations known to result in MM/LGMD2B may be utilized to screen individuals without a defined familial genotype. The analysis can be carried out on any genomic DNA derived from the patient, typically from a blood sample.

Instead of basing the diagnosis on analysis of the genomic DNA of a patient, one could seek evidence of the mutation in the level or nature of the relevant expression products. Well-known techniques for analyzing expression include mRNA-based methods, such as Northern blots and in situ hybridization (using a nucleic acid probe derived from the relevant cDNA), and quantitative PCR (as described in St-Jacques et al., 1994, Endocrinology 134:2645–57). One could also employ polypeptide based methods, including the use of antibodies specific for the polypeptide of interest. These techniques permit quantitation of the amount of expression of a given gene in the tissue of interest, at least relative to positive and negative controls. One would expect an individual who is heterozygous for a genetic defect affecting the level of expression of dysferlin to show up to a 50% loss of expression of this gene in such a hybridization or antibody-based assay. An antibody specific for the carboxy terminal end would be likely to pick up (by failure to bind to) most or all frameshift and premature termination signal mutations, as well as deletions of the carboxy terminal sequence. Use of a battery of monoclonal antibodies specific for different epitopes of dysferlin would be useful for rapidly screening cells to detect those expressing mutant forms of dysferlin (i.e., cells which bind to some dysferlin-specific monoclonal antibodies, but not to others), or for quantifying the level of dysferlin on the surface of cells. One could also use a protein truncation assay (Heim et al., 1994, Nature Genetics 8:218–19) to screen for any genetic defect which results in the production of a truncated polypeptide instead of the wild type protein.

Use of Immunodetection to Identify Normal and Disease-associated Dysferlin

In the following example, immunodetection methods are used to demonstrate a detectable difference in muscles homogenates between normal and disease-associated dysferlin alleles.

Frozen muscle samples (quadriceps) were homogenized in ten volumes of SDS-PAGE sample buffer and boiled for 5 minutes. The final loading volume of SDS-PAGE was adjusted after densitometric measurements (NIH Image) of myosin heavy chain on the Coomassie blue stained gels. Studies were performed on six MM, two LGMD-2B, and three normal muscle samples.

Immunocytochemistry was performed on 8 micron cryostat sections of the muscle that were fixed in 100% cold acetone for 5 minutes and preincubated with PBS containing 1% BSA, 5% heat-inactivated goat serum and 0.2% Triton®X-100. The sections were incubated with primary antibodies overnight at 4° C. and fluorescein-labeled secondary (TAGO Immunologicals) for 30 minutes at room temperature. The primary antibodies were applied in two double staining combinations: SalI-1 anti-dysferlin and anti-dystrophin antibodies, and SalI-2 anti-dysferlin and anti-δ-sarcoglycan antibodies. The sections were mounted in Slow-Fade (Molecular Probes).

The 230 kDA antigen was absent in samples from all five MM patient in immunoblot assays. All five patients had normal patterns of dystrophin expression. Genetic analysis of the dysferlin gene in the patients predicted that at least two of the five MM patients should have no full-length protein. Two of the other three patients had mutations in at least one allele that are predicted to eliminate normal dysferlin expression. In all five patients, absence of dysferlin immuno-staining was documented with at least two other anti-dysferlin anti-sera.

Immunostaining of dysferlin, dystrophin and δ-sarcoglycan proteins demonstrated distinct membrane-associated positivity for each protein in normal muscle. By contrast, in both MM and LGMD-2B muscle the dysferlin protein was absent, while the dystrophin and δ-sarcoglycan proteins appeared normal.

Therapeutic Treatment

A patient with MM/LGMD2B, or an individual genetically susceptible to contracting one or both of these diseases, can be treated by supplying dysferlin therapeutic agents of the present invention. Dysferlin therapeutic agents include a DNA or a subgenomic polynucleotide coding for a functional dysferlin protein. A DNA (e.g., a cDNA) is prepared which encodes the wild type form of the gene operably linked to expression control elements (e.g., promoter and enhancer) that induce expression in skeletal muscle cells or any other affected cells. The DNA may be incorporated into a vector appropriate for transforming the cells, such as a retrovirus, adenovirus, or adeno-associated virus. One of the many other known types of techniques for introducing DNA into cells in vivo may be used (e.g., liposomes). Particularly useful would be naked DNA techniques, since naked DNA is known to be readily taken up by skeletal muscle cells upon injection into muscle. Wildtype dysferlin protein can also be administered to an individual who either expresses mutant dysferlin protein or expresses an inadequate amount of dysferlin protein, e.g., a MM/LGMD2B patient.

Administration of the dysferlin therapeutic agents of the invention can include local or systemic administration, including injection, oral administration, particle gun, or catheterized administration, and topical administration. Various methods can be used to administer the therapeutic dysferlin composition directly to a specific site in the body. For example, a specific muscle can be located and the therapeutic dysferlin composition injected several times in several different locations within the body of the muscle.

The therapeutic dysferlin composition can be directly administered to the surface of the muscle, for example, by topical application of the composition. X-ray imaging can be used to assist in certain of the above delivery methods. Combination therapeutic agents, including a dysferlin protein or polypeptide or a subgenomic dysferlin polynucleotide and other therapeutic agents, can be administered simultaneously or sequentially.

Receptor-mediated targeted delivery of therapeutic compositions containing dysferlin subgenomic polynucleotides to specific tissues can also be used. Receptor-mediated DNA delivery techniques are described in, for example, Findeis et al. (1993), *Trends in Biotechnol.* 11, 202–05; Chiou et al. (1994), Gene Therapeutics: Methods and Applications of Direct Gene Transfer (J. A. Wolff, ed.); Wu & Wu (1988), *J. Biol. Chem.* 263, 621–24; Wu et al. (1994), *J. Biol. Chem.* 269, 542–46; Zenke et al. (1990), *Proc. Natl. Acad. Sci. U.S.A.* 87, 3655–59; Wu et al. (1991), *J. Biol. Chem.* 266, 338–42.

Alternatively, a dysferlin therapeutic composition can be introduced into human cells ex vivo, and the cells then implanted into the human. Cells can be removed from a variety of locations including, for example, from a selected muscle. The removed cells can then be contacted with the dysferlin therapeutic composition utilizing any of the above-described techniques, followed by the return of the cells to the human, preferably to or within the vicinity of a muscle. The above-described methods can additionally comprise the steps of depleting fibroblasts or other contaminating non-muscle cells subsequent to removing muscle cells from a human.

Both the dose of the dysferlin composition and the means of administration can be determined based on the specific qualities of the therapeutic composition, the condition, age, and weight of the patient, the progression of the disease, and other relevant factors. If the composition contains dysferlin protein or polypeptide, effective dosages of the composition are in the range of about 1 μg to about 100 mg/kg of patient body weight, e.g., about 50 μg to about 50 mg/kg of patient body weight, e.g., about 500 μg to about 5 mg/kg of patient body weight.

Therapeutic compositions containing dysferlin subgenomic polynucleotides can be administered in a range of about 0.1 μg to about 10 mg of DNA/dose for local administration in a gene therapy protocol. Concentration ranges of about 0.1 μg to about 10 mg, e.g., about 1 μg to about 1 mg, e.g., about 10 μg to about 100 μg of DNA can also be used during a gene therapy protocol. Factors such as method of action and efficacy of transformation and expression are considerations that will effect the dosage required for ultimate efficacy of the dysferlin subgenomic polynucleotides. Where greater expression is desired over a larger area of tissue, larger amounts of dysferlin subgenomic polynucleotides or the same amounts readministered in a successive protocol of administrations, or several administrations to different adjacent or close tissue portions of for example, a muscle site, may be required to effect a positive therapeutic outcome. In all cases, routine experimentation in clinical trials will determine specific ranges for optimal therapeutic effect.

Animal Model

A line of transgenic animals (e.g., mice, rats, guinea pigs, hamsters, rabbits, or other mammals) can be produced bearing a transgene encoding a defective form of dysferlin. Standard methods of generating such transgenic animals would be used, e.g., as described below.

Alternatively, standard methods of producing null (i.e., knockout) mice could be used to generate a mouse which bears one defective and one wild type allele encoding dysferlin. If desired, two such heterozygous mice could be crossed to produce offspring which are homozygous for the mutant allele. The homozygous mutant offspring would be expected to have a phenotype comparable to the human MM and/or LGMD2B phenotype, and so serve as models for the human disease.

For example, in one embodiment, dysferlin mutations are introduced into a dysferlin gene of a cell, e.g., a fertilized oocyte or an embryonic stem cell. Such cells can then be used to create non-human transgenic animals in which exogenous altered (e.g., mutated) dysferlin sequences have been introduced into their genome or homologously recombinant animals in which endogenous dysferlin nucleic acid sequences have been altered. Such animals are useful for studying the function and/or activity of dysferlin and for identifying and/or evaluating modulators of dysferlin function. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologously recombinant animal" is a non-human animal, preferably a mammal, more preferably a mouse, in which an endogenous dysferlin gene has been altered by homologous recombination between the endogenous gene and an exogenous DNA molecule introduced into a cell of the animal, e.g., an embryonic cell of the animal, prior to completed development of the animal.

A transgenic animal of the invention can be created by introducing a nucleic acid encoding a dysferlin mutation into the male pronuclei of a fertilized oocyte, e.g., by microinjection or retroviral infection, and allowing the oocyte to develop in a pseudopregnant female foster animal. A dysferlin cDNA sequence e.g., that of (SEQ ID NO:1 or SEQ ID NO:3) can be introduced as a transgene into the genome of a non-human animal. Alternatively, a nonhuman homologue of the human dysferlin gene can be isolated based on hybridization to the human dysferlin sequence (e.g., cDNA) and used as a transgene. Intronic sequences and polyadenylation signals can also be included in the transgene to increase the efficiency of expression of the transgene. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the mutant dysferlin transgene in its genome and/or expression of the mutant dysferlin mRNA in tissues or cells of the animals. A transgenic founder animal can then be used to breed additional animals carrying the transgene. Moreover, transgenic animals carrying a transgene encoding a mutant dysferlin can further be bred to other transgenic animals carrying other transgenes.

To create an homologously recombinant animal, a vector is prepared which contains at least a portion of a dysferlin gene into which a deletion, addition or substitution has been introduced to thereby alter a dysferlin gene. In a preferred embodiment, the vector is designed such that, upon homologous recombination, the endogenous dysferlin gene is functionally disrupted (i.e., no longer encodes a functional protein; also referred to as a "knock out" vector). Alternatively, the vector can be designed such that, upon homologous recombination, the endogenous dysferlin gene is mutated or otherwise altered (e.g., contains one of the mutations described in Table 2). In the homologous recombination vector, the altered portion of the dysferlin sequence is flanked at its 5' and 3' ends by additional nucleic acid of the dysferlin gene to allow for homologous recombination to occur between the exogenous dysferlin nucleic acid sequence carried by the vector and an endogenous dysferlin gene in an embryonic stem cell. The additional flanking dysferlin nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced dysferlin sequence has homologously recombined with the endogenous dysferlin gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A single stranded oligonucleotide of 14–50 nucleotides in length having a nucleotide sequence identical to a portion of SEQ ID NO:3, or a complement thereof.

* * * * *